US012606544B2

(12) United States Patent
Qi et al.

(10) Patent No.: US 12,606,544 B2
(45) Date of Patent: Apr. 21, 2026

(54) JAK1 SELECTIVE KINASE INHIBITOR

(71) Applicant: DIZAL (JIANGSU) PHARMACEUTICAL CO., LTD., Shanghai (CN)

(72) Inventors: Changhe Qi, Shanghai (CN); Honchung Tsui, Shanghai (CN); Qingbei Zeng, Shanghai (CN); Zhenfan Yang, Shanghai (CN); Xiaolin Zhang, Shanghai (CN)

(73) Assignee: DIZAL (JIANGSU) PHARMACEUTICAL CO., LTD., Shanghai (CN)

( * ) Notice: Subject to any disclaimer, the term of this patent is extended or adjusted under 35 U.S.C. 154(b) by 1058 days.

(21) Appl. No.: 17/604,442

(22) PCT Filed: Apr. 17, 2020

(86) PCT No.: PCT/CN2020/085338
§ 371 (c)(1),
(2) Date: Oct. 18, 2021

(87) PCT Pub. No.: WO2020/211839
PCT Pub. Date: Oct. 22, 2020

(65) Prior Publication Data

US 2022/0220096 A1 Jul. 14, 2022

(30) Foreign Application Priority Data

Apr. 19, 2019 (WO) ................ PCT/CN2019/083376

(51) Int. Cl.

| | |
|---|---|
| ***C07D 403/14*** | (2006.01) |
| ***A61K 9/00*** | (2006.01) |
| ***A61K 45/06*** | (2006.01) |
| ***C07D 401/14*** | (2006.01) |
| ***C07D 405/14*** | (2006.01) |
| ***C07D 413/14*** | (2006.01) |
| ***C07D 417/14*** | (2006.01) |
| ***C07D 471/04*** | (2006.01) |

(52) U.S. Cl.
CPC ............ *C07D 403/14* (2013.01); *A61K 9/007* (2013.01); *A61K 45/06* (2013.01); *C07D 401/14* (2013.01); *C07D 405/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

2013/0303563 A1* 11/2013 Adler .................. C12Q 1/6883 435/6.12

FOREIGN PATENT DOCUMENTS

| | | | | |
|---|---|---|---|---|
| CN | 108368091 A | 8/2018 | | |
| EP | 3854793 A1 | 7/2021 | | |
| WO | 2017/050938 A1 | 3/2017 | | |
| WO | WO-2018134213 A1 * | 7/2018 | ........... | A61K 31/506 |
| WO | WO-2020057669 A1 * | 3/2020 | ........... | A61K 31/506 |

OTHER PUBLICATIONS

Dengler et. al. "Lung-restricted inhibition of Janus kinase 1 is effective in rodent models of asthma" Sci. Transl. Med. 2018, 10, eaao2151, 1-11. DOI: 10.1126/scitranslmed.aao2151 (Year: 2018).*
Schwartz et. al. "JAK inhibition as a therapeutic strategy for immune and inflammatory diseases" Nat Rev Drug Discov. 2017, 17, 1, 78, 1-41. DOI: 10.1038/nrd.2017.267 (Year: 2017).*
Meyskens et. al. "Cancer Prevention: Obstacles, Challenges, and the Road Ahead" J Natl Cancer Inst 2016, 108, 2, djv309, 1-8. DOI: 10.1093/jnci/djv309 (Year: 2016).*
Qibin Su et al., "Discovery of (2R)-N-[3-[2-[(3-Methoxy-1-methyl-pyrazol-4-yl)amino]pyrimidin-4-yl]-1H-indol-7-yl]-2-(4-methylpiperazin-1-yl)propenamide (AZD4205) as a Potent and Selective Janus Kinase 1 Inhibitor", J.Med.Chem., Apr. 16, 2020 (Apr. 16, 2020), vol. 63, 4517-4527.
Neil P. Grimster et al., "Discovery and Optimization of a Novel Series of Highly Selective JAK1 Kinase Inhibitors", J. Med.Chem., Jun. 1, 2018 (Jun. 1, 2018), vol. 61, 5235-5244.
International Search Report of PCT/CN2020/085338, mailed on Jul. 15, 2020.
The partial supplementary European search report for the corresponding EP application 20790639.7, issued on Dec. 16, 2022.

* cited by examiner

*Primary Examiner* — Jennifer A Berrios
*Assistant Examiner* — Sophia Reilly
(74) *Attorney, Agent, or Firm* — Junhe Law Office P.C.; Zhaohui Wang

(57) ABSTRACT

Disclosed herein are compounds of Formula (I), and pharmaceutically acceptable salts thereof, that are useful as JAK kinase inhibitors. Also disclosed are pharmaceutical compositions comprising one or more compounds of Formula (I), and methods of using such compounds or compositions to treat respiratory conditions (e.g., asthma or COPD).

25 Claims, No Drawings

JAK1 SELECTIVE KINASE INHIBITOR

CROSS-REFERENCE TO RELATED APPLICATIONS

This application is a national phase application, filed pursuant to 35 U.S.C. § 371 of International Application No. PCT/CN2020/085338, filed on Apr. 17, 2020, which claims foreign priority of PCT Patent Application No. PCT/CN2019/083376, filed on Apr. 19, 2019, now abandoned. Each of these applications is hereby incorporated by reference herein in its entirety.

FIELD OF THE DISCLOSURE

The present disclosure relates to novel compounds selectively inhibiting JAK1 kinase. The present disclosure also relates to pharmaceutical compositions comprising one or more of the compounds as an active ingredient, and use of the compounds in the treatment of JAK1-related disorders, for example, respiratory conditions, such as asthma or COPD.

BACKGROUND

Janus kinase (JAK) is a family of intracellular, nonreceptor tyrosine kinases that transduce cytokine-mediated signals via the JAK-STAT pathway. After cytokines bind to their receptors, the receptors oligomerize to bring the JAK kinases, which associate with the cytoplasmic tails of the receptors, into proximity and facilitate trans-phosphorylation and activation of the tyrosine residues on the JAK kinase. The phosphorylated JAK kinases bind and activate various Signal Transducer and Activator of Transcription (STAT) proteins, which then dimerize and translocate to the nucleus to activate the transcription of cytokine-responsive genes.

The JAK family includes JAK1, JAK2, JAK3 and TYK2. JAK1 is essential for signaling of certain type I and type II cytokines, thus playing a critical role in initiating responses of multiple major cytokine receptor families. For example, JAK1 interacts with the common gamma chain (γc) of type I cytokine receptors to elicit signals from the IL-2 receptor family (e.g., IL-2R, IL-7R, IL-9R and IL-15R), the IL-4 receptor family (e.g., IL-4R and IL-13R) and the gp130 receptor family (e.g., IL-6R, IL-11R, LIF-R CNTF-R and neurotrophin-1 receptor). JAK1 is also important for transducing a signal by type I interferons (IFN-α/β), type II interferon (IFN-γ) and members of the IL-10 family via type II cytokine receptors. JAK1 has been demonstrated to relate to disorders such as cancer, autoimmune diseases, transplant rejection, and inflammation.

Given that JAK family members have different roles, there is therapeutic potential of targeting them selectively. However, developing selective JAK1 inhibitors has been challenging, and compounds identified as selective JAK1 inhibitors demonstrate only marginal JAK1 selectivity (Menet et al., *Future Med Chem* (2015) 7:203-35). Therefore, there is a need to develop highly potent and selective JAK1 inhibitors to treat JAK1-related disorders, for instance, asthma or COPD, with no real or perceived side effects associated with off-target activity, such as anaemia.

SUMMARY

In one aspect, the present disclosure provides a compound represented by Formula (I):

Formula (I)

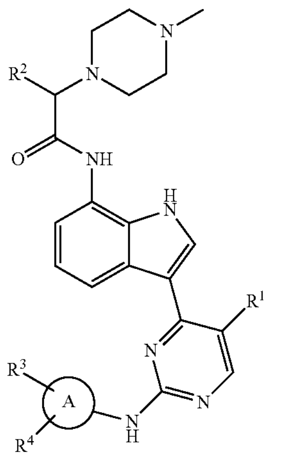

or a pharmaceutically acceptable salt thereof, wherein Ring A, $R^1$, $R^2$, $R^3$, $R^4$ are as herein defined.

In another aspect, the present disclosure provides a compound represented by Formula (Ia):

Formula (Ia)

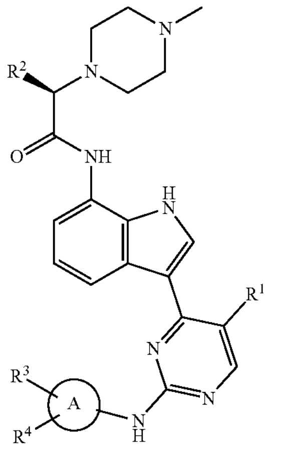

or a pharmaceutically acceptable salt thereof, wherein or a pharmaceutically acceptable salt thereof, wherein Ring A, $R^1$, $R^2$, $R^3$, $R^4$ are as herein defined.

In another aspect, the present disclosure provides a pharmaceutical composition comprising one or more compounds of Formula (I), Formula (Ia), or a pharmaceutically acceptable salts thereof, as an active ingredient.

In another aspect, the present disclosure further provides a compound of Formula (I), Formula (Ia), or a pharmaceutically acceptable salt thereof, or a pharmaceutical composition of one or more of the foregoing, for use in inhibiting JAK-1 kinase.

In yet another aspect, the present disclosure provides use of the compounds of Formula (I), Formula (Ia), or a pharmaceutically acceptable salts thereof, or a pharmaceutical composition of one or more of the foregoing in the manufacture of a medicament for inhibiting JAK-1 kinase in a subject.

In another aspect, the present disclosure provides a method for inhibiting JAK-1 kinase, by using one or more compounds of Formula (I), Formula (Ia), or a pharmaceutically acceptable salts thereof or the pharmaceutical composition of one or more of the foregoing.

In another aspect, the present disclosure provides a method for treating a JAK-1-related disorder (e.g., respiratory disease, such as asthma or COPD), by using the compounds of Formula (I), Formula (Ia), or a pharmaceutically acceptable salts thereof or the pharmaceutical composition of one or more of the foregoing. In a further aspect, the present disclosure provides a compound of Formula (I), Formula (Ia), or a pharmaceutically acceptable salt thereof, in combination with a second therapeutic agent, preferably an anti-inflammation agent.

In another aspect, the present disclosure provides a combined use of a compound of Formula (I), Formula (Ia), or a pharmaceutically acceptable salt thereof, and a second therapeutic agent, preferably an anti-inflammation agent.

DETAILED DESCRIPTION

Compounds

In one aspect, the present disclosure provides compounds of Formula (I):

Formula (I)

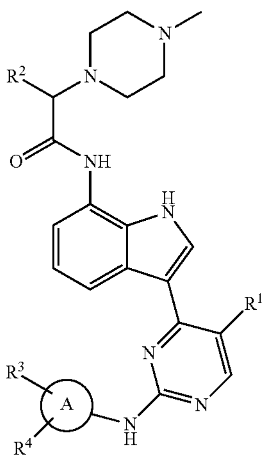

or a pharmaceutically acceptable salt thereof, wherein,

Ring A is a monocyclic heteroaryl or saturated or unsaturated 8-10 membered bicyclic ring having 0-5 ring heteroatoms selected from oxygen, sulfur and nitrogen, wherein one or more ring forming —$CH_2$— group of the aryl, the heteroaryl, or the bicyclic ring may be replaced by a —C(O)— group;

$R^1$ is hydrogen, halogen, hydroxyl, amino, cyano, or $C_{1-3}$ alkyl;

$R^2$ is hydrogen or $C_{1-12}$ alkyl optionally mono- or multi-substituted by halogen, hydroxyl, amino, cyano, or $C_{1-12}$ alkoxyl;

each $R^3$ and $R^4$ is independently absent, or halogen, hydroxyl, $C_{1-6}$ alkyl, carboxyl, $C_{1-6}$ alkoxyl, $C_{1-6}$ alkoxycarbonyl, —$NR^aR^b$, —C(O)$NR^aR^b$, sulfinyl, $C_{1-6}$ alkylsulfinyl, sulfonyl, $C_{1-6}$ alkylsulfonyl, sulfonoxyl, sulfoximinyl, $C_{1-6}$ alkylsulfoximinyl, sulfonimidoyl, S—($C_{1-6}$ alkyl)sulfonimidoyl, N—($C_{1-6}$ alkyl)sulfonimidoyl, N, S—($C_{1-6}$ alkyl)$_2$ sulfonimidoyl, phosphinoyl, $C_{1-6}$ alkylphosphinoyl, ($C_{1-6}$ alkyl)$_2$ phosphinoyl, $C_{1-6}$ alkylphosphonyl, 3-10 membered saturated or unsaturated carbocyclyl, 3-10 membered saturated or unsaturated heterocyclyl, which can be optionally mono- or independently multi-substituted by halogen, hydroxyl, $C_{1-6}$ alkyl, $C_{1-6}$ alkoxyl, $C_{1-6}$ carboxyl, $C_{1-6}$ alkoxycarbonyl, —$NR^aR^b$, —C(O)$NR^aR^b$, sulfonyl, $C_{1-6}$ alkylsulfonyl, carbamoyl, N—($C_{1-6}$ alkyl)carbamoyl, or N,N—($C_{1-6}$ alkyl)$_2$carbamoyl, phosphinoyl, $C_{1-6}$ alkylphosphinoyl, ($C_{1-6}$ alkyl)$_2$ phosphinoyl, wherein one or more ring forming —$CH_2$— group of the carbocyclyl or heterocyclyl may be replaced by a —C(O)— group;

wherein, each $R^a$ and $R^b$ is independently selected from hydrogen, $C_{1-6}$ alkyl, $C_{1-6}$ alkylcarbonyl, which can be optionally mono- or independently multi-substituted by halogen, hydroxyl, or $C_{1-6}$ alkoxy.

In some embodiments, the compounds provided herein have a structure of Formula (Ia)

Formula (I)

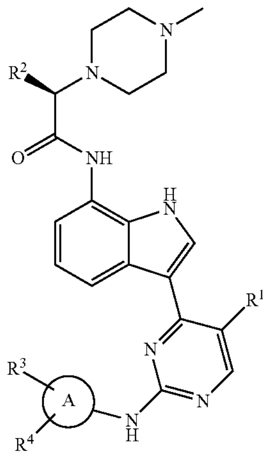

or a pharmaceutically acceptable salt thereof, wherein,

Ring A is a monocyclic heteroaryl or saturated or unsaturated 8-10 membered bicyclic ring having 0-5 ring heteroatoms selected from oxygen, sulfur and nitrogen, wherein one or more ring forming —$CH_2$— group of the aryl, the heteroaryl, or the bicyclic ring may be replaced by a —C(O)— group;

$R^1$ is hydrogen, halogen, hydroxyl, amino, cyano, or $C_{1-3}$ alkyl;

$R^2$ is hydrogen or $C_{1-12}$ alkyl optionally mono- or multi-substituted by halogen, hydroxyl, amino, cyano, or $C_{1-12}$ alkoxyl;

each $R^3$ and $R^4$ is independently absent, or halogen, hydroxyl, $C_{1-6}$ alkyl, carboxyl, $C_{1-6}$ alkoxyl, $C_{1-6}$ alkoxycarbonyl, —$NR^aR^b$, —C(O)$NR^aR^b$, sulfinyl, $C_{1-6}$ alkylsulfinyl, sulfonyl, $C_{1-6}$ alkylsulfonyl, sulfonoxyl, sulfoximinyl, $C_{1-6}$ alkylsulfoximinyl, sulfonimidoyl, S—($C_{1-6}$ alkyl)sulfonimidoyl, N—($C_{1-6}$ alkyl)sulfonimidoyl, N, S—($C_{1-6}$ alkyl)$_2$ sulfonimidoyl, phosphinoyl, $C_{1-6}$ alkylphosphinoyl, ($C_{1-6}$ alkyl)$_2$ phosphinoyl, $C_{1-6}$ alkylphosphonyl, 3-10 membered saturated or unsaturated carbocyclyl, 3-10 membered saturated or unsaturated heterocyclyl, which can be optionally mono- or independently multi-substituted by halogen, hydroxyl, $C_{1-6}$ alkyl, $C_{1-6}$ alkoxyl, $C_{1-6}$ carboxyl, $C_{1-6}$ alkoxycarbonyl, —$NR^aR^b$, —C(O)$NR^aR^b$, sulfonyl, $C_{1-6}$ alkylsulfonyl, carbamoyl, N—($C_{1-6}$ alkyl)carbamoyl, or N,N—($C_{1-6}$ alkyl)$_2$carbamoyl, phosphinoyl, $C_{1-6}$ alkylphosphinoyl, ($C_{1-6}$ alkyl)$_2$ phosphinoyl, wherein one or more ring forming —$CH_2$— group of the carbocyclyl or heterocyclyl may be replaced by a —C(O)— group;

wherein, each $R^a$ and $R^b$ is independently selected from hydrogen, $C_{1-6}$ alkyl, $C_{1-6}$ alkylcarbonyl, which can be optionally mono- or independently multi-substituted by halogen, hydroxyl, or $C_{1-6}$ alkoxy.

In some embodiments, Ring A is a phenyl or pyridinyl fused bicyclic heteroaryl ring having 0-5 ring heteroatoms selected from oxygen, sulfur and nitrogen, wherein one or more ring forming —$CH_2$— group of the bicyclic ring may be replaced by a —C(O)— group.

In some embodiments, Ring A is selected from the group consisting of:

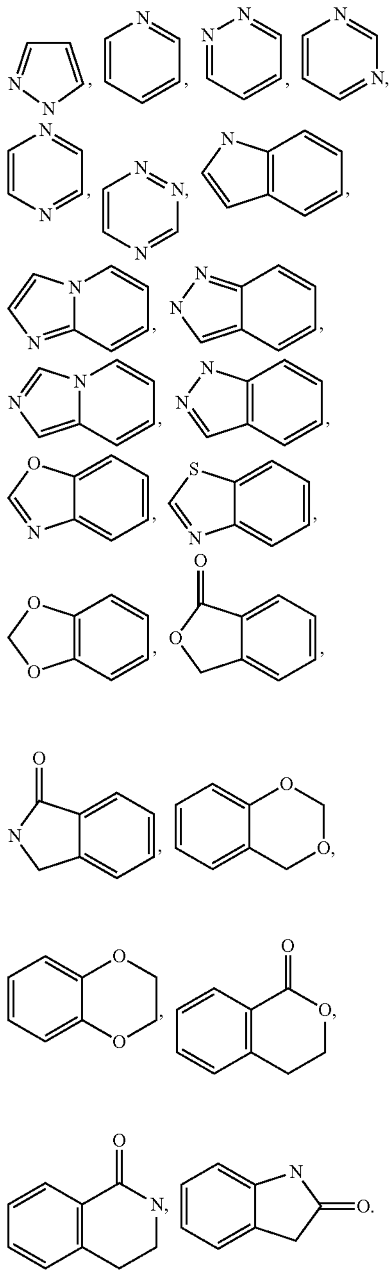

In some embodiments, Ring A is a monocyclic heteroaryl selected from pyrazolyl, pyridinyl, pyridazinyl, pyrimidinyl, pyrazinyl, or triazinyl. In some embodiments, Ring A is pyrimidinyl.

In some embodiments, Ring A is selected from pyrimidin-3-yl, pyrimidin-4-yl, 1H-pyrazolo[4,3-b]pyridin-6-yl, 6-(oxazol-2-yl)pyridin-3-yl, 1H-pyrazol-4-yl, benzo[d]thiazol-5-yl.

In some embodiments, $R^1$ is halogen selected from bromo, fluoro, chloro, and iodo. In some embodiments, $R^1$ is fluoro.

In some embodiments, $R^2$ is $C_{1-6}$ alkyl optionally mono- or multi-substituted by $C_{1-6}$ alkoxyl. In some embodiments, $R^2$ is $R^2$ is $C_{1-3}$ alkyl optionally mono- or multi-substituted by $C_{1-3}$ alkoxyl. In some embodiments, $R^2$ is methoxymethyl.

In some embodiments, each $R^3$ and $R^4$ is independently absent, or $C_{1-6}$ alkyl, $C_{1-6}$ alkoxyl, carboxyl, $C_{1-6}$ alkoxycarbonyl, —C(O)$NR^aR^b$, which can be optionally mono- or independently multi-substituted by halogen, hydroxyl, $C_{1-6}$ alkyl, $C_{1-6}$ alkoxyl, $C_{1-6}$ alkyl-carboxyl, $C_{1-6}$ alkoxycarbonyl, —$NR_aR_b$, —C(O)$NR_aR_b$, sulfonyl, $C_{1-6}$ alkylsulfonyl, carbamoyl, N—($C_{1-6}$ alkyl)carbamoyl, or N,N—($C_{1-6}$ alkyl)$_2$ carbamoyl.

In some embodiments, at least one of $R^3$ and $R^4$ is absent.

In some embodiments, neither of $R^3$ or $R^4$ is absent, and said $R^3$ or $R^4$ are in ortho-positions. In some embodiments, neither of $R^3$ or $R^4$ is absent, and said $R^3$ or $R^4$ are in meta-positions.

In some embodiments, each $R^3$ and $R^4$ is independently selected from absent, $C_{1-6}$ alkyl, $C_{1-6}$ alkoxycarbonyl, optionally substituted by hydroxyl or $C_{1-6}$ alkoxycarbonyl.

In some embodiments, each $R^3$ and $R^4$ is independently selected from absent, carboxyl, hydroxyl, carbamoyl, amino, methyl, methoxyl, ethoxyl, methoxymethyl, methoxyethoxyl, hydroxymethyl, hydroxyethyl, hydroxybutyl, hydroxymethoxyl, hydroxyethoxyl, carbamoylmethoxyl, methylcarbamoyl, hydroxyacetamido, (hydroxyethyl)carbamoyl, methylcarbamoylmethoxyl, dimethylcarbamoylethoxyl, carboxymethoxyl, methoxycarbonyl, ethoxycarbonyl, isopropoxycarbonyl, tertbutoxycarbonyl, methoxycarbonylmethyl, methoxycarbonylethyl, ethoxycarbonylmethyl, methoxycarbonylmethoxyl, methylamino, dimethylamino, dimethylaminoethyl, dimethylaminoethoxycarbonyl, dimethylaminomethyl, propionamido, methylcarbonylamino, dimethylaminoethoxycarbonyl, phosphinoyl, methylphosphinoyl, dimethylphosphinoyl, sulfonyl, methylsulfonyl, S-methyl-sulfonimidoyl, N,S-dimethylsulfonimidoyl, dimethylsulfoximinyl, methylsulfonoxyl, oxetanyl, oxetanyl-2-one, azetindin-2-yl, azetidin-3-yl-2-one, methylazetidin-3-yl-2-one, tetrahydrofuran-3-yl, or tetrahydropyran-4-yl.

In some embodiments, each $R^3$ and $R^4$ is selected from hydroxymethyl, methoxymethyl, hydroxyacetamido, or propionamido.

In some embodiments, when Ring A is pyrazolyl, neither of $R^3$ nor $R^4$ is $C_{1-3}$ alkyl or $C_{1-3}$ alkoxyl.

In some embodiments, $R^1$ is fluoro; $R^2$ is methoxymethyl; Ring A is selected from pyrimidin-3-yl, pyrimidin-4-yl, 1H-pyrazolo[4,3-b]pyridin-6-yl, 6-(oxazol-2-yl)pyridin-3-yl, 1H-pyrazol-4-yl, and benzo[d]thiazol-5-yl; each $R^3$ and $R^4$ is selected from hydroxymethyl, methoxymethyl, hydroxyacetamido, and propionamido.

Exemplary compounds 1-78 of Formula (I) are set forth in Table 1 below.

TABLE 1

| Exemplary Compounds 1-78 | | |
|---|---|---|
| Example number | structures | Name |
| 1 | 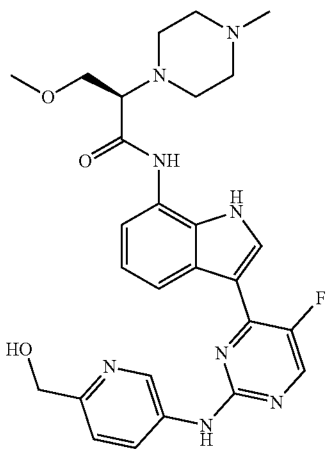 | (R)-N-(3-(5-fluoro-2-((6-(hydroxymethyl)pyridin-3-yl)amino)pyrimidin-4-yl)-1H-indol-7-yl)-3-methoxy-2-(4-methylpiperazin-1-yl)propanamide |
| 2 | 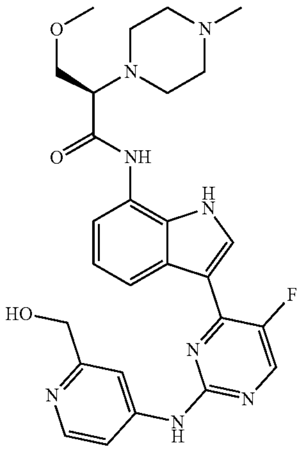 [SMILES: COC[C@H](C(=O)Nc1cccc2c(-c3nc(Nc4ccnc(CO)c4)ncc3F)c[nH]c12)N1CCN(C)CC1] | (R)-N-(3-(5-fluoro-2-((2-(hydroxymethyl)pyridin-4-yl)amino)pyrimidin-4-yl)-1H-indol-7-yl)-3-methoxy-2-(4-methylpiperazin-1-yl)propanamide |
| 3 | 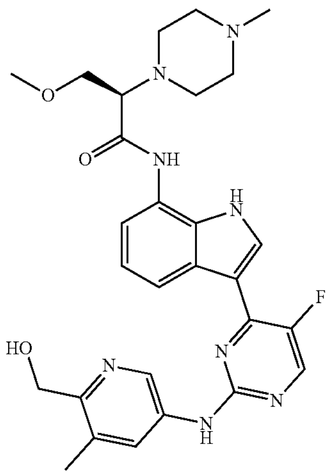 [SMILES: COC[C@H](C(=O)Nc1cccc2c(-c3nc(Nc4cnc(CO)c(C)c4)ncc3F)c[nH]c12)N1CCN(C)CC1] | (R)-N-(3-(5-fluoro-2-((6-(hydroxymethyl)-5-methylpyridin-3-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 4 | 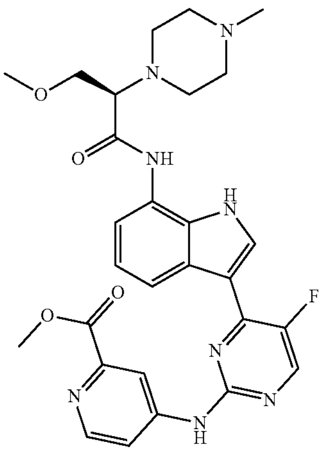 [SMILES: COC[C@H](C(=O)Nc1cccc2c(-c3nc(Nc4ccnc(C(=O)OC)c4)ncc3F)c[nH]c12)N1CCN(C)CC1] | Methyl-(R)-4-((5-fluoro-4-(7-(3-methoxy-2-(4-methylpiperazin-1-yl)propanamido)-1H-indol-3-yl)pyrimidin-2-yl)amino)picolinate |
| 5 | 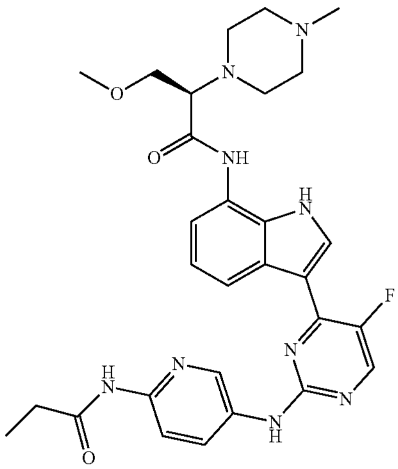 [SMILES: CCC(=O)Nc1ccc(Nc2ncc(F)c(-c3c[nH]c4c(NC(=O)[C@@H](COC)N5CCN(C)CC5)cccc34)n2)cn1] | (R)-N-(3-(5-fluoro-2-((6-propionamidopyridin-3-yl)amino)pyrimidin-4-yl)-1H-indol-7-yl)-3-methoxy-2-(4-methylpiperazin-1-yl)propanamide |
| 6 | 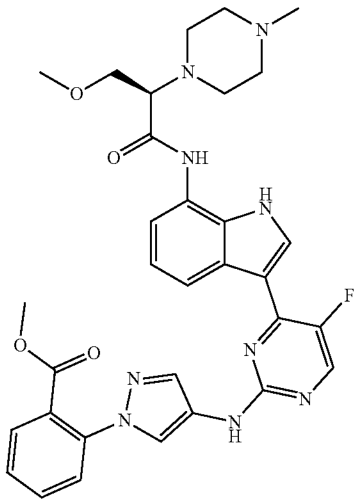 [SMILES: COC[C@H](C(=O)Nc1cccc2c(-c3nc(Nc4cnn(-c5ccccc5C(=O)OC)c4)ncc3F)c[nH]c12)N1CCN(C)CC1] | methyl (R)-2-(4-((5-fluoro-4-(7-(3-methoxy-2-(4-methylpiperazin-1-yl)propanamido)-1H-indol-3-yl)pyrimidin-2-yl)amino)-1H-pyrazol-1-yl)benzoate |

TABLE 1-continued

| Exemplary Compounds 1-78 | | |
|---|---|---|
| Example number | structures | Name |
| 7 | 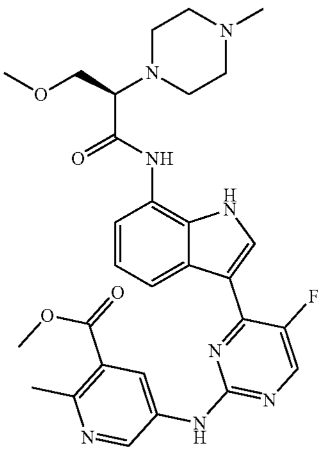 [SMILES: COC[C@H](C(=O)Nc1cccc2c(-c3nc(Nc4cnc(C)c(C(=O)OC)c4)ncc3F)c[nH]c12)N1CCN(C)CC1] | methyl (R)-5-((5-fluoro-4-(7-(3-methoxy-2-(4-methylpiperazin-1-yl)propanamido)-1H-indol-3-yl)pyrimidin-2-yl)amino)-2-methylnicotinate |
| 8 | 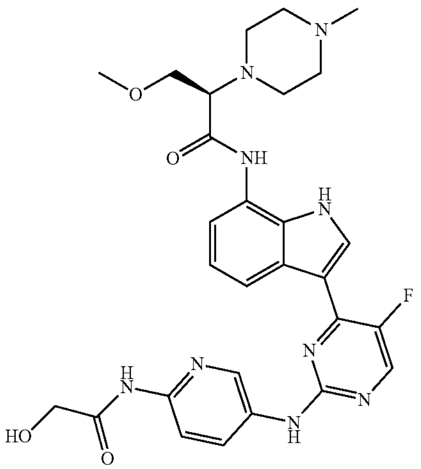 [SMILES: COC[C@H](C(=O)Nc1cccc2c(-c3nc(Nc4ccc(NC(=O)CO)nc4)ncc3F)c[nH]c12)N1CCN(C)CC1] | (R)-N-(3-(5-fluoro-2-((6-(2-hydroxyacetamido)pyridin-3-yl)amino)pyrimidin-4-yl)-1H-indol-7-yl)-3-methoxy-2-(4-methylpiperazin-1-yl)propanamide |
| 9 | 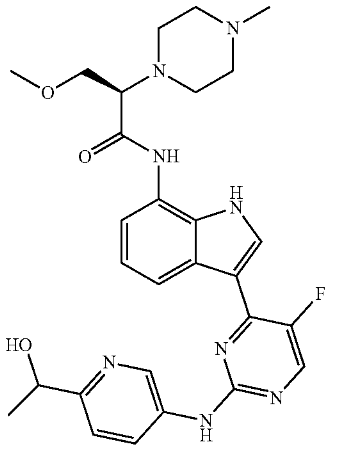 [SMILES: COC[C@H](C(=O)Nc1cccc2c(-c3nc(Nc4ccc(C(C)O)nc4)ncc3F)c[nH]c12)N1CCN(C)CC1] | (R)-N-(3-(5-fluoro-2-((6-(1-hydroxyethyl)pyridin-3-yl)amino)pyrimidin-4-yl)-1H-indol-7-yl)-3-methoxy-2-(4-methylpiperazin-1-yl)propanamide (isomer 2) |

TABLE 1-continued

| Exemplary Compounds 1-78 | | |
|---|---|---|
| Example number | structures | Name |
| 12 | 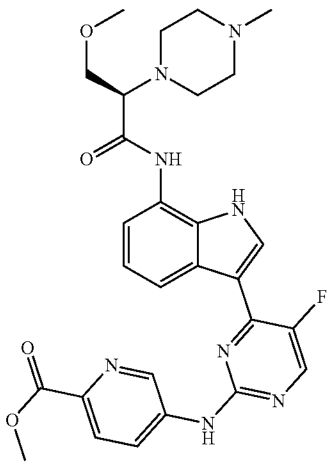 [SMILES: COC[C@H](C(=O)Nc1cccc2c(-c3nc(Nc4ccc(C(=O)OC)nc4)ncc3F)c[nH]c12)N1CCN(C)CC1] | methyl (R)-5-((5-fluoro-4-(7-(3-methoxy-2-(4-methylpiperazin-1-yl)propanamido)-1H-indol-3-yl)pyrimidin-2-yl)amino)picolinate |
| 13 | 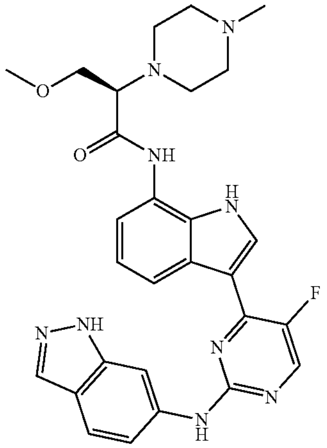 | (R)-N-(3-(2-((1H-indazol-6-yl)amino)-5-fluoropyrimidin-4-yl)-1H-indol-7-yl)-3-methoxy-2-(4-methylpiperazin-1-yl)propanamide |
| 14 | 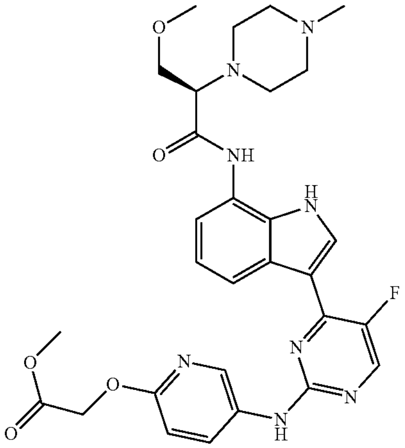 [SMILES: COC[C@H](C(=O)Nc1cccc2c(-c3nc(Nc4ccc(OCC(=O)OC)nc4)ncc3F)c[nH]c12)N1CCN(C)CC1] | methyl (R)-2-((5-((5-fluoro-4-(7-(3-methoxy-2-(4-methylpiperazin-1-yl)propanamido)-1H-indol-3-yl)pyrimidin-2-yl)amino)pyridin-2-yl)oxy)acetate |

TABLE 1-continued

| Exemplary Compounds 1-78 | | |
|---|---|---|
| Example number | structures | Name |
| 15 | 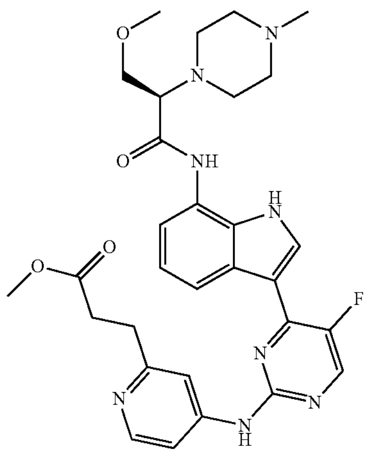 [SMILES: COC[C@H](C(=O)Nc1cccc2c(-c3nc(Nc4ccnc(CCC(=O)OC)c4)ncc3F)c[nH]c12)N1CCN(C)CC1] | methyl (R)-3-(4-((5-fluoro-4-(7-(3-methoxy-2-(4-methylpiperazin-1-yl)propanamido)-1H-indol-3-yl)pyrimidin-2-yl)amino)pyridin-2-yl)propanoate |
| 16 | 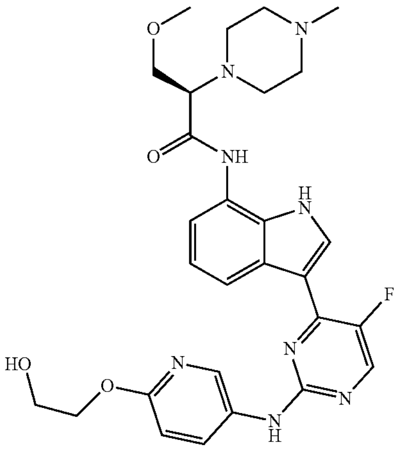 [SMILES: COC[C@H](C(=O)Nc1cccc2c(-c3nc(Nc4ccc(OCCO)nc4)ncc3F)c[nH]c12)N1CCN(C)CC1] | (R)-N-(3-(5-fluoro-2-((6-(2-hydroxyethoxy)pyridin-3-yl)amino)pyrimidin-4-yl)-1H-indol-7-yl)-3-methoxy-2-(4-methylpiperazin-1-yl)propanamide |
| 17 | 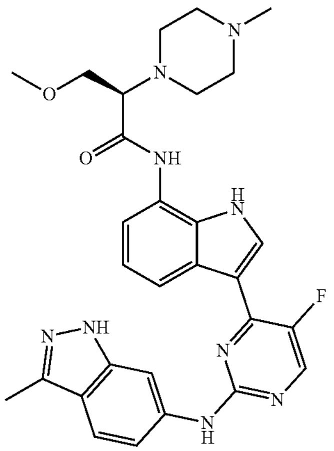 [SMILES: COC[C@H](C(=O)Nc1cccc2c(-c3nc(Nc4ccc5c(C)n[nH]c5c4)ncc3F)c[nH]c12)N1CCN(C)CC1] | (R)-N-(3-(5-fluoro-2-((3-methyl-1H-indazol-6-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 18 | 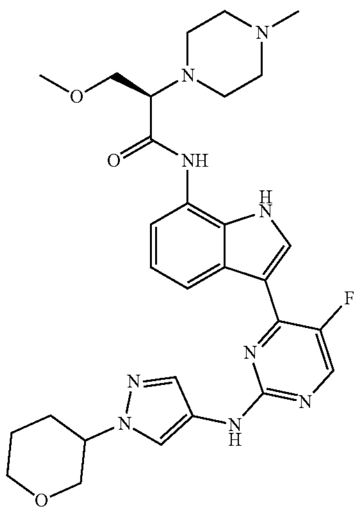 [SMILES: COC[C@H](C(=O)Nc1cccc2c(-c3nc(Nc4cnn(C5CCCOC5)c4)ncc3F)c[nH]c12)N1CCN(C)CC1] | (R)-N-(3-(5-fluoro-2-((1-(tetrahydro-2H-pyran-4-yl)-1H-pyrazol-4-yl)amino)pyrimidin-4-yl)-1H-indol-7-yl)-3-methoxy-2-(4-methylpiperazin-1-yl)propanamide |
| 19 | 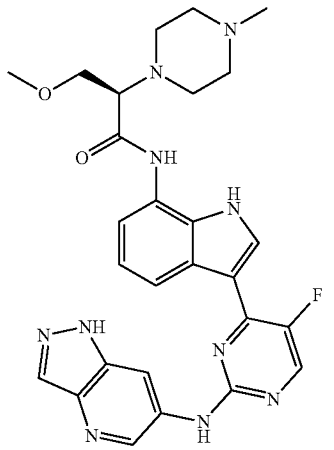 [SMILES: COC[C@H](C(=O)Nc1cccc2c(-c3nc(Nc4cnc5cn[nH]c5c4)ncc3F)c[nH]c12)N1CCN(C)CC1] | (R)-N-(3-(2-((1H-pyrazolo[4,3-b]pyridin-6-yl)amino)-5-fluoropyrimidin-4-yl)-1H-indol-7-yl)-3-methoxy-2-(4-methylpiperazin-1-yl)propanamide |
| 20 | 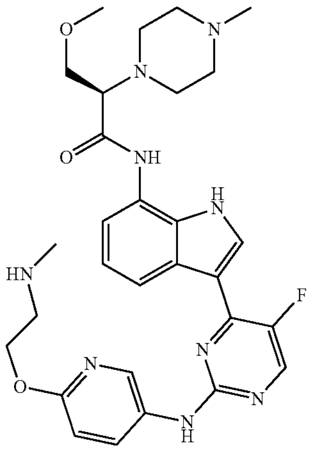 [SMILES: CNCCOc1ccc(Nc2ncc(F)c(-c3c[nH]c4c(NC(=O)[C@@H](COC)N5CCN(C)CC5)cccc34)n2)cn1] | (R)-N-(3-(5-fluoro-2-((6-(2-(methylamino)ethoxy)pyridin-3-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 21 | 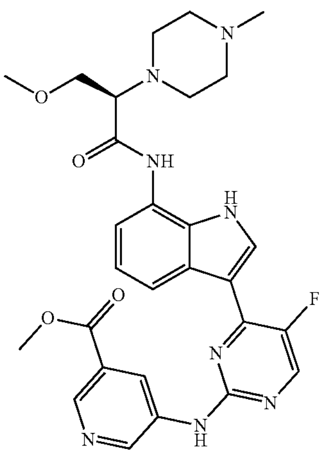 [SMILES: COC[C@H](C(=O)Nc1cccc2c(-c3nc(Nc4cncc(C(=O)OC)c4)ncc3F)c[nH]c12)N1CCN(C)CC1] | methyl (R)-5-((5-fluoro-4-(7-(3-methoxy-2-(4-methylpiperazin-1-yl)propanamido)-1H-indol-3-yl)pyrimidin-2-yl)amino)nicotinate |
| 22 | 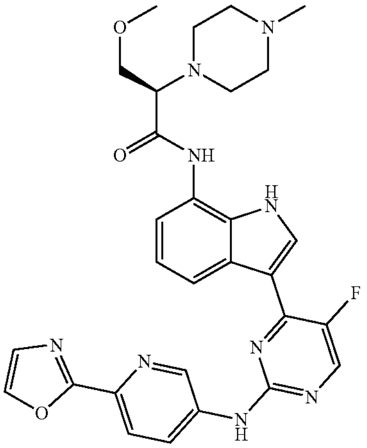 [SMILES: COC[C@H](C(=O)Nc1cccc2c(-c3nc(Nc4ccc(-c5ncco5)nc4)ncc3F)c[nH]c12)N1CCN(C)CC1] | (R)-N-(3-(5-fluoro-2-((6-(oxazol-2-yl)pyridin-3-yl)amino)pyrimidin-4-yl)-1H-indol-7-yl)-3-methoxy-2-(4-methylpiperazin-1-yl)propanamide |
| 24 | 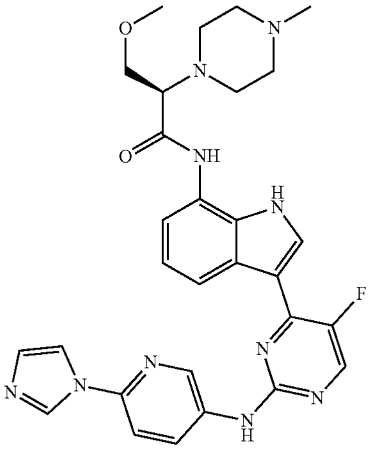 [SMILES: COC[C@H](C(=O)Nc1cccc2c(-c3nc(Nc4ccc(-n5ccnc5)nc4)ncc3F)c[nH]c12)N1CCN(C)CC1] | (R)-N-(3-(2-((6-(1H-imidazol-1-yl)pyridin-3-yl)amino)-5-fluoropyrimidin-4-yl)-1H-indol-7-yl)-3-methoxy-2-(4-methylpiperazin-1-yl)propanamide |

TABLE 1-continued

| Example number | structures | Name |
|---|---|---|
| 25 | 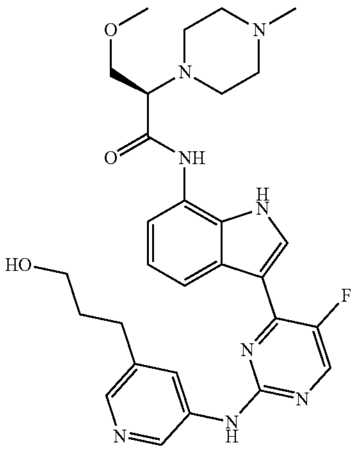 [SMILES: COC[C@H](C(=O)Nc1cccc2c(-c3nc(Nc4cncc(CCCO)c4)ncc3F)c[nH]c12)N1CCN(C)CC1] | (R)-N-(3-(5-fluoro-2-((5-(3-hydroxypropyl)pyridin-3-yl)amino)pyrimidin-4-yl)-1H-indol-7-yl)-3-methoxy-2-(4-methylpiperazin-1-yl)propanamide |
| 26 | 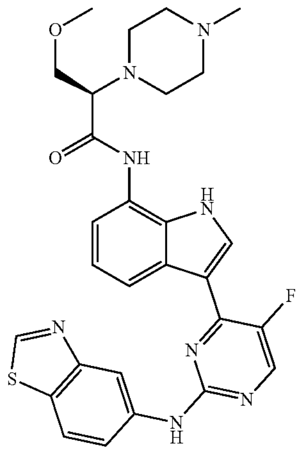 [SMILES: COC[C@H](C(=O)Nc1cccc2c(-c3nc(Nc4ccc5scnc5c4)ncc3F)c[nH]c12)N1CCN(C)CC1] | (R)-N-(3-(2-(benzo[d]thiazol-5-ylamino)-5-fluoropyrimidin-4-yl)-1H-indol-7-yl)-3-methoxy-2-(4-methylpiperazin-1-yl)propanamide |
| 28 | 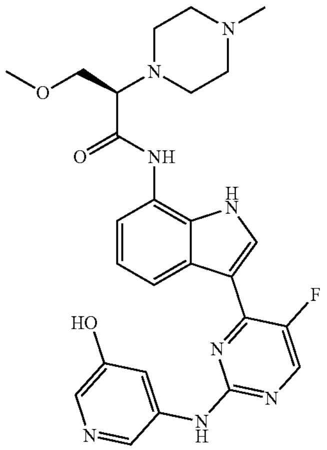 [SMILES: COC[C@H](C(=O)Nc1cccc2c(-c3nc(Nc4cncc(O)c4)ncc3F)c[nH]c12)N1CCN(C)CC1] | (R)-N-(3-(5-fluoro-2-((5-hydroxypyridin-3-yl)amino)pyrimidin-4-yl)-1H-indol-7-yl)-3-methoxy-2-(4-methylpiperazin-1-yl)propanainide |

Exemplary Compounds 1-78

TABLE 1-continued

| Exemplary Compounds 1-78 | | |
|---|---|---|
| Example number | structures | Name |
| 29 | 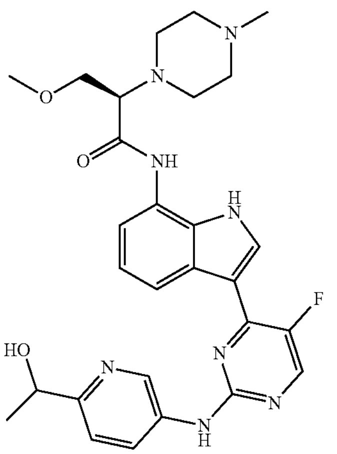 [SMILES: COC[C@H](C(=O)Nc1cccc2c(-c3nc(Nc4ccc(C(C)O)nc4)ncc3F)c[nH]c12)N1CCN(C)CC1] | 5-fluoro-2-((6-(1-hydroxyethyl)pyridin-3-yl)amino)pyrimidin-4-yl)-1H-indol-7-yl)-3-methoxy-2-(4-methylpiperazin-1-yl)propanamide (isomer 1) |
| 30 | 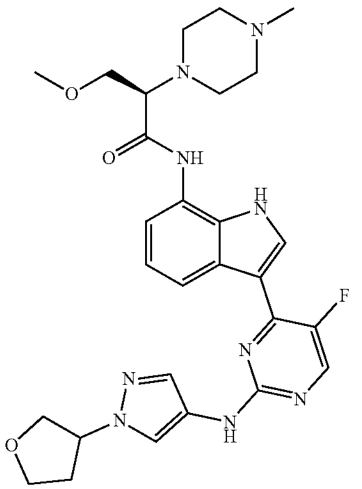 [SMILES: COC[C@H](C(=O)Nc1cccc2c(-c3nc(Nc4cnn(C5CCOC5)c4)ncc3F)c[nH]c12)N1CCN(C)CC1] | (R)-N-(3-(5-fluoro-2-((1-(tetrahydrofuran-3-yl)-1H-pyrazol-4-yl)amino)pyrimidin-4-yl)-1H-indol-7-yl)-3-methoxy-2-(4-methylpiperazin-1-yl)propanamide (isomer 1) |
| 31 | 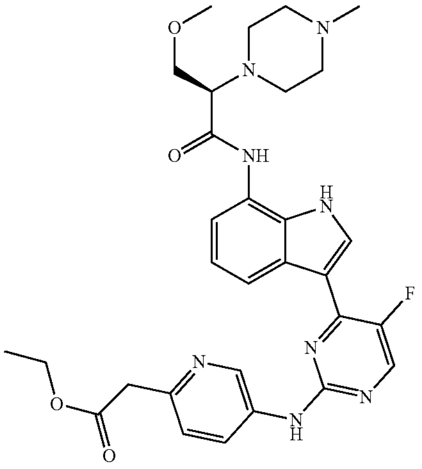 [SMILES: CCOC(=O)Cc1ccc(Nc2ncc(F)c(-c3c[nH]c4c(NC(=O)[C@@H](COC)N5CCN(C)CC5)cccc34)n2)cn1] | ethyl (R)-2-(5-((5-fluoro-4-(7-(3-methoxy-2-(4-methylpiperazin-1-yl)propanamido)-1H-indol-3-yl)pyrimidin-2-yl)amino)pyridin-2-yl)acetate |

TABLE 1-continued

| Example number | structures | Name |
|---|---|---|
| | Exemplary Compounds 1-78 | |
| 32 | 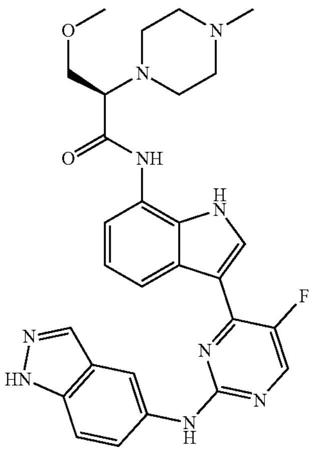 [SMILES: COC[C@H](C(=O)Nc1cccc2c(-c3nc(Nc4ccc5[nH]ncc5c4)ncc3F)c[nH]c12)N1CCN(C)CC1] | (R)-N-(3-(2-((1H-indazol-5-yl)amino)-5-fluoropyrimidin-4-yl)-1H-indol-7-yl)-3-methoxy-2-(4-methylpiperazin-1-yl)propanamide |
| 33 | 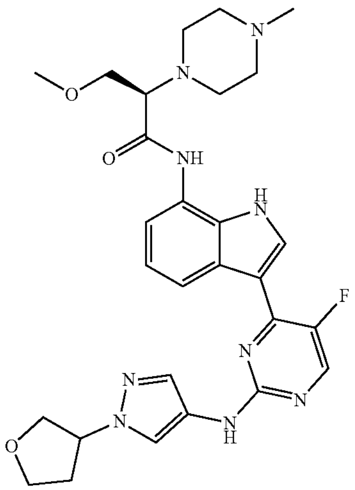 [SMILES: COC[C@H](C(=O)Nc1cccc2c(-c3nc(Nc4cnn(C5CCOC5)c4)ncc3F)c[nH]c12)N1CCN(C)CC1] | (R)-N-(3-(5-fluoro-2-((1-(tetrahydrofuran-3-yl)-1H-pyrazol-4-yl)amino)pyrimidin-4-yl)-1H-indol-7-yl)-3-methoxy-2-(4-methylpiperazin-1-yl)propanamide (isomer 2) |
| 34 | 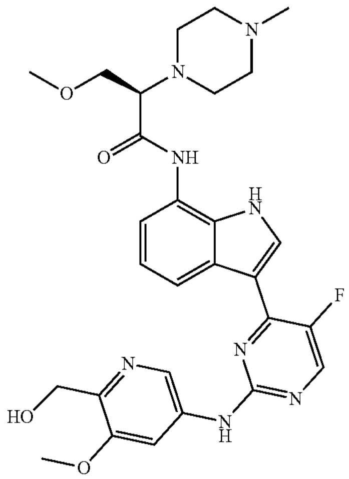 [SMILES: COC[C@H](C(=O)Nc1cccc2c(-c3nc(Nc4cnc(CO)c(OC)c4)ncc3F)c[nH]c12)N1CCN(C)CC1] | (R)-N-(3-(5-fluoro-2-((6-(hydroxymethyl)-5-methoxypyridin-3-yl)amino)pyrimidin-4-yl)-1H-indol-7-yl)-3-methoxy-2-(4-methylpiperazin-1-yl)propanamide |

TABLE 1-continued

| Example number | structures | Name |
|---|---|---|
| | Exemplary Compounds 1-78 | |
| 35 | 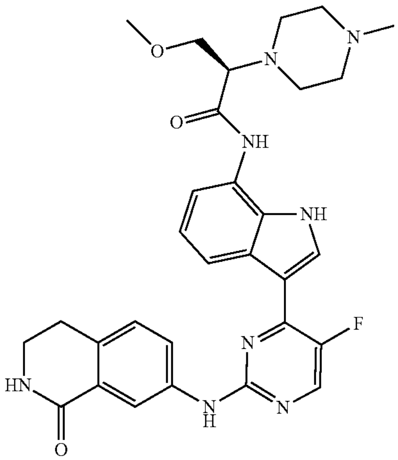 [SMILES: COC[C@H](C(=O)Nc1cccc2c(-c3nc(Nc4ccc5c(c4)C(=O)NCC5)ncc3F)c[nH]c12)N1CCN(C)CC1] | (R)-N-(3-(5-fluoro-2-((1-oxo-1,2,3,4-tetrahydroisoquinolin-7-yl)amino)pyrimidin-4-yl)-1H-indol-7-yl)-3-methoxy-2-(4-methylpiperazin-1-yl)propanamide |
| 36 | 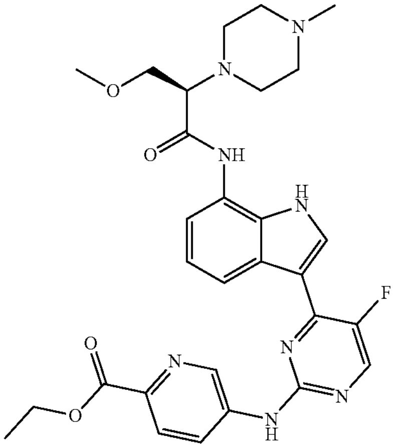 [SMILES: CCOC(=O)c1ccc(Nc2ncc(F)c(-c3c[nH]c4c(NC(=O)[C@@H](COC)N5CCN(C)CC5)cccc34)n2)cn1] | ethyl (R)-5-((5-fluoro-4-(7-(3-methoxy-2-(4-methylpiperazin-1-yl)propanamido)-1H-indol-3-yl)pyrimidin-2-yl)amino)picolinate |
| 37 | 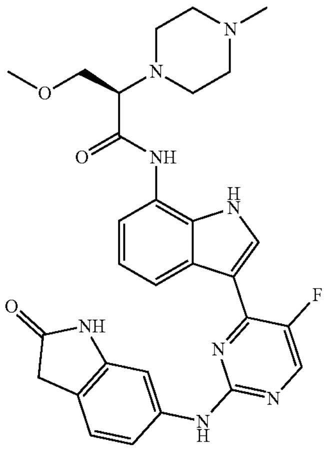 [SMILES: COC[C@H](C(=O)Nc1cccc2c(-c3nc(Nc4ccc5c(c4)NC(=O)C5)ncc3F)c[nH]c12)N1CCN(C)CC1] | (R)-N-(3-(5-fluoro-2-((2-oxoindolin-6-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 38 | 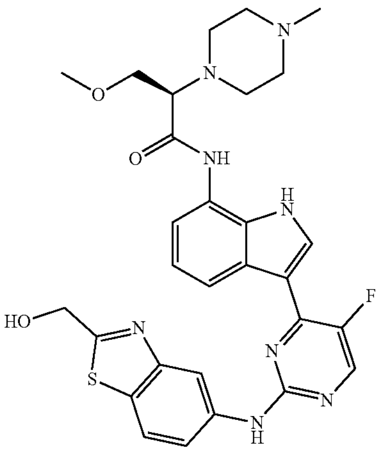 [SMILES: COC[C@H](C(=O)Nc1cccc2c(-c3nc(Nc4ccc5sc(CO)nc5c4)ncc3F)c[nH]c12)N1CCN(C)CC1] | (R)-N-(3-(5-fluoro-2-((2-(hydroxymethyl)benzo[d]thiazol-5-yl)amino)pyrimidin-4-yl)-1H-indol-7-yl)-3-methoxy-2-(4-methylpiperazin-1-yl)propanainide |
| 39 | 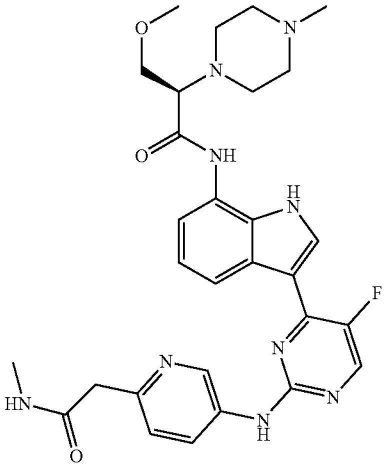 [SMILES: CNC(=O)Cc1ccc(Nc2ncc(F)c(-c3c[nH]c4c(NC(=O)[C@@H](COC)N5CCN(C)CC5)cccc34)n2)cn1] | (R)-N-(3-(5-fluoro-2-((6-(2-(methylamino)-2-oxoethyl)pyridin-3-yl)amino)pyrimidin-4-yl)-1H-indol-7-yl)-3-methoxy-2-(4-methylpiperazin-1-yl)propanamide |
| 40 | 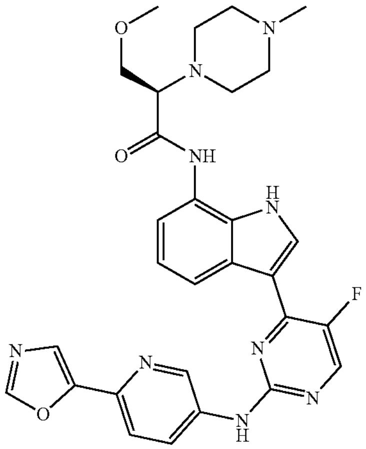 [SMILES: COC[C@H](C(=O)Nc1cccc2c(-c3nc(Nc4ccc(-c5cnco5)nc4)ncc3F)c[nH]c12)N1CCN(C)CC1] | (R)-N-(3-(5-fluoro-2-((6-(oxazol-5-yl)pyridin-3-yl)amino)pyrimidin-4-yl)-1H-indol-7-yl)-3-methoxy-2-(4-methylpiperazin-1-yl)propanamide |

TABLE 1-continued
| Exemplary Compounds 1-78 | | |
|---|---|---|
| Example number | structures | Name |
| 41 | 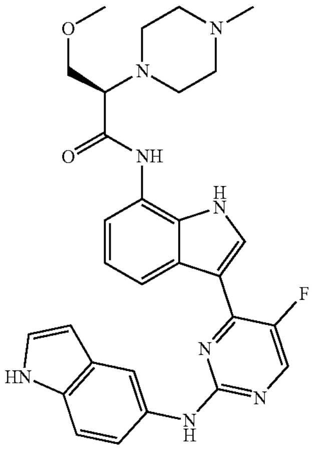 [SMILES: COC[C@H](C(=O)Nc1cccc2c(-c3nc(Nc4ccc5[nH]ccc5c4)ncc3F)c[nH]c12)N1CCN(C)CC1] | (R)-N-(3-(2-((1H-indol-5-yl)amino)-5-fluoropyrimidin-4-yl)-1H-indol-7-yl)-3-methoxy-2-(4-methylpiperazin-1-yl)propanamide |
| 42 | 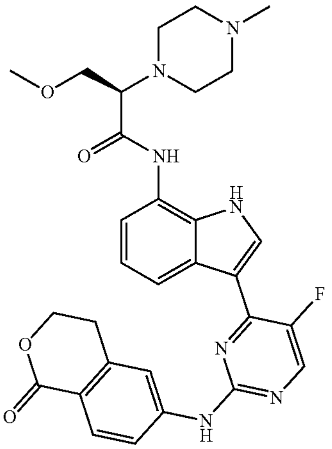 [SMILES: COC[C@H](C(=O)Nc1cccc2c(-c3nc(Nc4ccc5c(c4)CCOC5=O)ncc3F)c[nH]c12)N1CCN(C)CC1] | (R)-N-(3-(5-fluoro-2-((1-oxoisochroman-6-yl)amino)pyrimidin-4-yl)-1H-indol-7-yl)-3-methoxy-2-(4-methylpiperazin-1-yl)propanamide |
| 43 | 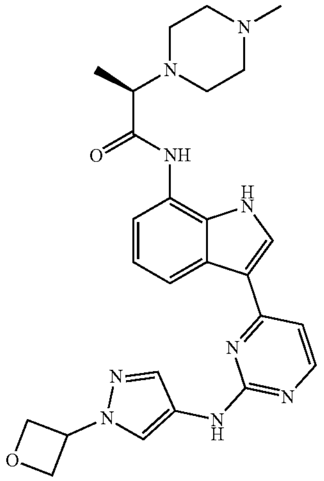 [SMILES: C[C@H](C(=O)Nc1cccc2c(-c3ccnc(Nc4cnn(C5COC5)c4)n3)c[nH]c12)N1CCN(C)CC1] | (R)-2-(4-methylpiperazin-1-yl)-N-(3-(2-((1-(oxetan-3-yl)-1H-pyrazol-4-yl)amino)pyrimidin-4-yl)-1H-indol-7-yl)propanamide |

TABLE 1-continued

| Exemplary Compounds 1-78 | | |
|---|---|---|
| Example number | structures | Name |
| 44 | 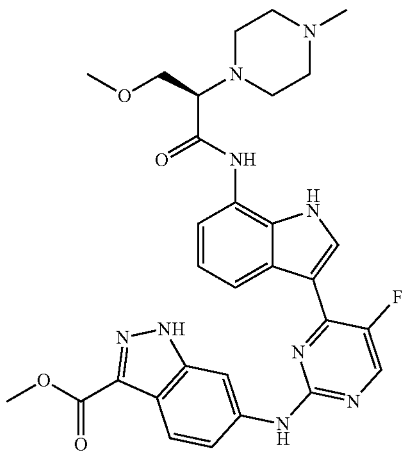 [SMILES: COC[C@H](C(=O)Nc1cccc2c(-c3nc(Nc4ccc5c(C(=O)OC)n[nH]c5c4)ncc3F)c[nH]c12)N1CCN(C)CC1] | methyl (R)-6-((5-fluoro-4-(7-(3-methoxy-2-(4-methylpiperazin-1-yl)propanamido)-1H-indol-3-yl)pyrimidin-2-yl)amino)-1H-indazole-3-carboxylate |
| 45 | 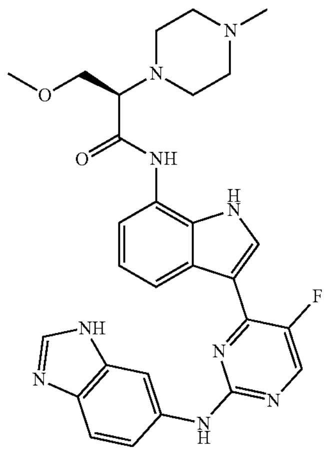 [SMILES: COC[C@H](C(=O)Nc1cccc2c(-c3nc(Nc4ccc5nc[nH]c5c4)ncc3F)c[nH]c12)N1CCN(C)CC1] | (R)-N-(3-(2-((1H-benzo[d]imidazol-6-yl)amino)-5-fluoropyrimidin-4-yl)-1H-indol-7-yl)-3-methoxy-2-(4-methylpiperazin-1-yl)propanamide |
| 46 | 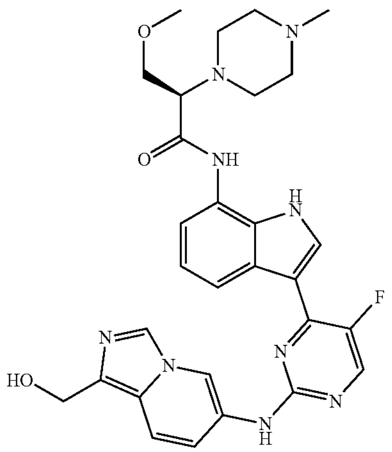 [SMILES: COC[C@H](C(=O)Nc1cccc2c(-c3nc(Nc4ccc5c(CO)ncn5c4)ncc3F)c[nH]c12)N1CCN(C)CC1] | (R)-N-(3-(5-fluoro-2-((1-(hydroxymethyl)imidazo[1,5-a]pyridin-6-yl)amino)pyrimidin-4-yl)-1H-indol-7-yl)-3-methoxy-2-(4-methylpiperazin-1-yl)propanainide |

TABLE 1-continued

| Exemplary Compounds 1-78 | | |
|---|---|---|
| Example number | structures | Name |
| 47 | 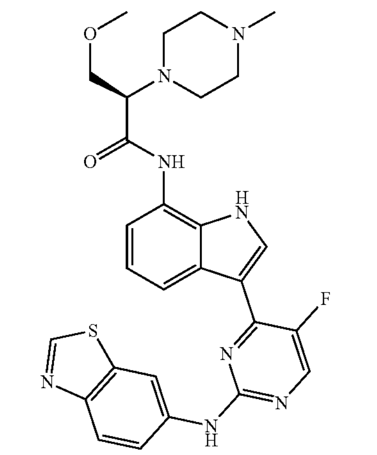 [SMILES: COC[C@H](C(=O)Nc1cccc2c(-c3nc(Nc4ccc5ncsc5c4)ncc3F)c[nH]c12)N1CCN(C)CC1] | (R)-N-(3-(2-(benzo[d]thiazol-6-ylamino)-5-fluoropyrimidin-4-yl)-1H-indol-7-yl)-3-methoxy-2-(4-methylpiperazin-1-yl)propanamide |
| 48 | 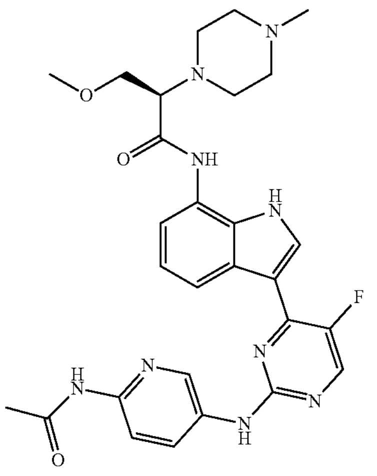 [SMILES: COC[C@H](C(=O)Nc1cccc2c(-c3nc(Nc4ccc(NC(C)=O)nc4)ncc3F)c[nH]c12)N1CCN(C)CC1] | (R)-N-(3-(2-((6-acetamidopyridin-3-yl)amino)-5-fluoropyrimidin-4-yl)-1H-indol-7-yl)-3-methoxy-2-(4-methylpiperazin-1-yl)propanamide |
| 50 | 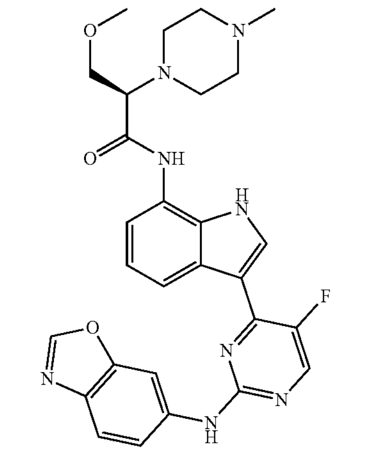 | (R)-N-(3-(2-(benzo[d]oxazol-6-ylamino)-5-fluoropyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 51 | 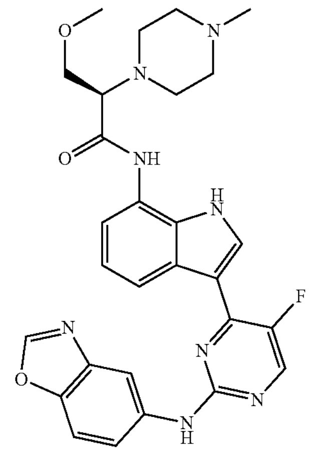 [SMILES: COC[C@H](C(=O)Nc1cccc2c(-c3nc(Nc4ccc5ocnc5c4)ncc3F)c[nH]c12)N1CCN(C)CC1] | (R)-N-(3-(2-(benzo[d]oxazol-5-ylamino)-5-fluoropyrimidin-4-yl)-1H-indol-7-yl)-3-methoxy-2-(4-methylpiperazin-1-yl)propanamide |
| 52 | 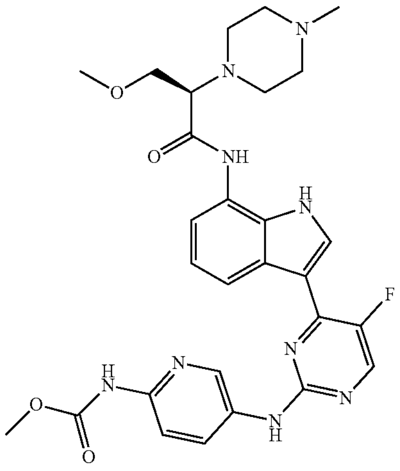 | methyl (R)-(5-((5-fluoro-4-(7-(3-methoxy-2-(4-methylpiperazin-1-yl)propanamido)-1H-indol-3-yl)pyrimidin-2-yl)amino)pyridin-2-yl)carbamate |
| 53 | 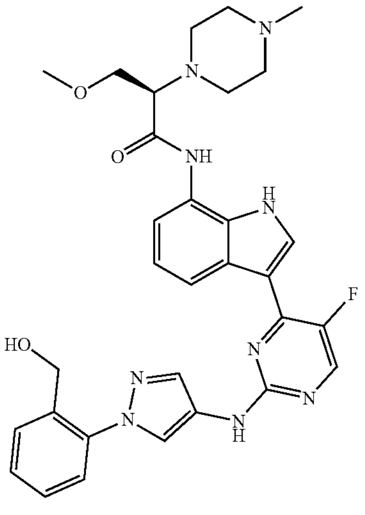 [SMILES: COC[C@H](C(=O)Nc1cccc2c(-c3nc(Nc4cnn(-c5ccccc5CO)c4)ncc3F)c[nH]c12)N1CCN(C)CC1] | (R)-N-(3-(5-fluoro-2-((1-(2-(hydroxymethyl)phenyl)-1H-pyrazol-4-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 54 | 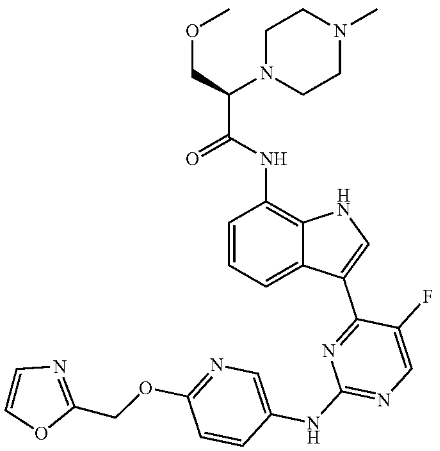 [SMILES: COC[C@H](C(=O)Nc1cccc2c(-c3nc(Nc4ccc(OCc5ncco5)nc4)ncc3F)c[nH]c12)N1CCN(C)CC1] | (R)-N-(3-(5-fluoro-2-((6-(oxazol-2-ylmethoxy)pyridin-3-yl)amino)pyrimidin-4-yl)-1H-indol-7-yl)-3-methoxy-2-(4-methylpiperazin-1-yl)propanamide |
| 55 | 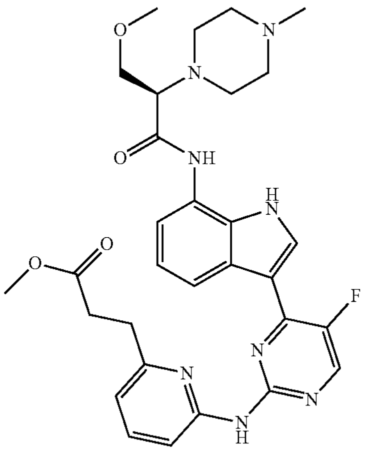 [SMILES: COC[C@H](C(=O)Nc1cccc2c(-c3nc(Nc4cccc(CCC(=O)OC)n4)ncc3F)c[nH]c12)N1CCN(C)CC1] | methyl (R)-3-(6-((5-fluoro-4-(7-(3-methoxy-2-(4-methylpiperazin-1-yl)propanamido)-1H-indol-3-yl)pyrimidin-2-yl)amino)pyridin-2-yl)propanoate |
| 57 | 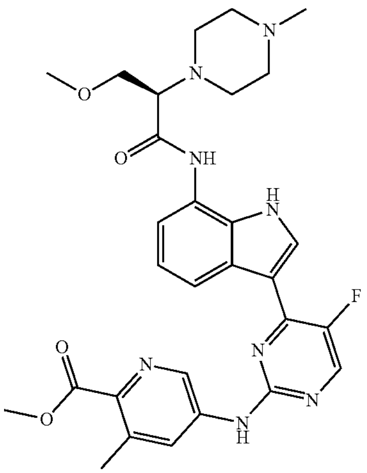 [SMILES: COC[C@H](C(=O)Nc1cccc2c(-c3nc(Nc4cnc(C(=O)OC)c(C)c4)ncc3F)c[nH]c12)N1CCN(C)CC1] | methyl (R)-5-((5-fluoro-4-(7-(3-methoxy-2-(4-methylpiperazin-1-yl)propanamido)-1H-indol-3-yl)pyrimidin-2-yl)amino)-3-methylpicolinate |

TABLE 1-continued

| Example number | structures | Name |
| --- | --- | --- |
| | Exemplary Compounds 1-78 | |
| 59 | 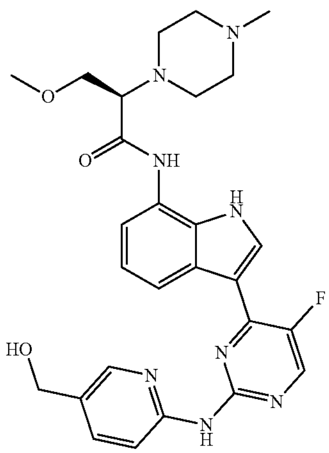 [SMILES: COC[C@H](C(=O)Nc1cccc2c(-c3nc(Nc4ccc(CO)cn4)ncc3F)c[nH]c12)N1CCN(C)CC1] | (R)-N-(3-(5-fluoro-2-((5-(hydroxymethyl)pyridin-2-yl)amino)pyrimidin-4-yl)-1H-indol-7-yl)-3-methoxy-2-(4-methylpiperazin-1-yl)propanamide |
| 60 | 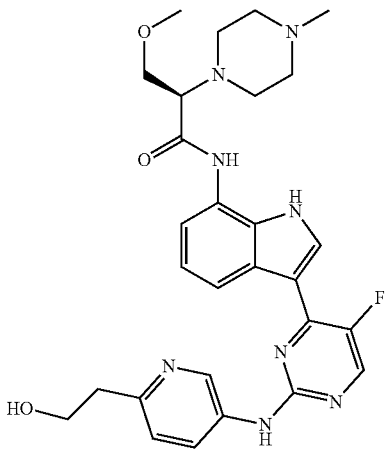 [SMILES: COC[C@H](C(=O)Nc1cccc2c(-c3nc(Nc4ccc(CCO)nc4)ncc3F)c[nH]c12)N1CCN(C)CC1] | (R)-N-(3-(5-fluoro-2-((6-(2-hydroxyethyl)pyridin-3-yl)amino)pyrimidin-4-yl)-1H-indol-7-yl)-3-methoxy-2-(4-methylpiperazin-1-yl)propanamide |
| 61 | 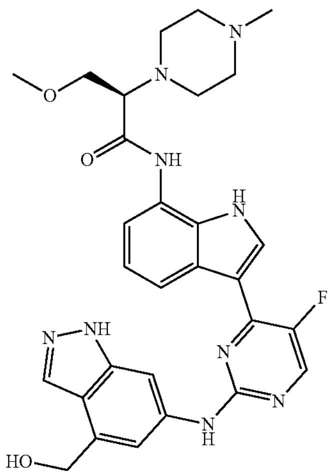 [SMILES: COC[C@H](C(=O)Nc1cccc2c(-c3nc(Nc4cc(CO)c5cn[nH]c5c4)ncc3F)c[nH]c12)N1CCN(C)CC1] | (R)-N-(3-(5-fluoro-2-((4-(hydroxymethyl)-1H-indazol-6-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 64 | 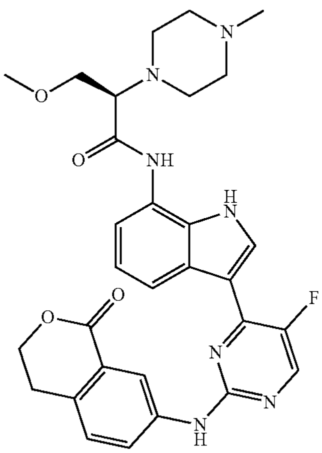 [SMILES: COC[C@H](C(=O)Nc1cccc2c(-c3nc(Nc4ccc5c(c4)C(=O)OCC5)ncc3F)c[nH]c12)N1CCN(C)CC1] | (R)-N-(3-(5-fluoro-2-((1-oxoisochroman-7-yl)amino)pyrimidin-4-yl)-1H-indol-7-yl)-3-methoxy-2-(4-methylpiperazin-1-yl)propanamide |
| 65 | 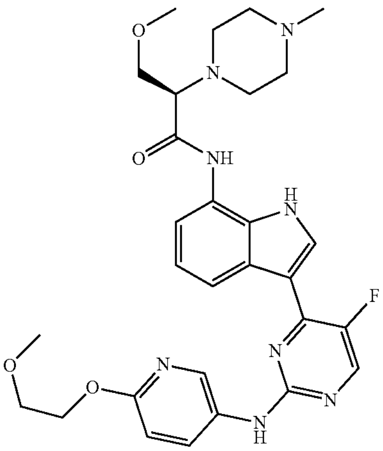 [SMILES: COCCOc1ccc(Nc2ncc(F)c(-c3c[nH]c4c(NC(=O)[C@@H](COC)N5CCN(C)CC5)cccc34)n2)cn1] | (R)-N-(3-(5-fluoro-2-((6-(2-methoxyethoxy)pyridin-3-yl)amino)pyrimidin-4-yl)-1H-indol-7-yl)-3-methoxy-2-(4-methylpiperazin-1-yl)propanamide |
| 66 | 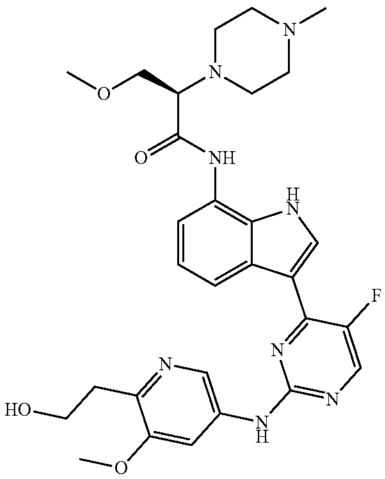 [SMILES: COC[C@H](C(=O)Nc1cccc2c(-c3nc(Nc4cnc(CCO)c(OC)c4)ncc3F)c[nH]c12)N1CCN(C)CC1] | (R)-N-(3-(5-fluoro-2-((6-(2-hydroxyethyl)-5-methoxypyridin-3-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 67 | 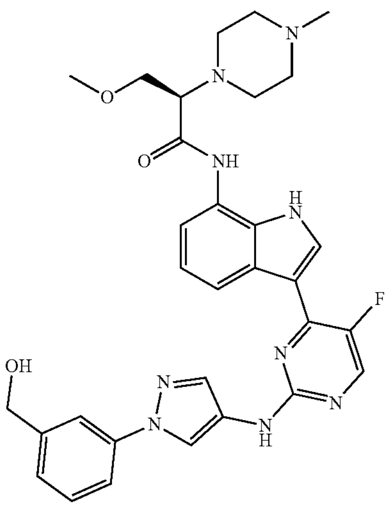 [SMILES: COC[C@H](C(=O)Nc1cccc2c(-c3nc(Nc4cnn(-c5cccc(CO)c5)c4)ncc3F)c[nH]c12)N1CCN(C)CC1] | (R)-N-(3-(5-fluoro-2-((1-(3-(hydroxymethyl)phenyl)-1H-pyrazol-4-yl)amino)pyrimidin-4-yl)-1H-indol-7-yl)-3-methoxy-2-(4-methylpiperazin-1-yl)propanamide |
| 68 | 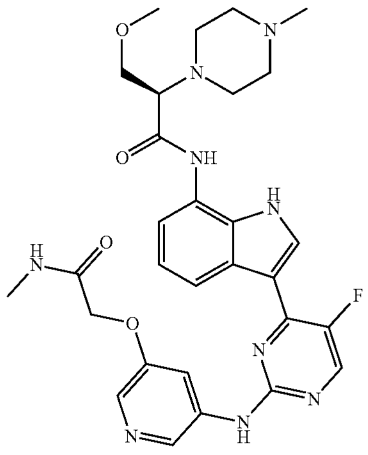 [SMILES: CNC(=O)COc1cncc(Nc2ncc(F)c(-c3c[nH]c4c(NC(=O)[C@@H](COC)N5CCN(C)CC5)cccc34)n2)c1] | (R)-N-(3-(5-fluoro-2-((5-(2-(methylamino)-2-oxoethoxy)pyridin-3-yl)amino)pyrimidin-4-yl)-1H-indol-7-yl)-3-methoxy-2-(4-methylpiperazin-1-yl)propanamide |
| 69 | 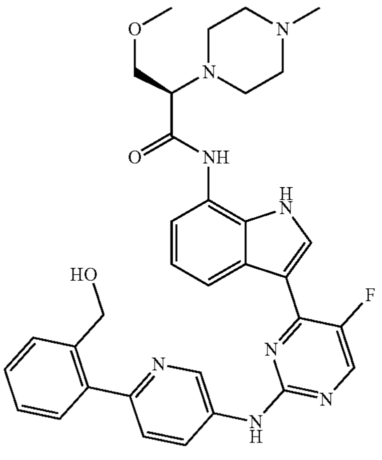 [SMILES: COC[C@H](C(=O)Nc1cccc2c(-c3nc(Nc4ccc(-c5ccccc5CO)nc4)ncc3F)c[nH]c12)N1CCN(C)CC1] | (R)-N-(3-(5-fluoro-2-((6-(2-(hydroxymethyl)phenyl)pyridin-3-yl)amino)pyrimidin-4-yl)-1H-indol-7-yl)-3-methoxy-2-(4-methylpiperazin-1-yl)propanamide |

TABLE 1-continued

| Exemplary Compounds 1-78 | | |
|---|---|---|
| Example number | structures | Name |
| 70 | 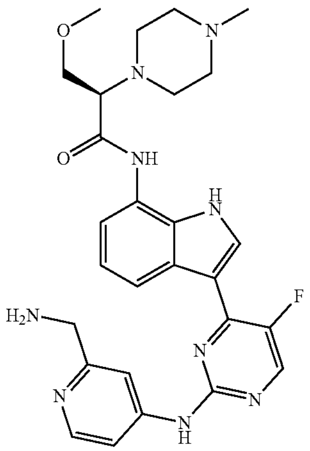 [SMILES: COC[C@H](C(=O)Nc1cccc2c(-c3nc(Nc4ccnc(CN)c4)ncc3F)c[nH]c12)N1CCN(C)CC1] | (R)-N-(3-(2-((2-(aminomethyl)pyridin-4-yl)amino)-5-fluoropyrimidin-4-yl)-1H-indol-7-yl)-3-methoxy-2-(4-methylpiperazin-1-yl)propanamide |
| 71 | 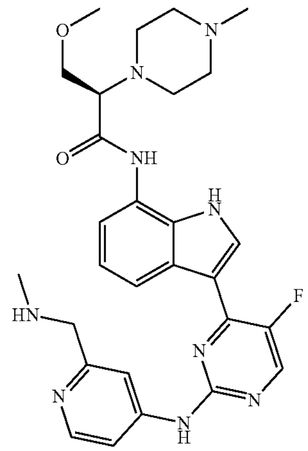 [SMILES: CNCc1cc(Nc2ncc(F)c(-c3c[nH]c4c(NC(=O)[C@@H](COC)N5CCN(C)CC5)cccc34)n2)ccn1] | (R)-N-(3-(5-fluoro-2-((2-((methylamino)methyl)pyridin-4-yl)amino)pyrimidin-4-yl)-1H-indol-7-yl)-3-methoxy-2-(4-methylpiperazin-1-yl)propanamide |
| 72 | 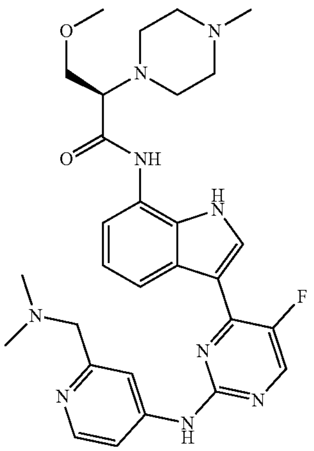 [SMILES: COC[C@H](C(=O)Nc1cccc2c(-c3nc(Nc4ccnc(CN(C)C)c4)ncc3F)c[nH]c12)N1CCN(C)CC1] | (R)-N-(3-(2-((2-((dimethylamino)methyl)pyridin-4-yl)amino)-5-fluoropyrimidin-4-yl)-1H-indol-7-yl)-3-methoxy-2-(4-methylpiperazin-1-yl)propanamide |

TABLE 1-continued

| Example number | structures | Name |
|---|---|---|
| Exemplary Compounds 1-78 | | |
| 73 | 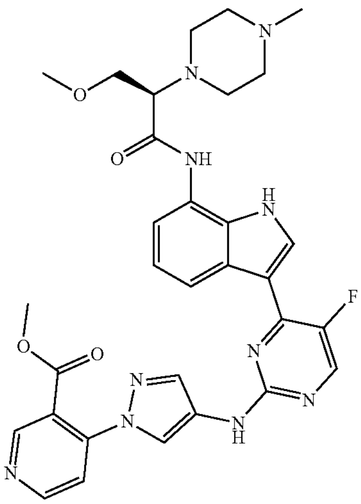 [SMILES: COC[C@H](C(=O)Nc1cccc2c(-c3nc(Nc4cnn(-c5ccncc5C(=O)OC)c4)ncc3F)c[nH]c12)N1CCN(C)CC1] | methyl (R)-4-(4-((5-fluoro-4-(7-(3-methoxy-2-(4-methylpiperazin-1-yl)propanamido)-1H-indol-3-yl)pyrimidin-2-yl)amino)-1H-pyrazol-1-yl)nicotinate |
| 74 | 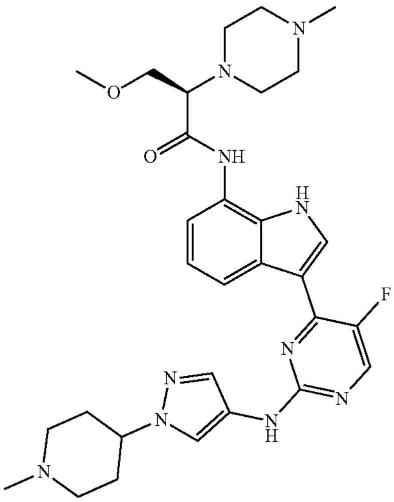 [SMILES: COC[C@H](C(=O)Nc1cccc2c(-c3nc(Nc4cnn(C5CCN(C)CC5)c4)ncc3F)c[nH]c12)N1CCN(C)CC1] | (R)-N-(3-(5-fluoro-2-((1-(1-methylpiperidin-4-yl)-1H-pyrazol-4-yl)amino)pyrimidin-4-yl)-1H-indol-7-yl)-3-methoxy-2-(4-methylpiperazin-1-yl)propanamide |
| 75 | 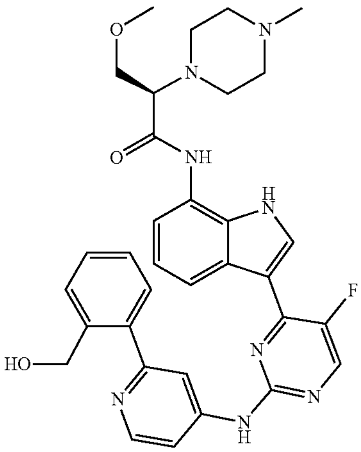 [SMILES: COC[C@H](C(=O)Nc1cccc2c(-c3nc(Nc4ccnc(-c5ccccc5CO)c4)ncc3F)c[nH]c12)N1CCN(C)CC1] | (R)-N-(3-(5-fluoro-2-((2-(2-(hydroxymethyl)phenyl)pyridin-4-yl)amino)pyrimidin-4-yI)-1H-indol-7-yl)-3-methoxy-2-(4-methylpiperazin-1-yl)propanamide |

TABLE 1-continued

| Example number | structures | Name |
| --- | --- | --- |
| | Exemplary Compounds 1-78 | |
| 76 | 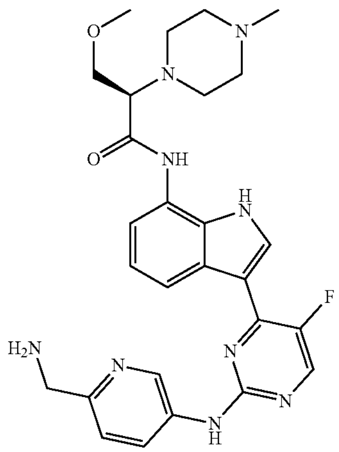 [SMILES: COC[C@H](C(=O)Nc1cccc2c(-c3nc(Nc4ccc(CN)nc4)ncc3F)c[nH]c12)N1CCN(C)CC1] | (R)-N-(3-(2-((6-(aminomethyl)pyridin-3-yl)amino)-5-fluoropyrimidin-4-yl)-1H-indol-7-yl)-3-methoxy-2-(4-methylpiperazin-1-yl)propanamide |
| 77 | 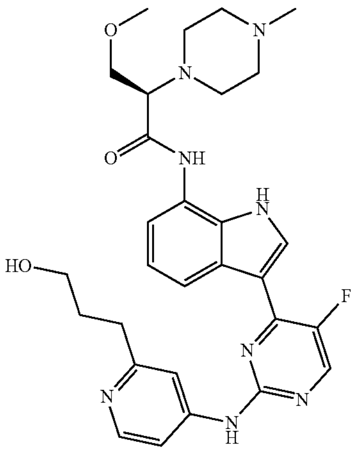 [SMILES: COC[C@H](C(=O)Nc1cccc2c(-c3nc(Nc4ccnc(CCCO)c4)ncc3F)c[nH]c12)N1CCN(C)CC1] | (R)-N-(3-(5-fluoro-2-((2-(3-hydroxypropyl)pyridin-4-yl)amino)pyrimidin-4-yl)-1H-indol-7-yl)-3-methoxy-2-(4-methylpiperazin-1-yl)propanamide |
| 78 | 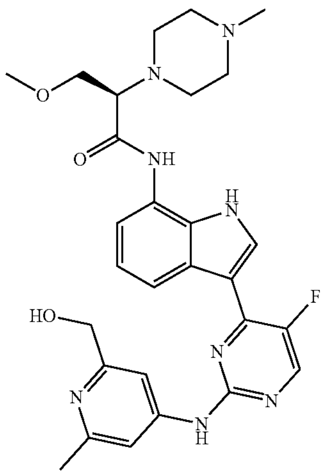 [SMILES: COC[C@H](C(=O)Nc1cccc2c(-c3nc(Nc4cc(C)nc(CO)c4)ncc3F)c[nH]c12)N1CCN(C)CC1] | (R)-N-(3-(5-fluoro-2-((2-(hydroxymethyl)-6-methylpyridin-4-yl)amino)pyrimidin-4-yl)-1H-indol-7-yl)-3-methoxy-2-(4-methylpiperazin-1-yl)propanamide |

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub combination.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, including 1 to 10, 1 to 8, 1 to 6, 1 to 5, 1 to 4, 1 to 3 or 1 to 2 carbon atoms.

As used herein, the term "alkyl", whether as part of another term or used independently, refers to a saturated or unsaturated hydrocarbon chain, while the latter may be further subdivided into hydrocarbon chain having at least one double or triple bonds (alkenyl or alkynyl). In some embodiments, alkyl refers to a saturated hydrocarbon chain. The hydrocarbon chain mentioned above may be straight-chain or branched-chain. The term "$C_{i-j}$ alkyl" refers to an alkyl having i to j carbon atoms. Examples of saturated alkyl group include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of unsaturated alkyl groups include, but are not limited to, ethenyl, n-propenyl, isopropenyl, n-butenyl, sec-butenyl, ethynyl, propyn-1-yl, propyn-2-yl, and the like. Examples of "$C_{1-6}$ alkyl" include, but are not limited to, methyl, ethyl, propyl, isopropyl, n-butyl, iso-butyl and tert-butyl. Examples of "$C_{1-3}$ alkyl" include, but are not limited to, methyl, ethyl, propyl, and isopropyl.

When "alkyl" represents a linking alkylene group, examples of alkylene groups include, but are not limited to, methylene, 1,1-ethylene, 1,2-ethylene, 1,1-propylene, 1,2-propylene, 1,3-propylene, 2,2-propylene, tertbutanylene and the like.

As used herein the term "amino" refers to the group of formula "$—NH_2$".

As used herein, the term "carbamoyl" refers to aminocarbonyl group (i.e., $NH_2—C(=O)—$).

As used herein the term "cyano" refers to the group of formula "—C≡N".

As used herein the terms "halo" and "halogen" refer to fluoro, chloro, bromo or iodo groups.

As used herein the term "hydroxyl" refers to the group of formula "—OH".

As used herein, the term "sulfinyl" refers to the group of formula "—S(=O)—".

As used herein, the term "sulfonyl" refers to the group of formula "$—S(=O)_2—$".

As used herein, the term "sulfonoxyl" refers to the group of formula "$—O—(S(=O)_2H)$".

As used herein, the term "sulfoximinyl" refers to the group of formula "—N=S=O".

As used herein, the term "sulfonimidoyl" refers to the group of formula "—S(=O)(=NH)—".

As used herein, the term "phosphinoyl" refers to the group of formula "$—P(=O)H_3$".

As used herein, the term "phosphonyl," refers to the group of formula "$—P(=O)(—OH)_2$".

As used herein, the term "alkoxy", whether as part of another term or used independently, refers to a group of formula —O-alkyl.

The term "$C_{i-j}$ alkoxy" means that the alkyl moiety of the alkoxy group has i to j carbon atoms. Examples of alkoxy groups include, but are not limited to, methoxyl, ethoxyl, propoxyl (e.g. n-propoxy and isopropoxy), t-butoxy, and the like. Examples of "$C_{1-12}$ alkoxyl" are methoxyl, ethoxyl and propoxyl.

As used herein, the term "hydroxy$C_{1-12}$ alky", refers to a group of formula "—$C_{1-12}$ alkyl-OH", wherein the alkyl moiety of the group has 1 to 12 carbon atoms, and one or more hydroxyl groups may be linked to any carbon atoms in the alkyl moiety. In some embodiments, "$C_{i-j}$ alky-OH" has one hydroxyl group. Examples of "$C_{1-12}$ alkyl-OH" are hydroxymethyl, 1-hydroxyethyl, 2-hydroxyethyl and 1-hydroxyisopropyl.

As used herein, the term "$C_{i-j}$ haloalkyl", refers to a halogen substituted (mono- or multi-substituted) $C_{i-j}$ alkyl group. Examples of "$C_{1-12}$ haloalkyl" are fluoromethyl, difluoromethyl, trifluoromethyl, fluoroethyl, difluoroethyl, trifluoroethyl, chloroethyl and bromoisopropyl. Examples of "difluoroethyl" are 1,1-difluoroethyl. Examples of "trifluoroethyl" are 2,2,2-trifluoroethyl and 1,2,2-trifluoroethlyl.

Examples of "$C_{i-j}$ haloalkoxyl" are fluoromethoxyl, difluoromethoxyl, or tri-fluoromethoxyl. Examples of "trifluoroethoxy" are 2,2,2-trifluoroethoxy and 1,2,2-trifluoroethoxy.

Examples of "N—($C_{1-12}$ alkyl)amino" are methylamino and ethylamino.

Examples of "N—($C_{1-12}$ haloalkyl)amino" are fluoromethylamino, difluoromethylamino, trifluoromethylamino, 2-chloroethylamino and 1-bromoisopropylamino.

As used herein, the term "$C_{1-6}$ alkoxycarbonyl" refers to the group of formula "$C_{1-6}$ alkyl-O—C(O)—".

Examples of "$C_{1-6}$ alkylsulfinyl" are methylsulfinyl, ethylsulfinyl, and propylsulfinyl.

Examples of "$C_{1-6}$ alkylsulfonyl" are methylsulfonyl and ethylsulfonyl.

Examples of "$C_{1-6}$ alkylsulfoximinyl" are methylsulfoximinyl and ethylsulfoximinyl.

Examples of "S—($C_{1-6}$ alkyl)sulfonimidoyl" are S-methylsulfoximidoyl and S-ethylsulfoximidoyl.

Examples of "N—($C_{1-6}$ alkyl)sulfonimidoyl" are N-methylsulfoximidoyl and N-ethylsulfoximidoyl.

Examples of "N, S—$(C_{1-6}$ alkyl$)_2$ sulfonimidoyl" are N, S-dimethyl-sulfonimidoyl, N-methyl-S-ethyl-sulfonimidoyl, and N-ethyl-S-methyl-sulfonimidoyl.

Examples of "$C_{1-6}$ alkylphosphinoyl" are methylphosphinoyl and ethylphosphinoyl Examples of "$(C_{1-6}$ alkyl$)_2$ phosphinoyl" are dimethylphosphinoyl, and diethylphosphinoyl.

Examples of "$C_{1-6}$ alkylphosphonyl" are methylphosphonyl and ethylphosphonyl.

As used herein, the term "$C_{i-j}$ alkanoyl" refers to $C_{i-j}$ alkylcarbonyl. Examples of "$C_{1-12}$ alkanoyl" are propionyl and acetyl.

Examples of "$C_{1-12}$ alkanoylamino" are formamido, acetamido and propionamido.

Examples of "$C_{1-12}$ alkanoyloxy" are acetoxy.

Examples of "$C_{1-12}$ alkoxycarbonyl" are methoxycarbonyl, ethoxycarbonyl, n- and t-butoxycarbonyl Examples of "N—($C_{1-12}$ alkyl)carbamoyl" are methylcarbamoyl and ethylcarbamoyl.

Examples of "N,N—($C_{1-12}$ alkyl$)_2$carbamoyl" are dimethylcarbamoyl and methylethylcarbamoyl.

Examples of "N,N—($C_{1-12}$ alkyl$)_2$amino" are di-(N-methyl)amino, di-(N-ethyl)amino and N-ethyl-N-methylamino.

As used herein, the term "aryl" or "aromatic", whether as part of another term or used independently, refers to a ring system with alternating double and single bonds between atoms forming rings. In the present disclosure the term "aryl" or "aromatic" also intends to include pseudoaromatic. The term "pseudoaromatic" refers to a ring system which is not strictly aromatic, but which is stabilized by means of delocalization of electrons and behaves in a similar manner to aromatic rings. An aryl or an aromatic group may have mono- or poly-ring(s). Examples of aryl groups include, but are not limited to, phenyl, naphthyl, tetrahydronaphthyl, indanyl and the like.

As used herein, the term "heteroaryl" as used herein refers to aryl which contains at least one ring forming heteroatom selected from O, S, N, P, and the like. Heteroaryl includes but are not limited to, furyl, thienyl, pyridinyl, triazinyl, pyridyl, pyrrolyl, oxazolyl, thiazolyl, imidazolyl, pyrazolyl, isoxazolyl, isothiazolyl, indolizinyl, indolyl, isoindolyl, indolinyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, quinazolinyl, isoquinazolinyl,1,3,5-triazinyl, 1H thieno[2,3-c]pyrazolyl, thieno[2,3-b]furyl, 3H-indolyl, benzo[b]furanyl, benzo[b]thiophenyl, 1H-indazolyl, benzimidazolyl, tetrazolyl, uridinyl, and cytosinyl.

As used herein, the term "carbocyclyl", whether as part of another term or used independently, refers to any ring, including mono- or poly-cyclic ring(s) (e.g. having 2 or 3 fused, bridged or spiro rings), in which all the ring atoms are carbon and which contains at least three ring forming carbon atoms. In some embodiments, the carbocyclyl may contain 3 to 12 ring forming carbon atoms (i.e. 3-12 membered carbon atoms), 3 to 10 ring forming carbon atoms, 3 to 9 ring forming carbon atoms or 4 to 8 ring forming carbon atoms. Carbocyclyl groups may be saturated, partially unsaturated or fully unsaturated. In some embodiments, the carbocyclyl group may be a saturated cyclic alkyl group. In some embodiments, the carbocyclyl group may be an unsaturated cyclic alkyl group that contains at least one double bond in its ring system. In some embodiments, an unsaturated carbocyclyl group may contains one or more aromatic rings. In some embodiments, one or more ring forming —$CH_2$— group of the saturated or unsaturated carbocyclyl may be replaced by a —C(O)— group.

In some embodiments, the carbocyclyl group is a monocyclic alkyl group. In some embodiments, the carbocyclyl group is a saturated monocyclic alkyl group. Examples of monocyclic saturated or unsaturated carbocyclyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, and the like.

As used herein, the term "spiro" rings refers to ring systems having two rings connected through one single common atom; the term "fused" rings refers to ring systems having two rings sharing two adjacent atoms; and the term "bridged" rings refers to ring systems with two rings sharing three or more atoms.

A 3-12, 3-10 or 5-6 "membered saturated or unsaturated carbocyclyl" is a saturated, partially unsaturated or fully unsaturated mono- or poly-cyclic ring system having 3 to 12, 3 to 10, or 5 to 6 ring forming carbon atoms respectively, wherein one or more ring forming —$CH_2$— group can optionally be replaced by a —C(O)— group.

Examples of "3-12 membered saturated or unsaturated carbocyclyl" are $C_{3-4}$ cycloalkyl, cyclohexyl, cyclohexenyl, cyclopentyl, phenyl, naphthyl and bicyclo[1.1.1]pentan-1-yl. Examples of "$C_{3-4}$ cycloalkyl" are cyclopropyl and cyclobutyl. Examples of "5-6 membered saturated or unsaturated carbocyclyl" are cyclopentyl and phenyl.

As used herein, the term "heterocyclyl" refers to a carbocyclyl group, wherein one or more (e.g. 1, 2 or 3) ring atoms are replaced by heteroatoms, which include, but are not limited to, O, S, N, P, and the like. In some embodiments, the heterocyclyl is a saturated heterocyclyl.

In some embodiments, the heterocyclyl is an unsaturated heterocyclyl having one or more double bonds in its ring system. In some embodiments, the heterocyclyl is a partially unsaturated heterocyclyl. In some embodiments, the heterocyclyl is a fully unsaturated heterocyclyl. In some embodiments, an unsaturated heterocyclyl group may contain one or more aromatic rings. In some embodiments, one or more ring forming —$CH_2$— group of the heterocyclyl can optionally be replaced by a —C(O)—, a —S—, a —S(O)—, or a —$S(O)_2$— group. In some embodiments, where the heterocyclyl contains a sulphur in its ring system, said ring forming sulphur atom may be optionally oxidised to form the S-oxides. In some embodiments the heterocyclyl is linked to the other portion of a compound through its ring forming carbon. In some embodiments the heterocyclyl is linked to the other portion of a compound through its ring forming nitrogen.

In some embodiments, 3-12 membered saturated or unsaturated mono- or poly-cyclic heterocyclyl having 1, 2, or 3 heteroatoms selected from N, O, or S.

A 3-12, 3-10 or 5-6 "membered saturated or unsaturated heterocyclyl" is a saturated, partially unsaturated or fully unsaturated mono- or poly-cyclic ring(s) (e.g. having 2 or 3 fused, bridged or spiro rings) system having 3 to 12, 3 to 10, or 5 to 6 ring forming atoms respectively, of which at least one ring forming atom is chosen from nitrogen, sulphur or oxygen, which may, unless otherwise specified, linked to the other portion of a compound through its ring forming carbon or nitrogen, wherein one or more ring forming —$CH_2$— group of the saturated or unsaturated heterocyclyl may be replaced by a —C(O)—, a —S—, a —S(O)—, or a —$S(O)_2$— group, and wherein when the heterocyclyl contains a sulphur in its ring system, said ring sulphur atom may be optionally oxidised to form the S-oxides.

Exemplary monocyclic heterocyclyl groups include, but are not limited to oxetanyl, pyranyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, triazinonyl, and the like.

Examples of spiro heterocyclyl include, but are not limited to, spiropyranyl, spirooxazinyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of bridged heterocyclyl include, but are not limited to, morphanyl, hexamethylenetetraminyl, 8-aza-bicyclo [3.2.1]octane, 1-aza-bicyclo[2.2.2]octane, 1,4-diazabicyclo [2.2.2]octane (DABCO), and the like.

Examples of "saturated or unsaturated 8-10 membered bicyclic ring" are indolyl, indazolyl, benzo[d]thiazol-5-yl, 2-oxoindolin-6-yl, benzo[d]thiazol-5-yl, benzo[d]thiazol-6-yl, 1-oxoisochroman-6-yl, 1H-pyrazolo[4,3-b]pyridin-6-yl, 1-oxo-1,2,3,4-tetrahydroisoquinolin-7-yl, 1-oxoisochroman-7-yl, benzo[d]oxazol-6-yl, 1H-benzo[d]imidazol-6-yl, imidazo[1,5-a]pyridin-6-yl, benzo[d]oxazol-5-yl, The "compound" of present disclosure is intended to encompass all stereoisomers, geometric isomers, and tautomers of the structures depicted unless otherwise specified.

The term "stereoisomer" refers to any of the various stereoisomeric configurations (e.g enantiomers, diastereomers and racemates) of an asymmetric compound (e.g. those having one or more asymmetrically substituted carbon atoms or "asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centers may give rise to enantiomers, diastereomers or other stereoisomeric forms that may be defined, in terms of absolute configuration, as (R)- or (S)- at each asymmetric center according to the Cahn-Ingold-Prelog R-S system. Resolved compounds whose absolute configuration is unknown can be designated using the term "or" at the asymmetric center. Methods on how to prepare optically active forms from racemic mixtures are known in the art, such as resolution by HPLC or stereoselective synthesis.

The terms "geometric isomers" or "cis and trans isomers" refer to compounds with same formula but their functional groups are rotated into a different orientation in three-dimensional space.

The term "tautomers" include prototropic tautomers that are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, the term "substituted by deuterium" or "deuterium substituted" to replace the other isoform of hydrogen (e.g. protium) in the chemical group with deuterium. In some embodiments, carbon includes $^{12}C$ and $^{13}C$. In some embodiments, "compound" of the present disclosure only encompasses the isotopes of hydrogen in the compound. In some embodiments, "compound" of the present disclosure only encompasses the isotopes of atoms in natural abundance.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, "pharmaceutically acceptable salts" refers to derivatives of the compounds of present disclosure wherein the parent compound is modified by converting an existing acidic moiety (e.g. carboxyl and the like) or base moiety (e.g. amine, alkali and the like) to its salt form. In many cases, compounds of present disclosure are capable of forming acid and/or base salts by virtue of the presence of amino and/or carboxyl groups or groups similar thereto. The pharmaceutically acceptable salts are acid and/or base salts that retain biological effectiveness and properties of the parent compound, which typically are not biologically or otherwise undesirable. Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). In some embodiments, the pharmaceutically acceptable salt of the compound of the present disclosure is a formic acid salt. In some embodiments, the pharmaceutically acceptable salt of the compound of the present disclosure is a TFA salt.

Suitable pharmaceutically acceptable salts of a compound of the present disclosure also include, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. Those skilled in the art would appreciate that adding acids or bases for forming acid/base-addition salts other than those shown in the examples may also be possible. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). In some embodiments, Suitable pharmaceutically acceptable salts of a compound of the present disclosure is inorganic bases salt.

The present disclosure also includes active intermediates, active metabolites and prodrugs of the compounds of present disclosure. As used herein, an "active intermediate" refer to intermediate compound in the synthetic process, which exhibits the same or essentially the same biological activity as the final synthesized compound.

As used herein, an "active metabolite" refers to a breakdown or end product of a compound of the present disclosure or its salt or prodrug produced through metabolism or biotransformation in the animal or human body, which exhibits the same or essentially the same biological activity as the specified compound. Such metabolites may result from, for example, oxidation, reduction, hydrolysis, amidation, deamidation, esterification, deesterification, enzymatic cleavage, and the like, of the administered compound or salt or prodrug.

As used herein, "prodrugs" refer to any compounds or conjugates which release the active parent drug when administered to an animal or human subject. Prodrugs can be prepared by modifying functional groups present in the compounds in such a way that the modifications are cleavable, either in routine manipulation or in vivo, from the parent compounds. Prodrugs include compounds wherein hydroxyl, amino, sulfhydryl, or carboxyl group is bonded to any group that, when administered to a mammalian subject, is cleavable to form a free hydroxyl, amino, sulfhydryl, or carboxyl group respectively. Examples of prodrugs include, but are not limited to, acetate, formate and benzoate derivatives of alcohol and amine functional groups in the compounds of the present disclosure. Preparation and use of prodrugs is discussed in THiguchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Disclosed herein are novel compounds or pharmaceutically acceptable salts which can selectively inhibit JAK1. Furthermore, these compounds can be partially effective for treating respiratory conditions when adapted for inhaled administration. And these compounds possess certain advantageous properties, for example excellent inhibitory properties, good pharmacokinetic profiles including uptake/absorption rate, low predicted human clearance etc. They may also possess favourable toxicity profiles, and/or favourable metabolic or pharmacokinetic profiles, in comparison with known JAK1 inhibitors.

Synthetic Method

Synthesis of the compounds provided herein, including salts, esters, hydrates, or solvates or stereoisomers thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized in China for the purposes of research and potentially submission to regulatory agencies.

The reactions for preparing compounds of the disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

Abbreviations as used herein, are defined as follows: "1×" or "×1" for once, "2×" or "×2" for twice, "3×" or "×3" for thrice, "4×" or "×4" for four times, "5×" or "×5" for five times, "° C." for degrees Celsius, "eq" or "eq." for equivalent or equivalents, "g" for gram or grams, "mg" for milligram or milligrams, "L" for liter or liters, "mL" or "ml" for milliliter or milliliters, "μL" for microliter or microliters, "N" for normal, "M" for molar, "mmol" for millimole or millimoles, "min" for minute or minutes, "h" or "hr" for hour or hours, "r.t." or "rt" for room temperature, "atm" for atmosphere, "psi" for pounds per square inch, "conc." for concentrate, "sat" or "sat'd" for saturated, "MS" or "Mass Spec" for mass spectrometry, "ESI" for electrospray ionization mass spectroscopy, "LCMS" for liquid chromatography mass spectrometry, "HPLC" for high pressure liquid chromatography, "RP" for reverse phase, "TLC" or "tlc" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, and "Hz" for hertz. "α", "β", "R", "S", "E", and "Z" are stereochemical designations familiar to one skilled in the art.

Pharmaceutical Composition

The present disclosure provides pharmaceutical compositions comprising at least one compound of the present disclosure. In some embodiments, the pharmaceutical composition comprises more than one compounds of the present disclosure. In some embodiments, the pharmaceutical composition comprises one or more compounds of the present disclosure, and a pharmaceutical acceptable carrier.

The pharmaceutically acceptable carriers are conventional medicinal carriers in the art which can be prepared in a manner well known in the pharmaceutical art. In some embodiments, the compounds of the present disclosure may be admixed with pharmaceutically acceptable carrier for the preparation of pharmaceutical composition.

The term "pharmaceutically acceptable carrier" as used herein refers to a pharmaceutically-acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and the like. Pharmaceutically acceptable carrier that can be employed in present disclosure includes those generally known in the art, such as those disclosed in "Remington Pharmaceutical Sciences" Mack Pub. Co., New Jersey (1991), which is incorporated herein by reference.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The form of pharmaceutical compositions depends on a number of criteria, including, but not limited to, route of administration, extent of disease, or dose to be administered. The pharmaceutical compositions can be formulated for oral, nasal, rectal, percutaneous, intravenous, or intramuscular administration. For example, dosage forms for nasal administration may conveniently be formulated as aerosols, solutions, drops, gels or dry powders; dosage forms for intranasal administration, may be formulated as a fluid formulation. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, ointment, paste, cream, lotion, gel, patche, inhalant, or suppository.

For compositions suitable and/or adapted for inhaled administration, it is preferred that the active substance is in a particle-size-reduced form, and more preferably the size-reduced form is obtained or obtainable by micronization. The preferable particle size of the size-reduced (e.g., micronised) compound or salt or solvate is defined by a $D_{50}$ value of about 0.5 to about 10 microns (for example as measured using laser diffraction). Dosage forms for inhaled administration may conveniently be formulated as aerosols or dry powders.

Aerosol formulations for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, such as a pressurized metered dose inhaler (pMDI) which releases a metered dose upon each actuation, it preferably contains a suitable propellant under pressure such as compressed air, carbon dioxide or an organic propellant such as hydrofluoroalkanes (HFAs), also known as hydrofluorocarbon (HFC). Suitable HFC propellants include 1,1,1,2,3,3,3-heptafluoropropane (HFA 227) and 1,1,1,2-tetrafluoroethane (HFA 134a). The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation. The composition may include other pharmaceutically acceptable excipients for inhalation use such as ethanol, oleic acid, polyvinylpyrrolidone and the like.

PMDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs.

Preferably, the dry powder inhalable formulation comprises a dry powder blend of the compound of formula I or pharmaceutically acceptable salt thereof (preferably in particle-size-reduced form, e.g., in micronised form), a powder base such as lactose, glucose, trehalose, mannitol or starch, and optionally a performance modifier such as L-leucine or another amino acid, and/or metals salts of stearic acid such as magnesium or calcium stearate. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines).

Optionally, a dry powder inhalable formulation can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS device (GlaxoSmithKline). Other dry powder inhalers are well known to those of ordinary skill in the art, and many such devices are commercially available, with representative devices including Aerolizer (Novartis), Airmax (WAX), ClickHaler (Innovata Biomed), Diskhaler (GlaxoSmithKline), Accuhaler (GlaxoSmithKline), Easyhaler (Orion Pharma), Eclipse (Aventis), FlowCaps (Hovione), Handihaler (Boehringer Ingelheim), Pulvinal (Chiesi), Rotahaler (GlaxoSmithKline), SkyeHaler or Certihaler (SkyePharma), Twisthaler (Schering-Plough), Turbuhaler (AstraZeneca), Ultrahaler (Aventis), and the like. The pharmaceutical compositions can also be formulated to provide quick, sustained or delayed release of the active ingredient after administration to the patient by employing procedures known in the art. In some embodiments, the pharmaceutical composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours. The pharmaceutical composition can be formulated in the form of tablet. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as disclosed in "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J Macromol Sci. Rev. Macromol Chem. 23:61; see also Levy et al., 1985, Science 228:190; During et al., 1989, Ann. Neurol. 25:351; Howard et al., 1989, J. Neurosurg. 71:105 can be used for sustained release. The above references are incorporated herein by reference in their entirety.

In certain embodiments, the pharmaceutical compositions comprise about 0.0001 mg to about 100 mg of the compounds of the present disclosure (e.g. about 0.0001 mg to about 10 mg, about 0.001 mg to about 10 mg, about 0.01 mg to about 10 mg, about 0.1 mg to about 10 mg, about 0.1 mg to about 5 mg, about 0.1 mg to about 4 mg, about 0.1 mg to about 3 mg, about 0.1 mg to about 2 mg, about 0.1 mg to about 1 mg, about 0.1 mg to about 0.5 mg, about 1 mg to about 10 mg, about 1 mg to about 5 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg,). Suitable dosages per subject per day can be from about 0.1 mg to about 10 mg, preferably about 0.1 mg to about 5 mg, about 5 mg to about 10 mg, or about 1 mg to about 5 mg.

In certain embodiments, the pharmaceutical compositions can be formulated in a unit dosage form, each dosage containing from about 0.0001 mg to about 10 mg, about 0.001 mg to about 10 mg, about 0.01 mg to about 10 mg, about 0.1 mg to about 10 mg, about 0.1 mg to about 5 mg, about 0.1 mg to about 4 mg, about 0.1 mg to about 3 mg, about 0.1 mg to about 2 mg, about 0.1 mg to about 1 mg, about 0.1 mg to about 0.5 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg of the compounds of the present disclosure. The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier.

In some embodiments, the pharmaceutical compositions comprise one or more compounds of the present disclosure as a first active ingredient, and further comprise a second active ingredient. The second active ingredient can be any anti-inflammatory or anti-hyperproliferative agents that is useful for treating JAK1-related disorders (e.g., asthma or COPD).

Examples of such anti-hyperproliferative agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would also be able to discern which combinations of agents would be useful based on the particular characteristics of the drugs and the cancer involved.

Examples of anti-inflammatory agents include but are not limited to, (1) TNF-αinhibitors such as Remicade and Enbrel); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Preferably this combination is for treatment and/or prophylaxis of asthma, COPD or allergic rhinitis. Representative examples of such a combination are a compound of formula I or a pharmaceutically acceptable salt thereof in combination with the components of Advair (salmeterol xinafoate and fluticasone propionate), Symbicort (budesonide and formoterol fumarate), or Dulera (mometasone furoate and formoterol fumarate), salmeterol or a pharmaceutically acceptable salt thereof (e.g., salmeterol xinafoate), or fluticasone propionate.

Method for Treatment

The present disclosure provides a method of treating JAK1-related disorders, comprising administering to a subject an effective amount of one or more compounds, pharmaceutically acceptable salts thereof or the pharmaceutical composition of the present disclosure.

The present disclosure also provides a method of treating JAK1-related disorders. In certain embodiments, the method comprises administering to a subject an effective amount of one or more compounds, pharmaceutically acceptable salts thereof or the pharmaceutical composition of the present disclosure.

As used herein, the term "JAK1-related disorders" refers to diseases whose onset or development or both are associated with the expression or activity of JAK1. Examples include but are not limited to, respiratory conditions, autoimmune diseases, hyperproliferative disorder (e.g., cancer) and other diseases.

JAK1-related disorders include, but are not limited to, (1) respiratory conditions, such as, asthma, bronchitis, bronchiectasis, silicosis, pneumoconiosis, acute respiratory distress syndrome, chronic eosinophilic pneumonia, and chronic obstructive pulmonary disease (COPD); (2) autoimmune diseases, such as psoriasis, scleroderma, rheumatoid arthritis, psoriatic arthritis, juvenile arthritis, myelofibrosis, Castleman's disease, lupus nephritis, systemic lupus erythematosus, Sjogren's syndrome, multiple sclerosis, inflammatory bowel disease, Behcet's disease, myasthenia gravis, type 1 diabetes mellitus, immunoglobulin nephropathy, autoimmune thyroid diseases; and (3) hyperproliferative disorder, such as cancer, for example, leukemia, glioblastoma, melanoma, chondrosarcoma, cholangiocarcinoma, osteosarcoma, lymphoma, lung cancer, adenoma, myeloma, hepatocellular carcinoma, adrenocortical carcinoma, pancreatic cancer, breast cancer, bladder cancer, prostate cancer, liver cancer, gastric cancer, colon cancer, colorectal cancer, ovarian cancer, cervical cancer, brain cancer, esophageal cancer, bone cancer, testicular cancer, skin cancer, kidney cancers, mesothelioma, neuroblastoma, thyroid cancer, head and neck cancers, esophageal cancers, eye cancers, prostate cancer, nasopharyngeal cancer, or oral cancer.

As used herein, the terms "treatment", "treat" and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to present or delay their recurrence.

In some embodiments, the one or more compounds, pharmaceutically acceptable salts thereof or the pharmaceutical composition provided herein is administered via a parenteral route or a non-parenteral route. In some embodiments, the one or more compounds pharmaceutically acceptable salts, hydrates, solvates or stereoisomers thereof or the pharmaceutical composition is administered orally, enterally, buccally, nasally, intranasally, transmucosally, epidermally, transdermally, dermally, ophthalmically, pulmonary, sublingually, rectally, vaginally, topically, subcutaneously, intravenously, intramuscularly, intraarterially, intrathecally, intracapsularly, intraorbitally, intracardiacally, intradermally, intraperitoneally, transtracheally, subcuticularly, intra-articularly, subcapsularly, subarachnoidly, intraspinally, or intrasternally.

The compounds provided herein can be administrated in pure form, in a combination with other active ingredients or in the form of pharmaceutically compositions of the present disclosure. In some embodiments, the compounds provided herein can be administered to a subject in need concurrently or sequentially in a combination with one or more anticancer or anti-inflammatory agent(s) known in the art. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

In some embodiments, the administration is conducted once a day, twice a day, three times a day, or once every two days, once every three days, once every four days, once every five days, once every six days, once a week.

In some embodiments, the one or more compounds, pharmaceutically acceptable salts thereof or the pharmaceutical composition provided herein is administered orally. For oral administration, any dose is appropriate that achieves the desired goals. In some embodiments, suitable daily dosages are between about 0.001-100 mg, preferably between 0.1 mg and 5 g, more preferably between 5 mg and 1 g, more preferably between 10 mg and 500 mg, and the administration is conducted once a day, twice a day, three times a day, every day, or 3-5 days a week. In some embodiments, the dose of the one or more compounds, pharmaceutically acceptable salts thereof or the pharmaceutical composition provided herein ranges between about 0.0001 mg, preferably, 0.001 mg, 0.01 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg per day.

Use of Compounds

In certain embodiments, the present disclosure provides use of the compounds, pharmaceutically acceptable salts thereof, or pharmaceutical composition of the present disclosure in the manufacture of medicaments for treating JAK1-related disorders. In certain embodiments, the JAK1-related disorders includes cancers.

The compounds and pharmaceutical compositions thereof in the present disclosure can be used in the prevention or treatment of the onset or development of any of JAK1-related disorders (expression or activities) in mammals especially in human.

In such situation, the present disclosure also provides a method of screening patient suitable for treating with the compounds or pharmaceutical composition of the present disclosure alone or combined with other ingredients (e.g. a second active ingredient, e.g. anti-inflammatory or anticancer agent). The method includes sequencing the tissue samples from patients and detecting the accumulation of JAK1 in the patient.

EXAMPLES

The followings further explain the general methods of the present disclosure. The compounds of the present disclosure may be prepared by the methods known in the art. The following illustrates the detailed preparation methods of the preferred compounds of the present disclosure. However, they are by no means limiting the preparation methods of the compounds of the present disclosure.

Synthetic Examples

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^{1}H$-NMR spectra is recorded in dimethyl sulfoxide-d6 (DMSO-d6) or $CDCl_3$ or $CD_3OD$ or $D_2O$ or Acetone_$d_6$ or $CD_3CN$ (from Innochem or Sigma-Aldrich or Cambridge Isotope Lab., Inc.) on Bruker AVANCE NMR (300 MHz or 400 MHz) spectrometers using ICON-NMR (under TopSpin program control) with tetramethylsilane as an internal standard.

MS measurement is carried out using Shimadzu 2020 Mass Spectrometer with an electrospray source at positive and negative ion mode.

High Performance Liquid Chromatography (HPLC) measurement is carried out on Shimadzu LC-20AD systems or Shimadzu LC-20ADXR systems or Shimadzu LC-30AD systems using Shim-pack XR-ODS C18 column (3.0×50 mm, 2.2 μm), or Ascentis Express C18 column (2.1×50 mm, 2.7 μm), or Agilent Poroshell HPH-C18 column (3.0×50 mm, 2.7 μm).

Thin layer chromatography is carried out using Sinopharm Chemical Reagent Beijing Co., Ltd. and Xinnuo Chemical silica gel plates. The silica gel plates used for thin layer chromatography (TLC) are 175-225 μm. The silica gel plates used for separating and purifying products by TLC are 1.0 mm.

Purified chromatographic column uses the silica gel as the carrier (100~200, 200~300 or 300~400 mesh, produced by Rushanshi Shangbang Xincailiao Co., Ltd. or Rushan Taiyang Desiccant Co., Ltd. etc.), or flash column (reversed phase C18 column 20-45 μm, produced by Agela Technologies) in Agela Technologies flash system. The size of columns are adjusted according to the amount of compounds.

The known starting materials of the present disclosure can be synthesized by using or according to the known methods in the art, or can be purchased from Alfa Aesar, TCI, Sigma-Aldrich, Bepharm, Bide pharmatech, PharmaBlock, Enamine, Innochem and JW&Y PharmLab etc.

Unless otherwise specified, the reactions are all carried out under argon or nitrogen atmosphere. Argon or nitrogen atmosphere refers to that the reaction flask is connected to an argon or nitrogen balloon with a volume of about 1 L. Hydrogenation is usually carried out under pressure. Unless otherwise specified, the reaction temperature in the examples is ambient temperature, which is 10° C.~30° C. The reaction progress is monitored by TLC or/and LC-MS. The eluent systems used for the reactions include dichloromethane-methanol system and petroleum ether-ethyl acetate system. The volume ratios of the solvents are adjusted according to the different polarities of compounds.

The elution system of column chromatography used for purifying compounds and eluent system of TLC include dichloromethane-methanol system and petroleum ether-ethyl acetate system. The volume ratios of the solvents are adjusted according to the different polarities of compounds. A small amount of alkaline or acidic agents (0.1%~1%) such as formic acid, or acetic acid, or TFA, or ammonia can be added for adjustment.

Abbreviations for chemicals used in the synthesis of the compounds provided herein are listed below:

| | |
|---|---|
| $(Boc)_2O$ | Di-tert-butyl dicarbonate |
| Brettphos | 2-(Dicyclohexylphosphino)3,6-dimethoxy-2',4',6'-triisopropyl-1,1'-biphenyl |
| $CH_3CN$ | Acetonitrile |
| $Cs_2CO_3$ | Caesium carbonate |
| DCM | Dichloromethane |
| DIEA | N,N-Dii sopropylethylamine |
| DMF | N,N-Dimethylformamide |
| DMSO | Dimethyl sulfoxide |
| EtOAc | Ethyl acetate |
| EtOH | Ethanol |
| HATU | 1-[Bis(dimethylamino)methylene]-1H-1,2,3-triazolo[4,5-b]pyridinium 3-oxid hexafluorophosphate |
| $K_2CO_3$ | Potassium carbonate |
| LiOH | Lithium hydroxide |
| MeOH | Methanol |
| 2-MeTHF | 2-Methyltetrahydrofuran |

-continued

| | |
|---|---|
| $Mg(OTf)_2$ | Magnesium trifluoromethanesulfonate |
| MTBE | Methyl tert-butyl ether |
| $Na_2CO_3$ | Sodium Carbonate |
| NaCl | Sodium chloride |
| $NaHCO_3$ | Sodium bicarbonate |
| NaOH | Sodium hydroxide |
| $Pd(dppf)Cl_2$ | [1,1'-Bis(diphenylphosphino)ferrocene]dichloropalladium(II) |
| PE | Petroleum ether |
| TEA | Triethyl amine |
| TFA | Trifluoroacetic acid |
| THF | Tetrahydrofuran |
| TosMIC | toluenesulfonylmethyl isocyanide |

Example 1

Preparation of (R)—N-(3-(5-fluoro-2-((6-(hydroxymethyl)pyridin-3-yl)amino)pyrimidin-4-yl)-1H-indol-7-yl)-3-methoxy-2-(4-methylpiperazin-1-yl)propanamide

SCHEME 1

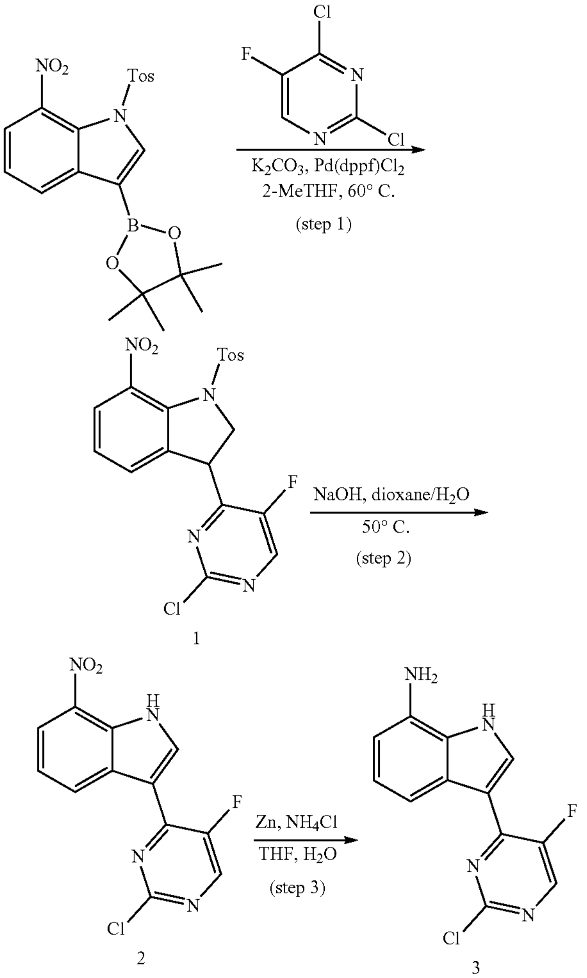

1

2

3

-continued

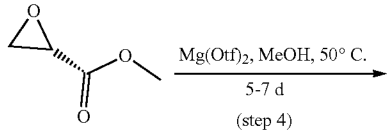

Sm2

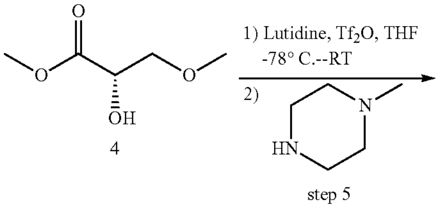

4

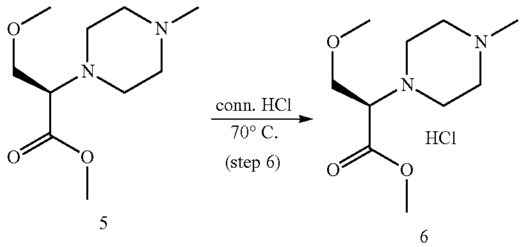

5

6

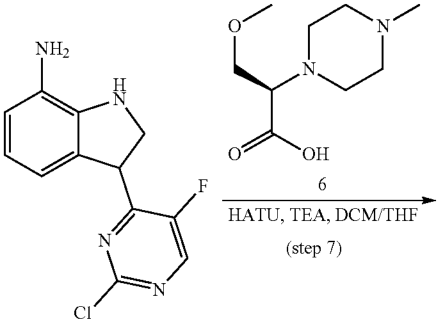

3

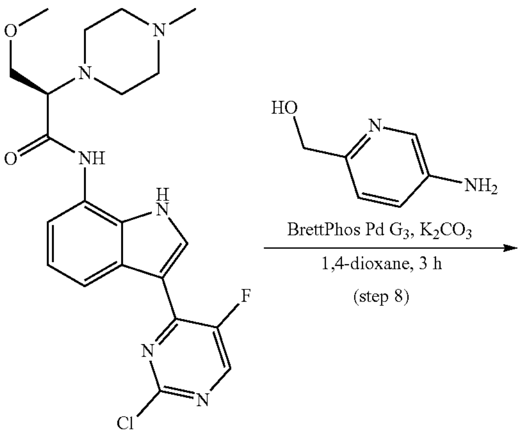

7

-continued

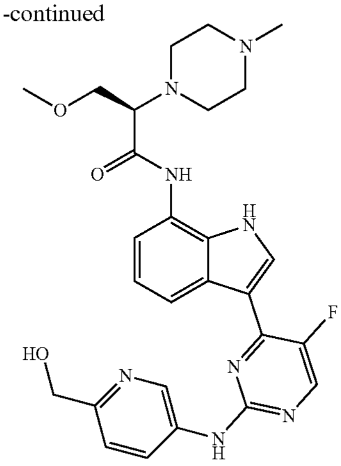

Example 1

Step 1. 3-(2-chloro-5-fluoropyrimidin-4-yl)-7-nitro-1-tosyl-1H-indole

To a solution of 1-(4-methylbenzenesulfonyl)-7-nitro-3-(4,4,5,5-tetramethyl-1,3,2-dioxaborolan-2-yl)-1H-indole (20.00 g, 45.219 mmol, 1.00 equiv) and 2,4-dichloro-5-fluoropyrimidine (9.81 g, 58.785 mmol, 1.30 equiv) in 2-Methyltetrahydrofuran (400.00 mL) and water (4.0 mL) were added $K_2CO_3$ (18.69 g, 135.205 mmol, 2.99 equiv) and $Pd(dppf)Cl_2 \cdot CH_2Cl_2$ (2.95 g, 3.618 mmol, 0.08 equiv). After stirring for 15 h at 60° C. under nitrogen atmosphere, the product was precipitated by the addition of water (300 mL). The precipitated solids were collected by filtration and washed with PE (1×40 mL). The resulting solid was dried under infrared light to afford 3-(2-chloro-5-fluoropyrimidin-4-yl)-1-(4-methylbenzenesulfonyl)-7-nitro-1H-indole (16 g, 79.19%) as an off-white solid. LCMS: m/z (ESI), $[M+H]^+$ =447.1. $^1$H-NMR (300 MHz, DMSO-$d_6$) δ 2.40 (3H, s), 7.50 (2H, d), 7.68 (1H, t), 7.98 (3H, dd), 8.72-8.85 (2H, m), 9.03 (1H, d).

Step 2. 3-(2-chloro-5-fluoropyrimidin-4-yl)-7-nitro-1H-indole

To a solution of 3-(2-chloro-5-fluoropyrimidin-4-yl)-1-(4-methylbenzenesulfonyl)-7-nitro-1H-indole (7.00 g, 15.666 mmol, 1.00 equiv) in 1,4-dioxane (210.00 mL) were added NaOH (6.27 g, 156.66 mmol, 10.0 equiv) in water (105 mL). After stirring for 5 h at 60° C., the mixture was acidified to pH6 with 2M HCl. The precipitated solids were collected by filtration and washed with PE (1×30 mL). This resulted in 3-(2-chloro-5-fluoropyrimidin-4-yl)-7-nitro-1H-indole (4.1 g, 89.43%) as a dark yellow solid. LCMS: m/z (ESI), $[M+H]^+$=293.0. $^1$H-NMR (300 MHz, DMSO-$d_6$) δ 7.53 (1H, t), 8.13-8.40 (2H, m), 8.83 (1H, d), 8.98 (1H, d), 12.82 (1H, s).

Step 3. 3-(2-chloro-5-fluoropyrimidin-4-yl)-1H-indol-7-amine

To a solution of 3-(2-chloro-5-fluoropyrimidin-4-yl)-7-nitro-1H-indole (10.00 g, 34.171 mmol, 1.00 equiv) in THF (400.00 mL) were added zinc power (17.9 g, 273.4 mmol, 8.0 equiv). Then $NH_4Cl$ (18.3 g, 341.7 mmol, 10.0 equiv) in water (100.00 mL) were added in the mixture. After stirring for 15 h at room temperature, the resulting mixture was filtered, the filter cake was washed with EA (3×20 mL). The filtrate was concentrated under reduced pressure to afford 3-(2-chloro-5-fluoropyrimidin-4-yl)-1H-indol-7-amine (5 g, 55.71%) as a reddish brown solid. LCMS: m/z (ESI), $[M+H]^{+=}$263.1. $^1$H-NMR (300 MHz, DMSO-$d_6$) δ 5.30 (2H, s), 6.48 (1H, dd), 6.96 (1H, t), 7.76 (1H, d), 8.27 (1H, t), 8.62 (1H, d), 11.84 (1H, s).

Step 4. (2S)-2-hydroxy-3-methoxypropanoate

A mixture of methyl (2S)-oxirane-2-carboxylate (20.00 g, 195.907 mmol, 1.00 equiv) and magnesium ditrifluoromethanesulfonate (18.95 g, 58.772 mmol, 0.30 equiv) in MeOH (500 mL) was stirred for 3 days at 50° C. under nitrogen atmosphere. The mixture was allowed to cool down to room temperature, concentrated under reduced pressure. The residue was dissolved in DCM (350 mL), and washed with 1×300 mL of water. The aqueous layer was extracted with $CH_2Cl_2$/MeOH (10/1) (5×200 mL), and dried over anhydrous $Na_2SO_4$. After filtration, the filtrate was concentrated under reduced pressure. The residue was purified by silica gel column chromatography, and eluted with PE/EtOAc (1:1) to afford methyl (2S)-2-hydroxy-3-methoxypropanoate (20.6 g, 78.39%) as a colorless oil. $^1$H-NMR (300 MHz, DMSO-$d_6$) δ 3.41 (3H, s), 3.63-3.78 (2H, m), 3.83 (3H, s), 4.33 (1H, t), 5.56 (1H, d).

Step 5. (R)-3-methoxy-2-(4-methylpiperazin-1-yl) propanoate

To a stirred solution of methyl (2S)-2-hydroxy-3-methoxypropanoate (8.00 g, 59.643 mmol, 1.00 equiv) and 2,6-lutidine (9.73 mL, 90.761 mmol, 1.4 equiv) in DCM (150.00 mL) was added trifluoromethanesulfonyl trifluoromethanesulfonate (21.88 g, 77.536 mmol, 1.3 equiv) dropwise at −78° C. under nitrogen atmosphere. The resulting mixture was stirred for 1 h at room temperature under nitrogen atmosphere. To the above mixture was added 1-methylpiperazine (12.55 g, 125.293 mmol, 2.10 equiv) dropwise over 10 min at 0° C. The resulting mixture was stirred for additional 15 h at room temperature. The reaction was quenched by the addition of water (150 mL) at room temperature, extracted with $CH_2Cl_2$ (3×150 mL). The combined organic layers were dried over anhydrous $MgSO_4$. After filtration, the filtrate was concentrated under reduced pressure. The residue was purified by silica gel column chromatography, eluted with PE/EtOAc (10:1 to 0:1) to afford methyl (R)-3-methoxy-2-(4-methylpiperazin-1-yl) propanoate (12 g, 93.03%) as a brown oil. LCMS: m/z (ESI), $[M+H]^+$=217.3. $^1$H NMR (300 MHz, DMSO-$d_6$) δ 2.35 (3H, s), 2.57 (4H, s), 2.73 (4H, t), 3.37 (3H, s), 3.40-3.52 (1H, m), 3.65 (1H, dd), 3.69-3.79 (4H, m).

Step 6. (R)-3-methoxy-2-(4-methylpiperazin-1-yl) propanoic Acid

A solution of methyl (R)-3-methoxy-2-(4-methylpiperazin-1-yl)propanoate (10.00 g, 46.236 mmol, 1.00 equiv) in conc. HCl (37.97 mL, 1041.355 mmol, 10.00 equiv, 37%) was stirred for 30 h at 70° C. under nitrogen atmosphere. The resulting mixture was concentrated under vacuum. The residue was dissolved in iPrOH (150 mL). The resulting mixture was concentrated under vacuum, re-dissolved and concentrated 3 times to give (R)-3-methoxy-2-(4-methylpiperazin-1-yl)propanoic acid hydrochloride (1 g, 99.66%), which was used directly in the next step. LCMS: m/z (ESI), $[M+H]^{+=}$203.1.

Step 7. (R)—N-(3-(2-chloro-5-fluoropyrimidin-4-yl)-1H-indol-7-yl)-3-methoxy-2-(4-methylpiperazin-1-yl)propanamide To a stirred mixture of (R)-3-methoxy-2-(4-methylpiperazin-1-yl)propanoic acid dihydrochloride (17.29 g, 62.816 mmol, 1.50 equiv), HATU (16.72 g, 43.972 mmol, 1.05 equiv) and 3-(2-chloro-5-fluoropyrimidin-4-yl)-1H-indol-7-amine (11.00 g, 41.878 mmol, 1.00 equiv) in DCM (280.00 mL) and THF (140.00 mL) were added TEA (23.28 mL, 230.097 mmol, 4.00 equiv) dropwise at 0° C. under nitrogen atmosphere. The resulting mixture was stirred for 2 h at 25° C. under nitrogen atmosphere. The reaction was quenched by the addition of sat. $NaHCO_3$ (aq.) (150 mL). The resulting mixture was extracted with $CH_2Cl_2$ (2×150 mL). The combined organic layers were dried over anhydrous $Na_2SO_4$. After filtration, the filtrate was concentrated under reduced pressure. The residue was purified by silica gel column chromatography, eluted with $CH_2Cl_2$/MeOH (15:1). The crude product was washed by hexane/EtOAc (3:1) to afford (2R)—N-[3-(2-chloro-5-fluoropyrimidin-4-yl)-1H-indol-7-yl]-3-methoxy-2-(4-methylpiperazin-1-yl)propanamide (7.8 g, 41.68%) as an off-white solid. LCMS: m/z (ESI), $[M+H]^+$=447.3. $^1$H-NMR (300 MHz, DMSO-$d_6$) δ 1.25 (3H, s), 2.46 (3H, s), 2.70-2.90 (8H, m), 3.54-3.91 (3H, m), 7.25 (1H, t), 7.57 (1H, dd), 8.28-8.52 (2H, m), 8.73 (1H, d), 9.99 (1H, s), 11.81 (1H, s).

Step 8 (R)—N-[3-(5-fluoro-2-[[6-(hydroxymethyl) pyridin-3-yl]amino]pyrimidin-4-yl)-1H-indol-7-yl]-3-methoxy-2-(4-methylpiperazin-1-yl)propanamide (Ex. 1)

Into a 40 mL vial were added (2R)—N-[3-(2-chloro-5-fluoropyrimidin-4-yl)-1H-indol-7-yl]-3-methoxy-2-(4-methylpiperazin-1-yl)propanamide (200.00 mg, 0.448 mmol, 1.00 equiv), and (5-aminopyridin-2-yl)methanol (83.33 mg, 0.671 mmol, 1.50 equiv), BrettPhos Pd $G_3$ (40.57 mg, 0.045 mmol, 0.1 equiv), $K_2CO_3$ (123.70 mg, 0.895 mmol, 2 equiv) in 1,4-dioxane (15.00 mL) at room temperature. Then the mixture was stirred at 70° C. under nitrogen atmosphere for 3 h. The resulting mixture was diluted with water (20 mL), and extracted with EtOAc (3×20 mL). The combined organic layers were washed with brine (3×10 mL), and dried over anhydrous $Na_2SO_4$. After filtration, the filtrate was concentrated under reduced pressure. The crude product was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 2500 B to 40% B in 7 min; 254/220 nm; Rt: 5.77 min) to afford (R)—N— [3-(5-fluoro-2-[[6-(hydroxymethyl)pyri din-3-yl]amino]pyrimidin-4-yl)-1H-indol-7-yl]-3-methoxy-2-(4-methylpiperazin-1-yl) propanamide (30 mg, 12.54 L) as a white solid. LCMS: m/z (ESI), $[M+H]^+$ =535.4. $^1$H-NMR (300 MHz, DMSO-$d_6$) δ 2.14 (3H, s), 2.36 (4H, s), 2.63 (2H, s), 2.73 (2H, s), 3.30 (3H, s), 3.49-3.86 (1H, t), 3.67 (1H, dd), 3.79 (1H, dd), 4.52 (2H, d), 5.28 (1H, t), 7.13 (1H, t), 7.39 (1H, d), 7.53 (1H, d), 8.22 (2H, dd), 8.49 (2H, dd), 8.78 (1H, d), 9.65 (1H, s), 9.86 (1, H s), 11.47 (1H, s).

The following examples in the table are synthesized by the similar method mentioned in Example 1.

| Example number | Structure | LCMS [M + H]+ | $^1$H NMR |
|---|---|---|---|
| 2 | 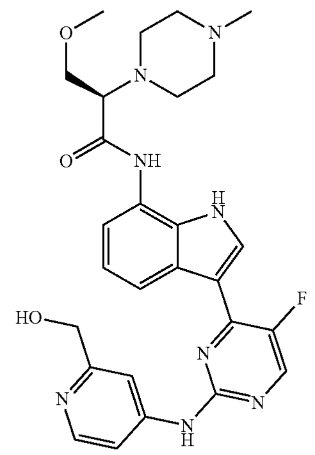 [SMILES: COC[C@H](C(=O)Nc1cccc2c(-c3nc(Nc4ccnc(CO)c4)ncc3F)c[nH]c12)N1CCN(C)CC1] | 535.4 | $^1$H-NMR (300 MHz, DMSO-$d_6$) δ 2.13 (3H, s), 2.34 (4H, s), 2.54-2.68 (2H, m), 2.73 (2H, d), 3.28 (3H, s), 3.49 (1H, t), 3.67 (1H, dd), 3.79 (1H, dd), 4.50 (2H, d), 5.30 (1H, t), 7.17 (1H, t), 7.54 (1H, d), 7.73 (1H, dd), 7.85 (1H, d), 8.26 (2H, t), 8.54 (1H, d), 8.62 (1H, dd), 9.86 (1H, s), 10.01 (1H, s), 11.50 (1H, s). |
| 4 | 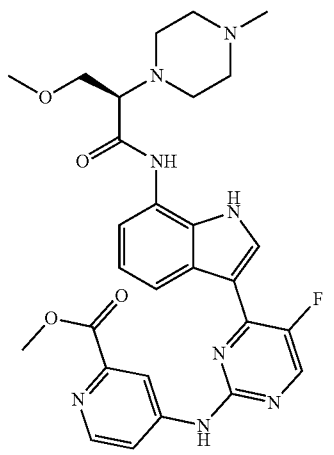 [SMILES: COC[C@H](C(=O)Nc1cccc2c(-c3nc(Nc4ccnc(C(=O)OC)c4)ncc3F)c[nH]c12)N1CCN(C)CC1] | 563.4 | $^1$H-NMR (400 MHz, DMSO-$d_6$) δ 2.13 (3H, s), 2.34 (4H, s), 2.54-2.69 (2H, m), 2.69-2.84 (2H, m), 3.32 (3H, s), 3.51 (1H, t), 3.66 (1H, dd), 3.73-3.93 (4H, m), 7.16 (1H, t), 7.56 (1H, d), 8.04 (1H, dd), 8.28 (1H, s), 8.43-8.51 (2H, m), 8.54-8.68 (2H, m), 9.91 (1H, s), 10.28 (1H, s), 11.63 (1H, s) |
| 7 | 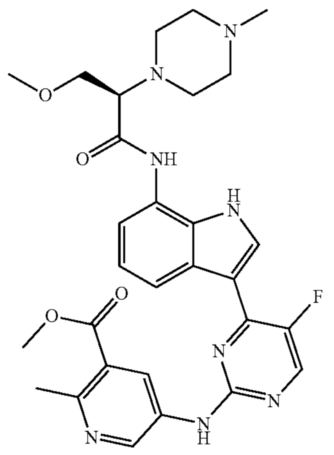 [SMILES: COC[C@H](C(=O)Nc1cccc2c(-c3nc(Nc4cnc(C)c(C(=O)OC)c4)ncc3F)c[nH]c12)N1CCN(C)CC1] | 577.3 | $^1$H-NMR (300 MHz, DMSO-d6) δ 2.15 (3H, s), 2.37 (4H, s), 2.66 (5H, s), 2.70-2.84 (2H, m), 3.28 (3H, s), 3.50 (1H, t), 3.67 (1H, dd), 3.80 (4H, s), 7.10 (1H, t), 7.53 (1H, d), 8 18-8.32 (1H, m), 8.37-8.58 (2H, m), 8.69 (1H, d), 8.94 (1H, d), 9.84 (2H, d), 11.50 (1H, s) |

-continued
| Example number | Structure | LCMS [M + H]+ | $^1$H NMR |
|---|---|---|---|
| 12 | 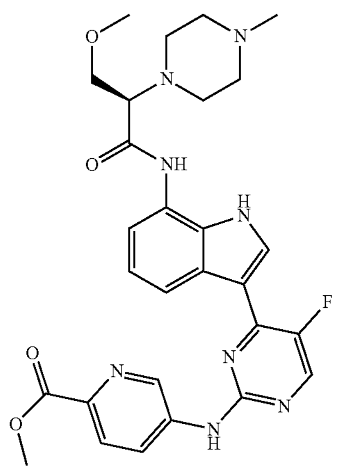 [SMILES: COC[C@H](C(=O)Nc1cccc2c(-c3nc(Nc4ccc(C(=O)OC)nc4)ncc3F)c[nH]c12)N1CCN(C)CC1] | 563.4 | $^1$H-NMR (300 MHz, DMSO-$d_6$) δ 2.13 (3H, s), 2.34 (4H, s), 2.62 (2H, d), 2.69-2.80 (2H, m), 3.31 (3H, s), 3.50 (1H, t), 3.67 (1H, dd), 3.74-3.82 (1H, m), 3.84 (3H, s), 7.18 (1H, t), 7.55 (1H, d), 8.02 (1H, d), 8.27 (1H, d), 8.43-8.64 (3H, m), 8.98 (1H, d), 9.87 (1H, s), 10.20 (1H, s), 11.54 (1H, s). |
| 21 | 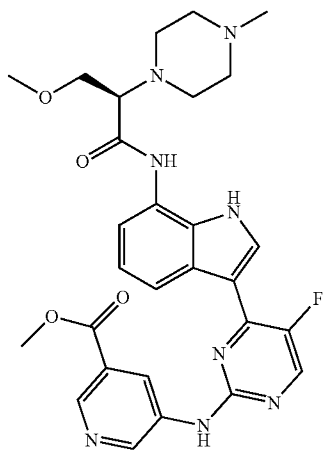 [SMILES: COC[C@H](C(=O)Nc1cccc2c(-c3nc(Nc4cncc(C(=O)OC)c4)ncc3F)c[nH]c12)N1CCN(C)CC1] | 563.4 | $^1$H-NMR (300 MHz, DMSO-$d_6$) δ 2.16 (3H, s), 2.37 (4H, s), 2.65 (2H, d), 2.69-2.84 (2H, m), 3.31 (3H, s), 3.52 (1H, t), 3.69 (1H, dd), 3.81 (1H, dd), 3.87 (3H, s), 7.14 (1H, t), 7.55 (1H, d), 8.28 (1H, s), 8.48-8.60 (2H, m), 8.70 (1H, d), 8.79-8.86 (1H, m), 9.16 (1H, d), 9.87 (1H, s), 9.99 (1H, s), 11.53 (1H, s) |
| 23 | 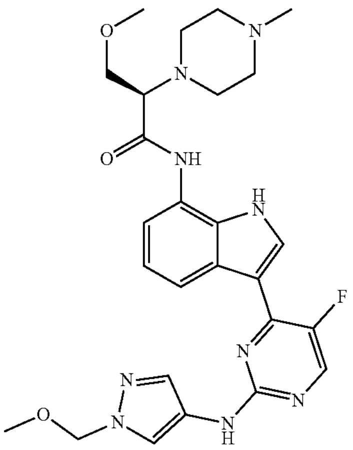 [SMILES: COC[C@H](C(=O)Nc1cccc2c(-c3nc(Nc4cnn(COC)c4)ncc3F)c[nH]c12)N1CCN(C)CC1] | 538.3 | $^1$H-NMR (300 MHz, DMSO-$d_6$) δ 2.15 (3H, s), 2.36 (4H, s), 2.56-2.69 (2H, m), 2.70-2.84 (2H, m), 3.24 (3H, s), 3.30 (3H, s), 3.51 (1H, t), 3.69 (1H, dd), 3.81 (1H, dd), 5.35 (2H, s), 7.16 (1H, t), 7.56 (1H, s), 7.64 (1H, d), 8.11 (1H, d), 8.21 (1H, d), 8.41 (1H, d), 8.54 (1H, S), 9.45 (1H, s), 9.87 (1 H, s), 11.45 (1H, s) |

-continued
| Example number | Structure | LCMS $[M+H]^+$ | $^1H$ NMR |
|---|---|---|---|
| 26 | 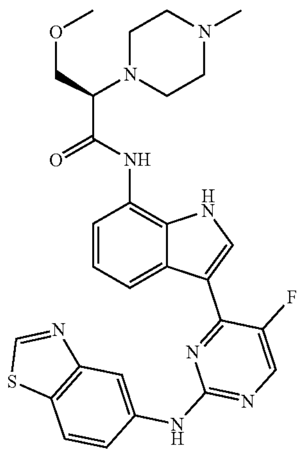 [SMILES: COC[C@H](C(=O)Nc1cccc2c(-c3nc(Nc4ccc5scnc5c4)ncc3F)c[nH]c12)N1CCN(C)CC1] | 561.3 | $^1H$-NMR (300 MHz, DMSO-$d_6$) δ 2.12 (3H, s), 2.44 (4H, s), 2.62 (2H, d), 2.71-2.76 (2H, m), 3.28 (3H, s), 3.49 (1H, t), 3.64-3.69 (1H, m), 3.76-3.81 (1H, m), 7.11 (1H.t), 7.52 (1H, d), 7.78-7.81 (1H.m), 8.03 (1H, d), 8.24 (1H, t), 8.49 (1H, d), 8.60 (1H, d), 8.69 (1H, d), 9.34 (1H, s), 9.76 (1H, s), 9.85 (1H, s), 11.48 (1H, s) |
| 28 | 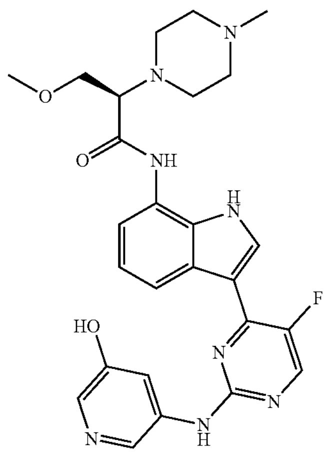 [SMILES: COC[C@H](C(=O)Nc1cccc2c(-c3nc(Nc4cncc(O)c4)ncc3F)c[nH]c12)N1CCN(C)CC1] | 521.2 | $^1H$-NMR (400 MHz, DMSO-$d_6$) δ 2.15 (3H, s), 2.36 (4H, s), 2.64 (2H, d), 2.74 (2H, m), 3.30 (3H, s), 3.51 (1H, t), 3.68 (1H, dd), 3.80 (1H, dd), 7.15 (1H, t), 7.54 (1H, dd), 7.77 (2H, dd), 8.24 (1H, m), 8.38 (1H, d), 8 47 (1H, d), 8.58 (1H, dd), 9.62 (1H, s), 9.73 (1H, s), 9.86 (1H, s), 11 48 (1H, m) |
| 31 | 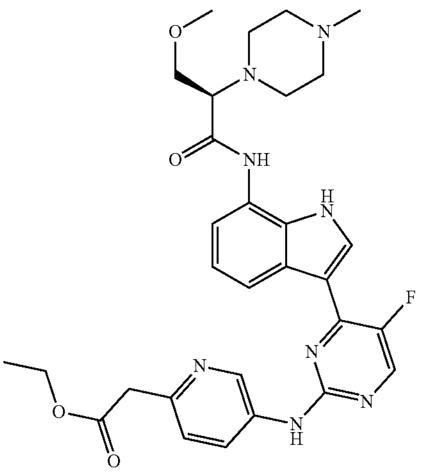 [SMILES: CCOC(=O)Cc1ccc(Nc2ncc(F)c(-c3c[nH]c4c(NC(=O)[C@@H](COC)N5CCN(C)CC5)cccc34)n2)cn1] | 591.3 | $^1H$-NMR (400 MHz, DMSO-$d_6$) δ 1.20 (3H, t), 2.16 (3H, s), 2.37 (4H, s), 2.64 (2H, s), 2.76 (2H, s), 3.30 (3H, s), 3.52 (1H, t), 3.69 (1H, dd), 3.76-3.85 (3H, m), 4.11 (2H, q), 7.16 (1H, t), 7.30 (1H, d), 7.56 (1H, d), 8.18-8.28 (2H, m), 8.47 (1H, d), 8.54 (1H, d), 9.70 (1H, s), 9.89 (1H, s), 11.52 (1H, s). |

-continued
| Example number | Structure | LCMS $[M + H]^+$ | $^1H$ NMR |
|---|---|---|---|
| 32 | 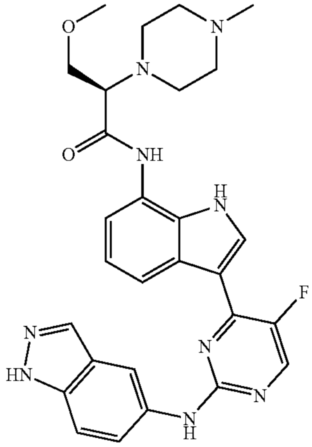 [SMILES: COC[C@H](C(=O)Nc1cccc2c(-c3nc(Nc4ccc5[nH]ncc5c4)ncc3F)c[nH]c12)N1CCN(C)CC1] | 544.4 | 1H-NMR (300 MHz, MeOD-d4) δ 2.34 (3H, s), 2.65 (4H, d), 2.88 (4H, d), 3.43 (3H, s), 3.51 (1H, t) 3.85-3.89 (1H, m), 3.94-3.97 (1H, m), 7.02 (1H, t), 7.15 (1H, m), 7.56 (2H, m), 8.00 (1H, s), 8.20 (3H, m), 8.56 (1H, d) |
| 35 | 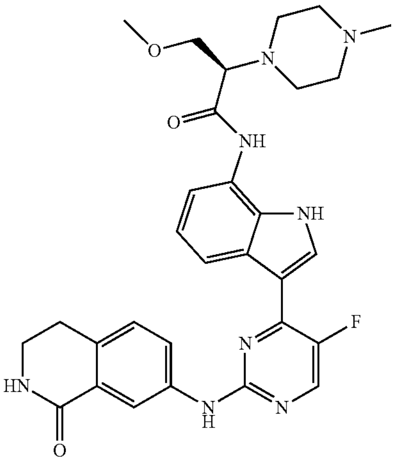 [SMILES: COC[C@H](C(=O)Nc1cccc2c(-c3nc(Nc4ccc5c(c4)C(=O)NCC5)ncc3F)c[nH]c12)N1CCN(C)CC1] | 573.4 | $^1H$-NMR (300 MHz, DMSO-$d_6$) δ 2.12 (3H, s), 2.34 (4H, s), 2.61 (2H, d), 2.74 (2H, t), 2.85 (2H, t), 3.28 (3H, s), 3.35-3.38 (2H, m), 3.49 (1H, t), 3.64-3.69 (1H, m), 3.76-3.81 (1H, m), 7.11 (1H.t), 7.21 (1H.d), 7.52 (1H, d), 7.89 (2H, t), 8.21 (2H, t), 8.43 (1H, d), 8.56 (1H, d), 9.61 (1H, s), 9.84 (1 H, s), 11.48 (1H, s) |
| 37 | 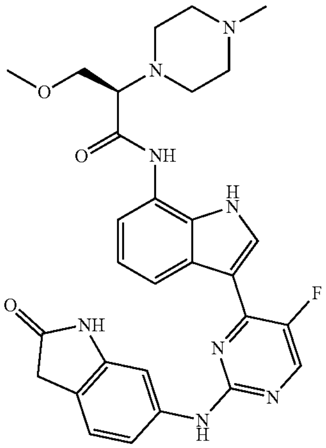 [SMILES: COC[C@H](C(=O)Nc1cccc2c(-c3nc(Nc4ccc5c(c4)NC(=O)C5)ncc3F)c[nH]c12)N1CCN(C)CC1] | 559.4 | $^1H$-NMR (300 MHz, DMSO-$d_6$) δ 2.16 (3H, s), 2.37 (4H, s), 2.64 (2H, s), 2.71-2.82 (2H, m), 3.30 (3H, s), 3.40 (2H, s), 3.52 (1H, t), 3.63-3.74 (1H, m), 3.75-3.87 (1H, m), 7.05-7.22 (2H, m), 7.28-7.37 (1H, m), 7.39-7.44 (1H, m), 7.55 (1H, d), 8.24 (1H, s), 8.43 (1H, d), 8.61 (1H, d), 9.51 (1H, s), 9.89 (1H, s), 10.37 (1H, s), 11.50 (1H, s). |

-continued
| Example number | Structure | LCMS [M + H]+ | $^1$H NMR |
|---|---|---|---|
| 38 | 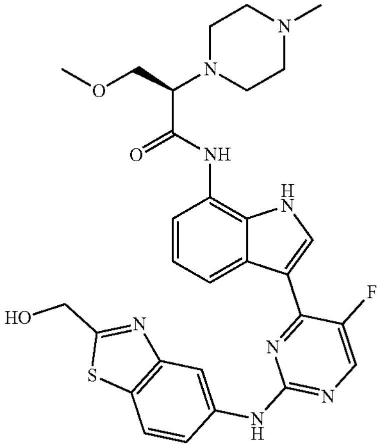 [SMILES: COC[C@H](C(=O)Nc1cccc2c(-c3nc(Nc4ccc5sc(CO)nc5c4)ncc3F)c[nH]c12)N1CCN(C)CC1] | 591.3 | $^1$H-NMR (300 MHz, DMSO-d$_6$) δ 2.13 (3H, s), 2.34 (4H, s), 2.56-2.68 (2H, m), 2.74 (2H, d), 3.30 (3H, s), 3.49 (1H, t), 3.67 (1H, dd), 3.79 (1H, dd), 4.84 (2H, d), 6.19 (1H, t), 7.11 (1H, t), 7.52 (1H, d), 7.75 (1H, dd), 7.95 (1H, d), 8.24 (1H, d), 8.48 (2H, dd), 8.59 (1H, d), 9.78 (2H, d), 11.47 (1H, s). |
| 43 | 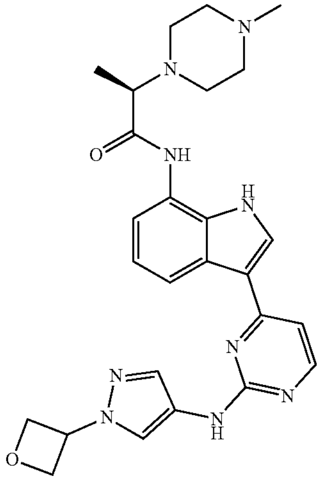 [SMILES: C[C@H](C(=O)Nc1cccc2c(-c3ccnc(Nc4cnn(C5COC5)c4)n3)c[nH]c12)N1CCN(C)CC1] | 502.3 | $^1$H-NMR (400 MHz, DMSO-d$_6$) δ 1.3 (3H, d), 2.2 (3H, s), 2.4 (4H, s), 2.6 (2H, s), 2.6 (2H, s), 3.3-3.4 (1H, m), 4.9-5.0 (4H, m), 5.6 (1H, p), 7.1 (1H, t), 7.2 (1H, d), 7.4 (1H, d), 7.7 (1H, s), 8.1 (1H, s), 8.3 (2H, dd), 8.4 (1H, s), 9.3 (1H, s), 9.7 (1H, s), 11.4 (1H, d). |
| 44 | 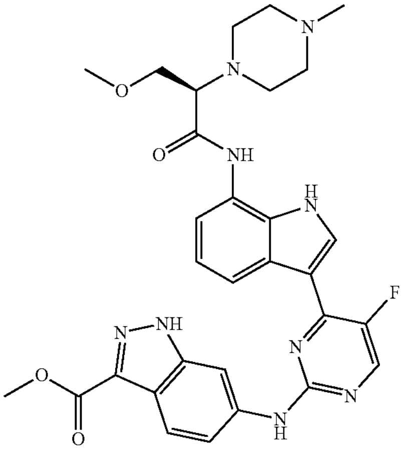 [SMILES: COC[C@H](C(=O)Nc1cccc2c(-c3nc(Nc4ccc5c(C(=O)OC)n[nH]c5c4)ncc3F)c[nH]c12)N1CCN(C)CC1] | 602.5 | $^1$H-NMR (300 MHz, DMSO-d$_6$) δ 2.16 (3H, s), 2.37 (4H, s), 2.64 (2H, d), 2.70-2.84 (2H, m), 3.32 (3H, s), 3.52 (1H, t), 3.69 (1H, dd), 3.81 (1H, dd), 3.93 (3H, s), 7.15 (1H, t), 7.50-7.60 (2H, m), 7.96 (1H, d), 8.27 (1H, d), 8.40 (1H, d), 8.53 (1H, d), 8.65 (1H, d), 9.87 (2H, d), 11.51 (1H, s), 13.65 (1H, s) |

-continued
| Example number | Structure | LCMS [M + H]+ | $^1$H NMR |
|---|---|---|---|
| 45 | 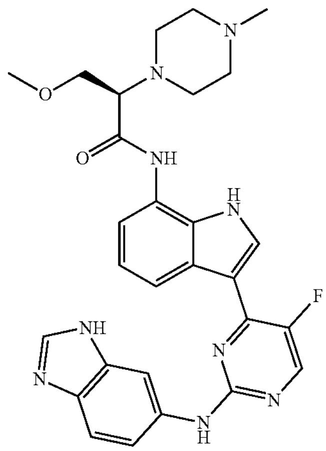 [SMILES: COC[C@H](C(=O)Nc1cccc2c(-c3nc(Nc4ccc5nc[nH]c5c4)ncc3F)c[nH]c12)N1CCN(C)CC1] | 544.4 | $^1$H-NMR (300 MHz, DMSO-$d_6$) δ 2.20 (3H, s), 2.44 (3H, s), 2.65 (2H, d), 2.72-2.86 (2H, m), 3.28 (4H, s), 3.56 (1H, t), 3.67 (1H, dd), 3.79 (1H, dd), 4.33 (2H, q), 7.18 (1H, t), 7.48 (1H, dd), 7.59 (1H, d), 8.15 (1H, s), 8.28 (1H, d), 8.49 (1H, d), 8.55-8.68 (2H, m), 9.06 (1H, d), 10.00 (1H, s), 10.19 (1H, s), 11.77 (1H, s). |
| 47 | 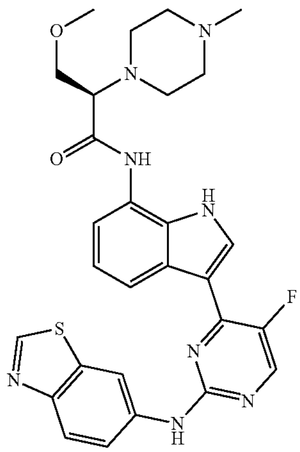 [SMILES: COC[C@H](C(=O)Nc1cccc2c(-c3nc(Nc4ccc5ncsc5c4)ncc3F)c[nH]c12)N1CCN(C)CC1] | 561.2 | $^1$H-NMR (400 MHz, MeOD-$d_4$) δ 2.34 (3H, s), 2.62 (4H, s), 2.84 (2H, s), 2.94 (2H, s), 3.44 (3H, s), 3.53 (1H, d), 3.86 (1H, d), 3.95-3.97 (1H, m), 7.18 (2H, dt), 7.71 (1H, d), 8.00 (1H, d), 8.21 (1H, d), 8.33 (1H, d), 8.68 (1H, d), 8.81 (1H, d), 9.10 (1H, s). |
| 48 | 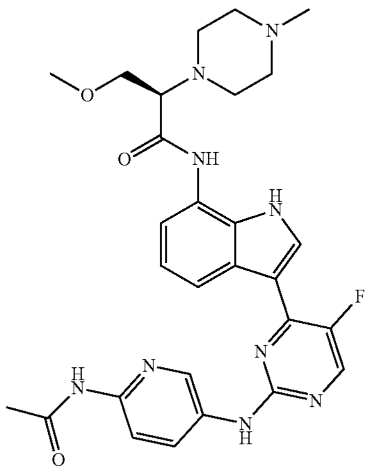 [SMILES: COC[C@H](C(=O)Nc1cccc2c(-c3nc(Nc4ccc(NC(C)=O)nc4)ncc3F)c[nH]c12)N1CCN(C)CC1] | 562.4 | $^1$H-NMR (300 MHz, DMSO-$d_6$) δ 2.09 (3H, s), 2.19 (3H, s), 2.18 (4H, s), 2.71 (4H, d), 3.53 (3H, t), 3.69 (2H, d), 3.81 (1H, d), 7.13 (1H, t), 7.54 (1H, d), 8.03 (1H, d), 8.12 (1H, d), 8.25 (1H, m), 8.47 (2H, m), 8 68 (1H, d), 9.59 (1H, s), 9 88 (1H, s), 10.39 (1H, s), 11.49 (1H, s) |

-continued
| Example number | Structure | LCMS [M + H]+ | $^1$H NMR |
|---|---|---|---|
| 50 | 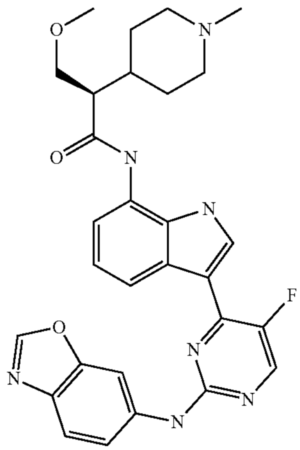 | 545.2 | $^1$H-NMR (300 MHz, DMSO-$d_6$) δ 2.16 (3H, s), 2.37 (4H, s), 2.65 (2H, s), 2.77 (2H, d), 3.32 (3 H, s), 3.52 (1H, t), 3.69 (1H, dd), 3 81 (1H, dd), 7 14 (1H, t), 7.55 (1 H, d), 7.61-7.78 (2H, m), 8.27 (1H, d), 8.45 (1H, d), 8.51 (1H, d), 8.60 (2H, d), 9.86 (2H, d), 11.51 (1H, s) |
| 51 | 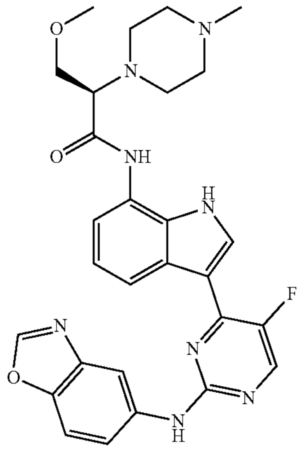 [SMILES: COC[C@H](C(=O)Nc1cccc2c(-c3nc(Nc4ccc5ocnc5c4)ncc3F)c[nH]c12)N1CCN(C)CC1] | 545.3 | $^1$H-NMR (300 MHz, DMSO-$d_6$) δ 2.15 (3H, s), 2.36 (4H, s), 2.63 (2H, d), 2.74 (2H, s), 3.30 (3H, s), 3.51 (1H, t), 3.68 (1H, dd), 3.80 (1H, dd), 7.11 (1H, t), 7.53 (1H, d), 7.70 (2H, d), 8.24 (1H, d), 8.34 (1H, d), 8.47 (1H, d), 8.57 (1H, d), 8.68 (1H, s), 9.66 (1H, s), 9.87 (1 H, s), 11.48 (1H, s). |
| 57 | 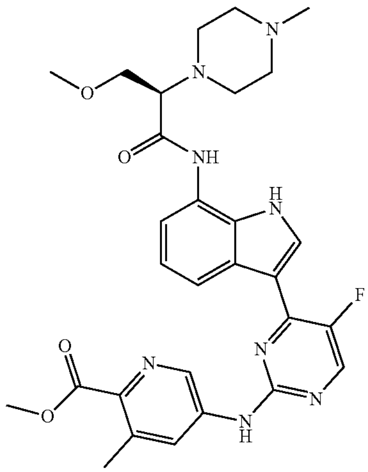 [SMILES: COC[C@H](C(=O)Nc1cccc2c(-c3nc(Nc4cnc(C(=O)OC)c(C)c4)ncc3F)c[nH]c12)N1CCN(C)CC1] | 577.4 | $^1$H-NMR (400 MHz, Chloroform-d) δ 2.40 (3H, s), 2.59-2.66 (4H, m), 2.70 (3H, s), 2.82 (2H, s), 2.95 (2H, s), 3.34-3.43 (4H, m), 3.87 (1H, dd), 3.97 (1H, dd), 4.00 (3H, s), 6.86 (1H, d), 7.22 (1H, t), 7.45 (1H, s), 8.14 (1H, t), 8.31 (1H, d), 8.50 (1H, d), 8.53-8.59 (2H, m), 9.94 (1H, s), 11.51 (1H, s) |

-continued
| Example number | Structure | LCMS $[M + H]^+$ | $^1$H NMR |
|---|---|---|---|
| 59 | 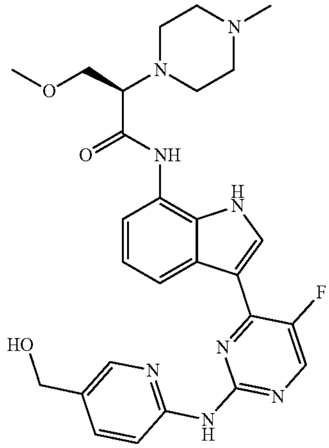 [SMILES: COC[C@H](C(=O)Nc1cccc2c(-c3nc(Nc4ccc(CO)cn4)ncc3F)c[nH]c12)N1CCN(C)CC1] | 535.3 | $^1$H-NMR (300 MHz, DMSO-$d_6$) δ 2.13 (3H, s), 2.34 (4H, s), 2.55-2.67 (2H, m), 2.73 (2H, q), 3.30 (3H, s), 3.49 (1H, t), 3.66 (1H, dd), 3.79 (1H, dd), 4.47 (2H, d), 5.18 (1H, d), 7.11 (1H, t), 7.54 (1H, dd), 7.68 (1H, dd), 8.17 (1H, d), 8.24 (2H, t), 8.46 (1H, d), 8.65-8.74 (1H, m), 9.90 (2H, s), 11.51 (1H, s). |
| 64 | 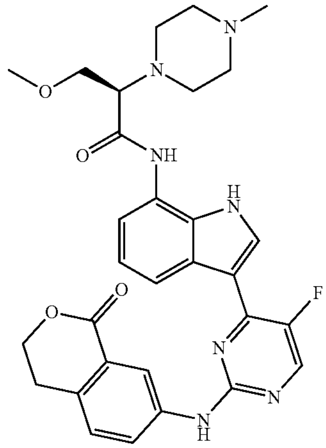 [SMILES: COC[C@H](C(=O)Nc1cccc2c(-c3nc(Nc4ccc5c(c4)C(=O)OCC5)ncc3F)c[nH]c12)N1CCN(C)CC1] | 574.4 | $^1$H-NMR (400 MHz, DMSO-$d_6$) δ 2.16 (3H, s), 2.38 (4H, s), 2.64 (2H, s), 2.70-2.87 (2H, m), 3.02 (2H, t), 3.32 (3H, s), 3.52 (1H, t), 3.69 (1H, dd), 3.81 (1H, dd), 4.52 (2H, t), 7.14 (1H, t), 7.36 (1H, d), 7.55 (1H, d), 8.03 (1H, dd), 8.22-8.37 (1H, m), 8.40 (1H, d), 8.49 (1H, d), 8.58 (1H, d), 9.82 (2H, d), 11.51 (1H, s) |
| 65 | 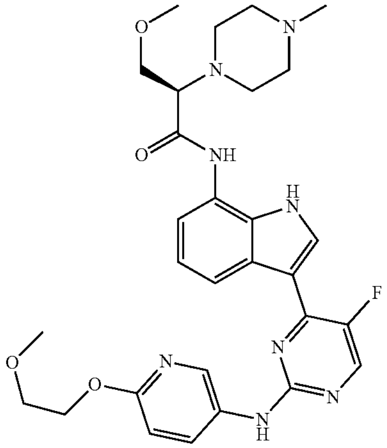 [SMILES: COCCOc1ccc(Nc2ncc(F)c(-c3c[nH]c4c(NC(=O)[C@@H](COC)N5CCN(C)CC5)cccc34)n2)cn1] | 579.4 | 1H-NMR (300 MHz, DMSO-d6) δ 2.15 (3H, s), 2.36 (4H, s), 2.64 (2H, d), 2.75 (2H, d), 3.33 (2H, s), 3.32 (3H, s), 3.35 (3H, s), 3.51 (1H, t), 3.63-3.74 (3H, m), 3.80 (1H, dd), 4.32-4.41 (2H, m), 6.84 (1H, d), 7.12 (1H, t), 7.54 (1H, d), 8.06 (1H, dd), 8.23 (1H, d), 8.37-8.51 (3H, m), 9.41 (1H, s), 9.87 (1H, s), 11.48 (1H, s) |

-continued

| Example number | Structure | LCMS [M + H]+ | $^1$H NMR |
|---|---|---|---|
| 77 | 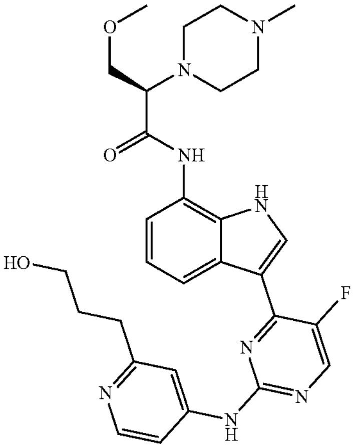 [SMILES: COC[C@H](C(=O)Nc1cccc2c(-c3nc(Nc4ccnc(CCCO)c4)ncc3F)c[nH]c12)N1CCN(C)CC1] | 563.4 | $^1$H-NMR (300 MHz, DMSO-$d_6$) δ 1.68-1.92 (32H, m), 2.13 (3H, s), 2.34 (4H, s), 2.54-2.81 (6H, m), 3 28 (3H, s), 3.38-3.56 (3H, m), 3.67 (1H, dd), 3.79 (1H, dd), 4.50 (1H, s), 7.17 (1H, t), 7.55 (2H, td), 7.71 (1H, d), 8.16-8.33 (2H, m), 8.46-8.65 (2H, m), 9.89 (2H, d), 11.52 (1H, s). |

Example 3

Preparation of (R)—N-(3-(5-fluoro-2-((6-(hydroxymethyl)-5-methylpyridin-3-yl)amino) pyrimidin-4-yl)-1H-indol-7-yl)-3-methoxy-2-(4-methylpiperazin-1-yl)propanamide

SCHEME 3

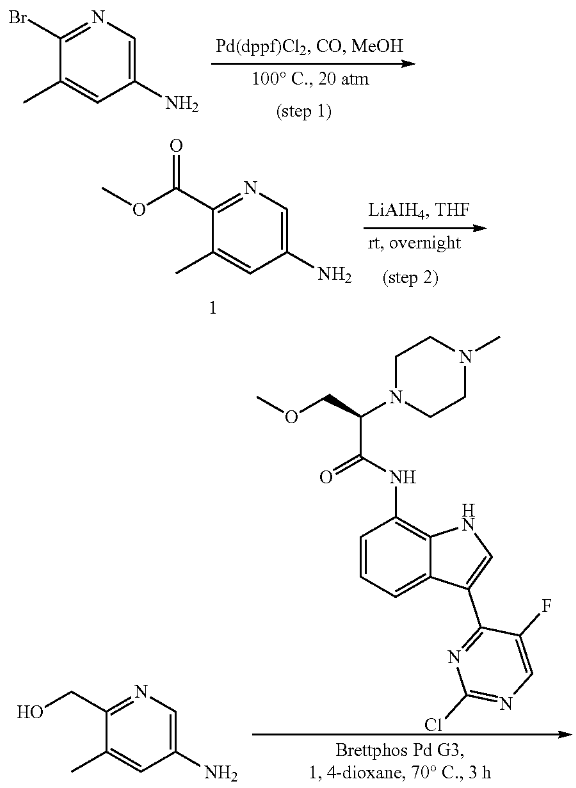

1

2

-continued

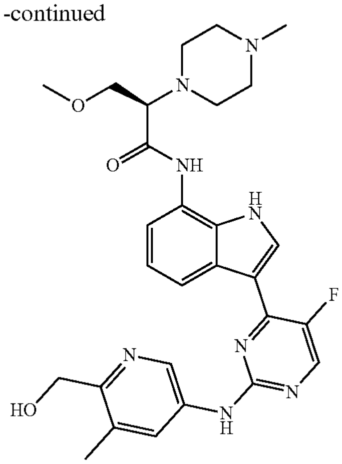

Example 3

Step 1. Methyl 5-amino-3-methylpicolinate

A mixture of 6-bromo-5-methylpyridin-3-amine (2000.00 mg, 10.693 mmol, 1.00 equiv) and Pd(dppf)$Cl_2$ (1564.80 mg, 2.139 mmol, 0.20 equiv) in MeOH (20.00 mL) was stirred for overnight at 100° C. under carbon monoxide atmosphere in 20 atm. The resulting mixture was concentrated under reduced pressure. The residue was purified by Prep-TLC ($CH_2Cl_2$/MeOH 20:1) to afford methyl 5-amino-3-methylpyridine-2-carboxylate (280 mg, 15.76%) as a white solid. LCMS: m/z (ESI), $[M+H]^{+}$=167.3.

Step 2. (5-amino-3-methylpyridin-2-yl)methanol

A mixture of methyl 5-amino-3-methylpyridine-2-carboxylate (200.00 mg, 1.204 mmol, 1.00 equiv) and Li AlH (137.03 mg, 3.610 mmol, 3.00 equiv) in THF (20.00 mL) was stirred for overnight at room temperature under air atmosphere. The resulting mixture was filtered, and the filter cake was washed with THF (2×5 mL). The filtrate was concentrated under vacuum. The crude product was used in the next step directly without further purification. LCMS: m/z (ESI), $[M+H]^{+}$=139.3.

Step 3. (R)—N-[3-(5-fluoro-2-[[6-(hydroxymethyl)-5-methylpyridin-3-yl]amino]pyrimidin-4-yl)-1H-indol-7-yl]-3-methoxy-2-(4-methylpiperazin-1-yl) propanamide (Ex. 3)

To a stirred mixture of (R)—N-[3-(2-chloro-5-fluoropyrimidin-4-yl)-1H-indol-7-yl]-3-methoxy-2-(4-methylpiperazin-1-yl)propanamide (200.00 mg, 0.448 mmol, 1.00 equiv) and (5-amino-3-methylpyridin-2-yl)methanol (92.75 mg, 0.671 mmol, 1.50 equiv) in dioxane (20.00 mL) were added BrettPhos Pd G3 (81.13 mg, 0.090 mmol, 0.20 equiv) and $Cs_2CO_3$ (437.43 mg, 1.343 mmol, 3.00 equiv) in portions at 70° C. under nitrogen atmosphere. The resulting mixture was concentrated under reduced pressure. The crude product (50 mg) was purified by Prep-HPLC with the following conditions (Column: XBridge Prep OBD $C_{18}$ Column, 30×150 mm, 5 μm; Mobile Phase A: Water (0.05% $NH_3H_2O$), Mobile Phase B: ACN; Flow rate: 60 mL/min; Gradient: 18 B to 38 B in 7 min; 254; 220 nm; RT1: 6.80) to afford (R)—N-[3-(5-fluoro-2-[[6-(hydroxymethyl)-5-methylpyridin-3-yl]amino]pyrimidin-4-yl)-1H-indol-7-yl]-3-methoxy-2-(4-methylpiperazin-1-yl)propanamide (15 mg, 6.11%) as a white solid. LCMS: m/z (ESI), $[M+H]^+$=549.4. $^1$H-NMR (400 Hz, Methanol-$d_4$) δ 2.33 (3H, s), 2.43 (3H, s), 2.60 (4H, s), 2.83 (2H, s), 2.92 (2H, s), 3.43 (3H, s), 3.51 (1H, t), 3.85 (1H, dd), 3.94 (1H, dd), 4.72 (2H, s), 7.16-7.23 (2H, m), 8.17 (1H, d), 8.20-8.24 (1H, m), 8.29 (1H, d), 8.62 (2H, dd).

Example 5

Preparation of (R)—N-(3-[5-fluoro-2-[(6-propanamidopyridin-3-yl)amino]pyrimidin-4-yl]-1H-indol-7-yl)-3-methoxy-2-(4-methylpiperazin-1-yl)propanamide

SCHEME 5

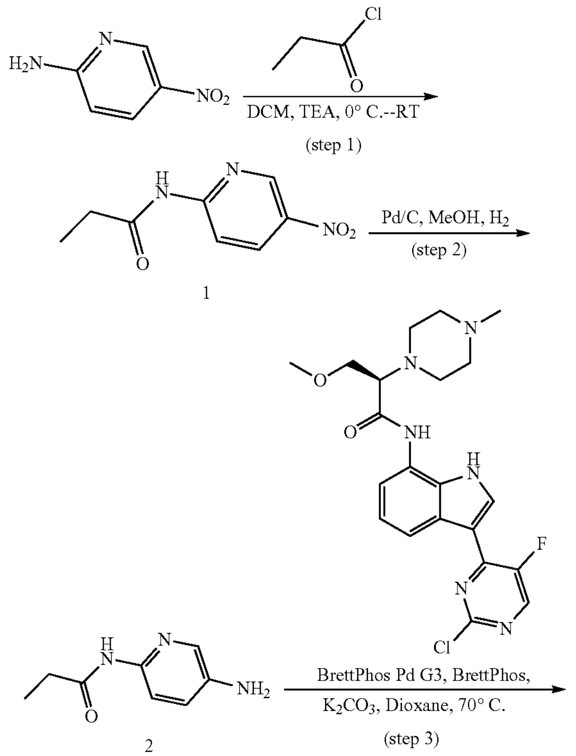

1

2

-continued

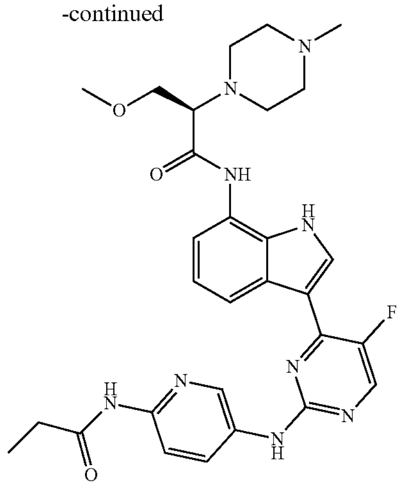

Example 5

Step 1. N-(5-nitropyridin-2-yl)propanamide

Into a 40 mL vial were added 5-nitropyridin-2-amine (800.00 mg, 5.751 mmol, 1.00 equiv), and propanoyl chloride (691.67 mg, 7.476 mmol, 1.30 equiv), TEA (1454.78 mg, 14.377 mmol, 2.5 equiv), DCM (20.00 mL) at room temperature. Then the mixture was stirred at 0° C. under nitrogen atmosphere for 3 h. The resulting mixture was extracted with EtOAc (3×20 mL). The combined organic layers were washed with brine (3×10 mL), dried over anhydrous $Na_2SO_4$. After filtration, the filtrate was concentrated under reduced pressure to afford N-(5-nitropyridin-2-yl)propanamide (145 mg, 12.92%) as a light yellow solid. LCMS: m/z (ESI), $[M+H]^+$=196.0.

Step 2. N-(5-aminopyridin-2-yl)propanamide

Into a 100 mL vial were added N-(5-nitropyridin-2-yl) propanamide (100.00 mg, 0.512 mmol, 1.00 equiv), and Pd/C (5.45 mg, 0.051 mmol, 0.10 equiv), MeOH (15.00 mL) at room temperature. Then the mixture was stirred at 0° C. under $H_2$ atmosphere for 3 h. The resulting mixture was filtered, and the filter cake was washed with DCM (3×20 mL). The filtrate was concentrated under reduced pressure to afford N-(5-aminopyridin-2-yl)propanamide (35 mg, 41.35%) as a light yellow solid. LCMS: m/z (ESI), $[M+H]^+$=166.2.

Step 3. (R)—N-(3-[5-fluoro-2-[(6-propanamidopyridin-3-yl)amino]pyrimidin-4-yl]-1H-indol-7-yl)-3-methoxy-2-(4-methylpiperazin-1-yl)propanamide (Ex. 5)

Into a 40 mL vial were added (R)—N-[3-(2-chloro-5-fluoropyrimidin-4-yl)-1H-indol-7-yl]-3-methoxy-2-(4-methylpiperazin-1-yl)propanamide (180.00 mg, 0.403 mmol, 1.00 equiv), and N-(5-aminopyridin-2-yl)propanamide (99.80 mg, 0.604 mmol, 1.50 equiv), BrettPhos Pd $G_3$ (36.51 mg, 0.040 mmol, 0.1 equiv), $K_2CO_3$ (111.33 mg, 0.806 mmol, 2 equiv), dioxane (20.00 mL) at room temperature. Then the mixture was stirred at 70° C. under nitrogen atmosphere for 3 h. The resulting mixture was extracted with EtOAc (3×20 mL). The combined organic layers were washed with brine (3×10 mL), dried over anhydrous $Na_2SO_4$. After filtration, the filtrate was concentrated under reduced pressure. The crude product was purified by Prep-HPLC with the following conditions (Column: XBridge Prep OBD C18 Column 30×150 mm, 5 μm; Mobile Phase A: Water (0.05% $NH_3 \cdot H_2O$), Mobile Phase B: ACN; Flow rate: 60 mL/min; Gradient: 25% B to 40% B in 7 min; 254/220 nm; Rt: 5.77 min) to afford (R)—N-(3-[5-fluoro-2-[(6-propanamidopyridin-3-yl)amino]pyrimidin-4-yl]-1H-indol-7-yl)-3-methoxy-2-(4-methylpiperazin-1-yl)propanamide (30 mg, 12.94%) as a light yellow solid. LCMS: m/z (ESI), $[M+H]^+$=576.4. $^1H$-NMR (300 MHz, DMSO-$d_6$) δ 1.07 (3H, t), 2.13 (3H, s), 2.37 (6H, dd), 2.54-2.66 (2H, m), 2.73 (2H, q), 3.32 (3H, s), 3.49 (1H, t), 3.66 (1H, dd), 3.79 (1H, dd), 7.11 (1H, t), 7.52 (1H, d), 7.97-8.17 (2H, m), 8.22 (1H, d), 8.45 (2, H dd), 8.66 (1H, d), 9.54 (1H, s), 9.85 (1H, s), 10.27 (1H, s), 11.47 (1H, s).

Example 6

Preparation of Methyl 2-[4-[(5-fluoro-4-[7-[(R)-3-methoxy-2-(4-methylpiperazin-1-yl)propanamido]-1H-indol-3-yl]pyrimidin-2-yl)amino]pyrazol-1-yl]benzoate

SCHEME 6

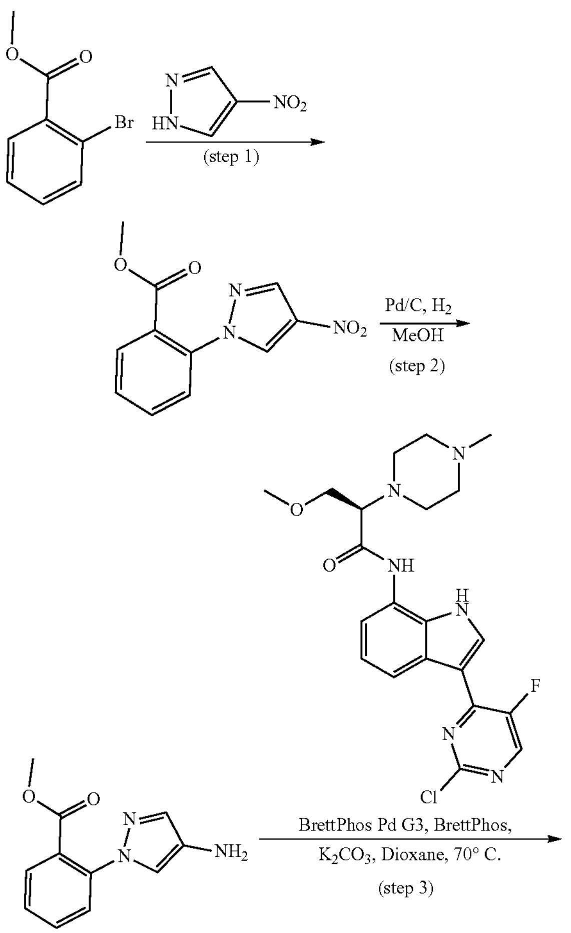

-continued

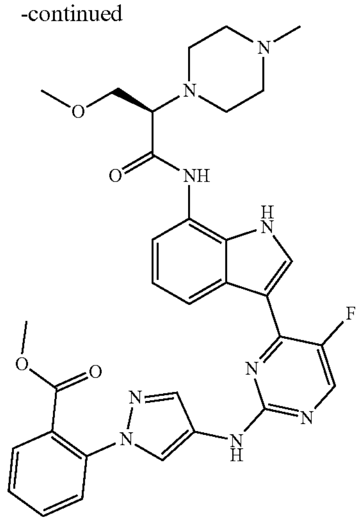

Example 6

Step 1. Methyl 2-(4-nitropyrazol-1-yl)benzoate

To a mixture of methyl 2-bromobenzoate (7.61 g, 35.374 mmol, 2.00 equiv) and 4-nitropyrazole (2.00 g, 17.687 mmol, 1.00 equiv) in dioxane (30.00 mL) were added $Cs_2CO_3$ (17288.54 mg, 53.062 mmol, 3.00 equiv), (1S, 2S)—N1,N2-dimethylcyclohexane-1,2-diamine (1509.56 mg, 10.612 mmol, 0.60 equiv) and CuI (1347.41 mg, 7.075 mmol, 0.40 equiv). After stirring for overnight at 110° C. under nitrogen atmosphere, the resulting mixture was filtered, and the filter cake was washed with DCM (3×20 mL). The filtrate was concentrated under reduced pressure. The residue was purified by silica gel column chromatography, eluted with PE/EtOAc (3:1) to afford methyl 2-(4-nitropyrazol-1-yl) benzoate (410 mg, 9.38%) as a white solid. $^1H$ NMR (300 MHz, $CDCl_3$-$d_1$) δ 3.79 (3H, s), 7.50-7.53 (1H, m), 7.60-7.64 (1H, m), 7.67-7.73 (1H, m), 8.00-8.02 (1H, m), 8.26 (1H, s), 8.41-8.47 (1H, m).

Step 2. Methyl 2-(4-aminopyrazol-1-yl)benzoate

Into a 50 mL round-bottom flask were added methyl 2-(4-nitropyrazol-1-yl)benzoate (410.00 mg, 1.659 mmol, 1.00 equiv) and Pd/C (353.00 mg, 3.317 mmol, 2.00 equiv) in MeOH (25.00 mL) at room temperature. The resulting mixture was stirred for 2 hs at room temperature under hydrogen atmosphere. The resulting mixture was filtered, and the filter cake was washed with MeOH (3×10 mL). The filtrate was concentrated under reduced pressure. This resulted in methyl 2-(4-aminopyrazol-1-yl)benzoate (360 mg, 79.3%) as a black oil. LCMS: m/z (ESI), $[M+H]^+$=218.2 $^1H$ NMR (400 MHz, $CDCl_3$-d) δ 3.79 (3H, s), 7.32-7.49 (4H, m), 7.53-7.57 (1H, m), 7.73-7.76 (1H, m).

Step 3. Methyl 2-[4-[(5-fluoro-4-[7-[(R)-3-methoxy-2-(4-methylpiperazin-1-yl)propanamido]-1H-indol-3-yl]pyrimidin-2-yl)amino]pyrazol-1-yl]benzoate (Ex. 6)

To a mixture of methyl 2-(4-aminopyrazol-1-yl)benzoate (94.78 mg, 0.436 mmol, 1.5 equiv) and (R)—N-[3-(2-chloro-5-fluoropyrimidin-4-yl)-1H-indol-7-yl]-3-methoxy-2-(4-methylpiperazin-1-yl)propanamide (130.00 mg, 0.291 mmol, 1.00 equiv) in dioxane (10.00 mL) were added BrettPhos Pd $G_3$ (26.37 mg, 0.029 mmol, 0.10 equiv), BrettPhos (15.61 mg, 0.029 mmol, 0.10 equiv) and $Cs_2CO_3$ (284.33 mg, 0.873 mmol, 3.00 equiv). After stirring for 2 h at 80° C. under a nitrogen atmosphere, the resulting mixture was concentrated under reduced pressure. The crude product (50 mg) was purified by Prep-HPLC with the following conditions (Column: CHIRALPAK IC-3, 4.6×50 mm, 3 μm; Mobile Phase A: (Hex:DCM=3:1)(0.1% DEA):EtOH=50:50, Flow rate: 1.5 mL/min) to afford methyl 2-[4-[(5-fluoro-4-[7-[(R)-3-methoxy-2-(4-methylpiperazin-1-yl)propanamido]-1H-indol-3-yl]pyrimidin-2-yl)amino]pyrazol-1-yl] benzoate (Ex. 6) (7 mg, 3.80%) as a white solid. LCMS: m/z (ESI), $[M+H]^+$=628.3 $^1$H-NMR (300 MHz, DMSO-$d_6$) δ 2.17 (3H, s), 2.38 (4H, s), 2.65 (4H, s), 2.75 (3H, s), 3.49-3.54 (1H, m), 3.67 (3H, s), 3.71 (1H, d), 3.78-3.84 (1H, m), 7.13 (1H, s), 7.42-7.58 (2H, m), 7.68 (3H, d), 7.83 (1H, s), 8.23 (1H, s), 8.39 (1H, s), 8.46 (1H, d), 8.47-8.48 (1H, m), 9.61 (1H, s), 9.87 (1H, s), 11.46 (1H, s).

Example 8

Preparation of (R)—N-(3-(5-fluoro-2-((6-(2-hydroxyacetamido)pyridin-3-yl)amino)pyrimidin-4-yl)-1H-indol-7-yl)-3-methoxy-2-(4-methylpiperazin-1-yl)propanamide

SCHEME 8

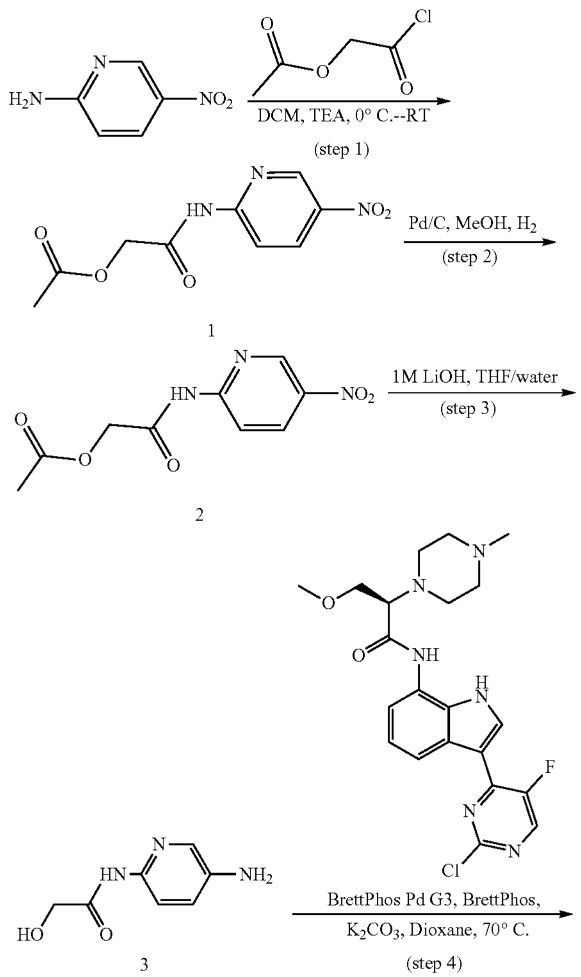

-continued

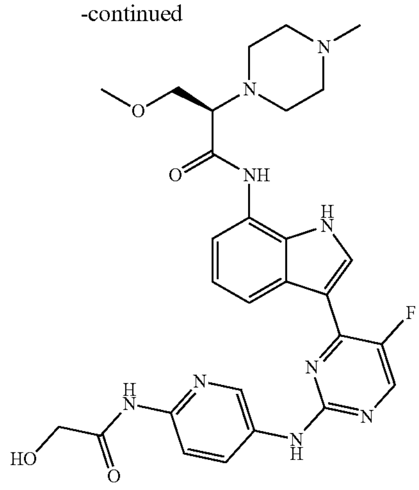

Example 8

Step 1. Preparation of 2-((5-nitropyridin-2-yl)amino)-2-oxoethyl Acetate

To a stirred mixture of 5-nitropyridin-2-amine (500.00 mg, 3.594 mmol, 1.00 equiv) and TEA (909.24 mg, 8.985 mmol, 2.50 equiv) in DCM (20.00 mL) was added 2-chloro-2-oxoethyl acetate (736.07 mg, 5.391 mmol, 1.50 equiv) dropwise at room temperature under nitrogen atmosphere. The resulting mixture was filtered, and the filter cake was washed with DCM (3×10 mL). The filtrate was concentrated under reduced pressure. The filtrate was concentrated under reduced pressure. The residue was purified by Prep-TLC ($CH_2Cl_2$/MeOH=10:1) to afford [(5-nitropyridin-2-yl)carbamoyl]methyl acetate (300 mg, 34.90%) as a Brown yellow solid. LCMS: m/z (ESI), $[M+H]^{+=}$240.3.

Step 2. Preparation of 2-((5-aminopyridin-2-yl)amino)-2-oxoethyl Acetate

To a stirred mixture of [(5-nitropyridin-2-yl)carbamoyl] methyl acetate (300.00 mg, 1.254 mmol, 1.00 equiv) and Pd/C (26.70 mg, 0.251 mmol, 0.20 equiv) in MeOH (20.00 mL) at room temperature under $H_2$ atmosphere. The resulting mixture was filtered, and the filter cake was washed with MeOH (3×10 mL). The filtrate was concentrated under reduced pressure to afford [(5-aminopyridin-2-yl)carbamoyl]methyl acetate (250 mg, 95.28%) as a yellow solid. LCMS: m/z (ESI), $[M+H]^{+=}$210.3.

Step 3. Preparation of N-(5-aminopyridin-2-yl)-2-hydroxyacetamide

To a stirred mixture of [(5-aminopyridin-2-yl)carbamoyl] methyl acetate (250.00 mg, 1.195 mmol, 1.00 equiv) and LiOH·$H_2O$ (250.73 mg, 5.975 mmol, 5.00 equiv) in THF (18.00 mL) and water (6.00 mL) in portions at room temperature under nitrogen atmosphere. The resulting mixture was filtered, the filter cake was washed with DCM (3×20 mL). The filtrate was concentrated under reduced pressure. The residue was purified by Prep-TLC ($CH_2Cl_2$/MeOH=10:1) to afford N-(5-aminopyridin-2-yl)-2-hydroxyacetamide (100 mg, 35.13%) as a yellow solid. LCMS: m/z (ESI), $[M+H]^+$=168.1.

Step 4. Preparation of (R)—N-(3-(5-fluoro-2-((5-hydroxy-6-(hydroxymethyl)pyridin-3-yl)amino)pyrimidin-4-yl)-1H-indol-7-yl)-3-methoxy-2-(4-methylpiperazin-1-yl)propanamide (Ex. 8)

To a stirred mixture of (R)—N-[3-(2-chloro-5-fluoropyrimidin-4-yl)-1H-indol-7-yl]-3-hydroxy-2-(4-methylpiperazin-1-yl)propanamide (150.00 mg, 0.347 mmol, 1.00 equiv) and N-(5-aminopyridin-2-yl)-2-hydroxyacetamide (86.89 mg, 0.520 mmol, 1.50 equiv) in dioxane (15.00 mL) was added BrettPhos Pd $G_3$ (31.41 mg, 0.035 mmol, 0.10 equiv), $K_2CO_3$ (95.78 mg, 0.693 mmol, 2.00 equiv) and BrettPhos (37.20 mg, 0.069 mmol, 0.20 equiv) in portions at 70° C. under nitrogen atmosphere. The resulting mixture was filtered, the filter cake was washed with DCM (3×20 mL). The filtrate was concentrated under reduced pressure. The residue was purified by Prep-TLC ($CH_2Cl_2$/MeOH=10:1) to afford the crude product (100 mg), which was purified by Prep-HPLC with the following conditions (Column: XBridge Prep OBD C18 Column 30×150 mm, 5 μm; Mobile Phase A: Water (0.05% $NH_3{\cdot}H_2O$), Mobile Phase B: ACN; Flow rate: 60 mL/min; Gradient: 31% B to 45% B in 7 min; 254/220 nm; Rt: 6.30 min) to afford (R)—N-[3-(5-fluoro-2-[[6-(2-hydroxyacetamido)pyridin-3-yl]amino]pyrimidin-4-yl)-1H-indol-7-yl]-3-methoxy-2-(4-methylpiperazin-1-yl)propanamide (25.1 mg, 12.45%) as an off-white solid. LCMS: m/z (ESI), $[M+H]^+$=578.4. $^1$H-NMR (300 MHz, DMSO-$d_6$) δ 2.16 (3H, s), 2.37 (4H, s), 2.64 (2H, d), 2.75 (2H, d), 3.30 (3H, s), 3.51 (1H, t), 3.69 (1H, dd), 3.81 (1H, dd), 4.05 (2H, d), 5.75 (1H, t), 7.14 (1H, t), 7.54 (1H, d), 8.07 (1H, d), 8.14-8.30 (2H, m), 8.40-8.57 (2H, m), 8.64-8.76 (1H, m), 9.56 (1H, s), 9.64 (1H, s), 9.87 (1H, s), 11.49 (1H, s).

Example 9/29

Preparation of (R)—N-(3-(5-fluoro-2-((6-(1-hydroxyethyl)pyridin-3-yl)amino)pyrimidin-4-yl)-1H-indol-7-yl)-3-methoxy-2-(4-methylpiperazin-1-yl)propanamide (Ex. 9 as Isomer 2 and Ex. 29 as Isomer 1)

SCHEME 9/29

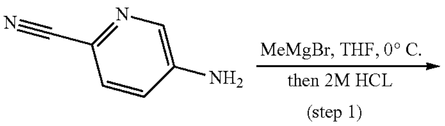

-continued

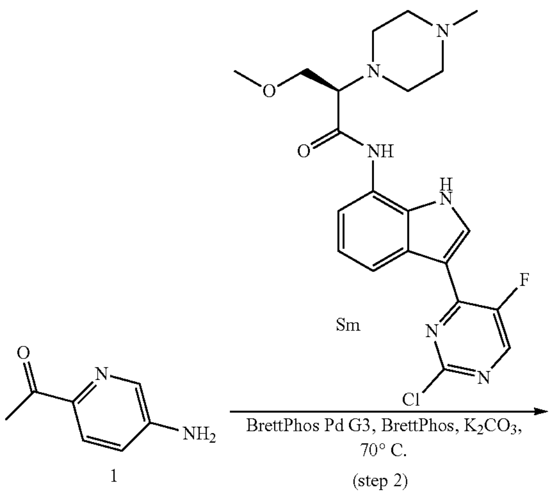

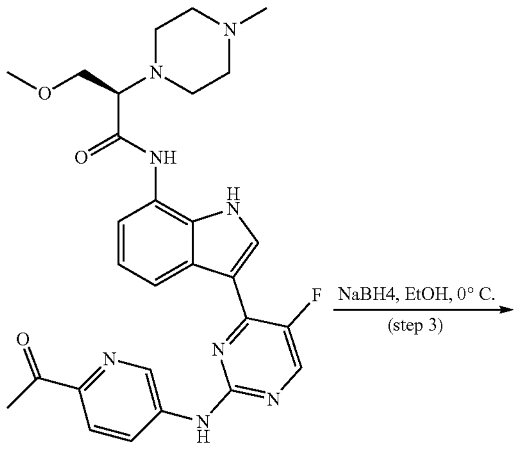

2

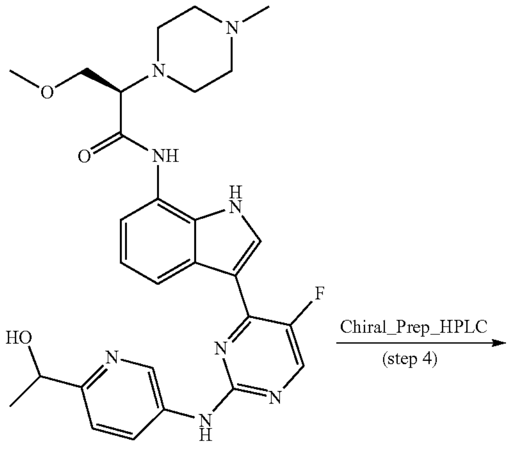

3

-continued

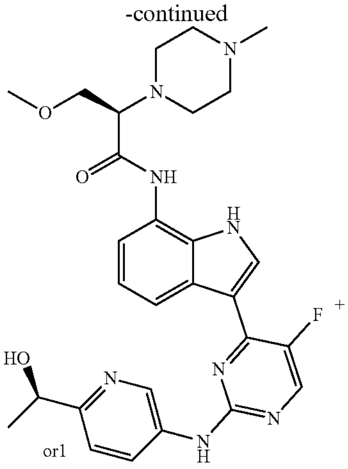

Example 29
isomer 1

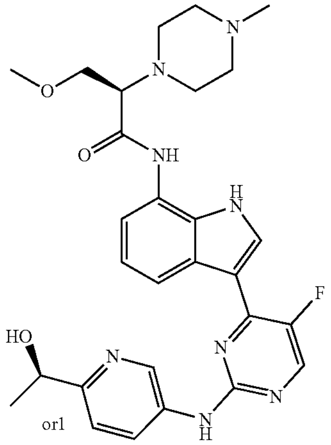

Example 9
isomer 2

Step 1. 1-(5-aminopyridin-2-yl)ethan-1-one

To a stirred solution of 5-aminopyridine-2-carbonitrile (800 mg, 6.716 mmol, 1.00 equiv) in THF (35.00 mL) was added bromo(methyl)magnesium (7.83 mL, 23.490 mmol, 3.50 equiv) dropwise at 0° C. under nitrogen atmosphere. The resulting mixture was stirred for 2 h at 0° C. under nitrogen atmosphere. The reaction was quenched with 2 M HCl (aq.) at 0° C. The resulting mixture was stirred for 4 h at room temperature. The mixture was basified to pH 8 with saturated $NaHCO_3$ (aq.). The resulting mixture was extracted with EtOAc (3×20 mL). The combined organic layers were washed with brine (1×50 mL), dried over anhydrous $Na_2SO_4$. After filtration, the filtrate was concentrated under reduced pressure. The residue was purified by silica gel column chromatography, eluted with PE/EtOAc (1:1) to afford 1-(5-aminopyridin-2-yl)ethanone (550 mg, 60.15%) as a light brown solid. LCMS: m/z (ESI), $[M+H]^+$=137.1. $^1$H-NMR (300 MHz, Chloroform-d) δ 2.66 (3H, s), 4.15 (2H, d), 7.01 (1H, dd), 7.93 (1H, d), 8.08 (1H, d).

Step 2. (R)—N-(3-(2-((6-acetylpyridin-3-yl)amino)-5-fluoropyrimidin-4-yl)-1H-indol-7-yl)-3-methoxy-2-(4-methylpiperazin-1-yl)propanamide A mixture of (R)—N-[3-(2-chloro-5-fluoropyrimidin-4-yl)-1H-indol-7-yl]-3-methoxy-2-(4-methylpiperazin-1-yl)

propanamide (220.00 mg, 0.492 mmol, 1.00 equiv), Brett-Phos Pd G3 (44.62 mg, 0.049 mmol, 0.10 equiv), BrettPhos (26.42 mg, 0.049 mmol, 0.10 equiv), $K_2CO_3$ (136.07 mg, 0.985 mmol, 2.00 equiv) and 1-(5-aminopyridin-2-yl)ethanone (100.54 mg, 0.738 mmol, 1.50 equiv) in 1,4-dioxane (10.00 mL) was stirred for 3 h at 80° C. under nitrogen atmosphere. The resulting mixture was filtered, the filter cake was washed with $CH_2Cl_2$ (2×5 mL). The filtrate was concentrated under reduced pressure. The residue was purified by Prep-TLC ($CH_2Cl_2$/MeOH 8:1) to afford (R)—N-(3-[2-[(6-acetylpyridin-3-yl)amino]-5-fluoropyrimidin-4-yl]-1H-indol-7-yl)-3-methoxy-2-(4-methylpiperazin-1-yl) propanamide (200 mg, 74.33%) as an off-white solid. LCMS: m/z (ESI), $[M+H]^+$=547.5.

Step 3. (R)—N-(3-(5-fluoro-2-((6-(1-hydroxyethyl) pyridin-3-yl)amino)pyrimidin-4-yl)-1H-indol-7-yl)-3-methoxy-2-(4-methylpiperazin-1-yl)propanamide To a stirred solution of (R)—N-(3-[2-[(6-acetylpyridin-3-yl)amino]-5-fluoropyrimidin-4-yl]-1H-indol-7-yl)-3-methoxy-2-(4-methylpiperazin-1-yl)propanamide (200.00 mg, 0.366 mmol, 1.00 equiv) in MeOH (10.00 mL) was added $NaBH_4$ (41.53 mg, 1.098 mmol, 3.00 equiv) in portions at 0° C. under nitrogen atmosphere. The resulting mixture was stirred for 1 h at 0° C. under nitrogen atmosphere. The reaction was quenched by the addition of Water/Ice. The resulting mixture was extracted with $CH_2Cl_2$ (3×15 mL). The combined organic layers were dried over anhydrous $Na_2SO_4$. After filtration, the filtrate was concentrated under reduced pressure. The crude product (180 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 23 B to 43 B in 7 min) to afford (R)—N-[3-(5-fluoro-2-[[6-(1-hydroxyethyl)pyridin-3-yl]amino]pyrimidin-4-yl)-1H-indol-7-yl]-3-methoxy-2-(4-methylpiperazin-1-yl) propanamide (120 mg, 59.78%) as a white solid. LCMS: m/z (ESI), $[M+H]^{+=}$549.0.

Step 4. (R)—N-(3-(5-fluoro-2-((6-(1-hydroxyethyl) pyridin-3-yl)amino)pyrimidin-4-yl)-1H-indol-7-yl)-3-methoxy-2-(4-methylpiperazin-1-yl)propanamide (Ex. 29/9)

The crude product (100 mg) was purified by Chiral-Prep-HPLC with the following conditions (Column: CHIRALPAK IC, 2×25 cm, 5 μm; Mobile Phase A: Hex:DCM=1:1 (10 mM NH3-MEOH)-HPLC, Mobile Phase B: IPA-HPLC; Flow rate: 20 mL/min; Gradient: 20 B to 20 B in 19 min; 254/220 nm; RT1: 14.362; RT2: 16.774; Injection Volume: 0.3 mL; Number Of Runs: 10) to afford (R)—N-[3-[5-fluoro-2-([6-[(1R)-1-hydroxyethyl]pyridin-3-yl]amino) pyrimidin-4-yl]-1H-indol-7-yl]-3-methoxy-2-(4-methylpiperazin-1-yl)propanamide (Ex. 29) (isomer 1, 40 mg, 40.00%) as a white solid LCMS m/z (ESI), $[M+H]^{+=}$549.4. $^1$H-NMR (400 MHz, DMSO-$d_6$) δ 1.38 (3H, d), 2.15 (3H, s), 2.36 (4H, s), 2.63 (2H, s), 2.68-2.84 (2H, m), 3.30 (3H, s), 3.51 (1H, t), 3.68 (1H, dd), 3.80 (1H, dd), 4.60-4.78 (1H, m), 5.23 (1H, d), 7.14 (1H, t), 7.44 (1H, d), 7.54 (1H, d), 8.09-8.29 (2H, m), 8.45 (1H, d), 8.53 (1H, d), 8.78 (1H, s), 9.63 (1H, s), 9.86 (1H, s), 11.48 (1H, s).

(R)—N-[3-[5-fluoro-2-([6-[1-hydroxyethyl]pyridin-3-yl] amino)pyrimidin-4-yl]-1H-indol-7-yl]-3-methoxy-2-(4-methylpiperazin-1-yl)propanamide (Ex. 9) (isomer 2, 45 mg, 44.55%) as a white solid, LCMS: m/z (ESI), $[M+H]^+$ =549.4. $^1$H-NMR (400 MHz, DMSO-$d_6$) δ 1.38 (3H, d), 2.15 (3H, s), 2.36 (4H, s), 2.63 (2H, s), 2.68-2.84 (2H, m), 3.30 (3H, s), 3.51 (1H, t), 3.68 (1H, dd), 3.80 (1H, dd), 4.60-4.78 (1H, m), 5.23 (1H, d), 7.14 (1H, t), 7.44 (1H, d), 7.54 (1H, d), 8.09-8.29 (2H, m), 8.45 (1H, d), 8.53 (1H, d), 8.78 (1H, s), 9.63 (1H, s), 9.86 (1H, s), 11.48 (1H, s).

Example 13

Preparation of (R)—N-[3-[5-fluoro-2-(1H-indazol-6-ylamino)pyrimidin-4-yl]-1H-indol-7-yl]-3-methoxy-2-(4-methylpiperazin-1-yl)propanamide

SCHEME 13

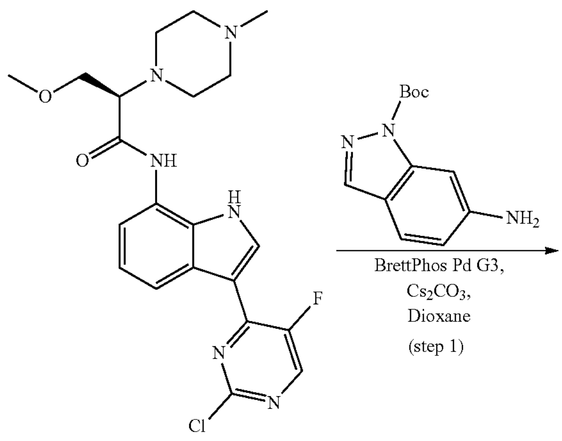

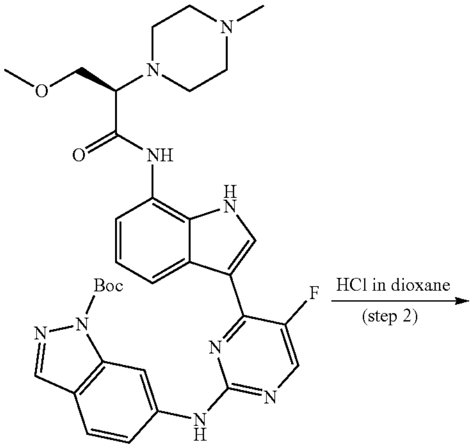

-continued

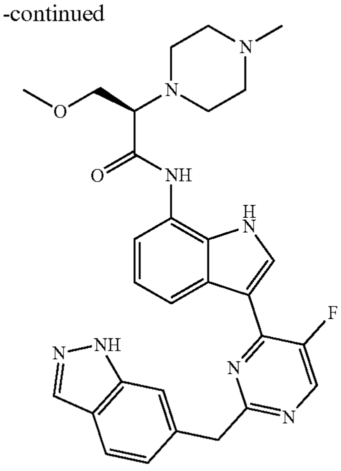

Example 13

Step 1. Tert-butyl 6-[(5-fluoro-4-[7-[(R)-3-methoxy-2-(4-methylpiperazin-1-yl) propanamido]-1H-indol-3-yl]pyrimidin-2-yl)amino]indazole-1-carboxylate A solution of (R)—N-[3-(2-chloro-5-fluoropyrimidin-4-yl)-1H-indol-7-yl]-3-methoxy-2-(4-methylpiperazin-1-yl) propanamide (150.00 mg, 0.336 mmol, 1.00 equiv) and tert-butyl 6-aminoindazole-1-carboxylate (117.44 mg, 0.503 mmol, 1.50 equiv), BrettPhos Pd G3 (30.43 mg, 0.034 mmol, 0.10 equiv), BrettPhos (18.02 mg, 0.034 mmol, 0.10 equiv), $Cs_2CO_3$ (218.72 mg, 0.671 mmol, 2.00 equiv) in Dioxane (5.00 mL) was stirred for 2 h at 100° C. under nitrogen atmosphere. The residue was purified by silica gel column chromatography, eluted with $CHCl_3$/MeOH (12:1) to afford tert-butyl 6-[(5-fluoro-4-[7-[(R)-3-methoxy-2-(4-methylpiperazin-1-yl)propanamido]-1H-indol-3-yl]pyrimidin-2-yl)amino]indazole-1-carboxylate (120 mg, 55.54%) as an off-white solid. LCMS: m/z (ESI), $[M+H]^{+}$=644.6

Step 2. (R)—N-[3-[5-fluoro-2-(1H-indazol-6-ylamino)pyrimidin-4-yl]-1H-indol-7-yl]-3-methoxy-2-(4-methylpiperazin-1-yl)propanamide (Ex. 13)

To a stirred solution of tert-butyl 6-[(5-fluoro-4-[7-[(R)-3-methoxy-2-(4-methylpiperazin-1-yl)propanamido]-1H-indol-3-yl]pyrimidin-2-yl)amino]indazole-1-carboxylate (110.00 mg, 0.171 mmol, 1.00 equiv) in HCl (gas) in 1,4-dioxane (10 mL) at room temperature under nitrogen atmosphere. The resulting mixture was concentrated under vacuum. The crude product was purified by Prep-HPLC with the following conditions (Column: XBridge Prep OBD C18 Column, 19×250 mm, 5 μm; Mobile Phase A: Water (0.05% $NH_3H_2O$), Mobile Phase B: ACN; Flow rate: 25 mL/min; Gradient: 31 B to 40 B in 10 min; 254,220 nm; RT 1:9.87) to afford (R)—N-[3-[5-fluoro-2-(1H-indazol-6-ylamino)pyrimidin-4-yl]-1H-indol-7-yl]-3-methoxy-2-(4-methylpiperazin-1-yl)propanamide (30 mg, 32.30%) as an off-white solid. LCMS: m/z (ESI), $[M+H]^{+}$=544.3. $^{1}$H-NMR (400 MHz, DMSO-$d_6$) δ 2.15 (3H, s), 2.36 (4H, s), 2.64 (2H, d), 2.75 (2H, q), 3.30 (3H, s), 3.51 (1H, t), 3.68 (1H, dd), 3.80 (1H, dd), 7.13 (1H, t), 7.37 (1H, dd), 7.54 (1H, dd), 7.64 (1H, d), 7.94 (1H, d), 8.25 (2H, dd), 8.49 (1H, d), 8.64 (1H, m), 9.67 (1H, s), 9.87 (1H, s), 11.47 (1H, m), 12.78 (1H, s).

Example 14

Preparation of Methyl 2-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]oxy)acetate

SCHEME 14

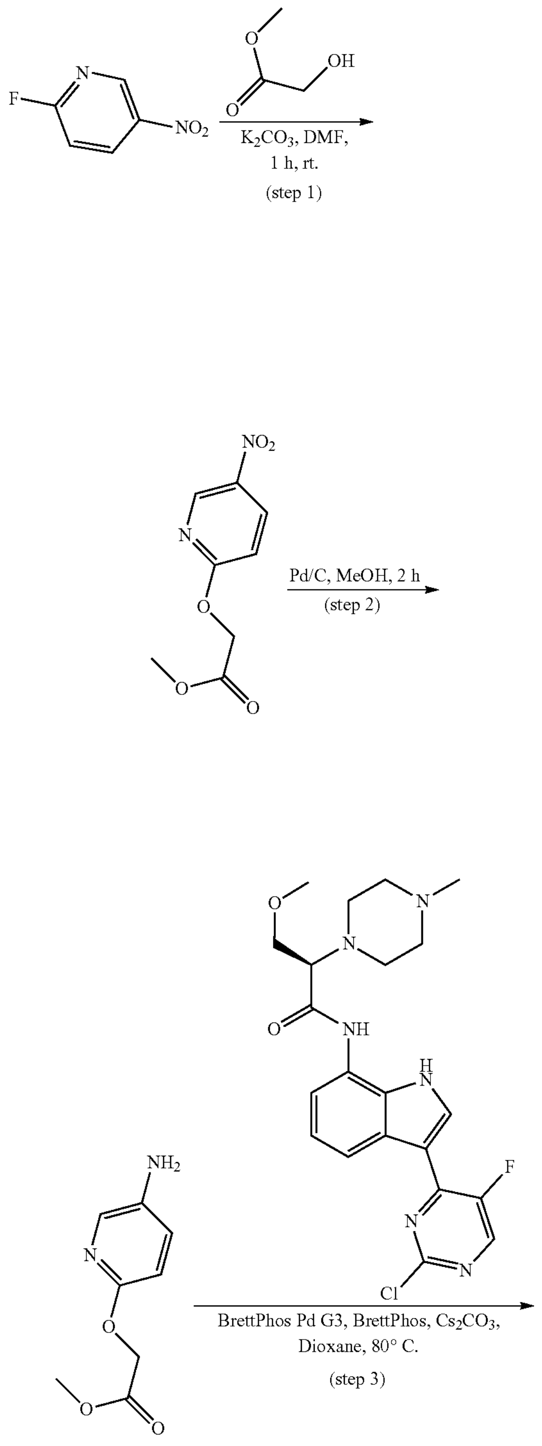

-continued

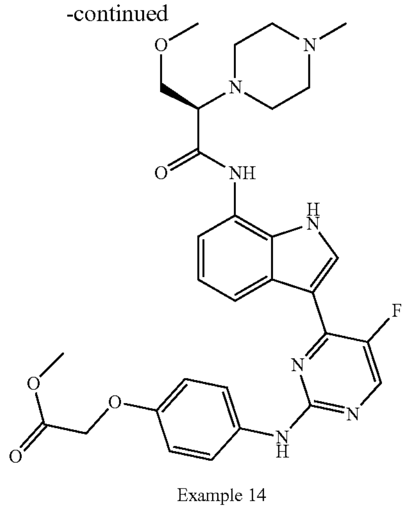

Example 14

Step 1. Methyl 2-[(5-nitropyridin-2-yl)oxy]acetate

To a stirred solution of 2-fluoro-5-nitropyridine (300.00 mg, 2.11 mmol, 1.00 equiv) and methyl 2-hydroxyacetate (380.4 mg, 4.22 mmol, 2.00 equiv) in DMF (20.00 mL) was added $K_2CO_3$ (583.6 mg, 4.22 mmol, 2.00 equiv) in portions at room temperature under air atmosphere. The resulting mixture was stirred for 1 h at room temperature under $N_2$ atmosphere. The resulting mixture was diluted with water (100 mL) and extracted with EtOAc (3×100 mL). The combined organic layers were washed with brine (1×30 mL), dried over anhydrous $Na_2SO_4$. After filtration, the filtrate was concentrated under reduced pressure. The residue was purified by Prep-TLC (PE/EtOAc 3:1) to afford methyl 2-[(5-nitropyridin-2-yl)oxy]acetate (200 mg, 26.79%) as a light brown solid. LCMS: m/z (ESI), $[M+H]^+$ =213.2.

Step 2. Methyl 2-[(5-aminopyridin-2-yl)oxy]acetate

A mixture of methyl 2-[(5-nitropyridin-2-yl)oxy]acetate (200.00 mg, 1 equiv) and Pd/C (30.00 mg) in MeOH (20.00 mL) was stirred for 2 h at room temperature under hydrogen atmosphere. The resulting mixture was filtered and the filtrate was concentrated under reduced pressure. This resulted in methyl 2-[(5-aminopyridin-2-yl)oxy]acetate (150 mg, 87.34%) as a light yellow solid. LCMS: m/z (ESI), $[M+H]^{+=}183.3$.

Step 3. Methyl 2-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]oxy)acetate (Ex. 14)

To a stirred mixture of (R)—N-[3-(2-chloro-5-fluoropyrimidin-4-yl)-1H-indol-7-yl]-3-methoxy-2-(4-methylpiperazin-1-yl)propanamide (140.00 mg, 0.313 mmol, 1.00 equiv) and methyl 2-[(5-aminopyridin-2-yl)oxy]acetate (114.14 mg, 0.627 mmol, 2 equiv) in dioxane (20.00 mL) were added BrettPhos Pd G3 (42.60 mg, 0.047 mmol, 0.15 equiv) and BrettPhos (25.22 mg, 0.047 mmol, 0.15 equiv), $Cs_2CO_3$ (21.87 mg, 0.067 mmol, 3.00 equiv) at room temperature under air atmosphere. The resulting mixture was stirred for 2 h at 80° C. under nitrogen atmosphere. The resulting mixture was concentrated under reduced pressure.

The crude product (30 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 38 B to 48 B in 7 min; 254; 220 nm; RT1: 5.93) to afford methyl 2-([5-[(5-fluoro-4-[7-[(R)-3-methoxy-2-(4-methylpiperazin-1-yl) propanamido]-1H-indol-3-yl]pyrimidin-2-yl)amino]pyridin-2-yl]oxy)acetate (21 mg, 11.31%) as a white solid. LCMS: m/z (ESI), $[M+H]^+$=593.3. $^1$H-NMR (300 MHz, MeOD-$d_4$) δ 2.34 (3H, s), 2.62 (4H, s), 2.84 (2H, s), 2.93 (2H, s), 3.43 (3H, s), 3.52 (1H, t), 3.78 (3H, s), 3.85 (1H, d), 3.94 (1H, d), 4.93 (2H, s), 6.91 (1H, d), 7.17 (2H, m), 8.07 (1H, d), 8.17 (1H, d), 8.23 (1H, d), 8.38 (1H, m), 8.53 (1H, d).

Example 15

Preparation of Methyl (R)-3-(4-((5-fluoro-4-(7-(3-methoxy-2-(4-methylpiperazin-1-yl) propanamido)-1H-indol-3-yl)pyrimidin-2-yl)amino)pyridin-2-yl) propanoate

SCHEME 15

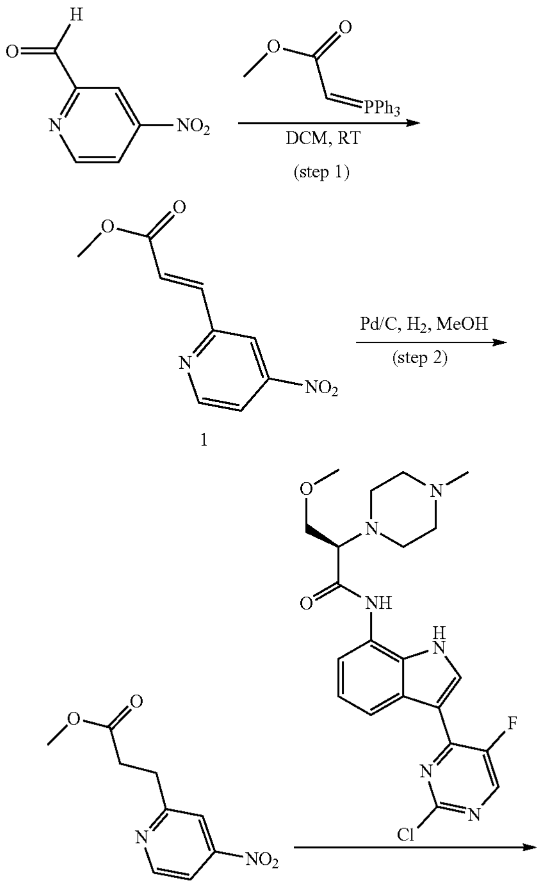

1

2

-continued

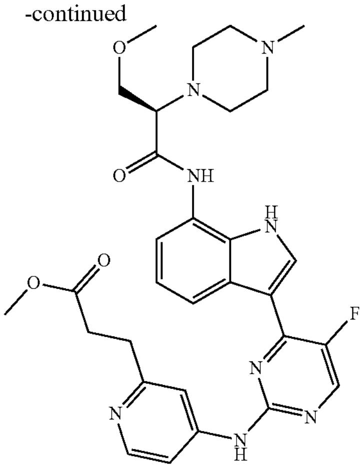

Example 15

Step 1. Methyl-3-(4-nitropyridin-2-yl)acrylate

To a stirred solution of 4-nitropyridine-2-carbaldehyde (0.50 g, 3.287 mmol, 1.00 equiv) and methyl 2-(triphenyl-lambda5-phosphanylidene)acetate (1.65 g, 4.935 mmol, 1.50 equiv) in DCM (10.00 mL) at room temperature under nitrogen atmosphere. The resulting mixture was concentrated under reduced pressure. The residue was purified by Prep-TLC ($CH_2Cl_2$/MeOH 15:1) to afford methyl (3-(4-nitropyridin-2-yl)prop-2-enoate (450 mg, 65.76%) as a yellow solid. LCMS: m/z (ESI), $[M+H]^{+}$=209.2.

Step 2. Preparation of Methyl 3-(4-aminopyridin-2-yl)propanoate

A mixture of methyl 3-(4-nitropyridin-2-yl)prop-2-enoate (200.00 mg, 0.961 mmol, 1.00 equiv) and Pd/C (20.45 mg, 0.192 mmol, 0.20 equiv) in MeOH (15.00 mL) was stirred at room temperature under $H_2$ for 1 h. The resulting mixture was filtered, and the filter cake was washed with MeOH (3×10 mL). The filtrate was concentrated under reduced pressure. The residue was purified by Prep-TLC ($CH_2Cl_2$/MeOH 10:1) to afford methyl 3-(4-aminopyridin-2-yl)propanoate (100 mg, 57.76%) as a yellow solid. LCMS: m/z (ESI), $[M+H]^+$=181.2.

Step 3. Methyl (R)-3-(4-((5-fluoro-4-(7-(3-methoxy-2-(4-methylpiperazin-1-yl)propanamido)-1H-indol-3-yl)pyrimidin-2-yl)amino)pyridin-2-yl) propanoate (Ex. 15)

To a mixture of (R)—N-[3-(2-chloro-5-fluoropyrimidin-4-yl)-1H-indol-7-yl]-3-methoxy-2-(4-methylpiperazin-1-yl) propanamide (130.00 mg, 0.291 mmol, 1.00 equiv) and methyl 3-(4-aminopyridin-2-yl)propanoate (78.63 mg, 0.436 mmol, 1.50 equiv) in dioxane (5.00 mL) were added BrettPhos Pd G3 (26.37 mg, 0.029 mmol, 0.10 equiv), BrettPhos (31.23 mg, 0.058 mmol, 0.20 equiv) and $K_2CO_3$ (80.40 mg, 0.582 mmol, 2.00 equiv) at rt under nitrogen atmosphere. The resulting mixture was stirred at 70° C. for 2 h under $N_2$. The resulting mixture was filtered, the filter cake was washed with DCM (3×20 mL). The filtrate was concentrated under reduced pressure. The residue was purified by Prep-TLC ($CH_2Cl_2$/MeOH 10:1) to afford a crude product (100 mg), which was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 31% B to 45% B in 7 min; 254; 220 nm; Rt: 6.30 min) to afford methyl 3-[4-[(5-fluoro-4-[7-[(R)-3-methoxy-2-(4-methyl-piperazin-1-yl)propanamido]-1H-indol-3-yl] pyrimidin-2-yl)amino]pyridin-2-yl]propanoate (40.8 mg, 23.13%) as an off-white solid. LCMS: m/z (ESI), $[M+H]^+$ =591.4 $^1$H-NMR (300 MHz, DMSO-$d_6$) 2.16 (3H, s), 2.38 (4H, s), 2.65 (2H, d), 2.76 (4H, t), 2.96 (2H, t), 3.32 (3H, d), 3.53 (1H, d), 3.61 (3H, s), 3.69 (1H, dd), 3.81 (1H, dd), 7.20 (1H, t), 7.57 (2H, dd), 7.79 (1H, d), 8.23-8.31 (2H, m), 8.53-8.63 (2H, m), 9.89 (1H, s), 9.98 (1H, s), 11.55 (1H, s).

Example 16

Preparation of (R)—N-[3-(5-fluoro-2-[[6-(2-hydroxyethoxy)pyridin-3-yl]amino]pyrimidin-4-yl)-1H-indol-7-yl]-3-methoxy-2-(4-methylpiperazin-1-yl)propanamide

SCHEME 16

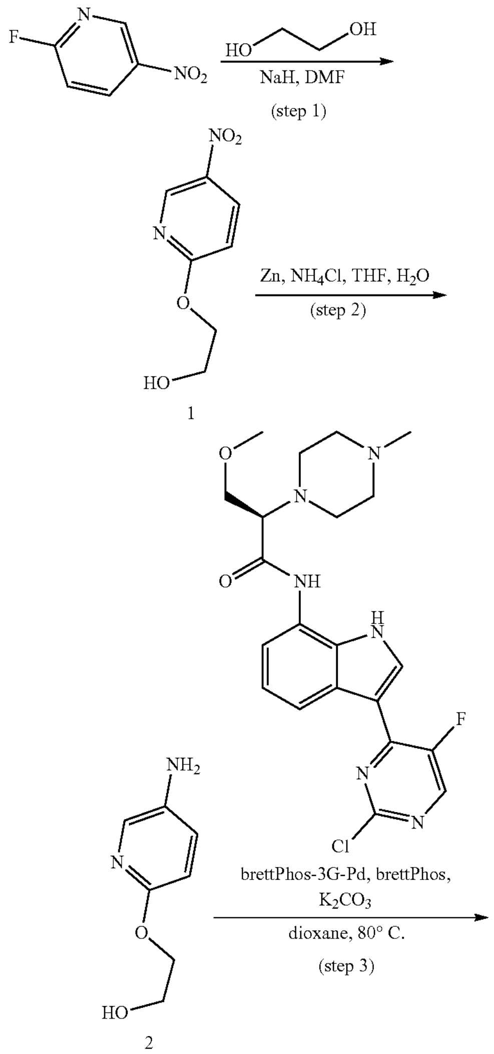

-continued

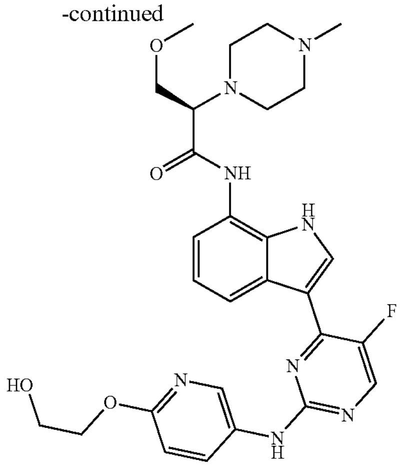

Example 16

Step 1. 2-[(5-nitropyridin-2-yl)oxy]ethanol

A mixture of 2-fluoro-5-nitropyridine (1.50 g, 10.557 mmol, 1.00 equiv), ethylene glycol (0.98 g, 15.835 mmol, 1.50 equiv) and NaH (0.63 g, 15.730 mmol, 1.49 equiv, 60%) in DMF (20.00 mL, 258.435 mmol, 24.48 equiv) was stirred for 2 h at 0° C. under nitrogen atmosphere. The resulting mixture was diluted with $H_2O$ (100 mL), and extracted with EA (3×100 mL), and the combined organic layers were washed with brine (2×20 mL), dried over anhydrous $Na_2SO_4$. After filtration, the filtrate was concentrated under reduced pressure. The residue was purified by Prep-TLC (PE/EtOAc 1:1) to afford 2-[(5-nitropyridin-2-yl)oxy]ethanol (1.78 g, 91.56%) as a yellow solid. LCMS: m/z (ESI), $[M+H]^+$=185.2. $^1$H-NMR (300 MHz, DMSO-$d_6$) δ 3.75 (2H, q), 4.31-4.51 (2H, m), 4.92 (1H, t), 7.04 (1H, dd), 8.48 (1H, dd), 9.08 (1H, d).

Step 2. 2-[(5-aminopyridin-2-yl)oxy]ethanol

A mixture of 2-[(5-nitropyridin-2-yl)oxy]ethanol (200.00 mg, 1.086 mmol, 1.00 equiv), Zn (710.38 mg, 10.861 mmol, 10.00 equiv) and $NH_4Cl$ (580.95 mg, 10.861 mmol, 10.00 equiv) in THF (4.00 mL) and $H_2O$ (2.00 mL) was stirred for 4 h at room temperature under nitrogen atmosphere. The resulting mixture was concentrated under reduced pressure. The resulting mixture was filtered, the filter cake was washed with MeOH (5 mL). The filtrate was concentrated under reduced pressure. This resulted in 2-[(5-aminopyridin-2-yl)oxy]ethanol (150 mg, 89.59%) as a yellow oil. LCMS: m/z (ESI), $[M+H]^{+=}$155.2.

Step 3. (R)—N-[3-(5-fluoro-2-[[6-(2-hydroxyethoxy)pyridin-3-yl]amino]pyrimidin-4-yl)-1H-indol-7-yl]-3-methoxy-2-(4-methylpiperazin-1-yl)propanamide (Ex. 16)

A mixture of (R)—N-[3-(2-chloro-5-fluoropyrimidin-4-yl)-1H-indol-7-yl]-3-methoxy-2-(4-methylpiperazin-1-yl) propanamide (150.00 mg, 0.336 mmol, 1.00 equiv), 2-[(5-aminopyridin-2-yl)oxy]ethanol (62.09 mg, 0.403 mmol, 1.20 equiv), BrettPhos Pd G3 (60.85 mg, 0.067 mmol, 0.20 equiv), BrettPhos (36.03 mg, 0.067 mmol, 0.20 equiv) and $K_2CO_3$ (115.97 mg, 0.839 mmol, 2.50 equiv) in dioxane (3.00 mL) was stirred for overnight at 80° C. under nitrogen atmosphere. The resulting mixture was concentrated under reduced pressure. The residue was purified by Prep-TLC ($CH_2Cl_2$/MeOH 10:1). The crude product (200 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 21 B to 41 B in 7 min; 254; 220 nm; RT1: 6.98) to afford (R)—N-[3-(5-fluoro-2-[[6-(2-hydroxyethoxy)pyridin-3-yl]amino]pyrimidin-4-yl)-1H-indol-7-yl]-3-methoxy-2-(4-methylpiperazin-1-yl) propanamide (110 mg, 58.04%) as a white solid. The crude product ((R)—N-[3-(5-fluoro-2-[[6-(2-hydroxyethoxy)pyridin-3-yl]amino]pyrimidin-4-yl)-1H-indol-7-yl]-3-methoxy-2-(4-methylpiperazin-1-yl)propanamide (110.00 mg)) was purified by Prep-CHIRAL-HPLC with the following conditions (Column: CHIRAL ART Cellulose-SB, 4.6×100 mm, 3 μm; Mobile Phase A: Hex(0.1% DEA):EtOH=50:50, Mobile Phase B; Flow rate: 1 mL/min; Gradient: 0 B to 0 B) to afford (R)—N-[3-(5-fluoro-2-[[6-(2-hydroxyethoxy)pyridin-3-yl]amino]pyrimidin-4-yl)-1H-indol-7-yl]-3-methoxy-2-(4-methyl-piperazin-1-yl)propanamide (53.07 mg, 48.25%) as a white solid. LCMS: m/z (ESI), $[M+H]^+$=565.4. $^1$H-NMR (300 MHz, DMSO-$d_6$) δ 2.16 (3H, s), 2.37 (4H, s), 2.54-2.66 (2H, m), 2.75 (2H, q), 3.32 (3H, s), 3.51 (1H, t), 3.65-3.90 (4H, m), 4.26 (2H, dd), 4.83 (1H, t), 6.82 (1H, d), 7.12 (1H, t), 7.53 (1H, dd), 8.05 (1H, dd), 8.17-8.31 (1H, m), 8.33-8.55 (3H, m), 9.40 (1H, s), 9.86 (1H, s), 11.47 (1H, s).

Example 17

Preparation of (R)—N-(3-(5-fluoro-2-((3-methyl-1H-indazol-6-yl)amino)pyrimidin-4-yl)-1H-indol-7-yl)-3-methoxy-2-(4-methylpiperazin-1-yl)propanamide

SCHEME 17

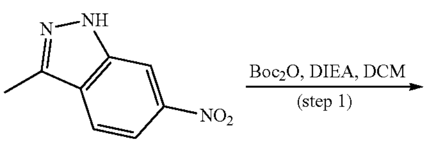

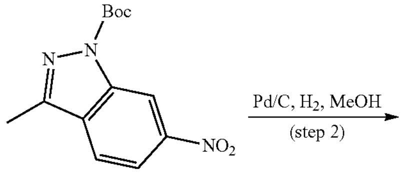

1

-continued

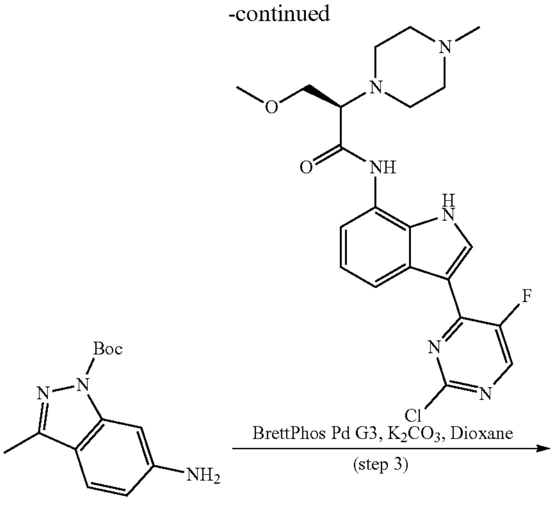

2

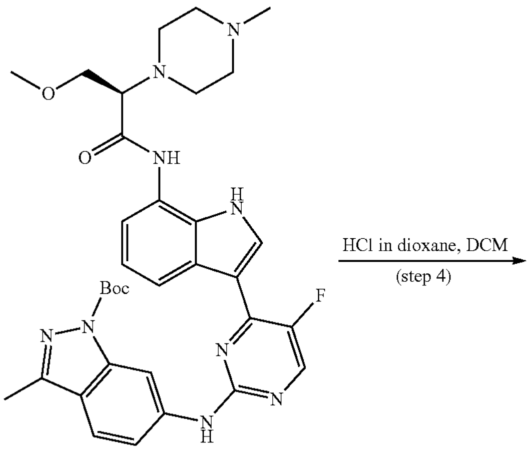

3

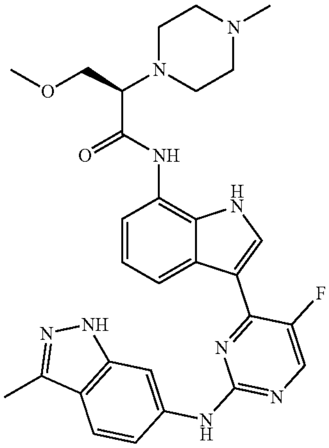

Example 17

Step 1. Tert-butyl 3-methyl-6-nitro-1H-indazole-1-carboxylate

A solution of 3-methyl-6-nitro-1H-indazole (500.00 mg, 2.822 mmol, 1.00 equiv) and $Boc_2O$ (923.92 mg, 4.233 mmol, 1.50 equiv), DIEA (729.52 mg, 5.645 mmol, 2.00 equiv) in DCM (10.00 mL) was stirred for overnight at room temperature under nitrogen atmosphere. The resulting mixture was quenched with water (10 mL), and extracted with $CH_3Cl$ (20 mL×3). The combined organic layers were washed with brine (10 mL×3), dried over anhydrous $Na_2SO_4$. After filtration, the filtrate was concentrated under reduced pressure. The residue was purified by silica gel column chromatography, eluted with PE/EtOAc (5:1) to afford tert-butyl 3-methyl-6-nitroindazole-1-carboxylate (550 mg, 70.28%) as an off-white solid. LCMS: m/z (ESI), $[M+H]^+$=278.3.

Step 2. Tert-butyl 6-amino-3-methylindazole-1-carboxylate

A solution of tert-butyl 3-methyl-6-nitroindazole-1-carboxylate (540.00 mg, 1.947 mmol, 1.00 equiv) and Pd/C (20.73 mg, 0.195 mmol, 0.10 equiv) in MeOH (10.00 mL) was stirred for 3 h at room temperature under hydrogen atmosphere. The resulting mixture was filtered, the filter cake was washed with MeOH (10 mL×3). The filtrate was concentrated under reduced pressure to afford tert-butyl 6-amino-3-methylindazole-1-carboxylate (400 mg, 83.05%) as an off-white solid. LCMS: m/z (ESI), $[M+H]^+$=248.1

Step 3. Tert-butyl 6-[(5-fluoro-4-[7-[(R)-3-methoxy-2-(4-methylpiperazin-1-yl) propanamido]-1H-indol-3-yl]pyrimidin-2-yl)amino]-3-methylindazole-1-carboxylate A solution of tert-butyl 6-amino-3-methylindazole-1-carboxylate (124.50 mg, 0.503 mmol, 1.50 equiv) and (R)—N-[3-(2-chloro-5-fluoropyrimidin-4-yl)-1H-indol-7-yl]-3-methoxy-2-(4-methylpiperazin-1-yl)propanamide (150.00 mg, 0.336 mmol, 1.00 equiv), BrettPhos Pd G3 (30.43 mg, 0.034 mmol, 0.10 equiv), $K_2CO_3$ (92.77 mg, 0.671 mmol, 2.00 equiv) in dioxane (4.00 mL) was stirred for 2 h at 70° C. under nitrogen atmosphere. The residue was purified by silica gel column chromatography, eluted with $CH_2Cl_2$/MeOH (7:1) to afford tert-butyl 6-[(5-fluoro-4-[7-[(R)-3-methoxy-2-(4-methylpiperazin-1-yl)propanamido]-1H-indol-3-yl]pyrimidin-2-yl)amino]-3-methylindazole-1-carboxylate (140 mg, 63.42%) as an off-white solid. LCMS: m/z (ESI), $[M+H]^+$=658.6.

Step 4. (R)—N-(3-[5-fluoro-2-[(3-methyl-1H-indazol-6-yl)amino]pyrimidin-4-yl]-1H-indol-7-yl)-3-methoxy-2-(4-methylpiperazin-1-yl)propanamide (Ex. 17)

A solution of tert-butyl 6-[(5-fluoro-4-[7-[(R)-3-methoxy-2-(4-methylpiperazin-1-yl)propanamido]-1H-indol-3-yl]pyrimidin-2-yl)amino]-3-methylindazole-1-carboxylate (140.00 mg, 0.213 mmol, 1.00 equiv) and HCl (gas) in 1,4-dioxane (2.00 mL) in DCM (2.00 mL) was stirred for 3 h at room temperature under nitrogen atmosphere. The resulting mixture was concentrated under reduced pressure. The crude product was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 30 B to 50 B in 7 min; 254; 220 nm; RT1: 6.63) to afford (R)—N-(3-[5-fluoro-2-[(3-methyl-1H-indazol-6-yl)amino]pyrimidin-4-yl]-1H-indol-7-yl)-3-methoxy-2-(4-methyl-piperazin-1-yl)propanamide (90 mg, 75.83%) as an off-white solid. LCMS: m/z (ESI), $[M+H]^+$ =558.3 $^1$H-NMR (300 MHz, DMSO-$d_6$) δ 2.14 (3H, s), 2.35 (4H, s), 2.44 (3H, s), 2.62 (2H, m), 2.74 (2H, m), 3.28 (3H, s), 3.50 (1H, t), 3.67 (1H, dd), 3.79 (1H, dd), 7.12 (1H, t), 7.32 (1H, dd), 7.54 (2H, m), 8.14 (1H, d), 8.23 (1H, m), 8.47 (1H, d), 8.62 (1H, dd), 9.63 (1H, s), 9.86 (1H, s), 11.47 (1H, s), 12.33 (1H, s).

Example 18

Preparation of (R)—N-[3-(5-fluoro-2-[[1-(oxan-4-yl)pyrazol-4-yl]amino]pyrimidin-4-yl)-1H-indol-7-yl]-3-methoxy-2-(4-methylpiperazin-1-yl)propanamide

SCHEME 18

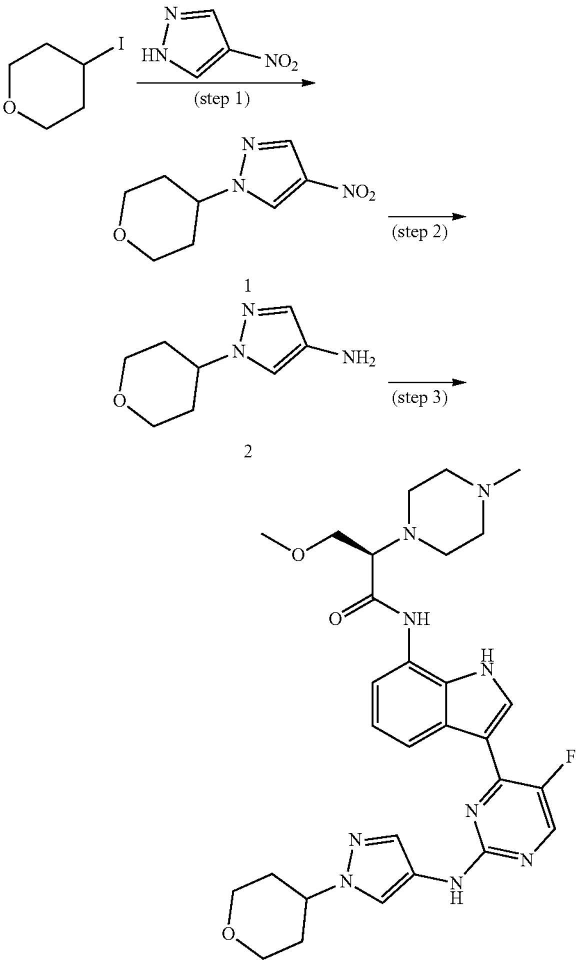

Example 18

Step 1. 4-nitro-1-(oxan-4-yl)pyrazole

To a stirred mixture of 4-iodooxane (2.06 g, 9.728 mmol, 1.10 equiv) and 4-nitropyrazole (1.00 g, 8.844 mmol, 1.00 equiv) in DMF (13.33 mL, 182.397 mmol, 19.48 equiv) was added $Cs_2CO_3$ (8.64 g, 26.531 mmol, 3.00 equiv) at room temperature under air atmosphere. The resulting mixture was stirred for 2 days at 80° C. under air atmosphere. The residue was purified by Prep-TLC ($CH_2Cl_2$/MeOH 20:1) to afford a crude solid. The residue was purified by silica gel column chromatography, eluted with $CH_2Cl_2$/MeOH (20:1) to afford 4-nitro-1-(oxan-4-yl)pyrazole (343 mg, 19.28%) as a light yellow solid. $^1$H-NMR (400 MHz, DMSO-$d_6$) δ 1.98-2.01 (4H, m), 3.43-3.49 (2H, m), 3.95-3.99 (2H, m), 4.48-4.56 (1H, m), 8.29 (1H, s), 8.96 (1H, s).

Step 2. 1-(oxan-4-yl)pyrazol-4-amine

Into a 100 mL round-bottom flask were added 4-nitro-1-(oxan-4-yl)pyrazole (315.00 mg, 1.597 mmol, 1.00 equiv) and Pd/C (3399.93 mg, 31.948 mmol, 20.00 equiv) in MeOH (20.00 mL) at room temperature. The resulting mixture was stirred for overnight at 120° C. under hydrogen atmosphere. The resulting mixture was filtered, the filter cake was washed with MeOH (3×10 mL). The filtrate was concentrated under reduced pressure. This resulted in 1-(oxan-4-yl)pyrazol-4-amine (200 mg, 67.39%) as a red solid. LCMS: m/z (ESI), $[M+H]^+$=168.2. $^1$H NMR (300 MHz, DMSO-$d_6$) δ 1.71-1.92 (4H, m), 3.22-3.53 (2H, m), 3.75 (2H, s), 3.87-3.89 (1H, m), 3.91-3.97 (1H, m), 4.11-4.18 (1H, m), 6.89 (1H, d), 7.05 (1H, d).

Step 3. (R)—N-[3-(5-fluoro-2-[[1-(oxan-4-yl)pyrazol-4-yl]amino]pyrimidin-4-yl)-1H-indol-7-yl]-3-methoxy-2-(4-methylpiperazin-1-yl)propanamide (Ex. 18)

To a solution of 1-(oxan-4-yl)pyrazol-4-amine (101.02 mg, 0.604 mmol, 1.50 equiv) and (R)—N-[3-(2-chloro-5-fluoropyrimidin-4-yl)-1H-indol-7-yl]-3-methoxy-2-(4-methylpiperazin-1-yl)propanamide (180.00 mg, 0.403 mmol, 1.00 equiv) in dioxane (5 mL) were added BrettPhos (6.01 mg, 0.011 mmol, 0.10 equiv), $Cs_2CO_3$ (393.69 mg, 1.208 mmol, 3.00 equiv) and BrettPhos Pd G3 (36.51 mg, 0.040 mmol, 0.10 equiv). After stirring for 2 h at 80° C. under nitrogen atmosphere, the resulting mixture was concentrated under reduced pressure. The residue was purified by Prep-TLC ($CH_2Cl_2$/MeOH 7:1). The crude product (105 mg) was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 31% B to 43% B in 7 min; 254; 220 nm; Rt: 6.75 min). The crude product (80 mg) was purified by Prep-Chiral-HPLC with the following conditions (Column: CHIRAL ART Cellulose-SB, 4.6×100 mm, 3 μm; Mobile Phase A: MtBE (0.1% DEA):EtOH=95:5, Mobile Phase B; Flow rate: 1 mL/min; Gradient: 0 B to 0 B) to afford (R)—N-[3-(5-fluoro-2-[[1-(oxan-4-yl)pyrazol-4-yl]amino]pyrimidin-4-yl)-1H-indol-7-yl]-3-methoxy-2-(4-methylpiperazin-1-yl)propanamide (37 mg, 15.74%) as a light yellow solid. LCMS: m/z (ESI), $[M+H]^+$=578.4. $^1$H-NMR (400 MHz, DMSO-$d_6$) δ 1.65-1.83 (4H, m), 1.95 (3H, s), 2.16 (4H, s), 2.40-2.47 (2H, m), 2.52-2.59 (2H, m), 3.21-3.35 (3H, m), 3.32 (3H, s), 3.47-3.51 (1H, m), 3.58-3.62 (1H, m), 3.77 (2H, d), 4.14-4.19 (1H, m), 6.92-6.95 (1H, m), 7.33-7.35 (2H, m), 7.80 (1H, s), 7.97-8.02 (1H, m), 8.18 (1H, d), 8.29 (1H, s), 9.11 (1H, s), 9.66 (1H, s), 11.23 (1H, s).

Example 19

Preparation of (R)—N-(3-(2-((1H-pyrazolo[4,3-b]pyridin-6-yl)amino)-5-fluoropyrimidin-4-yl)-1H-indol-7-yl)-3-methoxy-2-(4-methylpiperazin-1-yl)propanamide

SCHEME 19

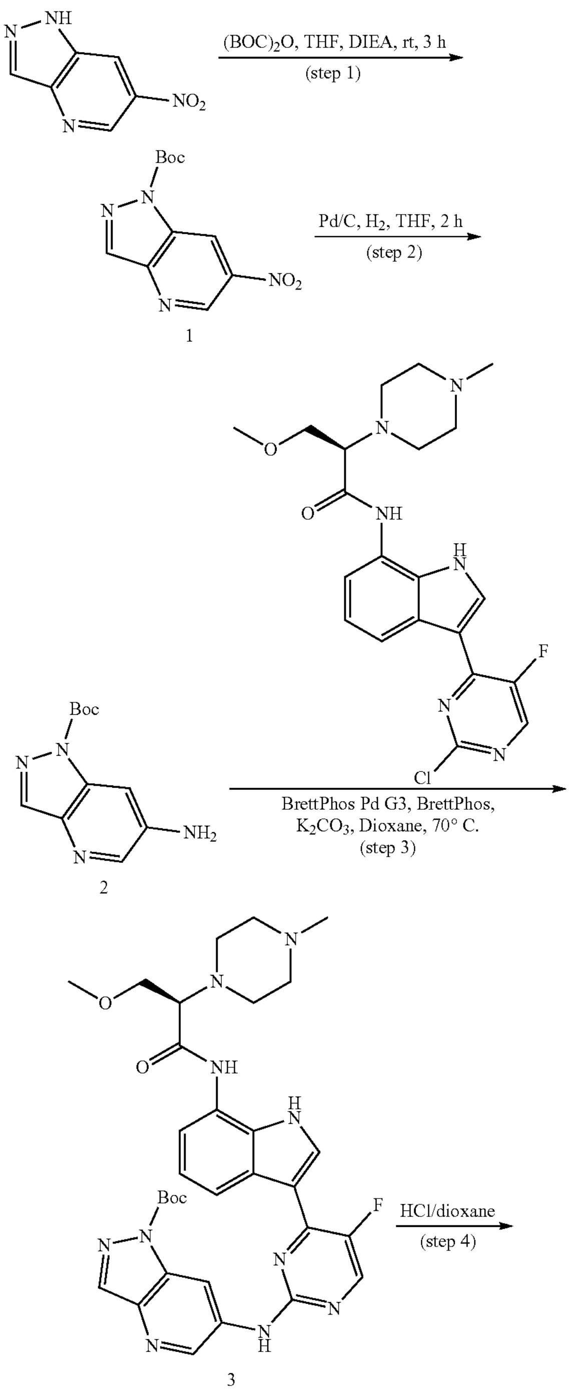

-continued

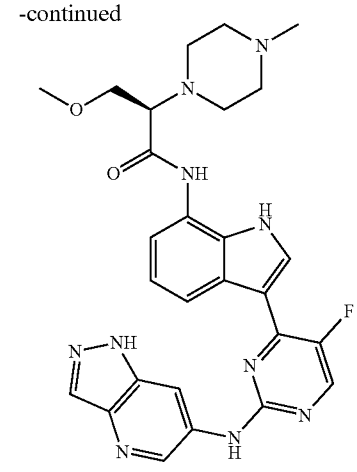

Example 19

Step 1. Tert-butyl 6-nitro-1H-pyrazolo[4,3-b]pyridine-1-carboxylate

To a stirred mixture of 6-nitro-1H-pyrazolo[4,3-b]pyridine (300.00 mg, 1.828 mmol, 1.00 equiv) and (B° C.)$_2$O (598.40 mg, 2.742 mmol, 1.50 equiv) in THF (40.00 mL) was added DIEA (708.73 mg, 5.484 mmol, 3.00 equiv) in portions at room temperature under air atmosphere. The resulting mixture was stirred for 3 h at room temperature under air atmosphere. The resulting mixture was concentrated under reduced pressure. The residue was purified by Prep-TLC (PE/EtOAc 2:1) to afford tert-butyl 6-nitropyrazolo[4,3-b]pyridine-1-carboxylate (310 mg, 64.18%) as a yellow solid. LCMS: m/z (ESI), $[M+H]^{+=}$265.0

Step 2. Tert-butyl 6-amino-1H-pyrazolo[4,3-b]pyridine-1-carboxylate

A mixture of tert-butyl 6-nitropyrazolo[4,3-b]pyridine-1-carboxylate (290.00 mg, 1.097 mmol, 1.00 equiv) and Pd/C (23.36 mg, 0.219 mmol, 0.20 equiv) in THF (30.00 mL) was stirred for overnight at room temperature under hydrogen atmosphere. The resulting mixture was filtered, and the filter cake was washed with MeOH (3×10 mL). The filtrate was concentrated under reduced pressure. The residue was purified by Prep-TLC ($CH_2Cl_2$/MeOH=12:1) to afford tert-butyl 6-aminopyrazolo[4,3-b]pyridine-1-carboxylate (200 mg, 77.79%) as a yellow solid LCMS: m/z (ESI), $[M+H]^+$ =235.1.

Step 3. Tert-butyl 6-[(5-fluoro-4-[7-[(R)-3-methoxy-2-(4-methylpiperazin-1-yl)propanamido]-1H-indol-3-yl]pyrimidin-2-yl)amino]pyrazolo[4,3-b]pyridine-1-carboxylate To a stirred mixture of (R)—N-[3-(2-chloro-5-fluoropyrimidin-4-yl)-1H-indol-7-yl]-3-methoxy-2-(4-methylpiperazin-1-yl)propanamide (200.00 mg, 0.448 mmol, 1.00 equiv) and tert-butyl 6-aminopyrazolo[4,3-b]pyridine-1-carboxylate (157.25 mg, 0.671 mmol, 1.50 equiv) in dioxane (30.00 mL) were added Brettphos Pd $G_3$ (81.13 mg, 0.090 mmol, 0.20 equiv) and $K_2CO_3$ (123.70 mg, 0.895 mmol, 2.00 equiv) in portions at 70° C. under nitrogen atmosphere. The resulting mixture was stirred for 2 h at 70° C. under nitrogen atmosphere. The resulting mixture was concentrated under reduced pressure. The residue was purified by Prep-TLC ($CH_2Cl_2$/MeOH=10:1) to afford tert-butyl 6-[(5-fluoro-4-[7-[(R)-3-methoxy-2-(4-methylpiperazin-1-yl)propanamido]-1H-indol-3-yl]pyrimidin-2-yl)amino]pyrazolo[4,3-b]pyridine-1-carboxylate (150 mg, 51.99%) as a yellow solid. LCMS: m/z (ESI), $[M+H]^+$=645.3.

Step 4. (R)—N-[3-(5-fluoro-2-[1H-pyrazolo[4,3-b]pyridin-6-ylamino]pyrimidin-4-yl)-1H-indol-7-yl]-3-methoxy-2-(4-methylpiperazin-1-yl)propanamide (Ex. 19)

A mixture of tert-butyl 6-[(5-fluoro-4-[7-[(R)-3-methoxy-2-(4-methylpiperazin-1-yl)propanamido]-1H-indol-3-yl]pyrimidin-2-yl)amino]pyrazolo[4,3-b]pyridine-1-carboxylate (130.00 mg, 0.202 mmol, 1.00 equiv) and HCl (gas) in 1,4-dioxane (7.35 mg, 0.202 mmol, 1.00 equiv) in DCM (20.00 mL) was stirred for 3 h at room temperature under air atmosphere. The resulting mixture was concentrated under reduced pressure. The crude product (80 mg) was purified by Prep-HPLC with the following conditions (Column: XBridge Prep OBD C18 Column, 30×150 mm, 5 μm; Mobile Phase A: Water (0.05% $NH_3·H_2O$), Mobile Phase B: ACN; Flow rate: 60 mL/min; Gradient: 22 B to 42 B in 7 min; 254/220 nm; RT1: 8.52) to afford (R)—N-[3-(5-fluoro-2-[1H-pyrazolo[4,3-b]pyridin-6-ylamino]pyrimidin-4-yl)-1H-indol-7-yl]-3-methoxy-2-(4-methylpiperazin-1-yl)propanamide (30 mg, 27.32%) as a yellow solid. LCMS: m/z (ESI), $[M+H]^{+=}$545.4. $^1$H NMR (400 MHz, DMSO-$d_6$) δ 2.15 (3H, s), 2.36 (4H, s), 2.63 (2H, s), 2.75 (2H, d), 3.32 (3H, s), 3.52 (1H, t), 3.68 (1H, dd), 3.80 (1H, dd), 7.15 (1H, t), 7.55 (1H, d), 8.16 (1H, s), 8.27 (1H, d), 8.54 (1H, d), 8.56-8.66 (2H, m), 8.72 (1H, d), 9.92 (2H, d), 11.54 (1H, s), 13.01 (1H, s)

Example 20

Preparation of (R)—N-(3-(5-fluoro-2-((6-(2-(methylamino)ethoxy)pyridin-3-yl)amino) pyrimidin-4-yl)-1H-indol-7-yl)-3-methoxy-2-(4-methylpiperazin-1-yl)propanamide

SCHEME 20

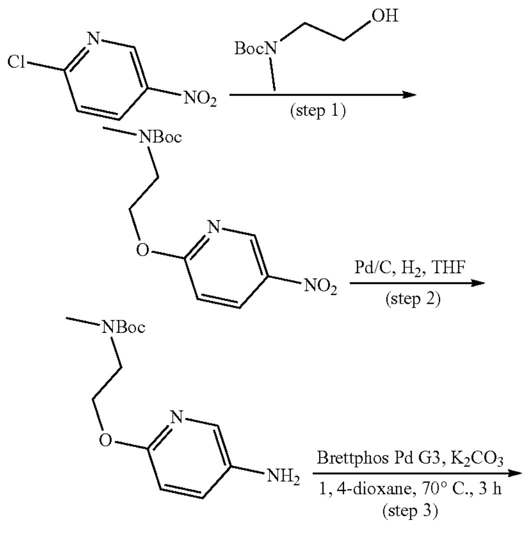

-continued

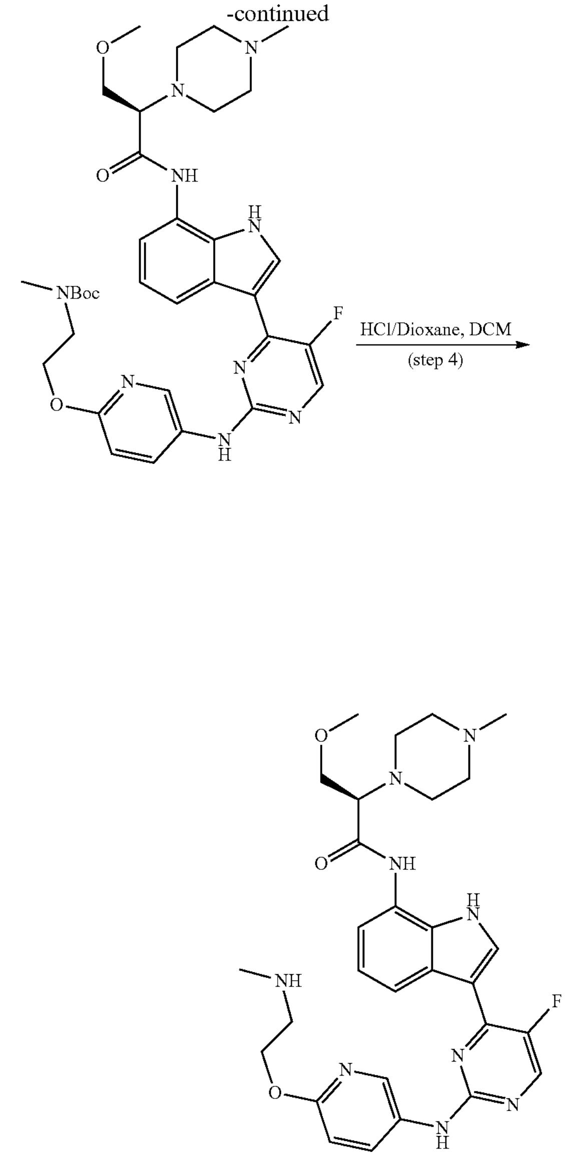

Example 20

Step 1. Tert-butyl N-methyl-N-[2-[(5-nitropyridin-2-yl)oxy]ethyl]carbamate

To a stirred mixture of 2-chloro-5-nitropyridine (200.00 mg, 1.262 mmol, 1.00 equiv) and tert-butyl N-(2-hydroxyethyl)-N-methylcarbamate (331.58 mg, 1.892 mmol, 1.50 equiv) in DMF (20.00 mL) was added NaH (30.27 mg, 1.262 mmol, 1.00 equiv) in portions at room temperature under air atmosphere. The resulting mixture was concentrated under reduced pressure. The residue was purified by Prep-TLC (PE/EtOAc=1:1) to afford tert-butyl N-methyl-N-[2-[(5-nitropyridin-2-yl)oxy]ethyl]carbamate (300 mg, 79.99%) as a yellow solid. LCMS: m/z (ESI), $[M+H]^+$=298.1.

Step 2. Tert-butyl N-[2-[(5-aminopyridin-2-yl)oxy]ethyl]-N-methylcarbamate

A mixture of tert-butyl N-methyl-N-[2-[(5-nitropyridin-2-yl)oxy]ethyl]carbamate (200.00 mg, 0.673 mmol, 1.00 equiv) and Pd/C (71.59 mg, 0.673 mmol, 1.00 equiv) in THF (20.00 mL) was stirred for 2 h at room temperature under hydrogen atmosphere. The resulting mixture was filtrated, the filtrate was concentrated under reduced pressure to afford tert-butyl N-[2-[(5-aminopyridin-2-yl)oxy]ethyl]-N-methylcarbamate (150 mg, 83.41%) as a white solid. LCMS: m/z (ESI), $[M+H]^+$=268.1.

Step 3. Tert-butyl N-[2-([5-[(5-fluoro-4-[7-[(R)-3-methoxy-2-(4-methylpiperazin-1-yl) propanamido]-1H-indol-3-yl]pyrimidin-2-yl)amino]pyridin-2-yl]oxy)ethyl]-N-methylcarbamate To a stirred mixture of (R)—N-[3-(2-chloro-5-fluoropyrimidin-4-yl)-1H-indol-7-yl]-3-methoxy-2-(4-methylpiperazin-1-yl)propanamide (200.00 mg, 0.448 mmol, 1.00 equiv) and tert-butyl N-[2-[(5-aminopyridin-2-yl)oxy]ethyl]-N-methylcarbamate (239.27 mg, 0.895 mmol, 2.00 equiv) in dioxane (20.00 mL) were added BrettPhos Pd $G_3$ (81.13 mg, 0.089 mmol, 0.20 equiv) and $K_2CO_3$ (123.70 mg, 0.895 mmol, 2 equiv) in portions at 70° C. under nitrogen atmosphere. The resulting mixture was concentrated under reduced pressure. The residue was purified by Prep-TLC ($CH_2Cl_2$/MeOH=10:1) to afford tert-butyl N-[2-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]oxy)ethyl]-N-methylcarbamate (50 mg, 16.48%) as a yellow solid. LCMS: m/z (ESI), $[M+Na]^+$=700.3.

Step 4. (R)—N-[3-[5-fluoro-2-([6-[2-(methylamino)ethoxy]pyridin-3-yl]amino)pyrimidin-4-yl]-1H-indol-7-yl]-3-methoxy-2-(4-methylpiperazin-1-yl)propanamide (Ex. 20)

A mixture of tert-butyl N-[2-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]oxy)ethyl]-N-methylcarbamate (50.00 mg, 0.074 mmol, 1.00 equiv) and HCl (gas) in 1,4-dioxane (8.07 mg, 0.221 mmol, 3.00 equiv) in DCM (10.00 mL) was stirred for 2 h at room temperature under air atmosphere. The resulting mixture was concentrated under reduced pressure. The crude product (30 mg) was purified by Prep-HPLC with the following conditions (Column: XBridge Prep OBD C18 Column, 30×150 mm, 5 μm; Mobile Phase A: Water (0.05% $NH_3 \cdot H_2O$), Mobile Phase B: ACN; Flow rate: 60 mL/min; Gradient: 21 B to 41 B in 7 min; RT1: 7.03) to afford (R)—N-[3-[5-fluoro-2-([6-[2-(methylamino)ethoxy]pyridin-3-yl]amino)pyrimidin-4-yl]-1H-indol-7-yl]-3-methoxy-2-(4-methylpiperazin-1-yl)propanamide (5 mg, 11.73%) as a white solid. LCMS: m/z (ESI), $[M+H]^+$=578.4. $^1$H-NMR (400 MHz, Methanol-$d_4$) δ 2.29 (3H, s), 2.48 (3H, s), 2.56 (4H, s), 2.70-2.84 (2H, m), 2.84-2.95 (2H, m), 2.95-3.07 (2H, m), 3.40 (3H, s), 3.47 (1H, t), 3.74-3.98 (2H, m), 4.33-4.45 (2H, m), 6.83 (1H, dd), 7.05-7.18 (2H, m), 8.02 (1H, dd), 8.11 (1H, d), 8.18 (1H, d), 8.37 (1H, dd), 8.49 (1H, dd).

Example 22

Preparation of (R)—N-(3-(5-fluoro-2-((6-(oxazol-2-yl)pyridin-3-yl)amino)pyrimidin-4-yl)-1H-indol-7-yl)-3-methoxy-2-(4-methylpiperazin-1-yl)propanamide

SCHEME 22

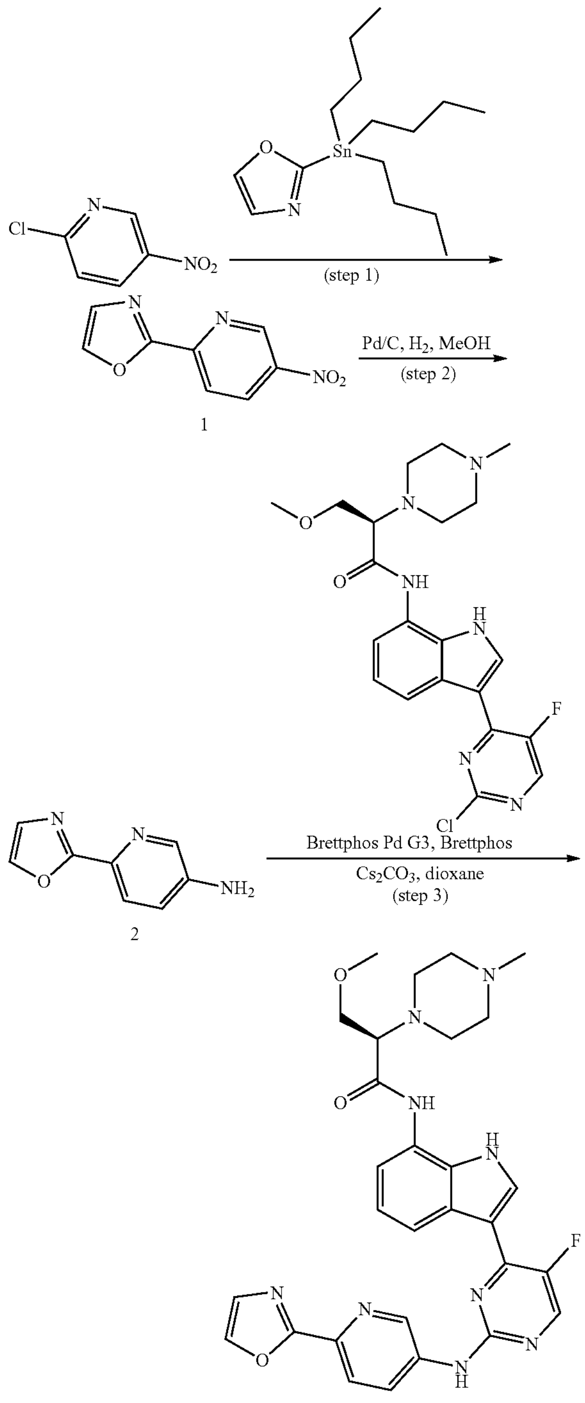

Example 22

Step 1. Preparation of 2-(5-nitropyridin-2-yl)oxazole

A mixture of pyridine, 2-chloro-5-nitro- (100.00 mg, 0.631 mmol, 1.00 equiv), $Pd(PPh_3)_4$ (72.89 mg, 0.063 mmol, 0.1 equiv) and 2-(tributylstannyl)-1,3-oxazole (293.65 mg, 0.820 mmol, 1.30 equiv) in dioxane (6.00 mL) was stirred for 16 h at 110° C. under nitrogen atmosphere. The resulting mixture was concentrated under vacuum. The residue was purified by Prep-TLC (PE/EtOAc=5:1) to afford 5-nitro-2-(1,3-oxazol-2-yl)pyridine (10 mg, 8.29%) as a light yellow solid. $^1$H-NMR (300 MHz, DMSO-$d_6$) δ 7.61 (1H, d), 8.35-8.37 (1H, m), 8.47 (1H, d), 8.75-8.77 (1H, m), 9.49-9.51 (1H, m).

Step 2. Preparation of 6-(oxazol-2-yl)pyridin-3-amine

A mixture of 5-nitro-2-(1,3-oxazol-2-yl)pyridine (200.00 mg, 1.046 mmol, 1.00 equiv) and Pd/C (200.43 mg, 1.883 mmol, 1.80 equiv) in MeOH (50.00 mL) was stirred for 2 h at room temperature under hydrogen atmosphere. The resulting mixture was filtered, the filter cake was washed with MeOH (2×10 mL). The filtrate was concentrated under reduced pressure. This gave 6-(1,3-oxazol-2-yl)pyridin-3-amine (160 mg, 94.88%) as alight yellow oil. LCMS: m/z (ESI), $[M+H]^+$=162.2. $^1$H-NMR (300 MHz, DMSO-$d_6$) δ 5.91 (2H, s), 7.00-7.03 (1H, m), 7.28 (1H, d), 7.76 (1H, d), 8.00 (1H, d), 8.10 (1H, d).

Step 3. Preparation of (R)—N-(3-(5-fluoro-2-((6-(oxazol-2-yl)pyridin-3-yl)amino) pyrimidin-4-yl)-1H-indol-7-yl)-3-methoxy-2-(4-methylpiperazin-1-yl)propanamide (Ex. 22)

A mixture of 6-(1,3-oxazol-2-yl)pyridin-3-amine (51.93 mg, 0.322 mmol, 1.2 equiv), (R)—N-[3-(2-chloro-5-fluoro-pyrimidin-4-yl)-1H-indol-7-yl]-3-methoxy-2-(4-methylpiperazin-1-yl)propanamide (120.00 mg, 0.269 mmol, 1.00 equiv), $K_2CO_3$ (111.33 mg, 0.806 mmol, 3.00 equiv), BrettPhos (28.83 mg, 0.054 mmol, 0.20 equiv) and BrettPhos Pd $G_3$ (24.34 mg, 0.027 mmol, 0.10 equiv) in dioxane (20.00 mL) was stirred for 2 h at 70° C. under nitrogen atmosphere. The resulting mixture was concentrated under reduced pressure. The residue was purified by silica gel column chromatography, eluted with $CH_2Cl_2$/MeOH (12:1) to afford crude solid. The crude product (90 mg) was purified by Prep-HPLC with the following conditions (Column: XBridge Prep OBD C18 Column, 30×150 mm, 5 μm; Mobile Phase A: Water (0.05% $NH_3 \cdot H_2O$), Mobile Phase B: ACN; Flow rate: 60 mL/min; Gradient: 30 B to 50 B in 7 min; RT1: 6.20) to afford (R)—N-[3-(5-fluoro-2-[[6-(1,3-oxazol-2-yl)pyridin-3-yl]amino]pyrimidin-4-yl)-1H-indol-7-yl]-3-methoxy-2-(4-methylpiperazin-1-yl)propanamide (65 mg) as a white solid. The crude product (65 mg) was purified by Prep-chiral-HPLC with the following conditions (Column: CHIRALPAK IC-3, 4.6×50 mm, 3 μm; Mobile Phase A: MTBE (0.1% DEA):MeOH=60:40, Flow rate: 1 mL/min) to afford (R)—N-[3-(5-fluoro-2-[[6-(1,3-oxazol-2-yl)pyridin-3-yl]amino]pyrimidin-4-yl)-1H-indol-7-yl]-3-methoxy-2-(4-methylpiperazin-1-yl)propanamide (52 mg, 33.88%) as a white solid. LCMS: m/z (ESI), $[M+H]^+$=572.4. $^1$H-NMR (300 MHz, MeOD-$d_4$) δ 2.37 (3H, s), 2.67 (4H, s), 2.89 (4H, d), 3.42 (3H, s), 3.52 (1H, t), 3.79-3.98 (2H, m), 7.15-7.26 (2H, m), 7.34 (1H, d), 7.99-8.09 (2H, m), 8.16 (1H, d), 8.33 (1H, d), 8.53 (1H, dd), 8.68 (1H, dd), 8.99 (1H, d).

Example 24

Preparation of (R)—N-(3-(2-((6-(1H-imidazol-1-yl)pyridin-3-yl)amino)-5-fluoropyrimidin-4-yl)-1H-indol-7-yl)-3-methoxy-2-(4-methylpiperazin-1-yl)propanamide (Ex. 24)

SCHEME 24

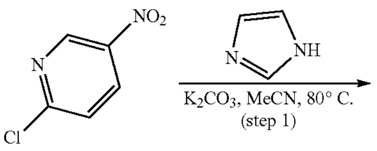

1

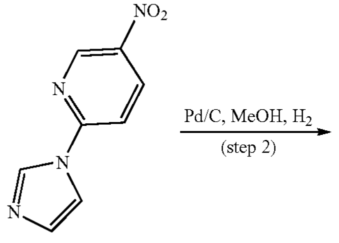

2

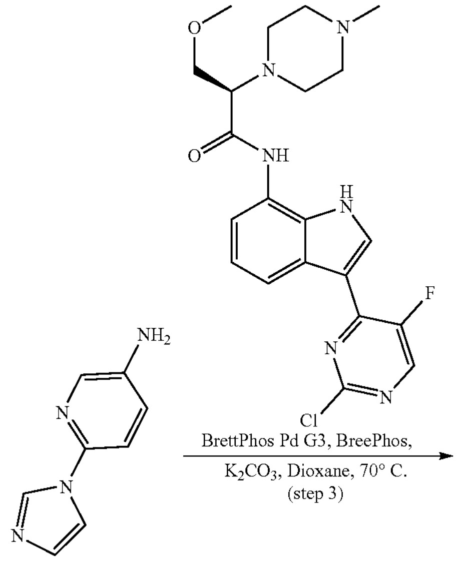

2

-continued

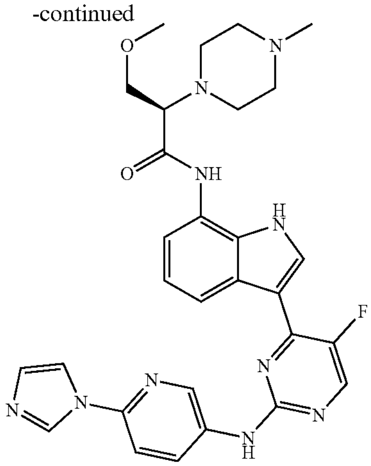

Example 24

Step 1. Preparation of 2-(1H-imidazol-1-yl)-5-nitropyridine

A mixture of 2-chloro-5-nitro-pyridine (500.00 mg, 3.154 mmol, 1.00 equiv), $K_2CO_3$ (1089.67 mg, 7.884 mmol, 2.50 equiv) and imidazole (429.41 mg, 6.308 mmol, 2.00 equiv) in MeCN (20.00 mL) was stirred for 2 h at 80° C. under nitrogen atmosphere. The precipitated solids were collected by filtration and washed with MeCN (3×10 mL) to afford 2-(imidazol-1-yl)-5-nitropyridine (375 mg, 60.46%) as a brown solid. LCMS: m/z (ESI), $[M+H]^+$=191.0

Step 2. Preparation of 6-(1H-imidazol-1-yl)pyridin-3-amine

A mixture of 2-(imidazol-1-yl)-5-nitropyridine (180.00 mg, 0.947 mmol, 1.00 equiv) and Pd/C (50.37 mg, 0.473 mmol, 0.50 equiv) in MeOH (15.00 mL) was stirred at room temperature under hydrogen atmosphere. The resulting mixture was filtered, the filter cake was washed with DCM (3×10 mL). The filtrate was concentrated under reduced pressure. The residue was purified by Prep-TLC ($CH_2Cl_2$/MeOH 10:1) to afford 6-(imidazol-1-yl)pyridin-3-amine (120 mg, 79.15%) as a yellow solid. LCMS: m/z (ESI), $[M+H]^+$=161.2.

Step 3. (R)—N-(3-(2-((6-(1H-imidazol-1-yl)pyridin-3-yl)amino)-5-fluoropyrimidin-4-yl)-1H-indol-7-yl)-3-methoxy-2-(4-methylpiperazin-1-yl)propanamide (Ex. 24)

To a stirred mixture of (R)—N-[3-(2-chloro-5-fluoropyrimidin-4-yl)-1H-indol-7-yl]-3-methoxy-2-(4-methylpiperazin-1-yl)propanamide (150.00 mg, 0.336 mmol, 1.00 equiv) and 6-(imidazol-1-yl)pyridin-3-amine (80.64 mg, 0.503 mmol, 1.50 equiv) in Dioxane (20.00 mL) were added BrettPhos Pd G3 (60.85 mg, 0.067 mmol, 0.20 equiv), BrettPhos (54.05 mg, 0.101 mmol, 0.30 equiv) and $K_2CO_3$ (115.97 mg, 0.839 mmol, 2.50 equiv). The mixture was stirred at 80° C. under nitrogen atmosphere. The resulting mixture was filtered, the filter cake was washed with DCM (3×20 mL). The filtrate was concentrated under reduced pressure. The residue was purified by Prep-TLC ($CH_2Cl_2$/MeOH 10:1) to afford a crude product (100 mg), which was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 31% B to 45% B in 7 min; 254; 220 nm; Rt: 6.30 min) to afford (R)—N-[3-(5-fluoro-2-[[6-(imidazol-1-yl)pyridin-3-yl]amino]pyrimidin-4-yl)-1H-indol-7-yl]-3-methoxy-2-(4-methylpiperazin-1-yl) propanamide (60.8 mg, 31.75%) as an off-white solid. LCMS: m/z (ESI), $[M+H]^{+}$=571.4 $^{1}$H-NMR (300 MHz, DMSO-$d_6$) δ 2.16 (3H, s), 2.37 (4H, s), 2.59-2.69 (2H, m), 2.71-2.82 (2H, m), 3.30 (3H, s), 3.51 (1H, t), 3.69 (1H, dd), 3.81 (1H, dd), 7.12 (1H, t), 7.19 (1H, t), 7.55 (1H, d), 7.78 (1H, d), 7.91 (1H, t), 8.27 (1H, d), 8.42 (1H, dd), 8.47 (1H, t), 8.50 (1H, d), 8.56 (1H, d), 8.80-8.89 (1H, m), 9.87 (2H, d), 11.50 (1H, s)

Example 25

Preparation of (R)—N-[3-(5-fluoro-2-[[5-(3-hydroxypropyl)pyridin-3-yl]amino]pyrimidin-4-yl)-1H-indol-7-yl]-3-methoxy-2-(4-methylpiperazin-1-yl)propanamide

SCHEME 25

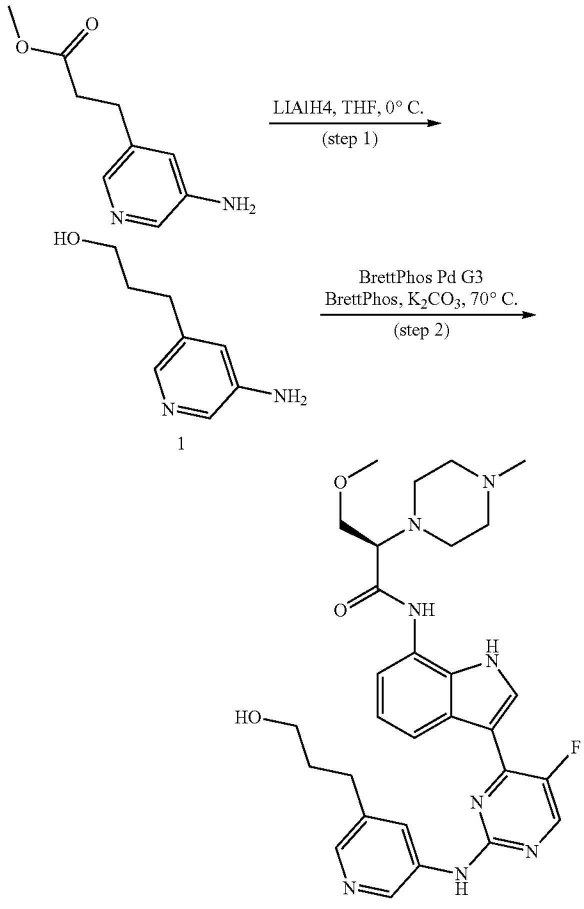

1

Example. 25

Step 1. 3-(5-aminopyridin-3-yl)propan-1-ol

To a stirred mixture of $LiAlH_4$ (44.23 mg, 1.165 mmol, 3 equiv) in THF (1 mL) were added methyl 3-(5-aminopyridin-3-yl)propanoate (70.00 mg, 0.388 mmol, 1.00 equiv) in THF (20.0 mL) dropwise at 0° C. The resulting mixture was stirred for 30 min at 0° C. Desired product could be detected by LCMS. The reaction was quenched by the addition of $Na_2SO_4.10H_2O$. The resulting mixture was filtered, and the filtered cake was washed with ethyl acetate (3×5 mL). The filtrate was concentrated under reduced pressure to afford 3-(5-aminopyridin-3-yl)propan-1-ol (56 mg, 94.72%) as a reddish brown oil. LCMS: m/z (ESI), $[M+H]^{+}$=153.3.

Step 2. (R)—N-[3-(5-fluoro-2-[[5-(3-hydroxypropyl)pyridin-3-yl]amino]pyrimidin-4-yl)-1H-indol-7-yl]-3-methoxy-2-(4-methylpiperazin-1-yl)propanamide (Ex. 25)

To a mixture of (R)—N-[3-(2-chloro-5-fluoropyrimidin-4-yl)-1H-indol-7-yl]-3-methoxy-2-(4-methylpiperazin-1-yl) propanamide (150.00 mg, 0.336 mmol, 1.00 equiv) and 3-(5-aminopyridin-3-yl)propan-1-ol (66.41 mg, 0.436 mmol, 1.30 equiv) in dioxane (20.0 mL) were added BrettPhos (36.03 mg, 0.067 mmol, 0.20 equiv), BrettPhos Pd $G_3$ (60.85 mg, 0.067 mmol, 0.20 equiv) and $K_2CO_3$ (92.77 mg, 0.671 mmol, 2.00 equiv). After stirring for 2 h at 80° C. under a nitrogen atmosphere, the residue was purified by TLC ($CH_2Cl_2$/MeOH=5:1) to afford crude solid. The crude product was purified by Prep-HPLC with the following conditions (Column: XBridge Prep OBD C18 Column, 30×150 mm, 5 μm; Mobile Phase A: Water (0.05% $NH_3{\cdot}H_2O$), Mobile Phase B: ACN; Flow rate: 60 mL/min; Gradient: 19 B to 39 B in 7 min; RT1: 6.53) to afford (R)—N-[3-(5-fluoro-2-[[5-(3-hydroxypropyl)pyridin-3-yl] amino]pyrimidin-4-yl)-1H-indol-7-yl]-3-methoxy-2-(4-methylpiperazin-1-yl)propanamide (16 mg, 8.47%) as a white solid. LCMS: m/z (ESI), $[M+H]^{+}$=563.4. $^{1}$H-NMR (300 MHz, DMSO-$d_6$) δ 1.60-1.82 (2H, m), 2.13 (3H, s), 2.34 (4H, s), 2.61 (4H, q), 2.67-2.81 (2H, m), 3.28 (3H, s), 3.41 (2H, q), 3.49 (1H, t), 3.67 (1H, dd), 3.79 (1H, dd), 4.48 (1H, t), 7.13 (1H, t), 7.52 (1H, d), 8.03 (1H, d), 8.11 (1H, t), 8.23 (1H, d), 8.38-8.56 (2H, m), 8.70 (1H, d), 9.63 (1H, s), 9.85 (1H, s), 11.47 (1H, s).

Example 30/33

Preparation of (R)—N-[3-[5-fluoro-2-([1-[oxolan-3-yl]pyrazol-4-yl]amino)pyrimidin-4-yl]-1H-indol-7-yl]-3-methoxy-2-(4-methylpiperazin-1-yl)propanamide (Ex. 30 as Isomer 1 and Ex. 33 as Isomer 2)

SCHEME 30/33

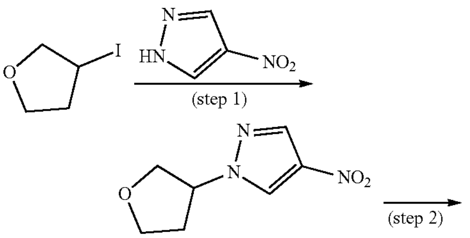

1

-continued

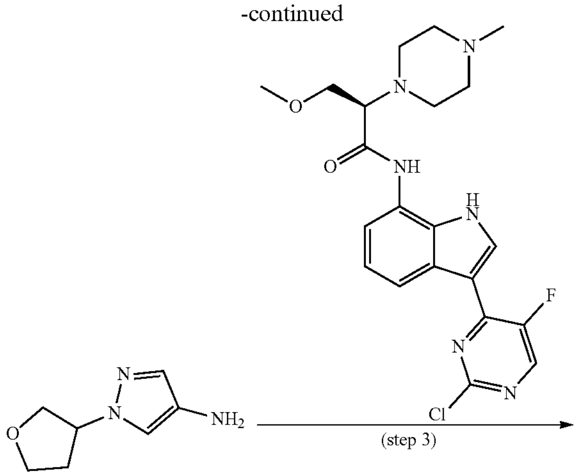

2

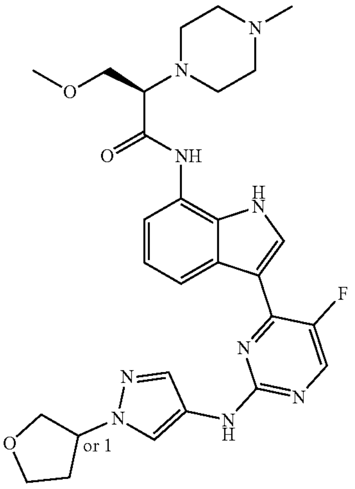

Example 30

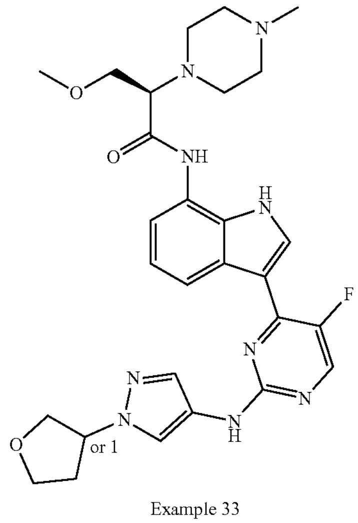

Example 33

Step 1. 4-nitro-1-(oxolan-3-yl)pyrazole

Into a 40 mL vial were added 3-iodooxolane (665 mg, 3.36 mmol, 1.00 equiv) and 4-nitropyrazole (380 mg, 3.36 mmol, 1.00 equiv) in DMF (20.00 mL) at room temperature. The final reaction mixture was stirred for overnight at 80° C. The resulting mixture was concentrated under reduced pressure. The residue was purified by Prep-TLC ($CH_2Cl_2$/MeOH 10:1) to afford 4-nitro-1-(oxolan-3-yl)pyrazole (600 mg, 59.02%) as a light yellow solid. LCMS: m/z (ESI), $[M+H]^+$ =184.3. $^1$H-NMR (300 MHz, MeOD-$d_4$) δ 2.36-2.39 (1H, m), 2.52 (1H, dtd), 3.91-3.94 (1H, m), 4.00-4.11 (2H, m), 4.06-4.19 (1H, m), 5.08-5.12 (1H, m), 8.13 (1H, s), 8.57-8.63 (1H, m).

Step 2. 1-(oxolan-3-yl)pyrazol-4-amine

A mixture of 4-nitro-1-(oxolan-3-yl)pyrazole (600 mg, 3.27 mmol, 1.00 equiv) and Pd/C (0.03 g, 0.327 mmol, 0.10 equiv) in MeOH (20.00 mL) was stirred for 1 h at room temperature under hydrogen atmosphere. The resulting mixture was filtered, the filter cake was washed with MeOH (2×10 mL). The filtrate was concentrated under reduced pressure. This resulted in 1-(oxolan-3-yl)pyrazol-4-amine (500 mg, 92.67%) as a purple oil. LCMS: m/z (ESI), $[M+H]^{+}$=154.1. $^1$H-NMR (300 MHz, DMSO-$d_6$) δ 2.05-2.21 (1H, m), 2.23-2.28 (1H, m), 3.58-4.04 (6H, m), 4.74-4.82 (1H, m), 6.91 (1H, d), 7.03 (1H, d).

Step 3. (R)—N-[3-[5-fluoro-2-([1-[oxolan-3-yl] pyrazol-4-yl]amino)pyrimidin-4-yl]-1H-indol-7-yl]-3-methoxy-2-(4-methylpiperazin-1-yl)propanamide (Ex. 30 and Ex. 33)

To a solution of 1-(oxolan-3-yl)pyrazol-4-amine (102.83 mg, 0.671 mmol, 1.50 equiv) and (R)—N-[3-(2-chloro-5-fluoropyrimidin-4-yl)-1H-indol-7-yl]-3-methoxy-2-(4-methyl-piperazin-1-yl)propanamide (200.00 mg, 0.448 mmol, 1.00 equiv) in dioxane (20.00 mL) were added BrettPhos (24.02 mg, 0.045 mmol, 0.10 equiv), BrettPhos Pd G3 (40.57 mg, 0.045 mmol, 0.10 equiv) and $Cs_2CO_3$ (437.43 mg, 1.343 mmol, 3.00 equiv). After stirring for 3 h at 80° C. under nitrogen atmosphere, the resulting mixture was concentrated under reduced pressure. The crude product (40 mg) was purified by Prep-HPLC with the following conditions (Column: CHIRAL ART Cellulose-SB, 4.6×100 mm, 3 μm; Mobile Phase A: (Hex:DCM=5:1) (0.1% DEA): IPA=85:15, Mobile Phase B; Flow rate: 1 mL/min; Gradient: 0 B to 0 B) to afford (R)—N-[3-[5-fluoro-2-([1-[oxolan-3-yl]pyrazol-4-yl]amino)pyrimidin-4-yl]-1H-indol-7-yl]-3-methoxy-2-(4-methylpiperazin-1-yl)propanamide (Ex. 33) (11 mg, 4.32%) LCMS: m/z (ESI), $[M+H]^+$=564.4. $^1$H-NMR (300 MHz, DMSO-$d_6$) δ 2.32 (5H, s), 2.54-2.82 (8H, m), 3.30 (3H, s), 3.59 (1H, s), 3.56-3.74 (1H, m), 3.75-4.04 (2H, m), 3.83-4.00 (3H, m), 4.98 (1H, s), 7.12-7.17 (1H, m), 7.56 (2H, d), 7.99 (1H, s), 8.19 (1H, s), 8.39 (2H, d), 9.34 (1H, s), 9.94 (1H, s), 11.52 (1H, s) and (R)—N-[3-[5-fluoro-2-([1-[oxolan-3-yl]pyrazol-4-yl] amino) pyrimidin-4-yl]-1H-indol-7-yl]-3-methoxy-2-(4-methylpiperazin-1-yl)propanamide (Ex. 30) (7 mg, 13.86%) as a white solid. LCMS: m/z (ESI), $[M+H]^+$=564.4. $^1$H-NMR (300 MHz, DMSO-$d_6$) δ 1.24 (3H, s), 1.95-2.06 (1H, m), 2.16 (3H, s), 2.25 (1H, s), 2.28-2.47 (4H, m), 2.64 (2H, d), 2.75 (2H, d), 3.51 (1H, t), 3.65-3.69 (1H, m), 3.74-3.87 (2H, m), 3.84-4.04 (3H, m), 4.95-5.03 (1H, m), 7.11-7.17 (1H, m), 7.53 (2H, d), 7.99 (1H, s), 8.18-8.20 (1H, m), 8.38-8.39 (1H, m), 8.49 (1H, s), 9.34 (1H, s), 9.85 (1H, s), 11.42 (1H, s).

Example 34

Preparation of (R)—N-[3-(5-fluoro-2-[[6-(hydroxymethyl)-5-methoxypyridin-3-yl]amino]pyrimidin-4-yl)-1H-indol-7-yl]-3-methoxy-2-(4-methylpiperazin-1-yl)propanamide

SCHEME 34

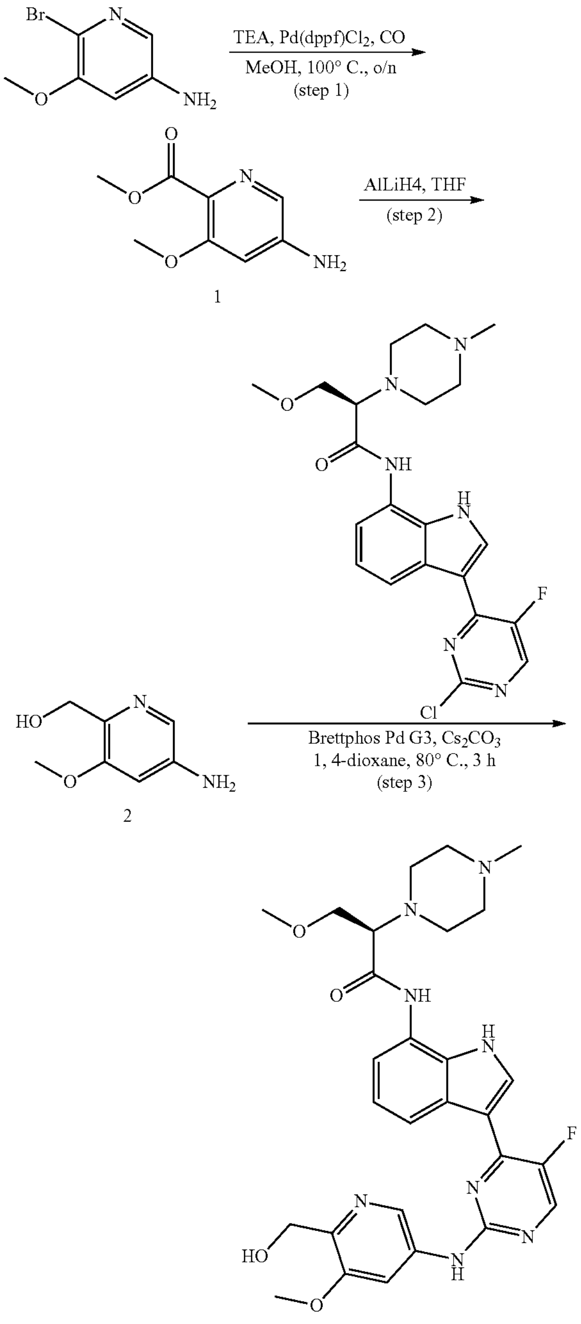

Example 34

Step 1. Methyl 5-amino-3-methoxypyridine-2-carboxylate

To a stirred mixture of 6-bromo-5-methoxypyridin-3-amine (1000.00 mg, 4.925 mmol, 1.00 equiv) and TEA (996.75 mg, 9.850 mmol, 2.00 equiv) in MeOH (100.00 mL) was added Pd(dppf)$Cl_2$ (720.75 mg, 0.985 mmol, 0.20 equiv) The resulting mixture was stirred at 100° C. under carbon monoxide atmosphere. The resulting mixture was stirred for overnight at 100° C. under carbon monoxide atmosphere. The resulting mixture was concentrated under reduced pressure. The residue was purified by Prep-TLC ($CH_2Cl_2$/MeOH 20:1) to afford methyl 5-amino-3-methoxypyridine-2-carboxylate (700 mg, 78.02%) as a light brown solid. LCMS: m/z (ESI), $[M+H]^+$=183.2

Step 2. (5-amino-3-methoxypyridin-2-yl)methanol

A mixture of methyl 5-amino-3-methoxypyridine-2-carboxylate (300.00 mg, 1.647 mmol, 1.00 equiv) and Li $AlH_4$ (187.50 mg, 4.940 mmol, 3.00 equiv) in THF (30.00 mL) was stirred for overnight at room temperature under air atmosphere. The reaction was quenched with Water/Ice at room temperature. The resulting mixture was filtered, the filter cake was washed with THF (3×10 mL). The filtrate was concentrated under reduced pressure. The crude product was used in the next step directly without further purification to afford (5-amino-3-methoxypyridin-2-yl)methanol (200 mg, 78.78%) as a yellow solid. LCMS: m/z (ESI), $[M+H]^+$ =155.3.

Step 3. (R)—N-[3-(5-fluoro-2-[[6-(hydroxymethyl)-5-methoxypyridin-3-yl]amino]pyrimidin-4-yl)-1H-indol-7-yl]-3-methoxy-2-(4-methylpiperazin-1-yl) propanamide To a stirred mixture of (R)—N-[3-(2-chloro-5-fluoropyrimidin-4-yl)-1H-indol-7-yl]-3-methoxy-2-(4-methylpiperazin-1-yl)propanamide (120.00 mg, 0.269 mmol, 1.00 equiv) and (5-amino-3-methoxypyridin-2-yl)methanol (82.79 mg, 0.537 mmol, 2.00 equiv) in dioxane (20.00 mL) were added $Cs_2CO_3$ (262.46 mg, 0.806 mmol, 3.00 equiv) and BrettPhos Pd G3 (48.68 mg, 0.054 mmol, 0.20 equiv) in portions at 80° C. under nitrogen atmosphere. The resulting mixture was stirred for 2 h at 80° C. under nitrogen atmosphere. The resulting mixture was concentrated under reduced pressure. The crude product (80 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 26 B to 36 B in 7 min; 254; 220 nm; RT1: 7.28) to afford (R)—N-[3-(5-fluoro-2-[[6-(hydroxymethyl)-5-methoxypyridin-3-yl]amino]pyrimidin-4-yl)-1H-indol-7-yl]-3-methoxy-2-(4-methylpiperazin-1-yl)propanamide (10 mg, 6.60%) as a white solid. LCMS: m/z (ESI), $[M+H]^+$=565.4. $^1$H-NMR (400 MHz, DMSO-$d_6$) δ 2.13 (3H, s), 2.34 (4H, s), 2.54-2.67 (2H, m), 2.73 (2H, d), 3.28 (3H, s), 3.49 (1H, t), 3.66 (1H, dd), 3.72-3.85 (4H, m), 4.48 (2H, d), 4.73 (1H, t), 7.13 (1H, t), 7.53 (1H, dd), 7.93 (1H, d), 8.24 (1H, d), 8.39-8.58 (3H, m), 9.78 (2H, d), 11.43 (1H, s)

Example 36

Preparation of Ethyl 5-[(5-fluoro-4-[7-[(R)-3-methoxy-2-(4-methylpiperazin-1-yl) propanamido]-1H-indol-3-yl]pyrimidin-2-yl)amino]pyridine-2-carboxylate

SCHEME 36

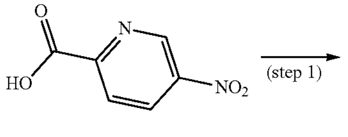

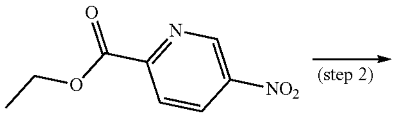

1

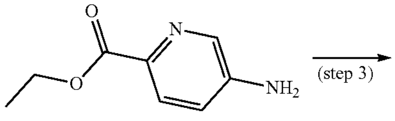

2

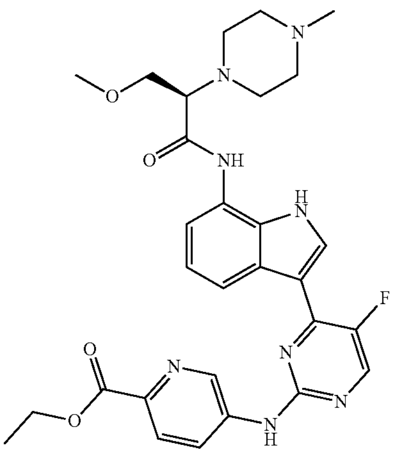

Example 36

Step 1. Ethyl 5-nitropyridine-2-carboxylate

To a stirred solution of 5-nitropyridine-2-carboxylic acid (700.00 mg, 4.164 mmol, 1.00 equiv) in EtOH (20.00 mL) was added $SOCl_2$ (1.01 mL, 7.480 mmol, 3.00 equiv) dropwise at 0° C. under air atmosphere. The resulting mixture was stirred for 2 h at 80° C. under air atmosphere. The resulting mixture was concentrated under reduced pressure. The reaction was quenched by the addition of saturated aqueous $NaHCO_3$ (50 mL) at room temperature. The mixture was extracted with EtOAc (2×25 mL). The combined organic layers were washed with brine (1×20 mL), dried over anhydrous $Na_2SO_4$. After filtration, the filtrate was concentrated under reduced pressure. This resulted in ethyl 5-nitropyridine-2-carboxylate (600 mg, 72.72%) as a light yellow solid. LCMS: m/z (ESI), $[M+H]^+$=197.2. $^1$H-NMR (300 MHz, MeOD-$d_4$) δ 1.40-1.47 (3H, m), 4.44-4.52 (2H, m), 8.33-8.38 (1H, m), 8.74-8.79 (1H, m), 9.43-9.46 (1H, m).

Step 2. Ethyl 5-aminopyridine-2-carboxylate

A mixture of ethyl 5-nitropyridine-2-carboxylate (400.00 mg, 2.039 mmol, 1.00 equiv) and Pd/C (434.01 mg, 4.078 mmol, 2.00 equiv) in MeOH (25.00 mL) was stirred at room temperature under hydrogen atmosphere for 1 h. The resulting mixture was filtered, the filter cake was washed with MeOH (3×15 mL). The filtrate was concentrated under reduced pressure. This resulted in ethyl-5-aminopyridine-2-carboxylate (312 mg, 91.15%) as a grey solid. LCMS: m/z (ESI), $[M+H]^+$=167.3. $^1$H-NMR (300 MHz, DMSO-$d_6$) δ 1.25 (3H, t), 4.17-4.31 (2H, m), 6.21 (2H, s), 6.89-6.93 (1H, m), 7.72 (1H, d), 7.96 (1H, d).

Step 3. Ethyl 5-[(5-fluoro-4-[7-[(R)-3-methoxy-2-(4-methylpiperazin-1-yl) propanamido]-1H-indol-3-yl]pyrimidin-2-yl)amino]pyridine-2-carboxylate (Ex. 36)

To a solution of ethyl 5-aminopyridine-2-carboxylate (55.78 mg, 0.336 mmol, 1.50 equiv) and (R)—N-[3-(2-chloro-5-fluoropyrimidin-4-yl)-1H-indol-7-yl]-3-methoxy-2-(4-methyl-piperazin-1-yl)propanamide (100.00 mg, 0.224 mmol, 1.00 equiv) in dioxane (10.00 mL) were added BrettPhos (12.01 mg, 0.022 mmol, 0.10 equiv), $Cs_2CO_3$ (218.72 mg, 0.671 mmol, 3.00 equiv) and BrettPhos Pd G3 (20.28 mg, 0.022 mmol, 0.10 equiv). After stirring for 2 h at 80° C. under nitrogen atmosphere, the resulting mixture was concentrated under reduced pressure. The residue was purified by silica gel column chromatography, eluted with $CH_2Cl_2$/MeOH (20:3). The crude product (100 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 30 B to 50 B in 7 min; 254; 220 nm; RT1: 7.43) to afford ethyl-5-[(5-fluoro-4-[7-[(R)-3-methoxy-2-(4-methylpiperazin-1-yl)propanamido]-1H-indol-3-yl]pyrimidin-2-yl)amino]pyridine-2-carboxylate (20 mg, 15.35%) as a white solid. LCMS: m/z (ESI), $[M+H]^+$=577.5. $^1$H-NMR (300 MHz, DMSO-$d_6$) δ 1.29-1.34 (3H, m), 2.13 (3H, s), 2.34 (4H, s), 2.62 (2H, s), 3.47-3.52 (2H, m), 3.32 (3H, s), 3.64-3.69 (1H, m), 3.76-3.81 (2H, m), 4.29-4.34 (2H, m), 7.15-7.20 (1H, m), 7.54 (1H, d), 8.02 (1H, d), 8.27 (1H, s), 8.45-8.62 (3H, m), 8.97 (1H, d), 9.87 (1H, s), 10.19 (1H, s), 11.53 (1H, s).

Example 39

Preparation of (R)—N-(3-(5-fluoro-2-((6-(2-(methylamino)-2-oxoethyl)pyridin-3-yl)amino) pyrimidin-4-yl)-1H-indol-7-yl)-3-methoxy-2-(4-methylpiperazin-1-yl)propanamide

SCHEME 39

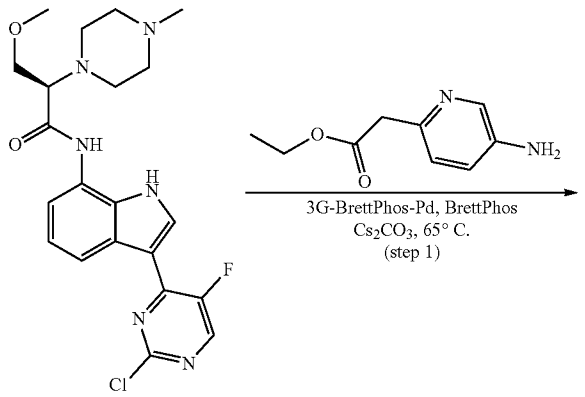

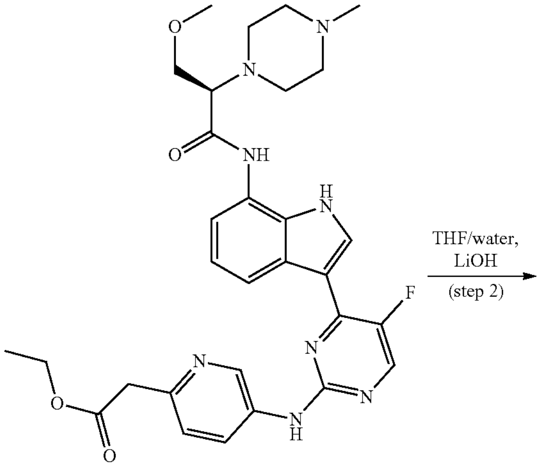

1

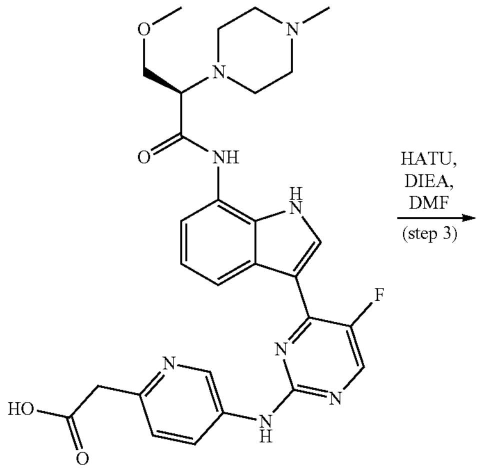

2

-continued

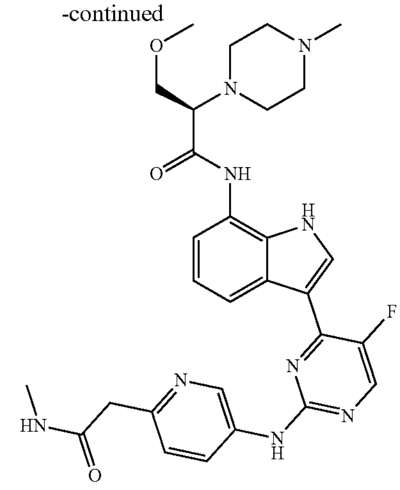

Example 39

Step 1. Ethyl (R)-2-(5-((5-fluoro-4-(7-(3-methoxy-2-(4-methylpiperazin-1-yl) propanamido)-1H-indol-3-yl)pyrimidin-2-yl)amino)pyridin-2-yl)acetate Into a 40 mL vial were added ethyl 2-(5-aminopyridin-2-yl)acetate (72.58 mg, 0.403 mmol, 1.20 equiv) and (R)—N-[3-(2-chloro-5-fluoropyrimidin-4-yl)-1H-indol-7-yl]-3-methoxy-2-(4-methylpiperazin-1-yl)propanamide (150.00 mg, 0.336 mmol, 1.00 equiv), BrettPhos (18.02 mg, 0.034 mmol, 0.10 equiv), BrettPhos Palladacycle (26.81 mg, 0.034 mmol, 0.10 equiv), $Cs_2CO_3$ (218.72 mg, 0.671 mmol, 2.00 equiv) in dioxane (10.00 mL) at room temperature. The resulting mixture was stirred for 2 h at 80° C. under nitrogen atmosphere. The resulting mixture was filtered, the filter cake was washed with DCM (2×10 mL). The filtrate was concentrated under reduced pressure. The residue was purified by Prep-TLC ($CH_2Cl_2$/MeOH 200:15) to afford ethyl-2-[5-[(5-fluoro-4-[7-[(R)-3-methoxy-2-(4-methylpiperazin-1-yl)propanamido]-1H-indol-3-yl]pyrimidin-2-yl)amino] pyridin-2-yl]acetate (120 mg, 60.6%) as a yellow solid. LCMS: m/z (ESI), $[M+H]^+$=591.3

Step 2. (R)-2-(5-((5-fluoro-4-(7-(3-methoxy-2-(4-methylpiperazin-1-yl)propanamido)-1H-indol-3-yl) pyrimidin-2-yl)amino)pyridin-2-yl)acetic Acid Into a 40 mL vial were added ethyl 2-[5-[(5-fluoro-4-[7-[(R)-3-methoxy-2-(4-methylpiperazin-1-yl)propanamido]-1H-indol-3-yl]pyrimidin-2-yl)amino]pyridin-2-yl]acetate (140.00 mg, 0.237 mmol, 1.00 equiv) in THF (3.00 mL) and LiOH (56.76 mg, 2.370 mmol, 10.00 equiv) in water (0.50 mL) at room temperature. The resulting mixture was stirred for 3 h at room temperature under air atmosphere. The reaction mixture was acidified by solution of HCl (1 M), then evaporated to afford a crude solid without purification. The crude solid was used directly in the next step. LCMS: m/z (ESI), $[M+H]^{+=}$563.4.

Step 3. (R)—N-(3-(5-fluoro-2-((6-(2-(methylamino)-2-oxoethyl)pyridin-3-yl)amino) pyrimidin-4-yl)-1H-indol-7-yl)-3-methoxy-2-(4-methylpiperazin-1-yl)propanamide (Ex. 39)

Into a 8 mL vial were added [5-[(5-fluoro-4-[7-[(R)-3-methoxy-2-(4-methylpiperazin-1-yl)propanamido]-1H-indol-3-yl]pyrimidin-2-yl)amino]pyridin-2-yl]acetic acid (80 mg, 0.142 mmol, 1.00 equiv) and methylamine (0.36 mL, 0.720 mmol, 5.06 equiv), HATU (108.13 mg, 0.284 mmol, 2.00 equiv), $Et_3N$ (43.17 mg, 0.427 mmol, 3.00 equiv) in DMF (2.00 mL) at room temperature. The resulting mixture was stirred for 2 h at room temperature under air atmosphere. The resulting mixture was diluted with water (10 mL). The aqueous layer was extracted with $CH_2Cl_2$ (3×10 mL). The combined organic layer was dried over anhydrous $Na_2SO_4$, filtered and evaporated to afford a yellow solid. The residue was purified by Prep-TLC ($CH_2Cl_2$/MeOH 8:1) to afford a yellow solid. The crude product (40 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 27 B to 37 B in 7 min; 254; 220 nm; RT1: 5.17) to afford (R)—N-[3-[5-fluoro-2-([6-[(methylcarbamoyl)methyl]pyridin-3-yl]amino)pyrimidin-4-yl]-1H-indol-7-yl]-3-methoxy-2-(4-methylpiperazin-1-yl)propanamide (10 mg, 12.22%) as a white solid. LCMS: m/z (ESI), $[M+H]^+$=576.3. $^1$H-NMR (400 MHz, DMSO-$d_6$) δ 2.16 (3H, s), 2.38 (4H, s), 2.61 (5H, d), 2.76 (2H, t), 3.30 (3H, s), 3.54 (3H, d), 3.69 (1H, dd), 3.81 (1H, dd), 7.16 (1H, t), 7.28 (1H, d), 7.55 (1H, d), 7.96 (1H, q), 8.16 (1H, dd), 8.22-8.29 (1H, m), 8.46 (1H, d), 8.54 (1H, d), 8.79 (1H, d), 9.65 (1H, s), 9.88 (1H, s), 11.50 (1H, d)

Example 40

Preparation of (R)—N-[3-(5-fluoro-2-[[6-(1,3-oxazol-5-yl)pyridin-3-yl]amino]pyrimidin-4-yl)-1H-indol-7-yl]-3-methoxy-2-(4-methylpiperazin-1-yl)propanamide

SCHEME 40

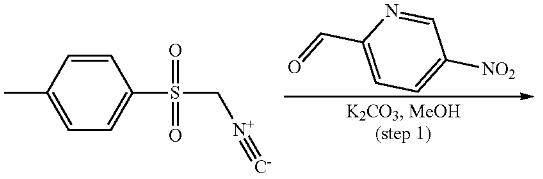

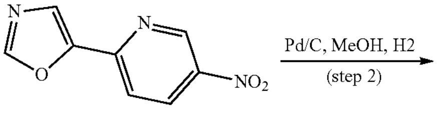

1

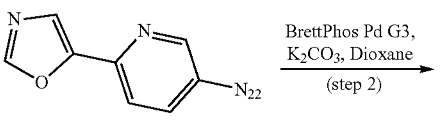

2

-continued

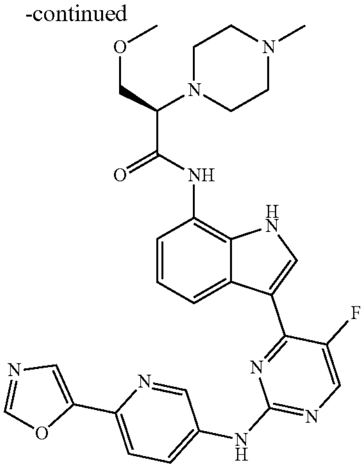

Example 40

Step 1. 5-nitro-2-(1,3-oxazol-5-yl)pyridine

A mixture of TosMIC (1.00 g, 5.122 mmol, 1.00 equiv) and 5-nitropyridine-2-carbaldehyde (779.09 mg, 5.122 mmol, 1.00 equiv), $K_2CO_3$ (1061.81 mg, 7.683 mmol, 1.50 equiv) in MeOH (20.00 mL) was stirred for 5 h at 75° C. under nitrogen atmosphere. The residue was purified by silica gel column chromatography, eluted with PE/EtOAc (5:1) to afford 5-nitro-2-(1,3-oxazol-5-yl)pyridine (500 mg, 51.07%) as an off-white solid. LCMS: m/z (ESI), $[M+H]^+$=192.2

Step 2. 6-(1,3-oxazol-5-yl)pyridin-3-amine

A mixture of 5-nitro-2-(1,3-oxazol-5-yl)pyridine (250.00 mg, 1.308 mmol, 1.00 equiv) and Pd/C (27.84 mg, 0.262 mmol, 0.20 equiv) in MeOH (10.00 mL) was stirred for 3 h at room temperature under hydrogen atmosphere. The resulting mixture was filtered, the filter cake was washed with MeOH (10 mL×3). The filtrate was concentrated under reduced pressure to afford 6-(1,3-oxazol-5-yl)pyridin-3-amine (180 mg, 85.39%) as an off-white solid. LCMS: m/z (ESI), $[M+H]^+$=162.3

Step 3. (R)—N-[3-(5-fluoro-2-[[6-(1,3-oxazol-5-yl)pyridin-3-yl]amino]pyrimidin-4-yl)-1H-indol-7-yl]-3-methoxy-2-(4-methylpiperazin-1-yl)propanamide (Ex. 40)

A mixture of (R)—N-[3-(2-chloro-5-fluoropyrimidin-4-yl)-1H-indol-7-yl]-3-methoxy-2-(4-methylpiperazin-1-yl)propanamide (120.00 mg, 0.269 mmol, 1.00 equiv) and 6-(1,3-oxazol-5-yl)pyridin-3-amine (64.91 mg, 0.403 mmol, 1.50 equiv), BrettPhos Pd $G_3$ (24.34 mg, 0.027 mmol, 0.10 equiv), $K_2CO_3$ (74.22 mg, 0.537 mmol, 2.00 equiv) in dioxane (4.00 mL) was stirred for 2 h at 70° C. under nitrogen atmosphere. The residue was purified by Prep-TLC ($CH_2Cl_2$/MeOH=15:1) to afford crude product. The crude product was purified by Prep-HPLC with the following conditions (Column: XBridge Prep OBD C18 Column, 19×250 mm, 5 μm; Mobile Phase A: Water (0.05% $NH_3·H_2O$), Mobile Phase B: ACN; Flow rate: 25 mL/min; Gradient: 32 B to 52 B in 7 min; RT1: 6.40) to afford (R)—N-[3-(5-fluoro-2-[[6-(1,3-oxazol-5-yl)pyridin-3-yl]amino]pyrimidin-4-yl)-1H-indol-7-yl]-3-methoxy-2-(4- methylpiperazin-1-yl)propanamide (100 mg, 65.15%) as an white solid. LCMS: m/z (ESI), $[M+H]^+$=572.2 $^1$H-NMR (400 MHz, DMSO-$d_6$) δ 2.15 (3H, s), 2.36 (4H, s), 2.64 (2H, d), 2.76 (2H, m), 3.30 (3H, s), 3.51 (1H, t), 3.68 (1H, dd), 3.80 (1H, dd), 7.17 (1H, t), 7.56 (1H, d), 7.65 (1H, s), 7.73 (1H, d), 8.27 (1H, d), 8.44 (1H, dd), 8.47 (1H, s), 8.50 (1H, d), 8.57 (1H, d), 8.96 (1H, d), 9.89 (1H, s), 9.95 (1H, s), 11.54 (1H, s).

Example 41

Preparation of (R)—N-[3-[5-fluoro-2-(1H-indol-5-ylamino)pyrimidin-4-yl]-1H-indol-7-yl]-3-methoxy-2-(4-methylpiperazin-1-yl)propanamide

SCHEME 41

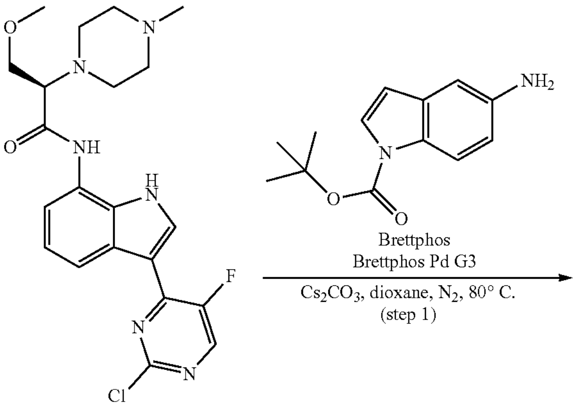

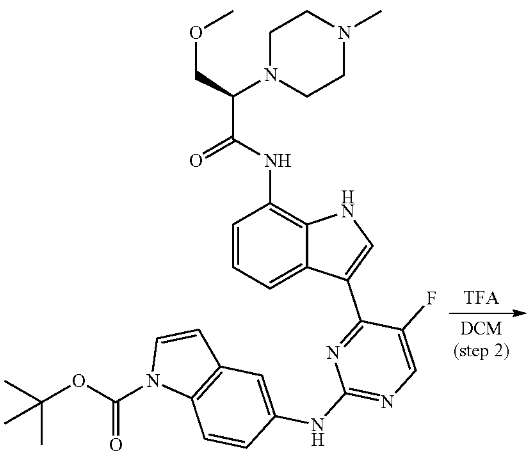

1

-continued

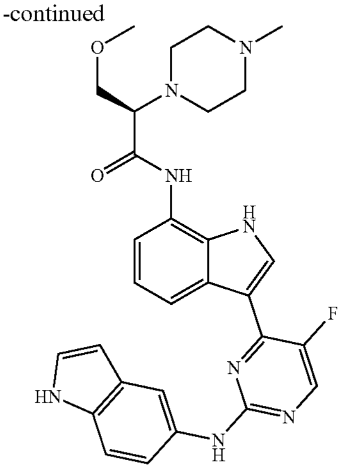

Example 41

Step 1. Tert-butyl 5-[(5-fluoro-4-[7-[(R)-3-methoxy-2-(4-methylpiperazin-1-yl)propanamido]-1H-indol-3-yl]pyrimidin-2-yl)amino]indole-1-carboxylate To a solution of (R)—N-[3-(2-chloro-5-fluoropyrimidin-4-yl)-1H-indol-7-yl]-3-methoxy-2-(4-methylpiperazin-1-yl) propanamide (180.00 mg, 0.403 mmol, 1.00 equiv) and tert-butyl 5-aminoindole-1-carboxylate (121.62 mg, 0.524 mmol, 1.3 equiv) in dioxane (10.0 mL) were added Brett-Phos (43.24 mg, 0.081 mmol, 0.2 equiv) and BrettPhos Pd G3 (73.02 mg, 0.081 mmol, 0.2 equiv) and $Cs_2CO_3$ (262.46 mg, 0.806 mmol, 2 equiv). After stirring for 16 h at 80° C. under a nitrogen atmosphere. The residue was purified by TLC ($CH_2Cl_2$/MeOH 8:1) to afford tert-butyl 5-[(5-fluoro-4-[7-[(R)-3-methoxy-2-(4-methylpiperazin-1-yl)propanamido]-1H-indol-3-yl]pyrimidin-2-yl)amino]indole-1-carboxylate (130 mg, 50.22%) as a reddish brown solid. LCMS: m/z (ESI), $[M+H]^+$=643.4.

Step 2. (R)—N-[3-[5-fluoro-2-(1H-indol-5-ylamino) pyrimidin-4-yl]-1H-indol-7-yl]-3-methoxy-2-(4-methylpiperazin-1-yl)propanamide (Ex. 41)

To a stirred solution of tert-butyl 5-[(5-fluoro-4-[7-[(R)-3-methoxy-2-(4-methyl-piperazin-1-yl)propanamido]-1H-indol-3-yl]pyrimidin-2-yl)amino]indole-1-carboxylate (130.00 mg, 0.202 mmol, 1.00 equiv) in DCM (6.0 mL) were added TFA (2.00 mL, 26.926 mmol, 133.13 equiv). The resulting mixture was stirred for 2 h at room temperature. The resulting mixture was concentrated under reduced pressure. The mixture was basified to pH8 with saturated $NaHCO_3$ (aq.). The resulting mixture was extracted with $CH_2Cl_2$ (8×30 mL), and the combined organic layers were dried over anhydrous $Na_2SO_4$. After filtration, the filtrate was concentrated under reduced pressure to afford (R)—N-[3-[5-fluoro-2-(1H-indol-5-ylamino)pyrimidin-4-yl]-1H-indol-7-yl]-3-methoxy-2-(4-methylpiperazin-1-yl)propanamide (54 mg, 49.20%) as a reddish brown oil. The crude product (54 mg) was purified by Chiral-Prep-HPLC with the following conditions (Column: CHIRAL ART Cellulose-SB, 2×25 cm, 5 μm; Mobile Phase A: MTBE (10 mM $NH_3$-MEOH)-HPLC, Mobile Phase B: EtOH-HPLC; Flow rate: 20 mL/min; Gradient: 10 B to 10 B in 12 min; 220/254 nm; RT1: 8.928; RT2: 10.344; Injection Volume: 0.6 mL; Number Of Runs: 20) to afford (R)—N-[3-[5-fluoro-2-(1H- indol-5-ylamino)pyrimidin-4-yl]-1H-indol-7-yl]-3-methoxy-2-(4-methylpiperazin-1-yl)propanamide (32.96 mg, 72.30%) as a light yellow solid. LCMS: m/z (ESI), $[M+H]^+$=543.3. $^1$H-NMR (300 MHz, DMSO-$d_6$) δ 2.14 (3H, s), 2.35 (4H, s), 2.63 (2H, d), 2.73 (2H, s), 3.29 (3H, s), 3.50 (1H, t), 3.68 (1H, dd), 3.80 (1H, dd), 6.36 (1H, t), 7.02 (1H, t), 7.23-7.42 (3H, m), 7.51 (1H, d), 8.01 (1H, s), 8.21 (1H, d), 8.38 (1H, d), 8.55 (1H, d), 9.22 (1H, s), 9.85 (1H, s), 10.95 (1H, s), 11.43 (1H, s).

Example 42

Preparation of (R)—N-(3-(5-fluoro-2-((1-oxoisochroman-6-yl)amino)pyrimidin-4-yl)-1H-indol-7-yl)-3-methoxy-2-(4-methylpiperazin-1-yl)propanamide

SCHEME 42

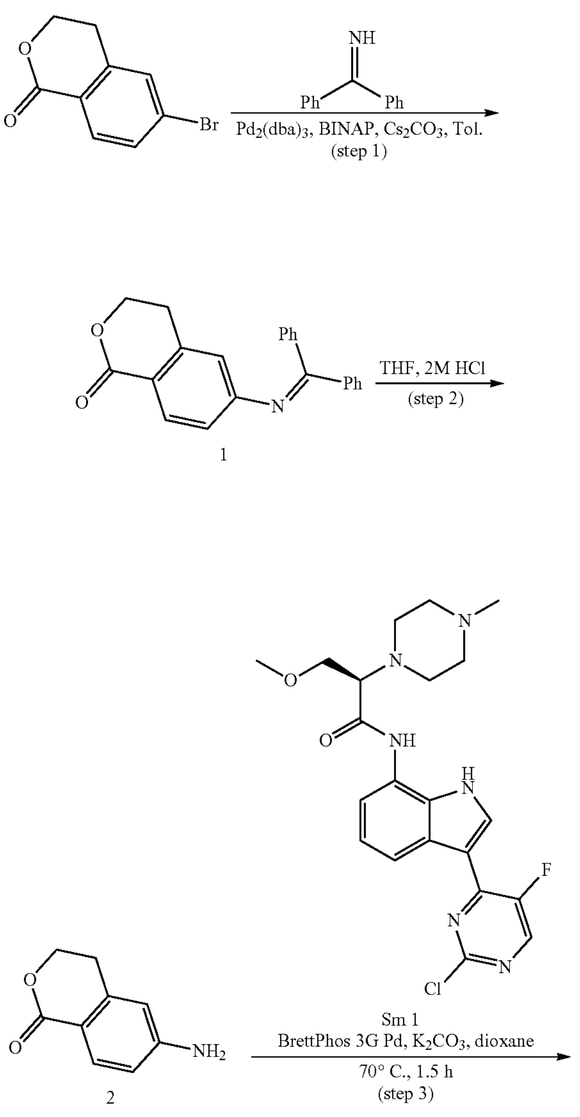

-continued

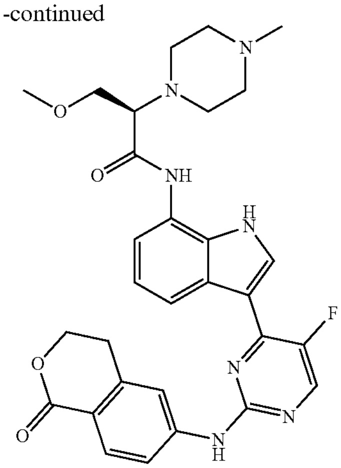

Example 42

Step1. 6-((diphenylmethylene)amino)isochroman-1-one

Into a 40 mL vial were added 6-bromo-3,4-dihydro-2-benzopyran-1-one (500.00 mg, 2.202 mmol, 1.00 equiv) and benzenemethanimine, ?-phenyl- (518.83 mg, 2.863 mmol, 1.30 equiv), $Pd_2(dba)_3$ (201.65 mg, 0.220 mmol, 0.10 equiv), BINAP (274.24 mg, 0.440 mmol, 0.20 equiv), $Cs_2CO_3$ (1434.97 mg, 4.404 mmol, 2.00 equiv) in Toluene (20.00 mL) at room temperature. The resulting mixture was stirred for 2 h at 90° C. under nitrogen atmosphere. The reaction mixture was allowed to cool down to rt, and the solid was filtered out and the filter cake was washed with MeOH (10 mL), and the filtrate was concentrated under reduced pressure. The residue was purified by TLC (EA: PE=1:3) to afford 6-[(diphenylmethylidene)amino]-3,4-dihydro-2-benzopyran-1-one (458 mg, 63.53%) as a yellow solid. LCMS: m/z (ESI), $[M+H]^+$=328.2

Step2. 6-aminoisochroman-1-one

Into a 50 mL round-bottom flask were added 6-[(diphenylmethylidene)amino]-3,4-dihydro-2-benzopyran-1-one (458.00 mg, 1.399 mmol, 1.00 equiv) in THF (10 mL), solution of HCl (2 M) in water (5 mL) was added to the above solution at room temperature. The resulting mixture was stirred for 1 h at room temperature under air atmosphere. The mixture was basified to pH8 with saturated $NaHCO_3$ (aq.). The aqueous layer was extracted with $CH_2Cl_2$ (3×20 mL). The combined organic layers were dried over anhydrous $Na_2SO_4$. After filtration, the filtrate was concentrated under reduced pressure. The residue was purified by Prep-TLC ($CH_2Cl_2$/MeOH 20:1) to afford 6-amino-3,4-dihydro-2-benzopyran-1-one (112 mg, 49.06%) as a yellow solid. LCMS: m/z (ESI), $[M+H]^+$=164.1

Step3. (R)—N-(3-(5-fluoro-2-((1-oxoisochroman-6-yl)amino)pyrimidin-4-yl)-1H-indol-7-yl)-3-methoxy-2-(4-methylpiperazin-1-yl)propanamide (Ex. 42)

Into a 40 mL vial were added 6-amino-3,4-dihydro-2-benzopyran-1-one (35.05 mg, 0.215 mmol, 1.20 equiv) and (R)—N-[3-(2-chloro-5-fluoropyrimidin-4-yl)-1H-indol-7-yl]-3-methoxy-2-(4-methylpiperazin-1-yl)propanamide (80.00 mg, 0.179 mmol, 1.00 equiv), BrettPhos Pd G3 (16.23 mg, 0.018 mmol, 0.10 equiv), $K_2CO_3$ (74.22 mg, 0.537 mmol, 3.00 equiv) in dioxane (2.00 mL) at room temperature. The resulting mixture was stirred for 2 h at 70° C. under nitrogen atmosphere. The resulting mixture was filtered, the filter cake was washed with MeOH (2×10 mL). The filtrate was concentrated under reduced pressure. The residue was purified by Prep-TLC ($CH_2Cl_2$/MeOH 10:1) to afford a yellow solid. The crude product (40 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 31 B to 51 B in 7 min; 254; 220 nm; RT1: 6.77) to afford (R)—N-(3-[5-fluoro-2-[(1-oxo-3,4-dihydro-2-benzopyran-6-yl)amino]pyrimidin-4-yl]-1H-indol-7-yl)-3-methoxy-2-(4-methylpiperazin-1-yl)propanamide (10 mg, 9.74%) as a white solid. LCMS: m/z (ESI), $[M+H]^+$=574.4 $^1$H-NMR (400 MHz, MeOD-$d_4$) 2.35 (3H, s), 2.63 (4H, s), 2.84 (2H, s), 2.94 (2H, s), 3.07 (2H, t), 3.43 (3H, s), 3.53 (1H, t), 3.85 (1H, dd), 3.94 (1H, dd), 4.56 (2H, t), 7.21 (2H, d), 7.67 (1H, dd), 7.95 (1H, d), 8.02 (1H, d), 8.19 (1H, d), 8.35 (1H, d), 8.69 (1H, q).

Example 46

Preparation of (R)—N-[3-(5-fluoro-2-[[6-(hydroxymethyl)pyridin-2-yl]amino]pyrimidin-4-yl)-1H-indol-7-yl]-3-methoxy-2-(4-methylpiperazin-1-yl)propanamide

SCHEME 46

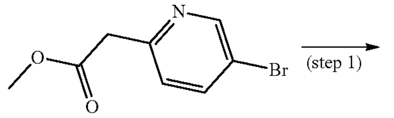

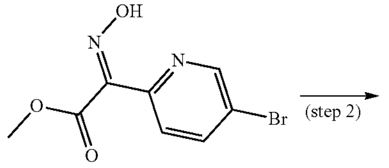

1

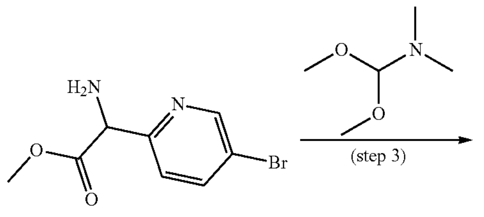

2

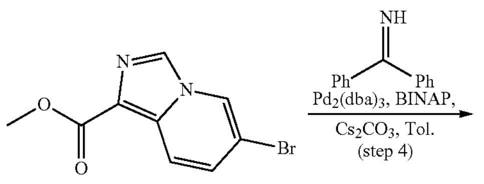

3

-continued

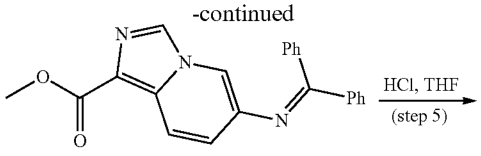

4

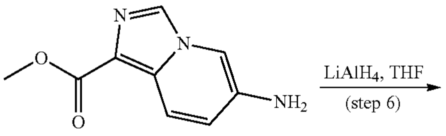

5

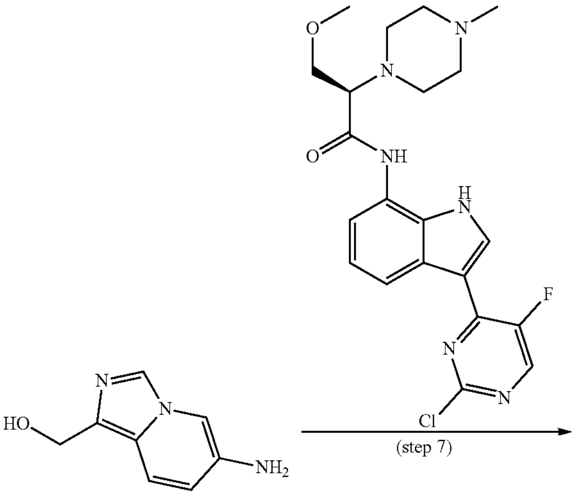

6

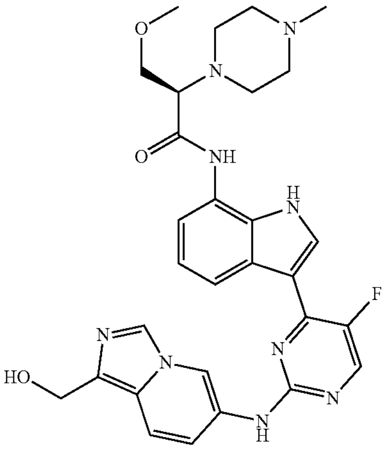

Example 46

Step 1. Methyl-2-(5-bromopyridin-2-yl)-2-(N-hydroxyimino)acetate

A mixture of methyl 2-(5-bromopyridin-2-yl)acetate (3.00 g, 13.040 mmol, 1.00 equiv) in AcOH (15.00 mL) was stirred for 30 min at 0° C. under air atmosphere. To the above mixture was added solution of $NaNO_2$ (0.90 g, 13.040 mmol, 1.00 equiv) in water (2 mL) dropwise over 1 min at room temperature. The resulting mixture was stirred for additional 1 h at room temperature. The resulting mixture was concentrated under reduced pressure. The resulting mixture was extracted with EtOAc (2×20 mL). The combined organic layers were washed with brine (1×20 mL), dried over anhydrous $Na_2SO_4$. After filtration, the filtrate was concentrated under reduced pressure. This resulted in methyl 2-(5-bromopyridin-2-yl)-2-(N-hydroxyimino)acetate (3 g, 87.92%) as a pink solid. LCMS: m/z (ESI), $[M+H]^+$=260.9.

Step 2. Methyl 2-amino-2-(5-bromopyridin-2-yl)acetate

Into a 250 mL round-bottom flask were added methyl-2-(5-bromopyridin-2-yl)-2-(N-hydroxyimino)acetate (5.00 g, 19.301 mmol, 1.00 equiv), Zn (3.16 g, 48.252 mmol, 2.50 equiv), formic acid (20.00 mL, 530.142 mmol, 27.47 equiv), MeOH (20.00 mL, 493.978 mmol, 25.59 equiv) and $H_2O$ (20.00 mL) at room temperature. The resulting mixture was stirred for overnight at room temperature under air atmosphere. The resulting mixture was concentrated under reduced pressure. The residue was neutralized to pH7 with saturated $NaHCO_3$ (aq.). The resulting mixture was extracted with EtOAc (3x15 mL). The combined organic layers were washed with brine (1x20 mL), dried over anhydrous $Na_2SO_4$. After filtration, the filtrate was concentrated under reduced pressure. This resulted in methyl 2-amino-2-(5-bromopyridin-2-yl)acetate (6 g, 60.89%) as a black oil. The crude product was used in next step without other purification. LCMS: m/z (ESI), $[M+H]^+$=244.9.

Step 3. Methyl 6-bromoimidazo[1,5-a]pyridine-1-carboxylate

Into a 250 mL round-bottom flask were added methyl-2-amino-2-(5-bromopyridin-2-yl)acetate (5.00 g, 20.402 mmol, 1.00 equiv) and (dimethoxymethyl)dimethylamine (2.67 g, 22.442 mmol, 1.10 equiv) in toluene (50 mL) at room temperature. The resulting mixture was stirred for overnight at 110° C. under air atmosphere. The resulting mixture was concentrated under reduced pressure. The residue was purified by silica gel column chromatography, eluted with PE/EtOAc (1:1) to afford methyl 6-bromoimidazo[1,5-a]pyridine-1-carboxylate (3.962 g, 74.61%) as a dark yellow solid. LCMS: m/z (ESI), $[M+H]^+$=254.9.

Step 4. Methyl 6-[(diphenylmethylidene)amino]imidazo[1,5-a]pyridine-1-carboxylate To a solution of methyl 6-bromoimidazo[1,5-a]pyridine-1-carboxylate (3.00 g, 11.761 mmol, 1.00 equiv) and diphenylmethanimine (3.20 g, 17.642 mmol, 1.50 equiv) in Toluene (25.00 mL) were added $Pd_2(dba)_3$ (1.08 g, 1.176 mmol, 0.10 equiv), BINAP (1.46 g, 2.352 mmol, 0.20 equiv) and $Cs_2CO_3$ (11.50 g, 35.284 mmol, 3.00 equiv). After stirring for 2 h at 90° C. under nitrogen atmosphere, the resulting mixture was concentrated under reduced pressure. The residue was purified by silica gel column chromatography, eluted with PE/EtOAc (5:1) to afford methyl-6-[(diphenylmethylidene)amino]imidazo[1,5-a]pyridine-1-carboxylate (1.9 g, 40.00%) as a dark yellow solid. $^1$H-NMR (300 MHz, $CDCl_3$-$d_1$) δ 1.18-1.32 (OH, m), 3.95 (3H, s), 6.66-6.70 (1H, m), 7.04-7.22 (3H, m), 7.34 (1H, s), 7.28-7.40 (2H, m), 7.40-7.48 (1H, m), 7.44-7.59 (3H, m), 7.72-7.86 (2H, m), 7.94 (2H, d).

Step 5. Methyl 6-aminoimidazo[1,5-a]pyridine-1-carboxylate

Into a 50 mL round-bottom flask were added methyl 6-[(diphenylmethylidene) amino]imidazo[1,5-a]pyridine-1-carboxylate (1.80 g, 5.065 mmol, 1.00 equiv), HCl (2M) (2.00 mL) and THF (20.00 mL) at room temperature. The resulting mixture was stirred for 1 h at room temperature under air atmosphere. The resulting mixture was concentrated under vacuum. The residue was neutralized to pH7 with saturated $NaHCO_3$ (aq.). The resulting mixture was concentrated under reduced pressure. The residue was purified by silica gel column chromatography, eluted with PE/EtOAc (3:1) to afford methyl 6-aminoimidazo[1,5-a]pyridine-1-carboxylate (731 mg, 73.23%) as a dark yellow solid. LCMS: m/z (ESI), $[M+H]^+$=192.2

Step 6. [6-aminoimidazo[1,5-a]pyridin-1-yl]methanol

Into a 40 mL vial were added methyl 6-aminoimidazo[1,5-a]pyridine-1-carboxylate (200.00 mg, 1.046 mmol, 1.00 equiv) and Li $AlH_4$ (119.11 mg, 3.138 mmol, 3 equiv) in THF (15.00 mL) at room temperature. The resulting mixture was stirred for 5 h at 65° C. under air atmosphere. The reaction was quenched by the addition of NaOH (120 mg in 1 mL) at room temperature. The resulting mixture was filtered, the filter cake was washed with DCM (3x8 mL). The filtrate was concentrated under reduced pressure. The residue was purified by Prep-TLC ($CHCl_3$/MeOH 10:1) to afford [6-aminoimidazo[1,5-a]pyridin-1-yl]methanol (53 mg, 42.34%) as a black oil. The crude product was used in next step without other purification. LCMS: m/z (ESI), $[M+H]^+$=164.0

Step 7. (R)—N-[3-(5-fluoro-2-[[1-(hydroxymethyl) imidazo[1,5-a]pyridin-6-yl]amino]pyrimidin-4-yl)-1H-indol-7-yl]-3-methoxy-2-(4-methylpiperazin-1-yl)propanamide (Ex. 46)

To a solution of (R)—N-[3-(2-chloro-5-fluoropyrimidin-4-yl)-1H-indol-7-yl]-3-methoxy-2-(4-methylpiperazin-1-yl) propanamide (100.00 mg, 0.224 mmol, 1.00 equiv) and [6-aminoimidazo[1,5-a]pyridin-1-yl]methanol (36.51 mg, 0.224 mmol, 1.00 equiv) in dioxane (10.00 mL) were added BrettPhos (12.01 mg, 0.022 mmol, 0.10 equiv), BrettPhos Pd G3 (20.28 mg, 0.022 mmol, 0.10 equiv) and $K_2CO_3$ (61.85 mg, 0.448 mmol, 2.00 equiv). After stirring for 2 hs at 80° C. under a nitrogen atmosphere, the resulting mixture was concentrated under reduced pressure. The residue was purified by Prep-TLC (DCM:MEOH 10:1). The crude product (20 mg) was purified by Prep-HPLC with the following conditions (Column: XBridge Prep OBD C18 Column, 30x150 mm, 5 μm; Mobile Phase A: Water (0.05% $NH_3H_2O$), Mobile Phase B: ACN; Flow rate: 60 mL/min; Gradient: 19 B to 39 B in 7 min; 254/220 nm; RT1: 6.47) to afford (R)—N-[3-(5-fluoro-2-[[1-(hydroxymethyl)imidazo[1,5-a]pyridin-6-yl]amino]pyrimidin-4-yl)-1H-indol-7-yl]-3-methoxy-2-(4-methylpiperazin-1-yl)propanamide (7 mg, 5.29%) as a white solid. LCMS: m/z (ESI), $[M+H]^+$=574.5 $^1$H-NMR (300 MHz, DMSO-$d_6$) δ 2.15 (3H, s), 2.37 (4H, s), 2.55-2.85 (2H, m), 3.30 (2H, s), 3.32 (3H, s), 3.49-3.53 (1H, m), 3.66-3.71 (1H, m), 3.78 (1H, d), 4.67 (2H, d), 4.89-4.93 (1H, m), 6.97 (1H, d), 7.10-7.15 (1H, m), 7.54 (1H, d), 7.60 (1H, d), 8.22 (2H, d), 8.49 (1H, d), 8.56 (1H, d), 9.06 (1H, s), 9.48 (1H, s), 9.87 (1H, s), 11.49 (1H, s).

Example 52

Preparation of Methyl-(R)-(5-((5-fluoro-4-(7-(3-methoxy-2-(4-methylpiperazin-1-yl)propanamido)-1H-indol-3-yl)pyrimidin-2-yl)amino)pyridin-2-yl) carbamate

SCHEME 52

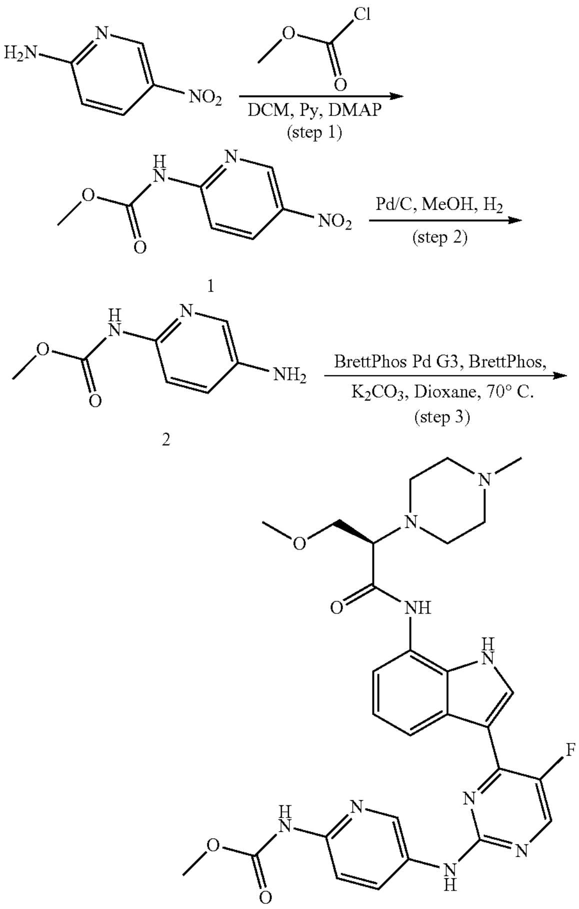

1

2

Example 52

Step1. Methyl (5-nitropyridin-2-yl)carbamate

To a stirred solution of 5-nitro-2-pyridinamine (500.00 mg, 3.594 mmol, 1.00 equiv), DMAP (87.82 mg, 0.719 mmol, 0.20 equiv) and pyridine (852.90 mg, 10.783 mmol, 3.00 equiv) in DCM (25.00 mL) was added methyl chloroformate (679.23 mg, 7.188 mmol, 2.00 equiv) dropwise at 0° C. under nitrogen atmosphere. The resulting mixture was stirred for 13 h at 30° C. under nitrogen atmosphere. The precipitated solids were collected by filtration and washed with $CH_2Cl_2$ (1×3 mL) to afford methyl N-(5-nitropyridin-2-yl)carbamate (300 mg, 42.34%) (crude) as a brown solid. LCMS: m/z (ESI), $[M+H]^+$=198.2.

Step 2. Methyl (5-aminopyridin-2-yl)carbamate

A mixture of methyl N-(5-nitropyridin-2-yl)carbamate (250.00 mg, 1.268 mmol, 1.00 equiv) and Pd/C (161.94 mg, 1.522 mmol, 2.00 equiv) in MeOH (15.00 mL) was stirred for 2 h at room temperature under hydrogen atmosphere. The resulting mixture was filtered, the filter cake was washed with MeOH (2×10 mL). The resulting mixture was concentrated under reduced pressure. The residue was purified by Prep-TLC ($CH_2Cl_2$/MeOH=20:1) to afford methyl N-(5-aminopyridin-2-yl)carbamate (89 mg, 41.98%) as a off-white solid. LCMS: m/z (ESI), $[M+H]^+$=168.2.

Step3. Methyl (R)-(5-((5-fluoro-4-(7-(3-methoxy-2-(4-methylpiperazin-1-yl) propanamido)-1H-indol-3-yl)pyrimidin-2-yl)amino)pyridin-2-yl)carbamate (Ex. 52)

A mixture of (R)—N-[3-(2-chloro-5-fluoropyrimidin-4-yl)-1H-indol-7-yl]-3-methoxy-2-(4-methylpiperazin-1-yl) propanamide (110.00 mg, 0.246 mmol, 1.00 equiv), RuPhos Palladacycle Gen.3 (20.59 mg, 0.025 mmol, 0.10 equiv), RuPhos (11.49 mg, 0.025 mmol, 0.10 equiv), $K_2CO_3$ (68.03 mg, 0.492 mmol, 2.00 equiv) and methyl-N-(5-aminopyridin-2-yl)carbamate (61.72 mg, 0.369 mmol, 1.50 equiv) in 1,4-dioxane (8.00 mL) was stirred for 2 h at 70° C. under nitrogen atmosphere. The resulting mixture was filtered, the filter cake was washed with $CH_2Cl_2$ (2×5 mL). The resulting mixture was concentrated under vacuum. The residue was purified by Prep-TLC ($CH_2Cl_2$/MeOH 8:1) to afford crude product (110 mg), which was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 28 B to 48 B in 7 min; 254; 220 nm; RT1: 5.82) to afford methyl-N-[5-[(5-fluoro-4-[7-[(R)-3-methoxy-2-(4-methylpiperazin-1-yl) propanamido]-1H-indol-3-yl]pyrimidin-2-yl)amino]pyridin-2-yl]carbamate (65 mg, 45.72%) as a white solid. LCMS: m/z (ESI), $[M+H]^+$=578.4. $^1$H-NMR (400 MHz, DMSO-$d_6$) δ 2.15 (3H, s), 2.35 (4H, s), 2.60-2.68 (2H, m), 2.74 (2H, s), 3.30 (3H, s), 3.51 (1H, t), 3.68 (4H, s), 3.80 (1H, dd), 7.12 (1H, t), 7.53 (1H, d), 7.77 (1H, d), 8.14 (1H, dd), 8.23 (1H, d), 8.43 (1H, d), 8.50 (1H, d), 8.60 (1H, d), 9.53 (1H, s), 9.86 (1H, s), 9.99 (1H, s), 11.48 (1H, s).

Example 53

Preparation of (R)—N-[3-[5-fluoro-2-([1-[2-(hydroxymethyl)phenyl]pyrazol-4-yl]amino) pyrimidin-4-yl]-1H-indol-7-yl]-3-methoxy-2-(4-methylpiperazin-1-yl)propanamide

SCHEME 53

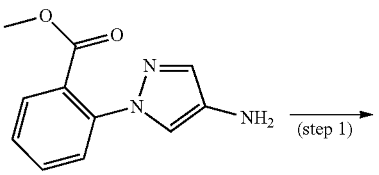

-continued

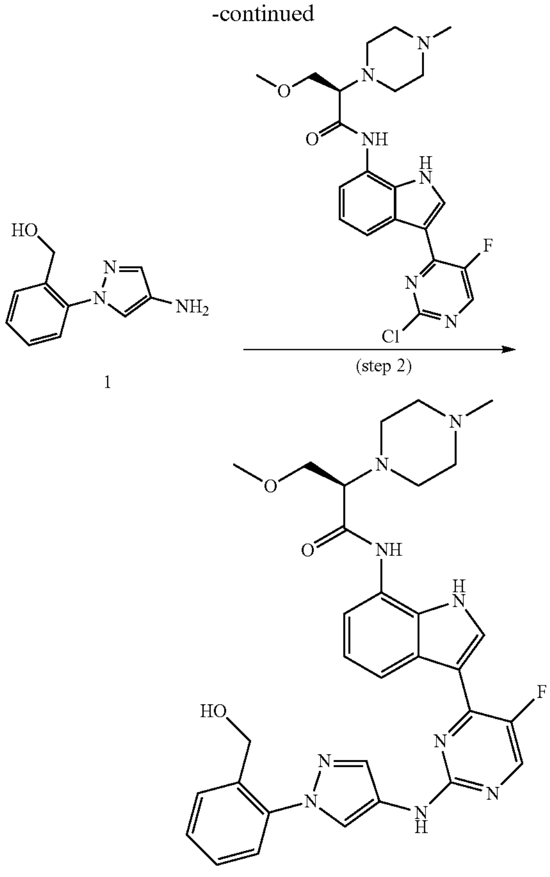

Example 53

Step 1. [2-(4-aminopyrazol-1-yl)phenyl]methanol

Into a 50 mL round-bottom flask were added methyl 2-(4-aminopyrazol-1-yl)benzoate (350.00 mg, 1.611 mmol, 1.00 equiv) and Li $AlH_4$ (183.46 mg, 4.834 mmol, 3.00 equiv) in THF (20.00 mL) at room temperature. The resulting mixture was stirred for 1 h at room temperature under air atmosphere. The reaction was quenched by addition of NaOH at room temperature. The resulting mixture was concentrated under reduced pressure. The crude product was used in the next step without other purification. LCMS: m/z (ESI), $[M+H]^+$=190.3

Step 2. (R)—N-[3-[5-fluoro-2-([1-[2-(hydroxymethyl)phenyl]pyrazol-4-yl]amino) pyrimidin-4-yl]-1H-indol-7-yl]-3-methoxy-2-(4-methylpiperazin-1-yl)propanamide (Ex. 53)

To a solution of (R)—N-[3-(2-chloro-5-fluoropyrimidin-4-yl)-1H-indol-7-yl]-3-methoxy-2-(4-methylpiperazin-1-yl) propanamide (50 mg, 0.112 mmol, 1.00 equiv) and [2-(4-aminopyrazol-1-yl)phenyl]methanol (31.75 mg, 0.168 mmol, 1.50 equiv) in dioxane (5.00 mL) were added BrettPhos Pd G3 (10.14 mg, 0.011 mmol, 0.10 equiv), BrettPhos (6.01 mg, 0.011 mmol, 0.10 equiv) and $Cs_2CO_3$ (109.36 mg, 0.336 mmol, 3.00 equiv). After stirring for 2 hs at 80° C. under a nitrogen atmosphere, the resulting mixture was concentrated under reduced pressure. The residue was purified by Prep-TLC ($CH_2Cl_2$/MeOH 10:1). The crude product (60 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 29 B to 49 B in 7 min; 254; 220 nm; RT1: 6.22). The crude product (30 mg) was purified by Prep-HPLC with the following conditions (Column: CHIRALPAK IC-3, 4.6×50 mm, 3 μm; Mobile Phase A: (Hex:DCM=3:1)(0.1% DEA):EtOH=50:50, Mobile Phase B; Flow rate: 1 mL/min; Gradient: 0 B to 0 B) to afford (R)—N-[3-[5-fluoro-2-([1-[2-(hydroxymethyl)phenyl]pyrazol-4-yl]amino)pyrimidin-4-yl]-1H-indol-7-yl]-3-methoxy-2-(4-methylpiperazin-1-yl) propanamide (7 mg, 10.43%) as a white solid. LCMS: m/z (ESI), $[M+H]^+$=600. 3 $^1$H-NMR (300 MHz, DMSO-$d_6$) δ 2.24 (3H, s), 2.49 (4H, s), 2.68 (2H, s), 2.78 (2H, s), 3.30 (3H, s), 3.53 (1H, t), 3.63-3.83 (2H, m), 4.51 (2H, d), 5.25-5.27 (1H, m), 7.11 (1H, s), 7.43 (3H, d), 7.52 (1H, d), 7.66 (1H, s), 7.85 (1H, s), 8.21 (1H, s), 8.31 (1H, s), 8.42 (2H, d), 9.53 (1H, s), 9.87 (1H, s), 11.45 (1H, s).

Example 54

Preparation of (R)—N-[3-(5-fluoro-2-[[6-(1,3-oxazol-2-ylmethoxy)pyridin-3-yl]amino]pyrimidin-4-yl)-1H-indol-7-yl]-3-methoxy-2-(4-methylpiperazin-1-yl)propanamide

SCHEME 54

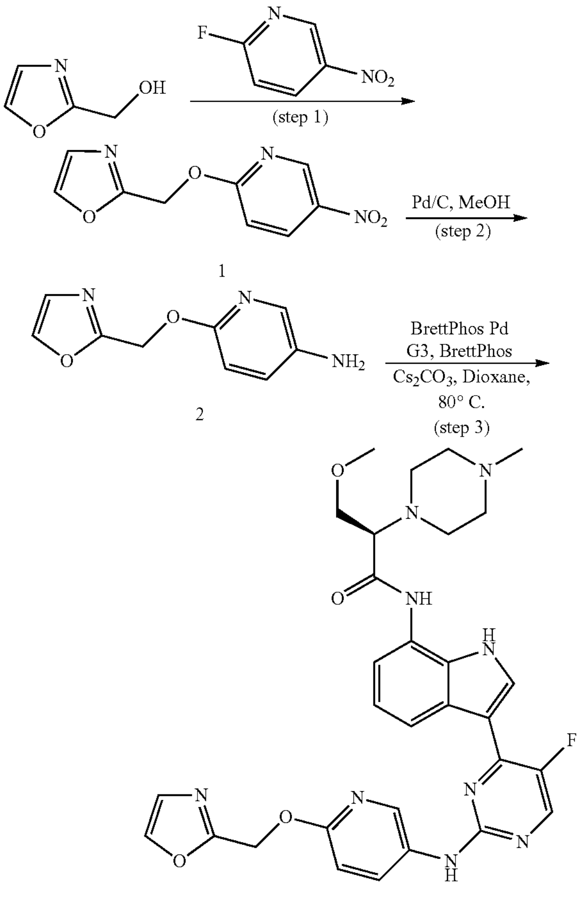

Example 54

Step 1. 5-nitro-2-(1,3-oxazol-2-ylmethoxy)pyridine

To a stirred mixture of 1,3-oxazol-2-ylmethanol (500.00 mg, 5.046 mmol, 1.00 equiv) and NaH (157.42 mg, 6.560 mmol, 1.30 equiv) at 0° C. in DMF (20.00 mL) was added 2-fluoro-5-nitropyridine (716.98 mg, 5.046 mmol, 1.00 equiv) dropwise at room temperature under air atmosphere. The resulting mixture was stirred for 2 h at room temperature under air atmosphere. The resulting mixture was diluted with water (150 mL) and extracted with EtOAc (3×200 mL). The combined organic layers were washed with brine (3×50 mL), dried over anhydrous $Na_2SO_4$. After filtration, the filtrate was concentrated under reduced pressure. This resulted in 5-nitro-2-(1,3-oxazol-2-ylmethoxy)pyridine (900 mg, 80.64%) as a light yellow solid. LCMS: m/z (ESI), $[M+H]^+$=222.2. $^1$H-NMR (300 MHz, MeOD-$d_4$) δ 5.63 (2H, s), 7.08 (1H, dd), 7.22 (1H, d), 7.97 (1H, d), 8.52 (1H, dd), 9.07 (1H, dd).

Step 2. 6-(1,3-oxazol-2-ylmethoxy)pyridin-3-amine

A mixture of 5-nitro-2-(1,3-oxazol-2-ylmethoxy)pyridine (500.00 mg) and Pd/C (20.00 mg) in MeOH (30.00 mL) was stirred at room temperature under hydrogen atmosphere for 1 h. The resulting mixture was filtered, the filter cake was washed with methanol (3×100 mL). The filtrate was concentrated under reduced pressure. The residue was purified by Prep-TLC ($CH_2Cl_2$/MeOH 10:1) to afford 6-(1,3-oxazol-2-ylmethoxy)pyridin-3-amine (420 mg, 97.2%) as a brown solid. LCMS: m/z (ESI), $[M+H]^+$=192.2. $^1$H NMR (300 MHz, MeOD-$d_4$) δ 5.34 (2H, s), 6.70 (1H, dd), 7.17 (3H, m), 7.61 (1H, dd), 7.92 (2H, d)

Step 3. (R)—N-[3-(5-fluoro-2-[[6-(1,3-oxazol-2-ylmethoxy)pyridin-3-yl]amino]pyrimidin-4-yl)-1H-indol-7-yl]-3-methoxy-2-(4-methylpiperazin-1-yl)propanamide (Ex. 54)

To a stirred solution of (R)—N-[3-(2-chloro-5-fluoropyrimidin-4-yl)-1H-indol-7-yl]-3-methoxy-2-(4-methylpiperazin-1-yl)propanamide (120.00 mg, 0.269 mmol, 1.00 equiv) and 6-(1,3-oxazol-2-ylmethoxy)pyridin-3-amine (102.67 mg, 0.537 mmol, 2.00 equiv) in dioxane (20.00 mL) were added BrettPhos Pd G3 (36.51 mg, 0.040 mmol, 0.15 equiv) and BrettPhos (21.62 mg, 0.040 mmol, 0.15 equiv) and $K_2CO_3$ (111.33 mg, 0.806 mmol, 3.00 equiv) at room temperature under nitrogen atmosphere. The resulting mixture was stirred for 2 h at 80° C. under nitrogen atmosphere. The residue was purified by Prep-TLC ($CH_2Cl_2$/MeOH 10:1) to afford a crude solid. The crude product (100 mg) was purified by Chiral-Prep-HPLC with the following conditions (Column: CHIRAL ART Cellulose-SB, 4.6×100 mm, 3 μm; Mobile Phase A: MtBE(0.1% DEA):EtOH=90:10, Mobile Phase B; Flow rate: 1 mL/min; Gradient: 0 B to OB) to afford (R)—N-[3-(5-fluoro-2-[[6-(1,3-oxazol-2-ylmethoxy)pyridin-3-yl]amino]pyrimidin-4-yl)-1H-indol-7-yl]-3-methoxy-2-(4-methylpiperazin-1-yl)propanamide (71.9 mg, 44.06%) as a white solid. LCMS: m/z (ESI), $[M+H]^+$=602.4. $^1$H NMR (300 MHz, DMSO-$d_6$) δ 2.16 (3H, s), 2.37 (4H, s), 2.63 (2H, m), 2.76 (2H, m), 3.51 (3H, t), 3.69 (2H, dd), 3.81 (1H, dd), 5.44 (2H, s), 6.93 (1H, d), 7.13 (1H, t), 7.26 (1H, d), 7.54 (1H, dd), 8.12 (2H, m), 8.24 (1H, d), 8.42 (1H, d), 8.48 (2H, m), 9.48 (1H, s), 9.86 (1H, s), 11.47 (1H, s).

Example 55

Preparation of Methyl (R)-3-(6-((5-fluoro-4-(7-(3-methoxy-2-(4-methylpiperazin-1-yl)propanamido)-1H-indol-3-yl)pyrimidin-2-yl)amino)pyridin-2-yl)propanoate

SCHEME 55

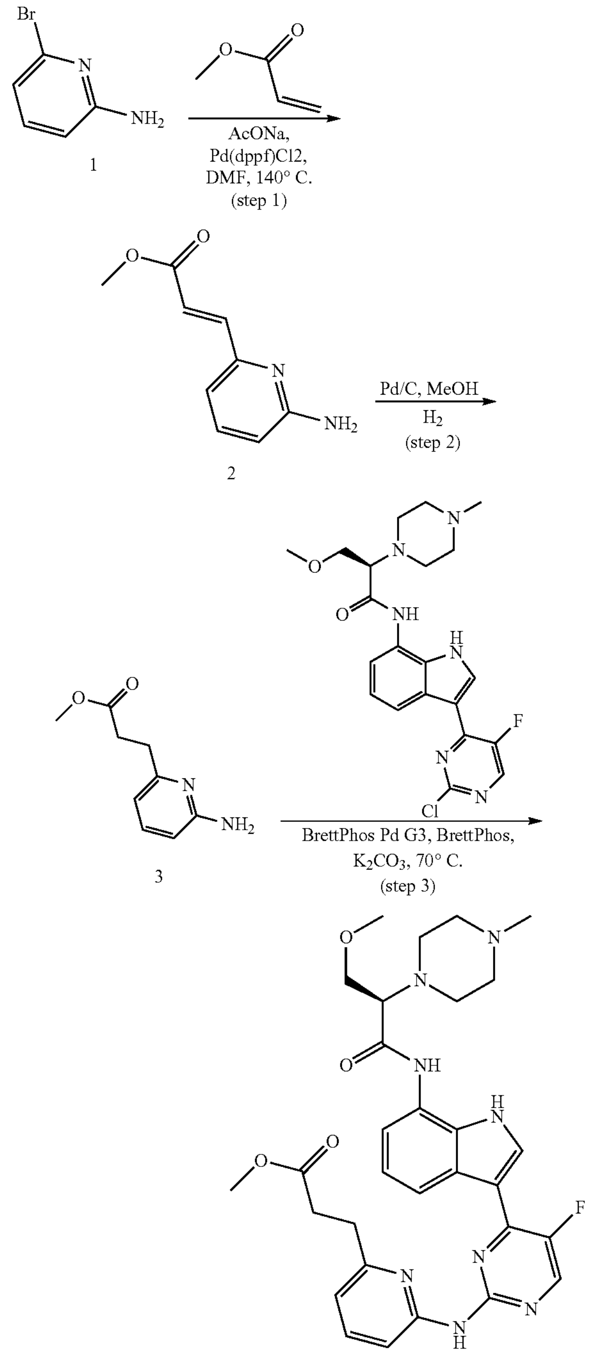

1

2

3

Example 55

Step 1. Preparation of Methyl-3-(6-aminopyridin-2-yl)acrylate

A mixture of methyl acrylate (0.75 g, 8.712 mmol, 1.51 equiv) and 6-bromopyridin-2-amine (1.00 g, 5.780 mmol, 1.00 equiv) in DMF (20.00 mL), AcONa (0.95 g, 11.581 mmol, 2.00 equiv) and Pd(dppf)$Cl_2$ (0.42 g, 0.574 mmol, 0.10 equiv) was stirred at 140° C. under nitrogen atmosphere. The resulting mixture was extracted with $CH_2Cl_2$ (3×20 mL). The combined organic layers were washed with water (3×50 mL), dried over anhydrous $Na_2SO_4$. After filtration, the filtrate was concentrated under reduced pressure. The residue was purified by Prep-TLC ($CH_2Cl_2$/MeOH 10:1) to afford methyl-3-(6-aminopyridin-2-yl)prop-2-enoate (450 mg, 40.02%) as a yellow solid. $[M+H]^+$=179.0

Step 2. Methyl 3-(6-aminopyridin-2-yl)propanoate

A mixture of methyl-3-(6-aminopyridin-2-yl)prop-2-enoate (80 mg, 0.449 mmol, 1.00 equiv) and Pd/C (9.56 mg, 0.090 mmol, 0.20 equiv) in MeOH (8.00 mL) was stirred at room temperature under hydrogen atmosphere for 1 h. The resulting mixture was filtered, the filter cake was washed with MeOH (3×10 mL). The filtrate was concentrated under reduced pressure. The residue was purified by Prep-TLC ($CH_2Cl_2$/MeOH 10:1) to afford methyl 3-(6-aminopyridin-2-yl)propanoate (135 mg, 64.54%) as a yellow solid. $[M+H]^{+=}$181.1

Step 3. Preparation of Methyl (R)-3-(6-((5-fluoro-4-(7-(3-methoxy-2-(4-methyl-piperazin-1-yl)propanamido)-1H-indol-3-yl)pyrimidin-2-yl)amino)pyridin-2-yl)propanoate (Ex. 55)

To a stirred mixture of (R)—N-[3-(2-chloro-5-fluoropyrimidin-4-yl)-1H-indol-7-yl]-3-methoxy-2-(4-methylpiperazin-1-yl)propanamide (150.00 mg, 0.336 mmol, 1.00 equiv) and methyl 3-(6-aminopyridin-2-yl)propanoate (90.73 mg, 0.503 mmol, 1.50 equiv) in dioxane (5.00 mL) were added BrettPhos Pd G3 (45.64 mg, 0.050 mmol, 0.15 equiv), $K_2CO_3$ (92.77 mg, 0.671 mmol, 2.00 equiv) and BrettPhos (36.03 mg, 0.067 mmol, 0.20 equiv). The resulting mixture was stirred at 70° C. under nitrogen atmosphere. The resulting mixture was filtered, the filter cake was washed with DCM (3×20 mL). The filtrate was concentrated under reduced pressure. The residue was purified by Prep-TLC ($CH_2Cl_2$/MeOH 10:1) to the crude product (100 mg), which was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 31% B to 45% B in 7 min; 254; 220 nm; Rt: 6.30 min) to afford methyl 3-[6-[(5-fluoro-4-[7-[(R)-3-methoxy-2-(4-methyl-piperazin-1-yl)propanamido]-1H-indol-3-yl]pyrimidin-2-yl)amino]pyridin-2-yl]propanoate (33.8 mg, 16.71%) as an off-white solid. $[M+H]^{+=}$591.4. $^1$H-NMR (300 MHz, DMSO-$d_6$) δ 2.16 (3H, s), 2.37 (4H, s), 2.64 (2H, d), 2.80 (4H, dd), 2.97 (2H, t), 3.30 (3H, s), 3.51 (1H, t), 3.61 (3H, s), 3.69 (1H, dd), 3.81 (1H, dd), 6.89 (1H, d), 7.15 (1H, t), 7.54 (1H, d), 7.60-7.72 (1H, m), 8.07 (1H, d), 8.27 (1H, s), 8.50 (1H, d), 8.69-8.78 (1H, m), 9.84 (2H, d), 11.48 (1H, s)

Example 60

Preparation of (R)—N-(3-(5-fluoro-2-((6-(2-hydroxyethyl)pyridin-3-yl)amino)pyrimidin-4-yl)-1H-indol-7-yl)-3-methoxy-2-(4-methylpiperazin-1-yl)propanamide (Ex. 60)

SCHEME 60

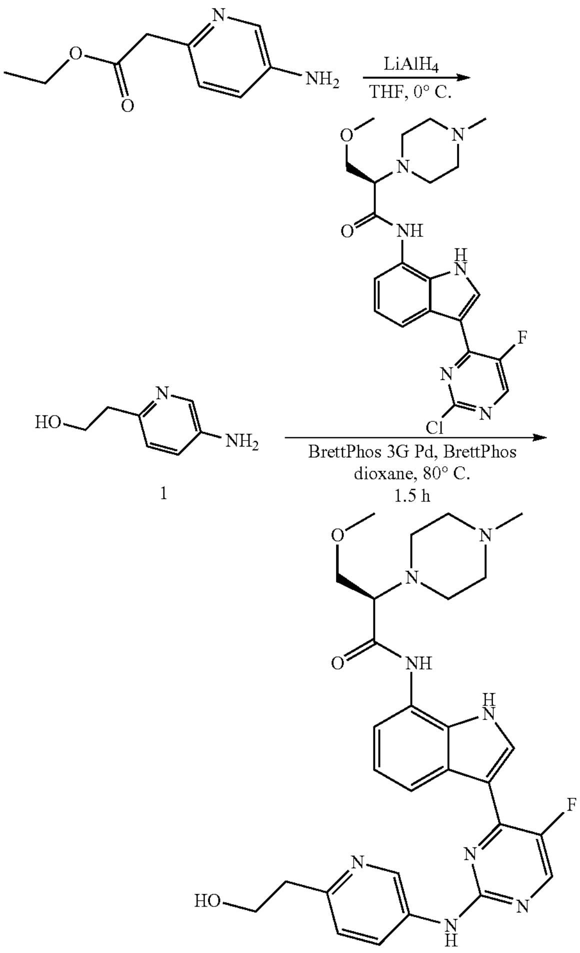

Example 60

Step1. 2-(5-aminopyridin-2-yl)ethan-1-ol

Into a 50 mL round-bottom flask were added Li $AlH_4$ (189.55 mg, 4.994 mmol, 3.00 equiv) in THF (13 mL) at room temperature. Solution of ethyl-2-(5-aminopyridin-2-yl)acetate (300.00 mg, 1.665 mmol, 1.00 equiv) in THF (7 mL) was added to the above mixture at 0° C. The resulting mixture was stirred for 0.5 h at 0° C. under air atmosphere. The reaction was quenched by the addition of Water (0.2 mL) at room temperature and then 15% NaOH (0.6 mL), water (0.2 mL). The resulting mixture was dried anhydrous mg $SO_4$, the solid was filtered out and the filtrate was evaporated out to afford 2-(5-aminopyridin-2-yl)ethanol (200 mg, 86.95%) as a yellow solid. $^1$H-NMR (400 MHz, $CDCl_3$) δ 2.91 (2H, t), 3.95-4.03 (2H, m), 6.91-7.00 (2H, m), 8.00 (1H, t)

Step 2. (R)—N-(3-(5-fluoro-2-((6-(2-hydroxyethyl)pyridin-3-yl)amino)pyrimidin-4-yl)-1H-indol-7-yl)-3-methoxy-2-(4-methylpiperazin-1-yl)propanamide (Ex. 60)

Into a 40 mL vial were added (R)—N-[3-(2-chloro-5-fluoropyrimidin-4-yl)-1H-indol-7-yl]-3-methoxy-2-(4-methylpiperazin-1-yl)propanamide (100.00 mg, 0.224 mmol, 1.00 equiv), 2-(5-aminopyridin-2-yl)ethanol (37.10 mg, 0.269 mmol, 1.20 equiv), BrettPhos (12.01 mg, 0.022 mmol, 0.10 equiv), BrettPhos Pd G3 (20.28 mg, 0.022 mmol, 0.10 equiv) and $Cs_2CO_3$ (218.72 mg, 0.671 mmol, 3.00 equiv) in dioxane (20 mL) at room temperature. The resulting mixture was stirred for 1.5 h at 80° C. The solid was filtered out and the filter cake was washed with MeOH (2×10 mL). The filtrate was concentrated under reduced pressure. The residue was purified by Prep-TLC ($CH_2Cl_2$/MeOH 7:1) to afford a crude solid. The crude product (80 mg) was purified by Prep-HPLC with the following conditions (Column: XBridge Prep OBD C18 Column, 30×150 mm, 5 μm; Mobile Phase A: Mobile Phase B; Flow rate: 60 mL/min; Gradient:% B; 254; 220 nm; RT1: 7.25) to afford (R)—N-[3-(5-fluoro-2-[[6-(2-hydroxyethyl)pyridin-3-yl]amino]pyrimidin-4-yl)-1H-indol-7-yl]-3-methoxy-2-(4-methyl-piperazin-1-yl)propanamide (25 mg, 20.37%) as a white solid. LCMS: m/z (ESI), $[M+H]^+$=549.3 $^1$H-NMR (400 MHz, DMSO-$d_6$) δ 2.15 (3H, s), 2.35 (4H, s), 2.58-2.66 (2H, m), 2.75 (2H, dt), 2.85 (2H, t), 3.30 (3H, s), 3.51 (1H, t), 3.64-3.84 (4H, m), 4.64 (1H, t), 7.08-7.27 (2H, m), 7.55 (1H, dd), 8.12 (1H, dd), 8.24 (1H, d), 8.44 (1H, d), 8.50-8.56 (1H, m), 8.78 (1H, dd), 9.59 (1H, s), 9.88 (1H, s), 11.47 (1H, s).

Example 61

Preparation of (R)—N-(3-(5-fluoro-2-((4-(hydroxymethyl)-1H-indazol-6-yl)amino)pyrimidin-4-yl)-1H-indol-7-yl)-3-methoxy-2-(4-methylpiperazin-1-yl)propanamide

SCHEME 61

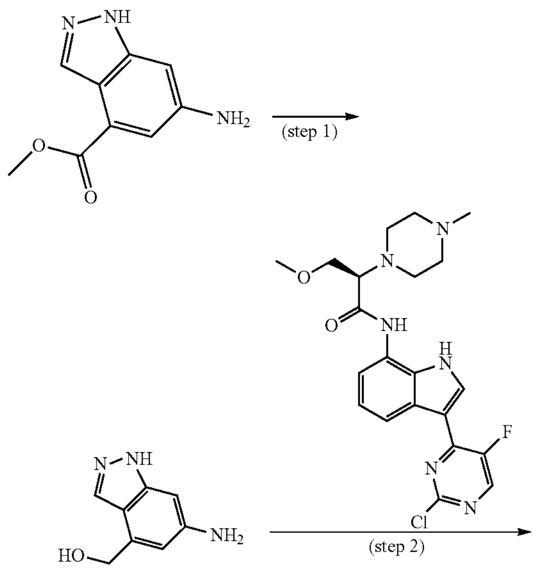

1

-continued

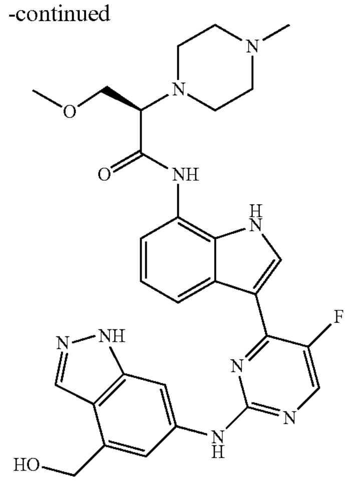

Example 61

Step 1. Preparation of (6-amino-1H-indazol-4-yl)methanol

To a stirred mixture of methyl 6-amino-1H-indazole-4-carboxylate (300.00 mg, 1.569 mmol, 1.00 equiv) in THF (5.00 mL) were added $LiAlH_4$ (178.66 mg, 4.707 mmol, 3.00 equiv) in portions at 0° C. The resulting mixture was stirred for 1 h at 70° C. The reaction was quenched by the addition of Water (0.08 mL) and NaOH (0.08 mL, 15%) at 0° C. The resulting mixture was filtered, the filter cake was washed with THF (3×10 mL). The filtrate was concentrated under reduced pressure. This gives (6-amino-1H-indazol-4-yl)methanol (100 mg, 39.06%) as a light yellow oil. LCMS: m/z (ESI), $[M+H]^+$=164.2.

Step 2. Preparation of (R)—N-(3-(5-fluoro-2-((4-(hydroxymethyl)-1H-indazol-6-yl)amino)pyrimidin-4-yl)-1H-indol-7-yl)-3-methoxy-2-(4-methylpiperazin-1-yl)propanamide (Ex. 61)

A mixture of (R)—N-[3-(2-chloro-5-fluoropyrimidin-4-yl)-1H-indol-7-yl]-3-methoxy-2-(4-methylpiperazin-1-yl)propanamide (50.00 mg, 0.112 mmol, 1.00 equiv), (6-amino-1H-indazol-4-yl)methanol (21.91 mg, 0.134 mmol, 1.20 equiv), $K_2CO_3$ (46.39 mg, 0.336 mmol, 3.00 equiv), BrettPhos (12.01 mg, 0.022 mmol, 0.20 equiv) and BrettPhos Pd G3 (10.14 mg, 0.011 mmol, 0.10 equiv) in dioxane (10.00 mL) was stirred for 2 h at 80° C. under nitrogen atmosphere. The resulting mixture was concentrated under reduced pressure. The residue was purified by Prep-TLC ($CH_2Cl_2$/MeOH 12:1) to afford (R)—N-[3-(5-fluoro-2-[[4-(hydroxymethyl)-1H-indazol-6-yl]amino]pyrimidin-4-yl)-1H-indol-7-yl]-3-methoxy-2-(4-methylpiperazin-1-yl)propanamide (20 mg, crude) as a light yellow solid. The crude product (20 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 21 B to 41 B in 7 min; 254/220 nm; RT1: 5.65) to afford (R)—N-[3-(5-fluoro-2-[[4-(hydroxymethyl)-1H-indazol-6-yl]amino]pyrimidin-4-yl)-1H-indol-7-yl]-3-methoxy-2-(4-methylpiperazin-1-yl)propanamide (2.5 mg, 3.90%) as a white solid. LCMS: m/z (ESI), $[M+H]^+$=574.4. $^1$H-NMR (300 MHz, MeOD-$d_4$) δ 2.31 (3H, s), 2.58 (4H, s), 2.86 (4H, d), 3.41 (3H, s), 3.49 (1H, t), 3.75-3.98 (2H, m), 7.04-7.22 (2H, m), 7.30 (1H, d), 8.07-8.19 (3H, m), 8.29 (1H, d), 8.67 (1H, dd)

Example 66

Preparation of (R)—N-[3-(5-fluoro-2-[[6-(2-hydroxyethyl)-5-methoxypyridin-3-yl]amino]pyrimidin-4-yl)-1H-indol-7-yl]-3-methoxy-2-(4-methylpiperazin-1-yl)propanamide

SCHEME 66

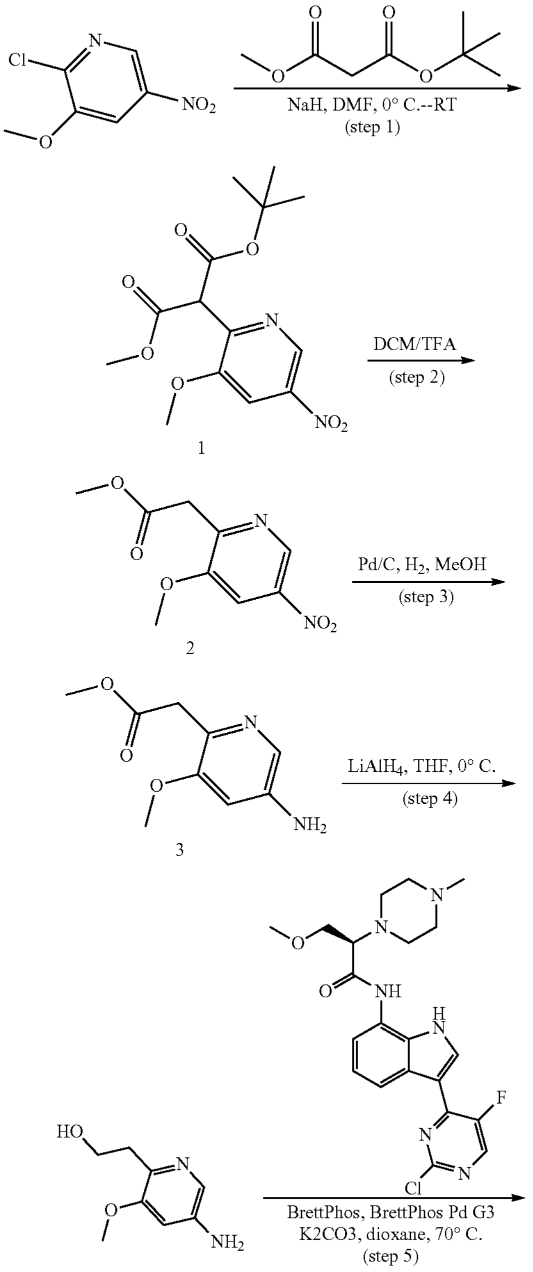

1

2

3

4

-continued

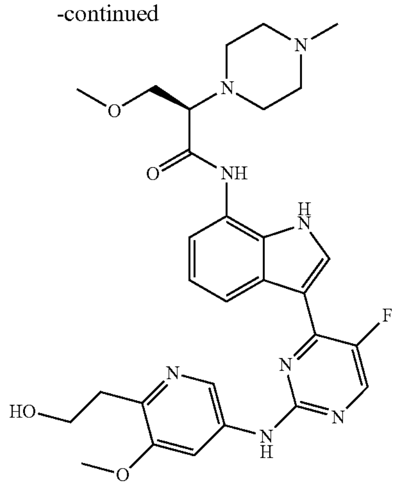

Example 66

Step 1. 1-tert-butyl 3-methyl 2-(3-methoxy-5-nitropyridin-2-yl)propanedioate A solution of 2-chloro-3-methoxy-5-nitropyridine (1.00 g, 5.303 mmol, 1.00 equiv) in DMF (100.0 mL) was treated with NaH (0.32 g, 13.258 mmol, 2.50 equiv) at 0° C. The solution was stirred for 10 min at room temperature. To the above mixture was added 1-tert-butyl 3-methyl propanedioate (1.52 g, 8.750 mmol, 1.65 equiv) dropwise at 0° C. The resulting mixture was stirred for 15 h at room temperature. The resulting mixture was quenched with water (30 mL), and extracted with EtOAc (3×35 mL). The combined organic layers were washed with brine (1×30 mL), dried over anhydrous $Na_2SO_4$. After filtration, the filtrate was concentrated under reduced pressure. The residue was purified by Prep-TLC (PE/EtOAc 5:1) to afford 1-tert-butyl-3-methyl-2-(3-methoxy-5-nitropyridin-2-yl)propanedioate (1.46 g, 84.37%) as a reddish brown oil. LCMS: m/z (ESI), $[M+H]^+$=327.3. $^1$H-NMR (300 MHz, Chloroform-d) δ 1.50 (9H, s), 3.82 (3H, s), 3.98 (3H, s), 5.09 (1H, s), 7.94 (1H, d), 9.02 (1H, d).

Step 2. Methyl 2-(3-methoxy-5-nitropyridin-2-yl)acetate

To a stirred solution of 1-tert-butyl 3-methyl 2-(3-methoxy-5-nitropyridin-2-yl)propanedioate (1.40 g, 4.290 mmol, 1.00 equiv) in DCM (20.0 mL) were added TFA (6.00 mL, 80.778 mmol, 18.83 equiv). The resulting mixture was stirred for 18 h at 25° C. The resulting mixture was concentrated under reduced pressure. The mixture was basified to pH8 with saturated $NaHCO_3$(aq.). The resulting mixture was extracted with $CH_2Cl_2$ (3×80 mL). The combined organic layer was dried over anhydrous $Na_2SO_4$. After filtration, the filtrate was concentrated under reduced pressure to afford methyl 2-(3-methoxy-5-nitropyridin-2-yl)acetate (0.88 g, 90.68%) as a reddish brown oil. LCMS: m/z (ESI), $[M+H]^{+}$=227.2. $^1$H-NMR (300 MHz, Chloroform-d) δ 3.74 (3H, s), 3.98 (3H, s), 4.00 (2H, s), 7.92 (1H, d), 9.01 (1H, d).

Step 3. Methyl 2-(5-amino-3-methoxypyridin-2-yl)acetate

To a solution of methyl 2-(3-methoxy-5-nitropyridin-2-yl)acetate (840.00 mg, 3.714 mmol, 1.00 equiv) in MeOH (50 mL) was added Pd/C (10%, 79.04 mg) under nitrogen atmosphere in a 250 mL round-bottom flask. The mixture was hydrogenated at room temperature for 1 h under hydrogen atmosphere using a hydrogen balloon, The mixture was filtered through a Celite pad and the filtrate was concentrated under reduced pressure to afford methyl 2-(5-amino-3-methoxypyridin-2-yl)acetate (445 mg, 61.07%) as a yellow solid. LCMS: m/z (ESI), $[M+H]^+$=197.2

Step 4. 2-(5-amino-3-methoxypyridin-2-yl)ethanol

To a stirred solution of $LiAlH_4$ (203.11 mg, 5.352 mmol, 3.00 equiv) in THF (10 mL) were added methyl 2-(5-amino-3-methoxypyridin-2-yl)acetate (350.00 mg, 1.784 mmol, 1.00 equiv) in THF (20 mL) dropwise at 0° C. The resulting mixture was stirred for 30 min at 0° C. The reaction was quenched by the addition of $Na_2SO_4.10H_2O$. The resulting mixture was filtered, the filter cake was washed with ethyl acetate (3×5 mL). The filtrate was concentrated under reduced pressure to afford 2-(5-amino-3-methoxypyridin-2-yl)ethanol (243 mg, 80.99%) as a light orange solid. LCMS: m/z (ESI), $[M+H]^{+=}$169.0

Step 5. (R)—N-[3-(5-fluoro-2-[[6-(2-hydroxyethyl)-5-methoxypyridin-3-yl]amino]pyrimidin-4-yl)-1H-indol-7-yl]-3-methoxy-2-(4-methylpiperazin-1-yl) propanamide (Ex. 66)

To a solution of (R)—N-[3-(2-chloro-5-fluoropyrimidin-4-yl)-1H-indol-7-yl]-3-methoxy-2-(4-methylpiperazin-1-yl) propanamide (130.00 mg, 0.291 mmol, 1.00 equiv) and 2-(5-amino-3-methoxypyridin-2-yl)ethanol (63.60 mg, 0.378 mmol, 1.3 equiv) in dioxane (10.0 mL) were added BrettPhos (31.23 mg, 0.058 mmol, 0.20 equiv) and BrettPhos Pd G3 (52.74 mg, 0.058 mmol, 0.20 equiv) and $K_2CO_3$ (80.40 mg, 0.582 mmol, 2.00 equiv). After stirring for 2 h at 70° C. under a nitrogen atmosphere. The residue was purified by TLC ($CH_2Cl_2$/MeOH 8:1) to afford (R)—N-[3-(5-fluoro-2-[[6-(2-hydroxyethyl)-5-methoxypyridin-3-yl] amino]pyrimidin-4-yl)-1H-indol-7-yl]-3-methoxy-2-(4-methylpiperazin-1-yl)propanamide (34.35 mg, 20.41%) as a white solid. LCMS: m/z (ESI), $[M+H]^+$=579.4. $^1$H-NMR (300 MHz, DMSO-$d_6$) δ 2.13 (3H, s), 2.22-2.44 (4H, m), 2.54-2.80 (4H, m), 2.86 (2H, t), 3.28 (3H, s), 3.49 (1H, t), 3.59-3.70 (3H, m), 3.72-3.84 (4H, m), 4.57 (1H, t), 7.11 (1H, t), 7.52 (1H, d), 7.85 (1H, d), 8.23 (1H, d), 8.30-8.64 (3H, m), 9.60 (1H, s), 9.86 (1H, s), 11.47 (1H, s).

Example 67

Preparation of (R)—N-(3-(5-fluoro-2-((1-(3-(hydroxymethyl)phenyl)-1H-pyrazol-4-yl)amino) pyrimidin-4-yl)-1H-indol-7-yl)-3-methoxy-2-(4-methylpiperazin-1-yl)propanamide

SCHEME 67

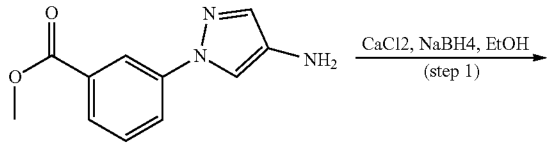

-continued

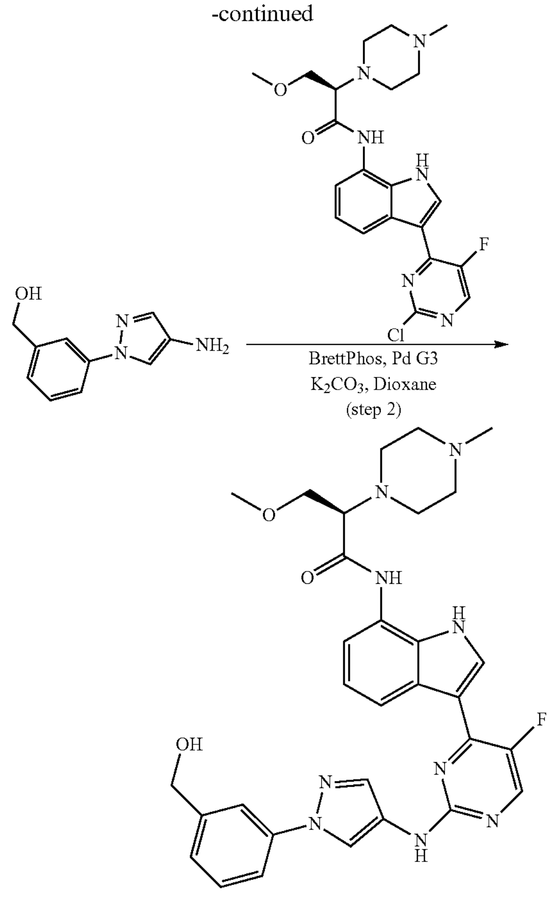

Example 67

Step1. (3-(4-amino-1H-pyrazol-1-yl)phenyl)methanol

Into a 40 mL vial were added methyl 3-(4-aminopyrazol-1-yl)benzoate (130.00 mg, 0.598 mmol, 1.00 equiv), and $CaCl_2$ (99.63 mg, 0.898 mmol, 1.50 equiv), $NaBH_4$ (67.92 mg, 1.795 mmol, 3 equiv), EtOH (15.00 mL) at room temperature. and the reaction mixture was stirred at 0° C. for 3 h. The resulting mixture was extracted with EtOAc (3×20 mL). The combined organic layers were washed with brine (3×10 mL), dried over anhydrous $Na_2SO_4$. After filtration, the filtrate was concentrated under reduced pressure. The crude product was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 25% B to 40% B in 7 min; 254/220 nm; Rt: 5.77 min) to afford [3-(4-aminopyrazol-1-yl)phenyl]methanol (80 mg, 70.65%) as a white solid. LCMS: m/z (ESI), $[M+H]^+$=190.3.

Step 2. (R)—N-[3-[5-fluoro-2-([1-[3-(hydroxymethyl)phenyl]pyrazol-4-yl]amino) pyrimidin-4-yl]-1H-indol-7-yl]-3-methoxy-2-(4-methylpiperazin-1-yl)propanamide (Ex. 67)

Into a 40 mL vial were added (R)—N-[3-(2-chloro-5-fluoropyrimidin-4-yl)-1H-indol-7-yl]-3-methoxy-2-(4-methylpiperazin-1-yl)propanamide (100.00 mg, 0.224 mmol, 1.00 equiv), and [3-(4-aminopyrazol-1-yl)phenyl] methanol (63.51 mg, 0.336 mmol, 1.50 equiv), BrettPhos Pd G3 (20.28 mg, 0.022 mmol, 0.1 equiv), $K_2CO_3$ (61.85 mg, 0.448 mmol, 2 equiv), Dioxane (15.00 mL) at room temperature. Then the mixture was stirred at 70° C. under nitrogen atmosphere for 3 h. And the LCMS is OK. The resulting mixture was diluted with water (10 mL), and extracted with EtOAc (3×20 mL). The combined organic layers were washed with brine (3×10 mL), dried over anhydrous $Na_2SO_4$. After filtration, the filtrate was concentrated under reduced pressure. The crude product was purified by Prep-HPLC with the following conditions (Column: XBridge Prep OBD C18 Column 30×150 mm, 5 μm; Mobile Phase A: Water (0.05% $NH_3H_2O$), Mobile Phase B: ACN; Flow rate: 60 mL/min; Gradient: 25% B to 40% B in 7 min) to afford (R)—N-[3-[5-fluoro-2-([1-[3-(hydroxymethyl) phenyl]pyrazol-4-yl]amino)pyrimidin-4-yl]-1H-indol-7-yl]-3-methoxy-2-(4-methylpiperazin-1-yl) propanamide (25 mg, 18.63%) as a white solid. LCMS: m/z (ESI), $[M+H]^+$ =600.4. $^1$H-NMR (300 MHz, DMSO-$d_6$) δ 2.14 (3H, s), 2.35 (4H, s), 2.56-2.68 (2H, m), 2.74 (2H, q), 3.30 (3H, s), 3.50 (1H, t), 3.67 (1H, dd), 3.79 (1H, dd), 4.56 (2H, d), 5.30 (1H, d), 7.11 (1H, t), 7.21 (1H, d), 7.41 (1H, t), 7.57 (2H, dd), 7.72 (1H, t), 7.82 (1H, s), 8.17-8.25 (1H, m), 8.43-8.63 (3H, m), 9.60 (1H, s), 9.87 (1H, s), 11.46 (1H, s).

Example 68

Preparation of (R)—N-(3-(5-fluoro-2-((5-(2-(methylamino)-2-oxoethoxy)pyridin-3-yl)amino) pyrimidin-4-yl)-1H-indol-7-yl)-3-methoxy-2-(4-methylpiperazin-1-yl)propanamide

SCHEME 68

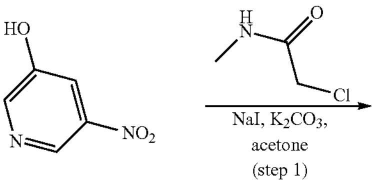

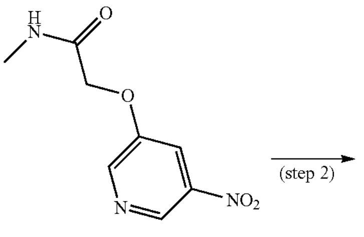

1

-continued

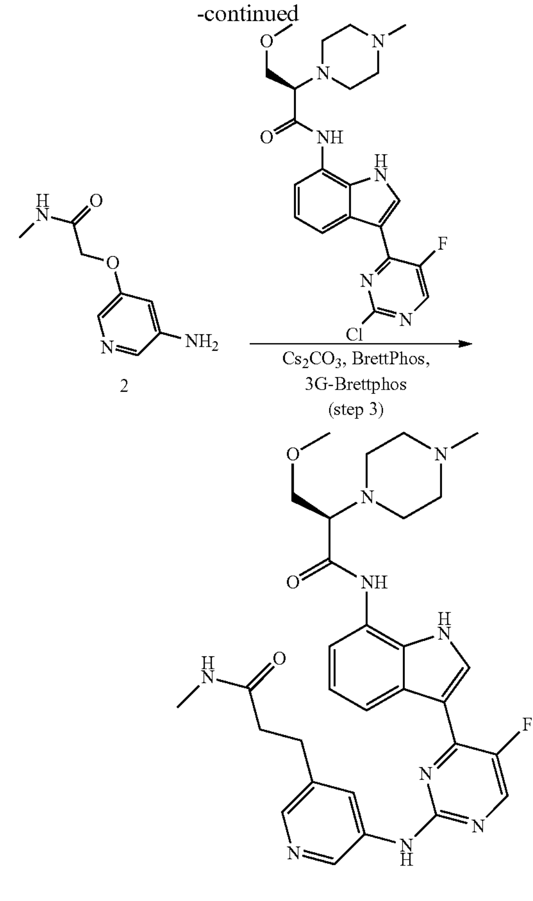

Example 68

Step 1. N-methyl-2-((5-nitropyridin-3-yl)oxy)acetamide

A mixture of 5-nitropyridin-3-ol (70.00 mg, 0.500 mmol, 1.00 equiv), NaI (7.49 mg, 0.050 mmol, 0.10 equiv), 2-chloro-N-methyl-acetamide (80.60 mg, 0.749 mmol, 1.50 equiv) and $K_2CO_3$ (138.11 mg, 0.999 mmol, 2.00 equiv) in propan-2-one (5.00 mL) was stirred for 2 hrs at 65° C. under air atmosphere. The resulting mixture was concentrated under vacuum. The crude product was re-crystallized from EtOAc/PE to afford N-methyl-2-[(5-nitropyridin-3-yl)oxy] acetamide (525 mg, 69.66%) as a yellow solid. LCMS: m/z (ESI), $[M+H]^+$=212.0. $^1$H-NMR (400 MHz, $CDCl_3$) δ 2.98 (3H, d), 4.66 (2H, s), 8.02 (1H, t), 8.70 (1H, d), 9.17 (1H, d).

Step 2. 2-((5-aminopyridin-3-yl)oxy)-N-methylacetamide

To a stirred solution of N-methyl-2-[(5-nitropyridin-3-yl) oxy]acetamide (240.00 mg, 1.136 mmol, 1.00 equiv) in MeOH (20.00 mL) were added Pd/C (120.94 mg, 1.136 mmol, 1.00 equiv). The resulting mixture was stirred for 4 h at room temperature under hydrogen atmosphere. The resulting mixture was filtered, the filter cake was washed with MeOH (3×20 mL). The filtrate was concentrated under reduced pressure to afford 2-[(5-aminopyridin-3-yl)oxy]-N-methylacetamide (201 mg, 97.61%) as yellow solid. LCMS: m/z (ESI), $[M+H]^+$=182.2.

Step 3. (R)—N-(3-(5-fluoro-2-((5-(2-(methylamino)-2-oxoethoxy)pyridin-3-yl)amino) pyrimidin-4-yl)-1H-indol-7-yl)-3-methoxy-2-(4-methylpiperazin-1-yl)propanamide (Ex. 68)

To a stirred mixture of (R)—N-[3-(2-chloro-5-fluoropyrimidin-4-yl)-1H-indol-7-yl]-3-methoxy-2-(4-methylpiperazin-1-yl)propanamide (150.00 mg, 0.336 mmol, 1.00 equiv) and 2-[(5-aminopyridin-3-yl)oxy]-N-methylacetamide (121.63 mg, 0.671 mmol, 2.00 equiv) in dioxane (2.00 mL) were added Brettphos (36.03 mg, 0.067 mmol, 0.20 equiv) and BrettPhos Pd G3 (60.85 mg, 0.067 mmol, 0.20 equiv), $Cs_2CO_3$ (328.07 mg, 1.007 mmol, 3.00 equiv). The resulting mixture was stirred for 2 h at 80° C. under nitrogen atmosphere. The resulting mixture was concentrated under vacuum. The residue was purified by Prep-TLC ($CH_2Cl_2$/MeOH 8:1) to afford crude product. The crude product (150 mg) was purified by Prep-HPLC with the following conditions (Column: XBridge Prep OBD C18 Column, 30×150 mm, 5 μm; Mobile Phase A: Water (0.05% $NH_3H_2O$), Mobile Phase B: ACN; Flow rate: 60 mL/min; Gradient: 29 B to 31 B in 7 min; 254; 220 nm; RT1: 5.85) to afford a solid. The crude product (80 mg) was purified by Prep-HPLC with the following conditions (Column: CHIRAL ART Cellulose-SB, 2×25 cm, 5 μm; Mobile Phase A: Hex(8 mmol/L $NH_3$·MeOH)-HPLC, Mobile Phase B: EtOH-HPLC; Flow rate: 20 mL/min; Gradient: 50 B to 50 B in 15 min; 254/220 nm; RT1: 8.698; RT2: 11.463; Injection Volume: 0.85 mL; Number Of Runs: 4) to afford (R)—N-[3-[5-fluoro-2-([5-[(methylcarbamoyl)methoxy] pyridin-3-yl]amino)pyrimidin-4-yl]-1H-indol-7-yl]-3-methoxy-2-(4-methylpiperazin-1-yl)propanamide (40 mg, 20.14%) as a white solid. LCMS: m/z (ESI), $[M+H]^+$=592.3. $^1$H-NMR (300 MHz, DMSO-$d_6$) δ 2.12 (3H, s), 2.34 (4H, s), 2.64-2.71 (5H, m), 2.72-2.75 (2H, m), 3.27 (3H, s), 3.49 (1H, t), 3.64-3.69 (1H, m), 3.76-3.81 (1H, m), 4.51 (2H, s), 7.14 1H. t), 7.53 (1H, d), 7.91-7.96 (2H, m), 8.06 (1H, d), 8.25 (1H, s), 8.47 (1H, d), 8.56 (2H, t), 9.76 (1H, s), 9.86 (1H, s), 11.50 (1H, s).

Example 69

Preparation of Methyl (R)—N-[3-[5-fluoro-2-([6-[2-(hydroxymethyl)phenyl]pyridin-3-yl]amino)pyrimidin-4-yl]-1H-indol-7-yl]-3-methoxy-2-(4-methylpiperazin-1-yl)propanamide (Ex. 69)

SCHEME 69

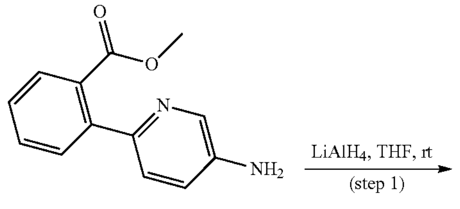

1

-continued

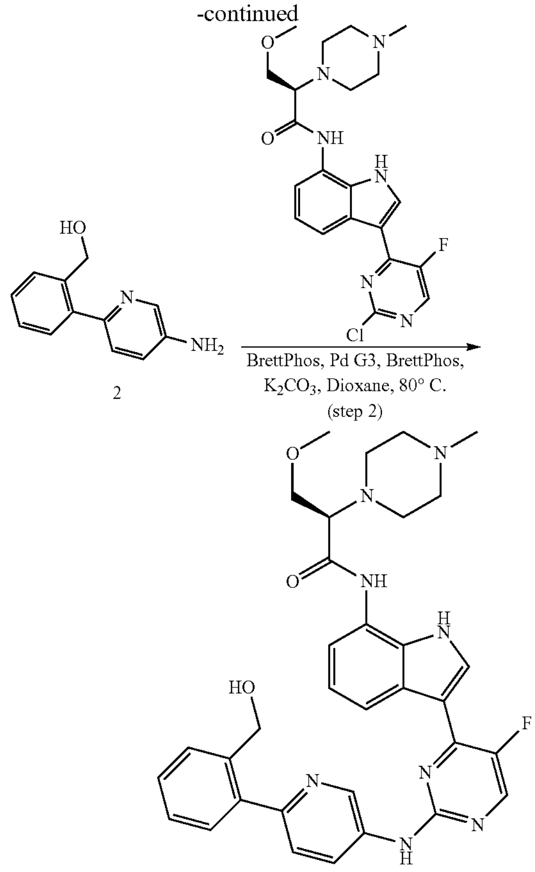

2

Example 69

Step 1. [2-(5-aminopyridin-2-yl)phenyl]methanol

To a stirred solution of methyl 2-(5-aminopyridin-2-yl) benzoate (400.00 mg, 1.752 mmol, 1.00 equiv) in THF (20.00 mL) was added $LiAlH_4$ (266.05 mg, 7.010 mmol, 4.00 equiv) in portions at room temperature under air atmosphere. The resulting mixture was stirred for 1 h at room temperature under air atmosphere. The reaction was quenched by the addition of Water (0.3 mL) at 0° C. The mixture was basified to pH7 with NaOH (266 mg). The resulting mixture was filtered, the filter cake was washed with $CH_2Cl_2$ (3×30 mL). The filtrate was concentrated under reduced pressure. The residue was purified by Prep-TLC ($CH_2Cl_2$/MeOH 20:1) to afford [2-(5-aminopyridin-2-yl) phenyl]methanol (135 mg, 38.47%) as a red solid. LCMS: m/z (ESI), $[M+H]^+$=201.2.

Step2. (R)—N-[3-[5-fluoro-2-([6-[2-(hydroxymethyl)phenyl]pyridin-3-yl]amino) pyrimidin-4-yl]-1H-indol-7-yl]-3-methoxy-2-(4-methylpiperazin-1-yl)propanamide (Ex. 69)

To a stirred mixture of (R)—N-[3-(2-chloro-5-fluoropyrimidin-4-yl)-1H-indol-7-yl]-3-methoxy-2-(4-methylpiperazin-1-yl)propanamide (120.00 mg, 0.269 mmol, 1.00 equiv) and 3-(5-aminopyridin-2-yl)-2-methylpenta-2,4-dien-1-ol (102.17 mg, 0.537 mmol, 2.00 equiv) in Dioxane (20.00 mL) were added BrettPhos Pd G3 (36.51 mg, 0.040 mmol, 0.15 equiv) and BrettPhos (21.62 mg, 0.040 mmol, 0.15 equiv) and $K_2CO_3$ (111.33 mg, 0.806 mmol, 3.00 equiv) at room temperature under air atmosphere. The resulting mixture was stirred for 2 h at 80° C. under nitrogen atmosphere. The resulting mixture was concentrated under reduced pressure. The residue was purified by Prep-TLC ($CH_2Cl_2$/MeOH 10:1). The crude product (100 mg) was purified by Prep-HPLC with the following conditions (Column: YMC-Actus Triart C18, 30×250, 5 μm; Mobile Phase A: Water (0.05% $NH_3H_2O$), Mobile Phase B: ACN; Flow rate: 60 mL/min; Gradient: 52 B to 72 B in 7 min; 254; 220 nm; RT1: 6.05) to afford (R)—N-[3-[5-fluoro-2-([6-[2-(hydroxymethyl)phenyl]pyridin-3-yl]amino)pyrimidin-4-yl]-1H-indol-7-yl]-3-methoxy-2-(4-methylpiperazin-1-yl)propanamide (52.3 mg, 31.89%) as a white solid. LCMS: m/z (ESI), $[M+H]^+$=611.4. $^1$H-NMR (300 MHz, DMSO-$d_6$) δ 2.13 (3H, s), 2.34 (4H, s), 2.63 (2H, s), 2.74 (2H, s), 3.49 (3H, t), 3.67 (1H, dd), 3.79 (2H, dd), 4.55 (2H, d), 5.45 (1H, t), 7.17 (1H, t), 7.37 (2H, m), 7.55 (4H, m), 8.26 (1H, d), 8.32 (1H, dd), 8.50 (1H, d), 8.56 (1H, d), 9.02 (1H, d), 9.85 (2H, d), 11.49 (1H, s).

Example 74

Preparation of (R)—N-[3-(5-fluoro-2-[[1-(1-methylpiperidin-4-yl)-1H-pyrazol-4-yl]amino]pyrimidin-4-yl)-1H-indol-7-yl]-3-methoxy-2-(4-methylpiperazin-1-yl)propanam-ide

SCHEME 74

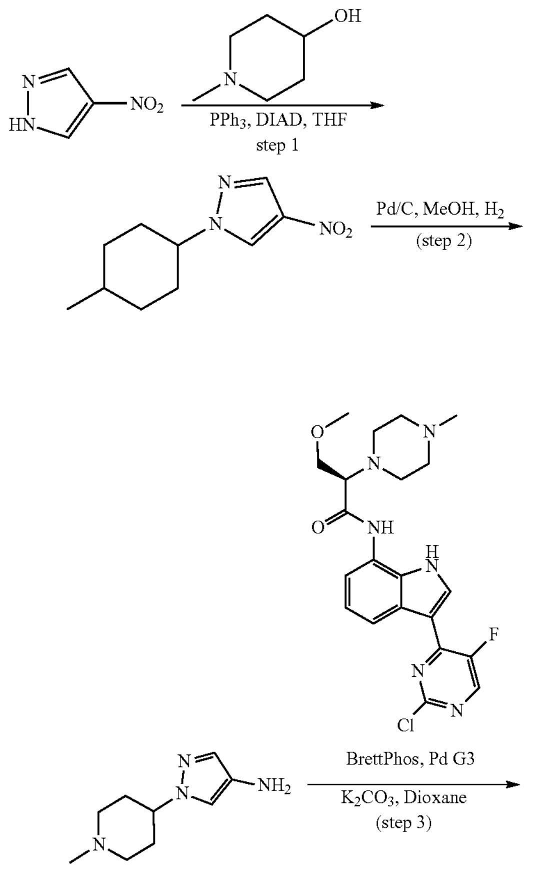

-continued

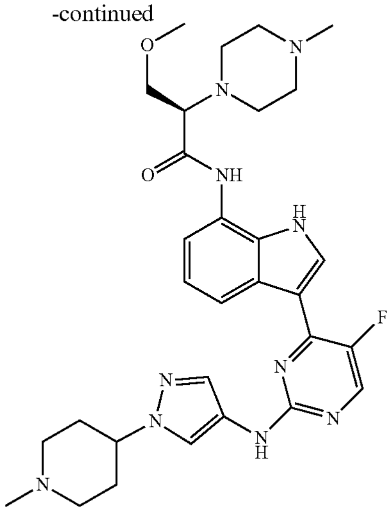

Example 74

Step 1. 1-methyl-4-(4-nitropyrazol-1-yl)piperidine

To a stirred mixture of 4-nitropyrazole (30.00 mg, 0.265 mmol, 1.00 equiv) and 1-methylpiperidin-4-ol (91.67 mg, 0.796 mmol, 3.00 equiv) in THF (2.00 mL) was added $PPh_3$ (208.76 mg, 0.796 mmol, 3.00 equiv) and DIAD (160.94 mg, 0.796 mmol, 3.00 equiv) in portions at room temperature under air atmosphere. The resulting mixture was stirred for 2 h at 70° C. under nitrogen atmosphere. The resulting mixture was concentrated under reduced pressure. The residue was purified by Prep-TLC ($CH_2Cl_2$/MeOH=1:1) to afford 1-methyl-4-(4-nitropyrazol-1-yl) piperidine (10.33 mg, 18.52%) as a brown solid. LCMS: m/z (ESI), $[M+H]^+$ =211.2.

Step2. 1-(1-methylpiperidin-4-yl)pyrazol-4-amine

To a stirred mixture of 1-methyl-4-(4-nitropyrazol-1-yl) piperidine (500.00 mg) and Pd/C (20.00 mg) in MeOH (20.00 mL) in portions at room temperature under air atmosphere. The resulting mixture was stirred for 1 h at room temperature under $H_2$ atmosphere. The resulting mixture was filtered, the filter cake was washed with MeOH (3×30 mL). The filtrate was concentrated under reduced pressure. The residue was purified by Prep-TLC ($CH_2Cl_2$/MeOH=1:1) to afford 1-(1-methylpiperidin-4-yl)pyrazol-4-amine (333 mg) as a reddish brown solid. LCMS: m/z (ESI), $[M+H]^{+}$=181.3.

Step 3. (R)—N-[3-(5-fluoro-2-[[1-(1-methylpiperidin-4-yl)pyrazol-4-yl]amino] pyrimidin-4-yl)-1H-indol-7-yl]-3-methoxy-2-(4-methylpiperazin-1-yl) propanamide (Ex. 74)

To a stirred mixture of (R)—N-[3-(2-chloro-5-fluoropyrimidin-4-yl)-1H-indol-7-yl]-3-methoxy-2-(4-methylpiperazin-1-yl)propanamide (120.00 mg, 0.269 mmol, 1.00 equiv) and 1-(1-methylpiperidin-4-yl)pyrazol-4-amine (72.60 mg, 0.403 mmol, 1.5 equiv) in dioxane (20.00 mL) were added BrettPhos Pd $G_3$ (36.51 mg, 0.040 mmol, 0.15 equiv) and BrettPhos (21.62 mg, 0.040 mmol, 0.15 equiv) and $K_2CO_3$ (111.33 mg, 0.806 mmol, 3 equiv) in portions at room temperature under air atmosphere. The resulting mixture was stirred for 2 h at 70° C. under nitrogen atmosphere. The resulting mixture was concentrated under reduced pressure. The residue was purified by Prep-TLC ($CH_2Cl_2$/MeOH=10:1). The crude product was purified by Prep-HPLC with the following conditions (Column: XBridge Prep OBD C18 Column, 30×150 mm, 5 μm; Mobile Phase A: Water (0.05% NH3. H2O), Mobile Phase B: ACN; Flow rate: 60 mL/min; Gradient: 37 B to 57 B in 7 min; RT1: 6.03) to afford (R)—N-[3-(5-fluoro-2-[[1-(1-methylpiperidin-4-yl)pyrazol-4-yl]amino]pyrimidin-4-yl)-1H-indol-7-yl]-3-methoxy-2-(4-methylpiperazin-1-yl)propanamide (24 mg, 15.13%) as a white solid. LCMS: m/z (ESI), $[M+H]^{+}$=591.4. $^{1}H$ NMR (300 MHz, DMSO-$d_6$) δ 1.99 (6H, m), 2.18 (6H, d), 2.36 (4H, s), 2.63 (2H, m), 2.74 (1H, s), 2.77 (1H, d), 2.86 (2H, d), 3.30 (3H, s), 3.51 (1H, t), 3.69 (1H, dd), 3.81 (1H, dd), 4.06 (1H, dq), 7.13 (1H, t), 7.53 (2H, m), 7.98 (1H, s), 8.20 (1H, s), 8.38 (1H, d), 8.40 (1H, s), 9.30 (1H, s), 9.86 (1H, s), 11.43 (1H, s).

Example 75

Preparation of (R)—N-[3-[5-fluoro-2-([2-[2-(hydroxymethyl)phenyl]pyridin-4-yl]amino) pyrimidin-4-yl]-1H-indol-7-yl]-3-methoxy-2-(4-methylpiperazin-1-yl)propanamide

SCHEME 75

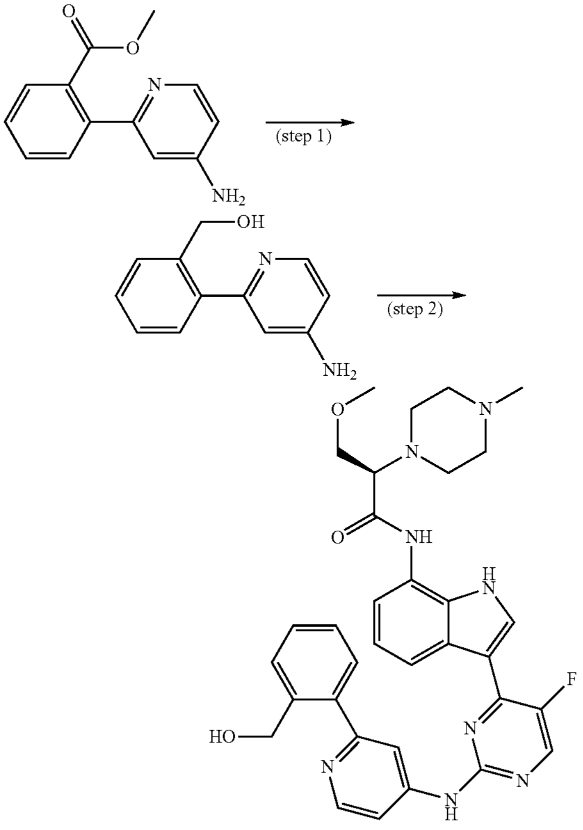

Example 75

Step 1. [2-(4-aminopyridin-2-yl)phenyl]methanol

Into a 50 mL round-bottom flask were added methyl 2-(4-aminopyridin-2-yl)benzoate (200.00 mg, 0.876 mmol, 1.00 equiv) and $LiAlH_4$ (133.03 mg, 3.505 mmol, 4.00 equiv) in THF (10.00 mL) at room temperature. The resulting mixture was stirred for overnight at 70° C. under air atmosphere. The reaction was quenched by the addition of NaOH (133 mg in water) at 5° C. The resulting mixture was concentrated under reduced pressure. The residue was purified by Prep-TLC ($CH_2Cl_2$/MeOH 10:1 with TEA) to afford [2-(4-aminopyridin-2-yl)phenyl]methanol (70 mg, 29.12%) as a black oil. LCMS: m/z (ESI), $[M+H]^{+}$=201.0

Step 2. (R)—N-[3-[5-fluoro-2-([2-[2-(hydroxymethyl)phenyl]pyridin-4-yl]amino) pyrimidin-4-yl]-1H-indol-7-yl]-3-methoxy-2-(4-methylpiperazin-1-yl)propanamide (Ex. 75)

To a solution of [2-(4-aminopyridin-2-yl)phenyl]methanol (67.21 mg, 0.336 mmol, 1.50 equiv) and (R)—N-[3-(2-chloro-5-fluoropyrimidin-4-yl)-1H-indol-7-yl]-3-methoxy-2-(4-methylpiperazin-1-yl)propanamide (100 mg, 0.224 mmol, 1.00 equiv) in dioxane (10.00 mL) were added BrettPhos Pd G3 (20.28 mg, 0.022 mmol, 0.10 equiv) BrettPhos (12.01 mg, 0.022 mmol, 0.10 equiv) and $K_2CO_3$ (61.85 mg, 0.448 mmol, 2.00 equiv). After stirring for 2 hs at 70° C. under a nitrogen atmosphere, the resulting mixture was concentrated under reduced pressure. The residue was purified by Prep-TLC (PE/EtOAc 3:1) to afford a crude solid. The crude solid was purified by Prep-HPLC with the following conditions (Column: YMC-Actus Triart C18, 30×250, 5 μm; Mobile Phase A: Water (0.05% $NH_3H_2O$), Mobile Phase B: ACN; Flow rate: 60 mL/min; Gradient: 52 B to 72 B in 7 min; 254; 220 nm; RT1: 6.05) to afford (R)—N-[3-[5-fluoro-2-([2-[2-(hydroxymethyl)phenyl]pyridin-4-yl]amino)pyrimidin-4-yl]-1H-indol-7-yl]-3-methoxy-2-(4-methylpiperazin-1-yl)propanamide (25 mg, 18.11%) as a white solid. LCMS: m/z (ESI), $[M+H]^{+}$=611.3 $^{1}H$-NMR (400 MHz, DMSO-$d_6$) δ 2.15 (3H, s), 2.36 (4H, s), 2.75 (4H, s), 3.28 (3H, s), 3.50 (1H, t), 3.69 (1H, dd), 3.76-3.84 (1H, m), 4.50 (2H, d), 5.62 (1H, t), 7.08 (1H, t), 7.35 (1H, t), 7.42 (1H, t), 7.50 (2H, dd), 7.58 (1H, d), 7.79-7.85 (1H, m), 8.05 (1H, d), 8.27 (1H, s), 8.44 (1H, d), 8.52-8.60 (2H, m), 9.86 (1H, s), 10.14 (1H, s), 11.51 (1H, s).

Example 76

Preparation of (R)—N-[3-(2-[[6-(aminomethyl)pyridin-3-yl]amino]-5-fluoropyrimidin-4-yl)-1H-indol-7-yl]-3-methoxy-2-(4-methylpiperazin-1-yl)propanamide

SCHEME 76

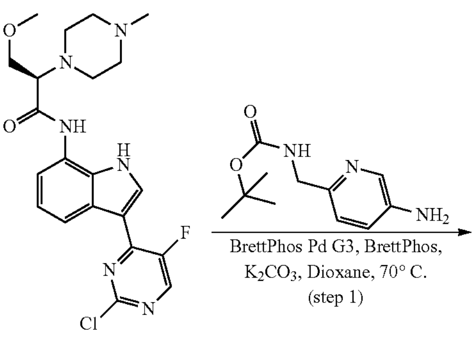

-continued

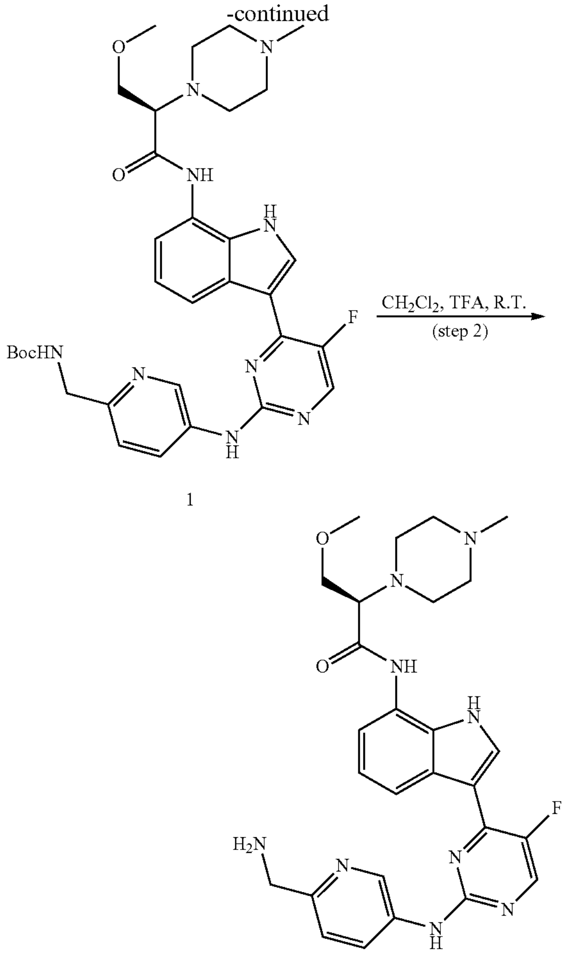

1

Example 76

Step 1. Tert-butyl N-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]methyl)carbamate To a stirred solution/mixture of (R)—N-[3-(2-chloro-5-fluoropyrimidin-4-yl)-1H-indol-7-yl]-3-methoxy-2-(4-methylpiperazin-1-yl)propanamide (150.00 mg, 0.336 mmol, 1.00 equiv) and tert-butyl N-[(5-aminopyridin-2-yl)methyl]carbamate (149.88 mg, 0.671 mmol, 2 equiv) in Dioxane (20.00 mL) were added BrettPhos Pd $G_3$ (45.64 mg, 0.050 mmol, 0.15 equiv) and BrettPhos (27.02 mg, 0.050 mmol, 0.15 equiv) and $K_2CO_3$ (139.16 mg, 1.007 mmol, 3 equiv) in portions at room temperature under air atmosphere. The resulting mixture was stirred for 2 h at 80° C. under nitrogen atmosphere. The residue was purified by Prep-TLC ($CH_2Cl_2$/MeOH=10:1) to afford tert-butyl N-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]methyl)carbamate (150 mg, 70.52%) as a brown solid. LCMS: m/z (ESI), $[M+H]^+$=634.4.

Step2. (R)—N-[3-[5-fluoro-2-([6-[2-(hydroxymethyl)phenyl]pyridin-3-yl]amino) pyrimidin-4-yl]-1H-indol-7-yl]-3-methoxy-2-(4-methylpiperazin-1-yl)propanamide (Ex. 76)

To a stirred solution of tert-butyl N-([5-[(5-fluoro-4-[7-[(R)-3-methoxy-2-(4-methylpiperazin-1-yl)propanamido]-1H-indol-3-yl]pyrimidin-2-yl)amino]pyridin-2-yl]methyl) carbamate (100.00 mg) in $CH_2Cl_2$ (3.00 mL) and TFA (10.00 mL) dropwise at room temperature under air atmosphere. The resulting mixture was stirred for 1 h at room temperature under air atmosphere. The resulting mixture was extracted with $CH_2Cl_2$ (3x30 mL). The combined organic layers were washed with brine (1x30 mL), dried over anhydrous $Na_2SO_4$. After filtration, the filtrate was concentrated under reduced pressure. The crude product (80 mg) was purified by Prep-HPLC with the following conditions (Column: XBridge Prep OBD C18 Column, 30x150 mm, 5 μm; Mobile Phase A: Water (0.05% $NH_3H_2O$), Mobile Phase B: ACN; Flow rate: 60 mL/min; Gradient: 17 B to 37 B in 7 min; 254/220 nm; RT1: 6.58) to afford (R)—N-[3-(2-[[6-(aminomethyl)pyridin-3-yl]amino]-5-fluoropyrimidin-4-yl)-1H-indol-7-yl]-3-methoxy-2-(4-methylpiperazin-1-yl)propanamide (24.1 mg) as a white solid. LCMS: m/z (ESI), $[M+H]^+$=534.2. $^1$H-NMR (300 MHz, MeOD-$d_4$) δ 2.33 (3H, s), 2.61 (4H, s), 2.85 (2H, s), 2.93 (2H, s), 3.44 (3H, s), 3.52 (1H, t), 3.90 (1H, m), 3.95 (3H, s), 7.21 (2H, m), 7.42 (1H, d), 8.19 (1H, d), 8.32 (2H, q), 8.65 (1H, m), 8.88 (1H, d).

Example 78

Preparation of (R)—N-[3-(5-fluoro-2-[[2-(hydroxymethyl)-6-methylpyridin-4-yl] amino]pyrimidin-4-yl)-1H-indol-7-yl]-3-methoxy-2-(4-methylpiperazin-1-yl)propanamide

SCHEME 78

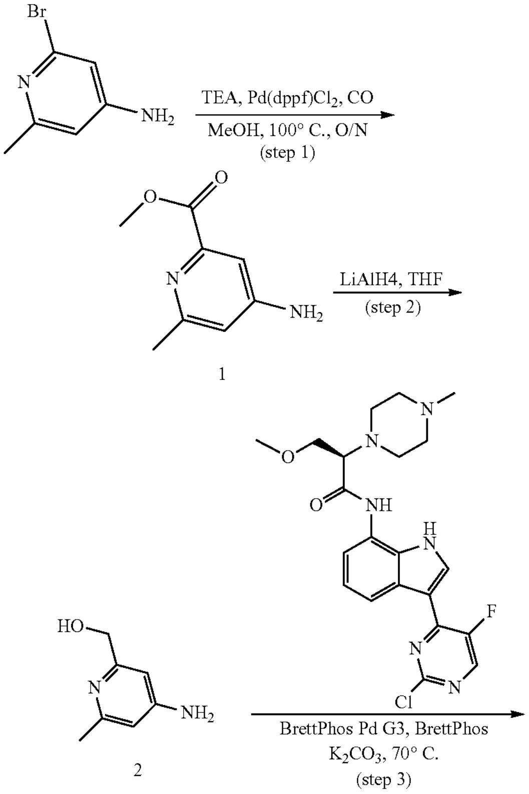

-continued

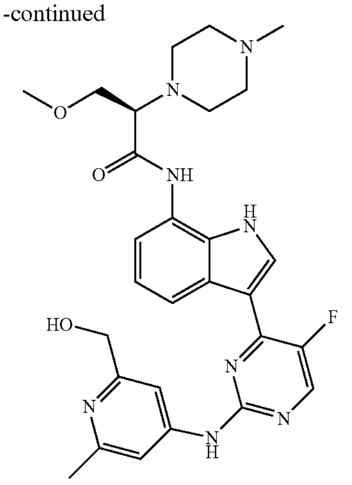

Example 78

Step 1. Methyl 4-amino-6-methylpyridine-2-carboxylate

Into a 250 mL pressure tank reactor were added 2-bromo-6-methylpyridin-4-amine (1.00 g, 5.346 mmol, 1.00 equiv), Pd(dppf)$Cl_2CH_2Cl_2$ (436.61 mg, 0.535 mmol, 0.10 equiv) and TEA (1.623 g, 16.039 mmol, 3.00 equiv) in MeOH (50.00 mL) under 20 atm CO (g) atmosphere at 100° C. for 6 h. Desired product could be detected by LCMS. The resulting mixture was concentrated under vacuum. The residue was purified by silica gel column chromatography, eluted with PE/EtOAc (1:1) to afford methyl 4-amino-6-methylpyridine-2-carboxylate (500 mg, 56.28%) as a yellow solid. LCMS: m/z (ESI), $[M+H]^+$=167.3.

Step2. (4-amino-6-methylpyridin-2-yl)methanol

Into a 40 mL sealed tube were added methyl 4-amino-6-methylpyridine-2-carboxylate (332.00 mg, 1.998 mmol, 1.00 equiv) and $LiAlH_4$ (151.65 mg, 3.996 mmol, 2.00 equiv) in THF (15.00 mL) at 0° C., then it was stirred at room temperature for 1 h. Desired product could be detected by LCMS. The reaction was quenched by the addition of water (1 mL) at 0° C. The precipitated solids were collected by filtration and washed with MeOH (2×50 mL). The resulting mixture was concentrated under reduced pressure. The residue was purified by Prep-TLC ($CH_2Cl_2$/MeOH=10:1) to afford (4-amino-6-methylpyridin-2-yl)methanol (210 mg, 76.08%) as a yellow solid. LCMS: m/z (ESI), $[M+H]^+$=139.2.

Step3. (R)—N-[3-(5-fluoro-2-[[2-(hydroxymethyl)-6-methylpyridin-4-yl]amino]pyrimidin-4-yl)-1H-indol-7-yl]-3-methoxy-2-(4-methylpiperazin-1-yl)propanamide (Ex. 78)

Into a 40 mL sealed tube were added (R)—N-[3-(2-chloro-5-fluoropyrimidin-4-yl)-1H-indol-7-yl]-3-methoxy-2-(4-methylpiperazin-1-yl)propanamide (120.00 mg, 0.269 mmol, 1.00 equiv), (4-amino-6-methylpyridin-2-yl)methanol (74.20 mg, 0.537 mmol, 2.00 equiv), BrettPhos (14.41 mg, 0.027 mmol, 0.1 equiv), BrettPhos Pd $G_3$ (24.34 mg, 0.027 mmol, 0.1 equiv) and $K_2CO_3$ (74.22 mg, 0.537 mmol, 2 equiv) in dioxane (8.00 mL) at 80° C. Desired product could be detected by LCMS. The resulting mixture was concentrated under vacuum. The residue was purified by Prep-TLC ($CH_2Cl_2$/MeOH=10:1) to afford crude solid. The crude product was purified by Prep-HPLC with the following conditions (Column: XBridge Prep OBD C18 Column, 30×150 mm, 5 μm; Mobile Phase A: Water (0.05% $NH_3 \cdot H_2O$), Mobile Phase B: ACN; Flow rate: 60 mL/min; Gradient: 34 B to 54 B in 7 min, RT1: 5.90) to afford (R)—N-[3-(5-fluoro-2-[[2-(hydroxymethyl)-6-methylpyridin-4-yl]amino]pyrimidin-4-yl)-1H-indol-7-yl]-3-methoxy-2-(4-methylpiperazin-1-yl)propanamide (65 mg, 44.12%) as a white solid. LCMS: m/z (ESI), $[M+H]^+$=549.4. 1H-NMR (300 MHz, DMSO-$d_6$) δ 2.13 (3H, s), 2.34 (4H, s), 2.37 (3H, s), 2.56-2.66 (2H, m), 2.69-2.79 (2H, m), 3.28 (3H, s), 3.49 (1H, t), 3.67 (1H, dd), 3.79 (1H, dd), 4.45 (2H, d), 5.24 (1H, t), 7.17 (1H, t), 7.49-7.60 (2H, m), 7.70 (1H, d), 8.26 (1H, d), 8.53 (1H, d), 8.59 (1H, dd), 9.89 (2H, d), 11.51 (1H, s).

Biological Examples

Exemplary compounds disclosed herein have been characterized in one or more of the following biological assays.

Example 79: Enzymatic Assay and Cellular p-STAT6 Assay

Recombinant JAK1, JAK2, JAK3 and TYK2 purchased from Carna Biosciences. The inhibition potency of compounds against JAK1, JAK2, JAK3 and TYK2 was assessed using Lance Ultra Kinase Assay.

In brief, recombinant kinases were pre-incubated in the presence or absence of compound at room temperature for 15 minutes. The reaction was initiated by the addition of 5 mM ATP and substrate peptide which could be phosphorylated by kinases in the reaction. After 60 minutes incubation, the reaction was stopped by the addition of the detection reagent mix containing EDTA. The fluorescence was measured at 615 nm and 665 nm, respectively with excitation wavelength at 320 nm. The calculated signal ratio of 665 nm/615 nm is proportional to the kinase activity. The concentration of compound producing 50% inhibition of the respective kinase ($IC_{50}$) was calculated using four-parameter logistic fit with XLfit.

To detect phosphorylated STAT6 (pSTAT6), THP-1 cells were harvested by centrifugation at 250 g for 5 min and resuspended in assay medium (RPMI1640+10% FBS) to $2\times10^5$ cells/well. Test compounds were applied to assay plates in serial dilution from 1 μM to 0.3 nM in DMSO. THP-1 cells were incubated with serial diluted compounds for 60 min at room temperature, followed by stimulation of interleukin (IL-13, 10 ng/ml) for 30 min, fixed in Cytofix buffer (BD Biosciences), and permeabilized in 90% methanol on ice. PE anti-pSTAT6 (BD Biosciences) antibodies were stained for 60 min at room temperature before being analyzed by flow cytometry. In the assay the compounds were thus diluted and dose-response curves for inhibition of the signal determine the $IC_{50}$ for the compounds.

The inhibitory activity of the tested compounds to JAK1, JAK2, JAK3, TYK2 kinases and to the phosphorylation of STAT6 are shown in Tables 2 below. JAK1/JAK2 selectivity ratios for all tested compounds are above 10 (upto 1000 or more) based on (JAK2 $IC_{50}$/JAK1 $IC_{50}$). The inhibition of STAT6 phosphorylation confirming the relevance of the JAK-STAT pathway in airway inflammation as reported in prior art. Compounds which have demonstrated potent JAK1 inhibitory activity were also proven to be efficacious in the inhibition of STAT6 phosphorylation.

TABLE 2

| Enzymatic potency of the test compounds | | | | | |
|---|---|---|---|---|---|
| Examples | JAK1 $IC_{50}$ (nM) | JAK2 $IC_{50}$ (nM) | JAK3 $IC_{50}$ (nM) | TYK2 $IC_{50}$ (nM) | pSTAT6 $IC_{50}$ (nM) |
| 1 | 0.13 | 85 | >10000 | 644 | 4.0 |
| 2 | 0.25 | 202 | >10000 | 1088 | 4.3 |
| 3 | 0.19 | 4 | 7696 | 156 | 4.5 |
| 4 | 0.26 | 81 | >10000 | 1828 | 5.1 |
| 5 | 0.19 | 268 | >10000 | 764 | 5.1 |
| 6 | 0.42 | 452 | >10000 | 4663 | 6.0 |
| 7 | 0.21 | 58 | >10000 | 634 | 6.2 |
| 8 | 0.16 | 183 | >10000 | 850 | 6.2 |
| 9 | 0.25 | 20 | 9946 | 330 | 6.5 |
| 12 | 0.17 | 469 | >10000 | 3769 | 7.2 |
| 13 | 0.33 | 88 | 8951 | 1394 | 7.2 |
| 14 | 0.20 | 336 | >10000 | 4204 | 7.3 |
| 15 | 0.19 | 20 | >10000 | 1442 | 7.3 |
| 16 | 0.36 | 138 | >10000 | 1995 | 7.4 |
| 17 | 0.18 | 43 | 7745 | 1207 | 7.6 |
| 18 | 0.14 | 22 | 7728 | 1094 | 7.6 |
| 19 | 0.27 | 215 | >10000 | 2456 | 7.7 |
| 20 | 0.65 | 135 | >10000 | 2401 | 7.9 |
| 21 | 0.20 | 125 | >10000 | 1152 | 8.4 |
| 22 | 0.24 | 467 | >10000 | 5252 | 8.5 |
| 24 | 0.82 | 403 | >10000 | 2569 | 8.9 |
| 25 | 0.20 | 9 | >10000 | 273 | 8.9 |
| 26 | 0.07 | 100 | >10000 | 1262 | 9.1 |
| 28 | 0.12 | 162 | >10000 | 1184 | 9.6 |
| 29 | 0.31 | 74 | >10000 | 939 | 9.8 |
| 30 | 0.15 | 95 | >10000 | 1177 | 10.3 |
| 31 | 0.15 | 218 | >10000 | 1311 | 10.4 |
| 32 | 0.16 | 87 | 9275 | 1492 | 10.6 |
| 33 | 0.14 | 110 | >10000 | 2174 | 11.1 |
| 34 | 0.18 | 12 | >10000 | 447 | 11.3 |
| 35 | 0.26 | 199 | >10000 | 2043 | 11.3 |
| 36 | 0.29 | 491 | >10000 | 4612 | 11.5 |
| 37 | 0.21 | 68 | 4763 | 996 | 11.5 |
| 38 | 0.13 | 65 | >10000 | 726 | 11.8 |
| 39 | 0.23 | 316 | >10000 | 974 | 11.9 |
| 40 | 0.21 | 219 | >10000 | 2515 | 12.1 |
| 41 | 0.22 | 110 | >10000 | 1428 | 12.6 |
| 42 | 0.07 | 16 | 5263 | 560 | 12.8 |
| 44 | 0.27 | 147 | >10000 | >10000 | 13.2 |
| 45 | 0.14 | 131 | >10000 | 1290 | 13.4 |
| 46 | 1.52 | 322 | >10000 | >10000 | 13.5 |
| 47 | 0.13 | 81 | >10000 | 556 | 14.0 |
| 48 | 0.27 | 379 | >10000 | 1697 | 14.0 |
| 50 | 0.11 | 119 | >10000 | 772 | 14.4 |
| 51 | 0.23 | 186 | >10000 | 1405 | 14.9 |
| 52 | 0.43 | 363 | >10000 | 2170 | 15.0 |
| 53 | 0.22 | 180 | >10000 | 1662 | 15.0 |
| 54 | 0.86 | 219 | >10000 | 4876 | 15.3 |
| 55 | 12.81 | 2714 | >10000 | >10000 | 15.3 |
| 57 | 0.16 | 44 | >10000 | 922 | 16.0 |
| 59 | 131.38 | 2217 | >10000 | >10000 | 17.4 |
| 60 | 0.25 | 158 | >10000 | 1342 | 17.6 |
| 61 | 0.11 | 8 | 3587 | 194 | 17.7 |
| 64 | 0.14 | 22 | >10000 | 512 | 18.4 |
| 65 | 0.32 | 198 | >10000 | 1256 | 18.8 |
| 66 | 0.35 | 12 | >10000 | 545 | 20.3 |
| 67 | 0.18 | 35 | 6774 | 609 | 20.6 |
| 68 | 0.22 | 71 | 5358 | 1234 | 20.9 |

Example 80: Metabolic Stability in Rat Hepatocytes and Human Liver Microsome

Rat hepatocytes in male gender and human liver microsome were obtained from commercial vendors (e.g., BioreclamationIVT) and stored at −150° C. prior to use.

For metabolic stability assay with rat heptatocytes, vials of cryopreserved hepatocytes or microsome were removed from storage, ensured that vials remain at cryogenic temperatures. 1 μM of each test compound (in Acetonitrile; 0.01% DMSO) was incubated with 250 μL of hepatocyte cells ($1\times10^6$ cells/ml) in a 96 deep well plate. Reaction was stopped at different time points (0, 0.5, 5, 15, 30, 45, 60, 80, 100 and 120 min) by addition of 3 volumes of chilled acetonitrile to 20 μL of reaction mixture and centrifuged at 4° C. for 15 min. 40 μL of supernatant was diluted to 200 μL with pure water and analyzed using LC-MS/MS.

For metabolic stability assay with human liver microsome, 1 μM of each test compound was incubated with 1 mg/mL of microsomes (Pooled HLM with 20 mg/ml protein cone) at 37° C. in 250 μL of buffer (100 mM phosphate buffer, pH-7.4) containing 1 mM NADPH solution. L of incubation mix was quenched with 5 volumes chilled acetonitrile at different time points 0, 0.5, 5, 10, 15, 20 and 30 min in a fresh 96 well plate. The quench plate was centrifuged at 4000 rpm for 15 min. 40 μL of supernatant was diluted to 200 μL with pure water and analyzed using LC-MS/MS.

In vitro hepatocyte clearance was estimated based on determination of elimination half-life ($T_{1/2}$) of compounds disappearance from their initial concentrations. Peak area ratios of each compound (test or control) to IS was calculated. Ln (% Control) versus Incubation Time (min) curve was plotted, and the slope of a linear fitting line was calculated. Drug elimination rate constant k (min−1), $T_{1/2}$ (min), and in vitro intrinsic clearance $CL_{int}$ (μL/min/E6) was calculated according to the following equations:

$$k=-\text{slope}$$

$$T_{1/2}=0.693/k$$

$$CL_{int}=k/C_{hep}$$

Where $C_{hep}$ (cells×μL$^{-1}$) is the cell concentration in the incubation system.

Data are shown as below in Table 3.

TABLE 3

| In vitro metabolic stability (rat hepatocytes and human liver microsome) | | |
|---|---|---|
| Examples | Rat Hepatocyte $CL_{int}$ (μl/min/l × $10^6$ cells) | Human liver microsome $CL_{int}$ (μl/min/mg) |
| 1 | 68.8 | 4.9 |
| 2 | 9.5 | 10.6 |
| 3 | 11.1 | 3.0 |
| 4 | >300 | 14.4 |
| 5 | 11.0 | 73.9 |
| 6 | 156.2 | 76.4 |
| 7 | 128.1 | 46.7 |
| 8 | 38.4 | 7.2 |
| 9 | 5.9 | 18.4 |
| 12 | 226.4 | >300 |
| 13 | 5.5 | 83.1 |
| 14 | 0.0 | >300 |
| 15 | 68.0 | >300 |
| 16 | 42.1 | 3.0 |
| 17 | 4.5 | 57.2 |
| 18 | 5.0 | 13.5 |
| 19 | 4.0 | 51.4 |
| 20 | 6.0 | 3.0 |
| 21 | >300 | 194.3 |
| 22 | 6.3 | <3 |
| 24 | <1 | 26.8 |
| 25 | 17.7 | 44.0 |
| 26 | 2.8 | <3 |
| 28 | 36.5 | 15.6 |
| 29 | 5.8 | 10.1 |
| 30 | 4.4 | 13.5 |

TABLE 3-continued

In vitro metabolic stability (rat hepatocytes and human liver microsome)

| Examples | Rat Hepatocyte $CL_{int}$ (μl/min/l × $10^6$ cells) | Human liver microsome $CL_{int}$ (μl/min/mg) |
|---|---|---|
| 31 | 0.0 | 135.1 |
| 32 | 6.0 | 26.1 |
| 33 | 6.8 | 11.1 |
| 34 | 210.5 | <3 |
| 35 | 2.2 | 9.2 |
| 36 | >300 | >300 |
| 37 | 6.3 | 11.7 |
| 38 | 117.1 | 10.9 |
| 39 | 2.2 | 4.9 |
| 40 | 36.4 | 50.4 |
| 41 | 3.4 | 11.4 |
| 42 | 3.8 | 26.1 |
| 43 | 4.0 | 4.8 |
| 44 | 18.2 | 17.9 |
| 45 | 2.7 | 45.2 |
| 47 | 2.8 | 29.0 |
| 48 | 1.6 | 69.1 |
| 50 | 15.7 | 195.7 |
| 51 | 3.7 | 8.3 |
| 52 | 2.7 | 6.7 |
| 53 | 17.4 | 27.9 |
| 55 | >300 | >300 |
| 57 | 24.0 | >300 |
| 59 | >300 | 10.7 |
| 60 | 4.6 | 7.0 |
| 61 | 3.5 | 27.9 |
| 64 | 4.0 | 21.9 |
| 65 | 6.2 | 7.9 |
| 66 | 12.7 | 25.0 |
| 67 | 153.6 | 19.5 |
| 68 | 4.0 | 19.0 |

Example 81: Pharmacokinetics in Plasma and Lung in Mouse

Lung PK of the compounds were tested via Intratracheal (IT) instillation administration in male CD1 Mice. Plasma and lung levels of test compounds and ratios thereof were determined in the following manner. Test compounds were dosed cassettely as the formulation of 0.4 mg/mL suspension of 0.5% HPMC, 0.1% Tween 80 in saline. The animal was anesthetized using 5% of isoflurane for 5 min, open its mouth and take out the tongue, the light was focused on the neck of the mouse and localize the trachea, and the syringe was inserted into the trachea while the trachea is in the open state, and the test compounds were inject into the trachea. At various time points (typically 5 min, 1, 4, 24 hours) post dosing, approximately 0.250 mL blood samples were removed via cardiac puncture and intact lungs were excised from the mice. Each blood sample was transferred into plastic micro centrifuge tubes containing $K_2$EDTA. Blood samples were then centrifuged (Eppendorf centrifuge, 5804R) for 4 minutes at approximately 12,000 rpm at 4° C. to collect plasma. The mice will be fully exsanguinated prior to tissue collection. Lung samples will be collected at adopted time point and the whole lung were weighted and homogenized. Concentrations of test compounds in the plasma and lung samples were analyzed using a LC-MS/MS method. WinNonlin (Phoenix™) or other similar software will be used for pharmacokinetic calculations. Tested compounds exhibited exposure in lung from one to two orders of magnitude greater than exposure in plasma in mouse.

TABLE 4

Mouse lung PK (intratracheal dose) data

| | % Dose in Lung | | Lung $T_{1/2}$ | Conc. Ratio (Lung/Plasma) | |
|---|---|---|---|---|---|
| Example | 5 min | 1 hr | (hr) | 5 min | 1 hr |
| 2 | 18.1% | 13.4% | 29.9 | 399 | 3262 |
| 5 | 101.6% | 54.0% | 6.1 | 2103 | 2935 |
| 8 | 62.7% | 13.4% | 3.5 | 296 | 1589 |
| 19 | 35.2% | 18.2% | 11.3 | 395 | 2455 |
| 21 | 13.8% | 3.0% | 1 | 713 | 835 |
| 22 | 20.5% | 9.5% | 3.6 | 233 | 609 |
| 38 | 79.9% | 19.4% | 3.9 | 965 | 1780 |
| 40 | 58.6% | 23.0% | 4.6 | 824 | 1441 |

Example 82: Murine Model of *Alternaria alternata*-Induced Eosinophilic Inflammation of the Lung Airway eosinophilia is a hallmark of human asthma. *Alternaria alternata* is a fungal aeroallergen that can exacerbate asthma in humans and induces eosinophilic inflammation in the lungs of mice (Havaux et al. Clin Exp Immunol. 2005, 139(2):179-88). In mice, it has been demonstrated that *alternaria* indirectly activates tissue resident type 2 innate lymphoid cells in the lung, which respond to (e.g. IL-2 and IL-7) and release JAK-dependent cytokines (e.g. IL-5 and IL-13) and coordinate eosinophilic inflammation (Bartemes et al. J Immunol. 2012, 188(3):1503-13).

Seven- to nine-week old male C57 mice from Taconic are used in the study. On the day of study, animals are lightly anesthetized with isoflurane and administered either vehicle or test compound (0.1-1.0 mg/mL, 50.mu.L total volume over several breaths) via oropharyngeal aspiration. Animals are placed in lateral recumbency post dose and monitored for full recovery from anesthesia before being returned to their home cage. One hour later, animals are once again briefly anesthetized and challenged with either vehicle or *alternaria* extract (200 ug total extract delivered, 50 mL total volume) via oropharyngeal aspiration before being monitored for recovery from anesthesia and returned to their home cage. Forty-eight hours after *alternaria* administration, bronchoalveolar lavage fluid (BALF) is collected and eosinophils are counted in the BALF using the Advia 120 Hematology System (Siemens).

Exemplary compounds disclosed herein are tested in this *alternaria* assay. Activity in the model is evidenced by a decrease in the level of eosinophils present in the BALF of treated animals at forty-eight hours compared to the vehicle treated, *alternaria* challenged control animals. Data are expressed as percent inhibition of the vehicle treated, *alternaria* challenged BALF eosinophils response. To calculate percent inhibition, the number of BALF eosinophils for each condition is converted to percent of the average vehicle treated, *alternaria* challenged BALF eosinophils and subtracted from one-hundred percent. The test compounds demonstrate inhibition of *alternaria*-induced BALF eosinophils.

While the present disclosure has been particularly shown and described with reference to specific embodiments (some of which are preferred embodiments), it should be understood by those skilled in the art that various changes in form and detail may be made therein without departing from the spirit and scope of the present disclosure as disclosed herein.

What is claimed is:

1. A compound of Formula (I):

Formula (I)

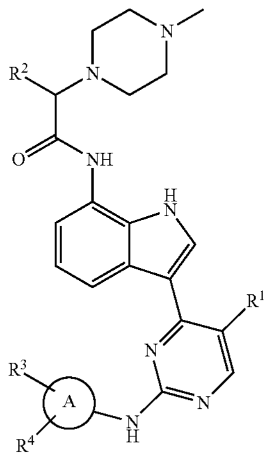

or a pharmaceutically acceptable salt thereof, wherein,

Ring A is a 6-membered monocyclic heteroaryl or saturated or unsaturated 8-10 membered bicyclic ring having 0-5 ring heteroatoms selected from oxygen, sulfur and nitrogen, wherein one or more ring forming —$CH_2$— group of the heteroaryl, or the bicyclic ring may be replaced by a —C(O)— group;

$R^1$ is hydrogen, halogen, hydroxyl, amino, cyano, or $C_{1-3}$ alkyl;

$R^2$ is hydrogen, $C_{1-12}$ alkyl or $C_{1-12}$ alkoxyl optionally mono- or multi-substituted by halogen, hydroxyl, amino, cyano, or $C_{1-12}$ alkoxyl;

each $R^3$ and $R^4$ is independently absent, or halogen, hydroxyl, $C_{1-6}$ alkyl, carboxyl, $C_{1-6}$ alkoxyl, $C_{1-6}$ alkoxycarbonyl, —$NR^aR^b$, —C(O)$NR^aR^b$, sulfinyl, $C_{1-6}$ alkylsulfinyl, sulfonyl, $C_{1-6}$ alkylsulfonyl, sulfonoxyl, sulfoximinyl, $C_{1-6}$ alkylsulfoximinyl, sulfonimidoyl, S—($C_{1-6}$ alkyl) sulfonimidoyl, N—($C_{1-6}$ alkyl) sulfonimidoyl, N, S—($C_{1-6}$ alkyl)$_2$ sulfonimidoyl, phosphinoyl, $C_{1-6}$ alkylphosphinoyl, ($C_{1-6}$ alkyl)$_2$ phosphinoyl, $C_{1-6}$ alkylphosphonyl, 3-10 membered saturated or unsaturated carbocyclyl, 3-10 membered saturated or unsaturated heterocyclyl, which can be optionally mono- or independently multi-substituted by halogen, hydroxyl, $C_{1-6}$ alkyl, $C_{1-6}$ alkoxyl, $C_{1-6}$ carboxyl, $C_{1-6}$ alkoxycarbonyl, —$NR^aR^b$, —C(O)$NR^aR^b$, sulfonyl, $C_{1-6}$ alkylsulfonyl, carbamoyl, N—($C_{1-6}$ alkyl) carbamoyl, or N,N—($C_{1-6}$ alkyl)$_2$carbamoyl, phosphinoyl, $C_{1-6}$ alkylphosphinoyl, ($C_{1-6}$ alkyl)$_2$ phosphinoyl, wherein one or more ring forming —$CH_2$— group of the carbocyclyl or heterocyclyl may be replaced by a —C(O)— group;

wherein, each $R^a$ and $R^b$ is independently selected from hydrogen, $C_{1-6}$ alkyl, $C_{1-6}$ alkylcarbonyl, which can be optionally mono- or independently multi-substituted by halogen, hydroxyl, or $C_{1-6}$ alkoxy.

2. The compound of claim 1 having a structure of Formula (Ia)

Formula (Ia)

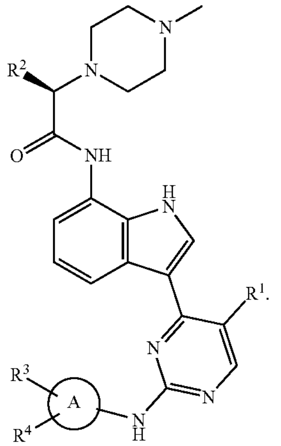

3. The compound of claim 1, wherein Ring A is a phenyl fused bicyclic heteroaryl ring or a pyridinyl fused bicyclic heteroaryl ring wherein the bicyclic Ring A has 0-5 ring heteroatoms selected from oxygen, sulfur and nitrogen, wherein one or more ring forming —$CH_2$— group of the bicyclic Ring A may be replaced by a —C(O)— group.

4. The compound of claim 1, wherein Ring A is selected from the group consisting of:

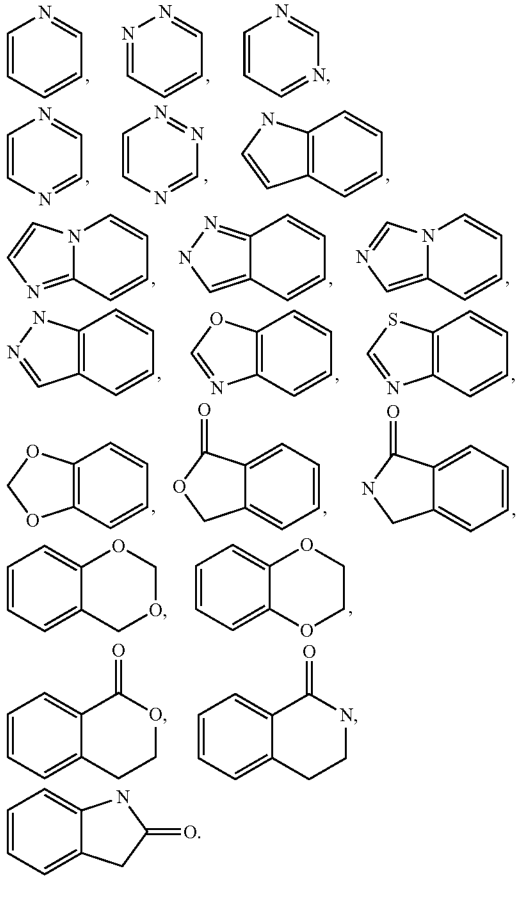

5. The compound of claim 1, wherein Ring A is a monocyclic heteroaryl selected from pyridinyl, pyridazinyl, pyrimidinyl, pyrazinyl, or triazinyl.

6. The compound of claim 1, wherein each $R^3$ and $R^4$ is independently absent, or $C_{1-6}$ alkyl, $C_{1-6}$ alkoxyl, carboxyl, $C_{1-6}$ alkoxycarbonyl, —C(O)$NR^aR^b$, which can be optionally mono- or independently multi-substituted by halogen, hydroxyl, $C_{1-6}$ alkyl, $C_{1-6}$ alkoxyl, $C_{1-6}$ alkyl-carboxyl, $C_{1-6}$ alkoxycarbonyl, —$NR^aR^b$, —C(O)$NR^aR^b$, sulfonyl, $C_{1-6}$ alkylsulfonyl, carbamoyl, N—($C_{1-6}$ alkyl) carbamoyl, or N,N—($C_{1-6}$ alkyl)$_2$ carbamoyl.

7. The compound of claim 1, wherein at least one of $R^3$ and $R^4$ is absent.

8. The compound of claim 1, wherein neither $R^3$ nor $R^4$ is absent, and said $R^3$ or $R^4$ are in ortho-positions.

9. The compound of claim 1, wherein each $R^3$ and $R^4$ is independently selected from absent, $C_{1-6}$ alkyl, $C_{1-6}$ alkoxy-carbonyl, optionally substituted by hydroxyl or Cie alkoxy-carbonyl.

10. The compound of claim 1, wherein each $R^3$ and $R^4$ is independently absent, or carboxyl, hydroxyl, carbamoyl, amino, methyl, methoxyl, ethoxyl, methoxymethyl, methoxyethoxyl, hydroxymethyl, hydroxyethyl, hydroxybutyl, hydroxymethoxyl, hydroxyethoxyl, carbamoylmethoxyl, methylcarbamoyl, hydroxyacetamido, (hydroxyethyl) carbamoyl, methylcarbamoylmethoxyl, dimethylcarbamoylethoxyl, carboxymethoxyl, methoxycarbonyl, ethoxycarbonyl, isopropoxycarbonyl, tertbutoxycarbonyl, methoxycarbonylmethyl, methoxycarbonylethyl, ethoxycarbonylmethyl, methoxycarbonylmethoxyl, methylamino, dimethylamino, dimethylaminoethyl, dimethylaminoethoxycarbonyl, dimethylaminomethyl, propionamido, methylcarbonylamino, dimethylaminoethoxycarbonyl, phosphinoyl, methylphosphinoyl, dimethylphosphinoyl, sulfonyl, methylsulfonyl, S-methyl-sulfonimidoyl, N,S-dimethyl-sulfonimidoyl, dimethylsulfoximinyl, methylsulfonoxyl, oxetanyl, oxetanyl-2-one, azetindin-2-yl, azetidin-3-yl-2-one, methylazetidin-3-yl-2-one, tetrahydrofuran-3-yl, or tetrahydropyran-4-yl.

11. The compound of claim 1, wherein each $R^3$ and $R^4$ is independently absent, methyl, methoxycarbonyl, or hydroxymethyl.

12. A compound selected from the group consisting of

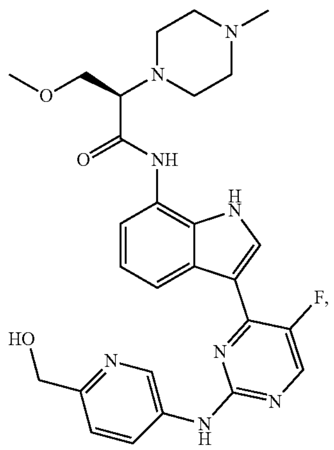

-continued

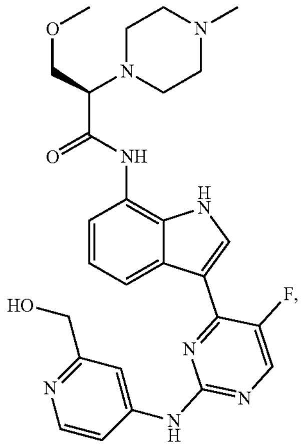

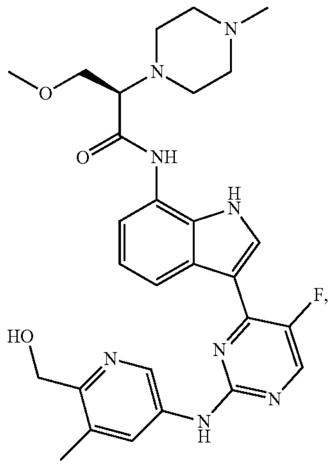

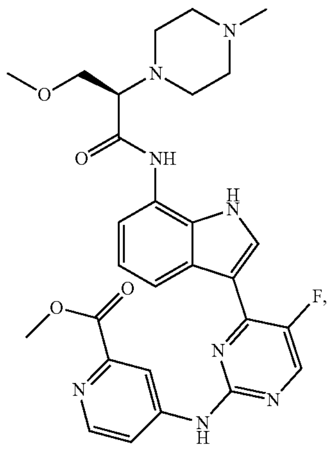

-continued
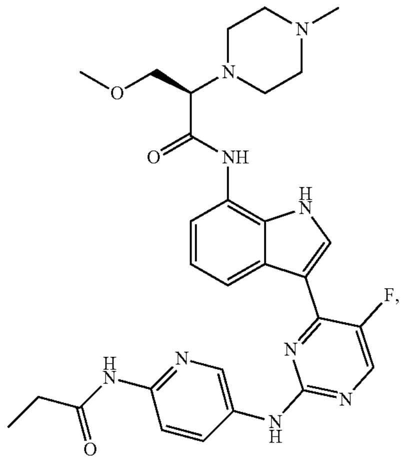
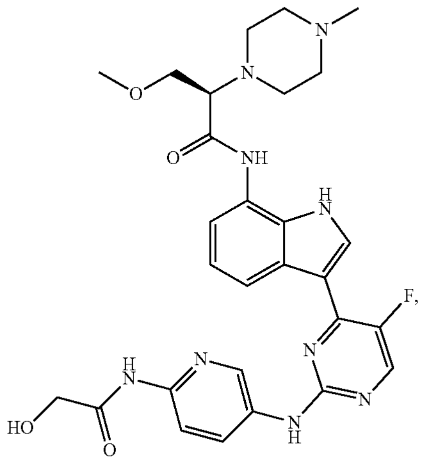
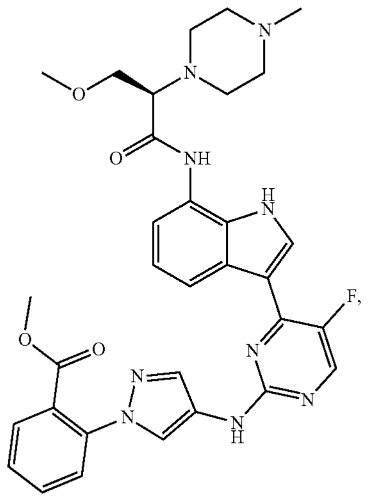
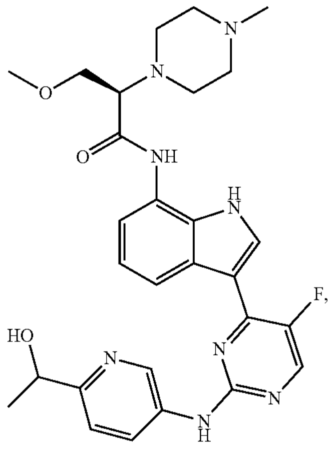
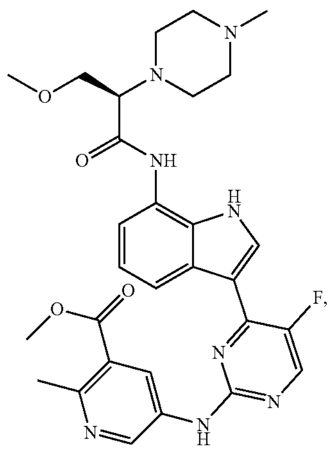
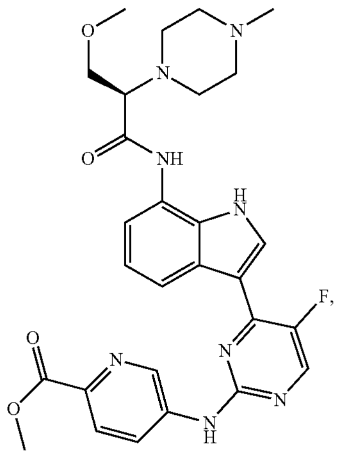

-continued
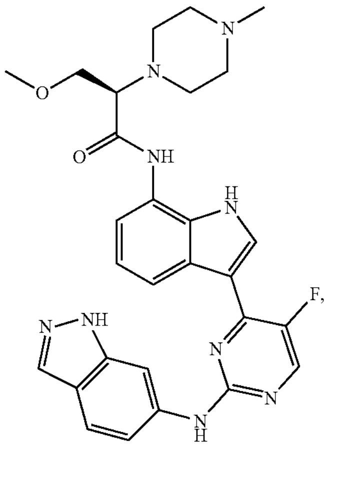
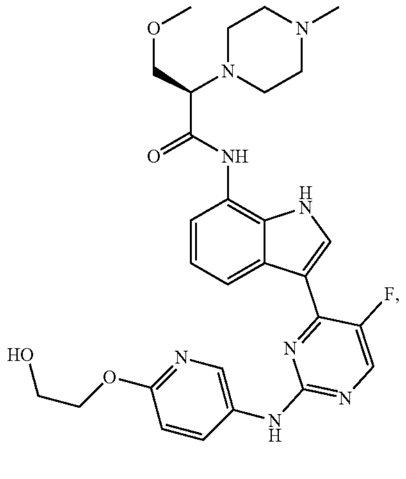
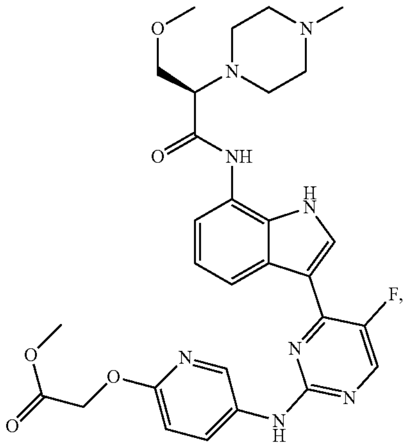
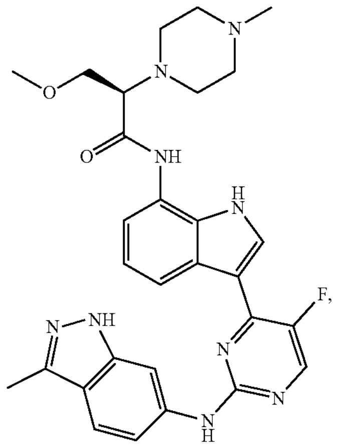
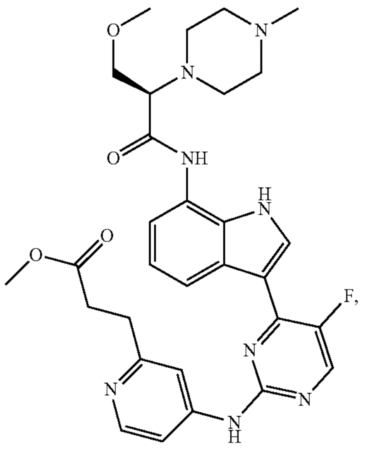
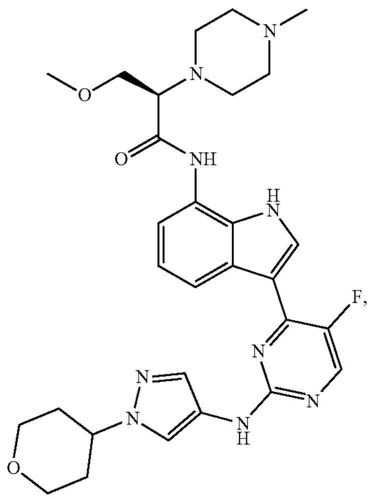

-continued
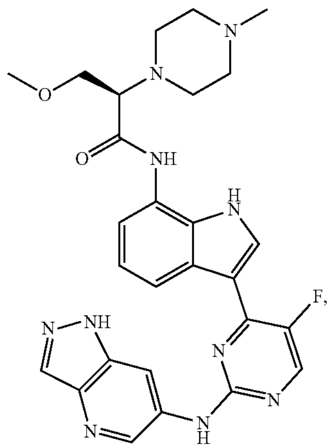
-continued
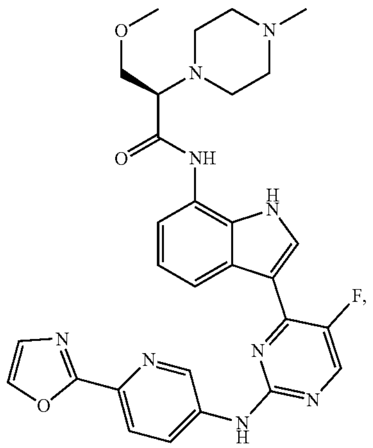
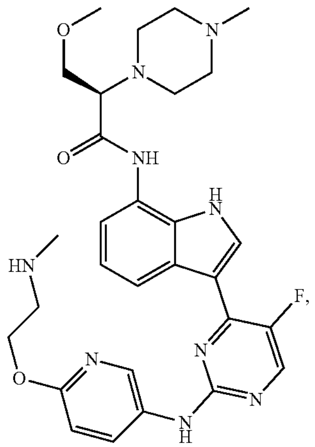
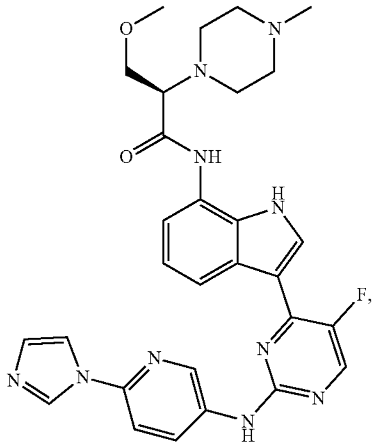
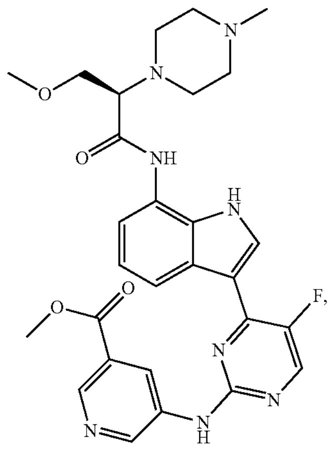
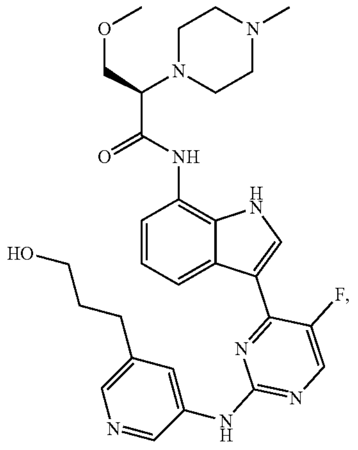

-continued
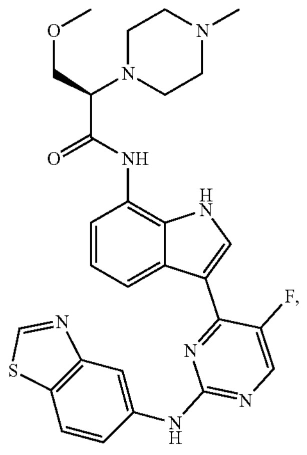
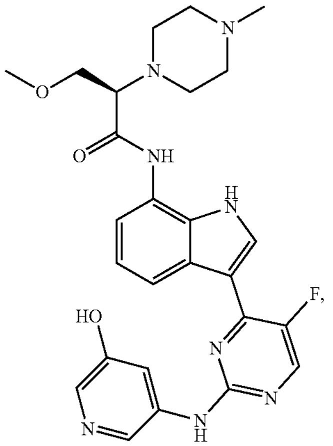
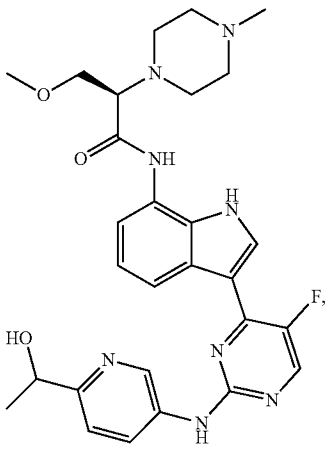
-continued
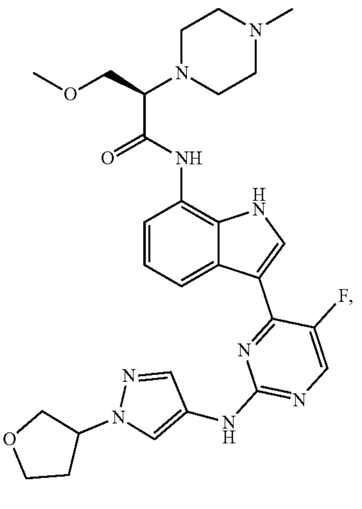
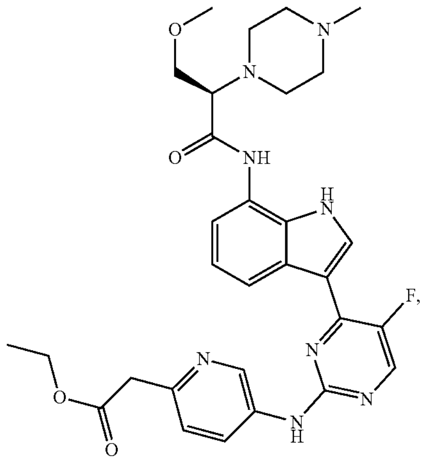
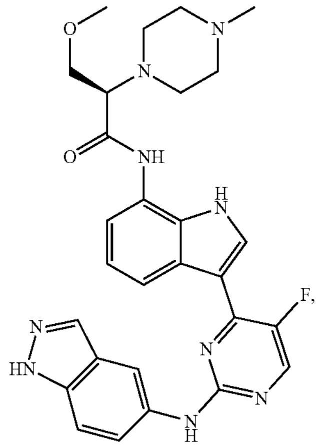

-continued
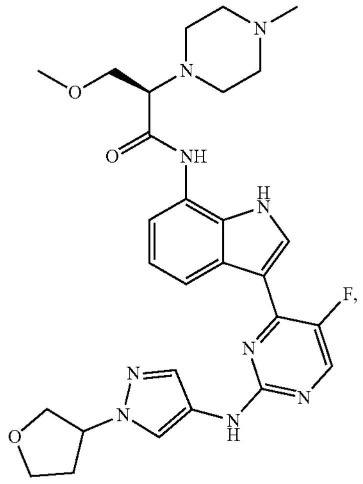
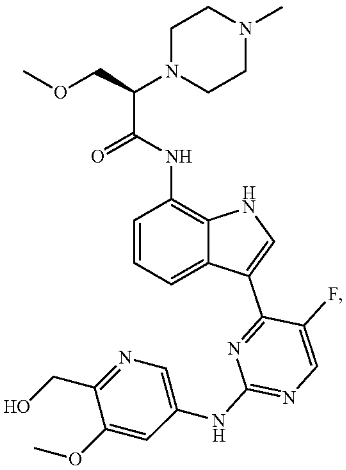
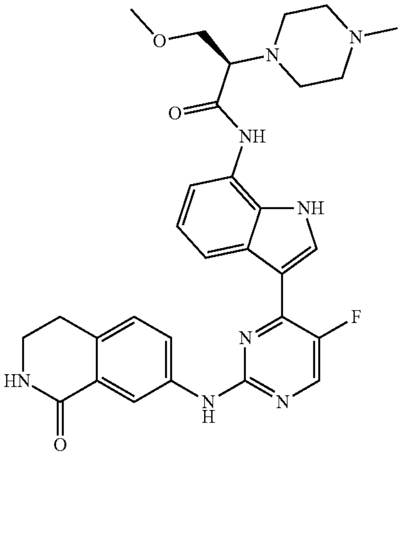
,
-continued
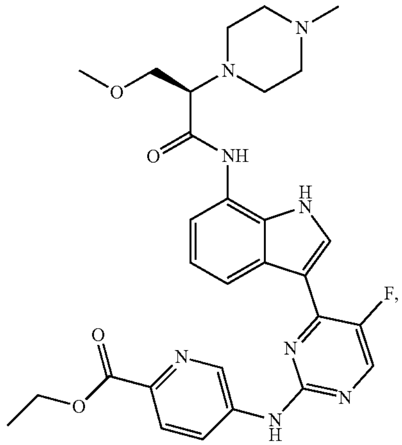
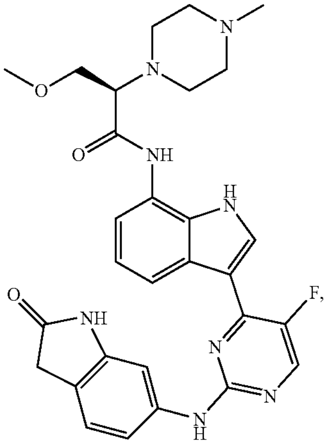
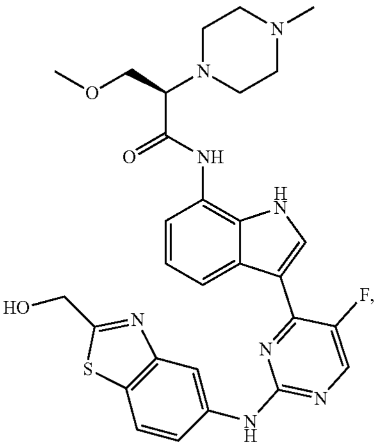

-continued
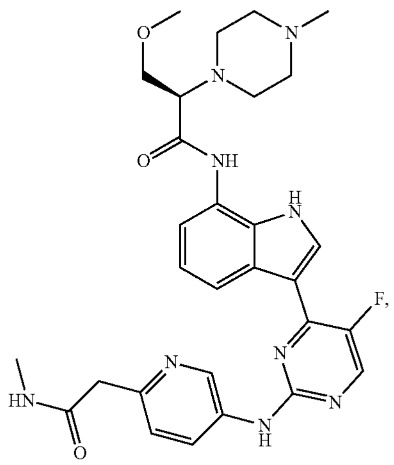
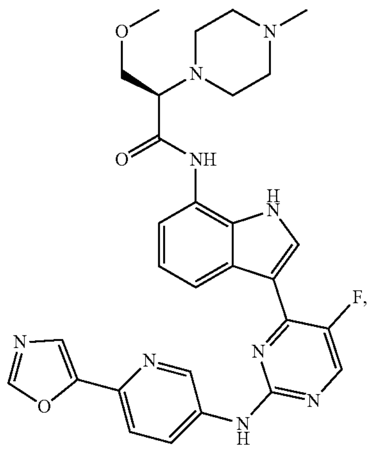
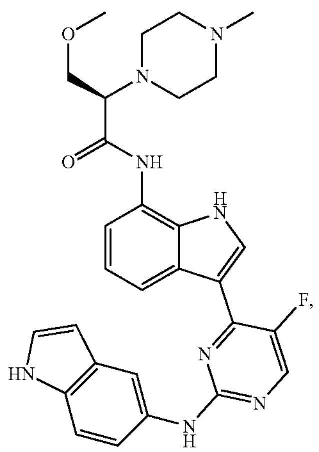
-continued
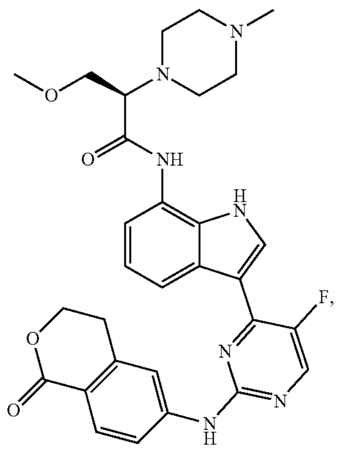
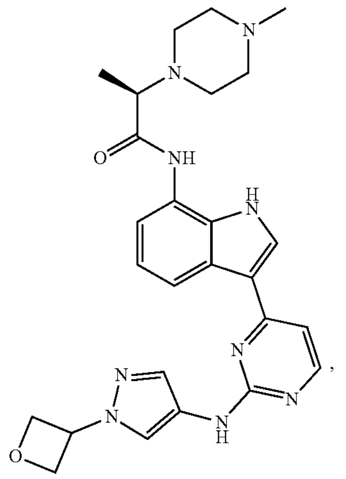
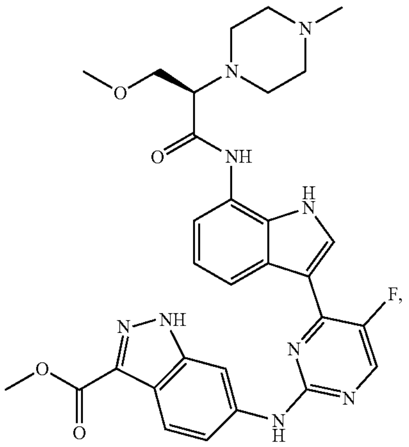

-continued
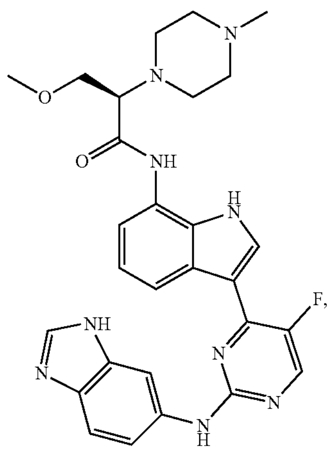
-continued
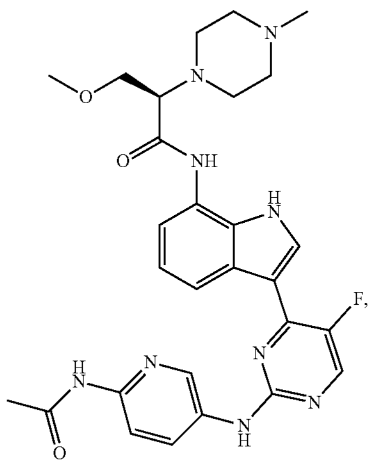
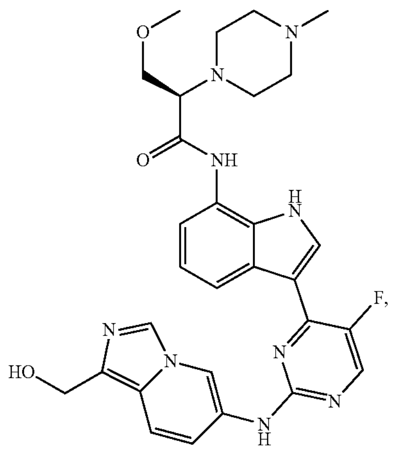
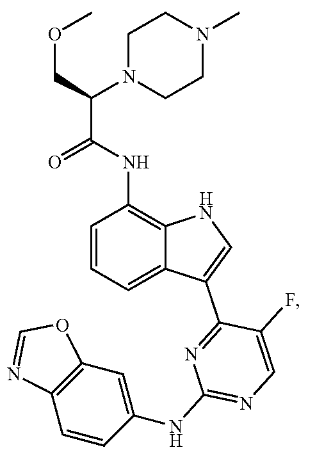
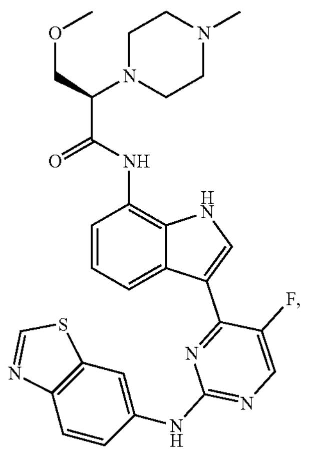
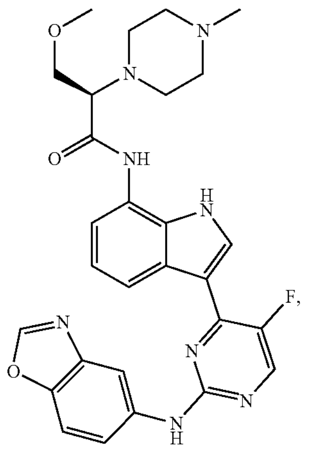

-continued
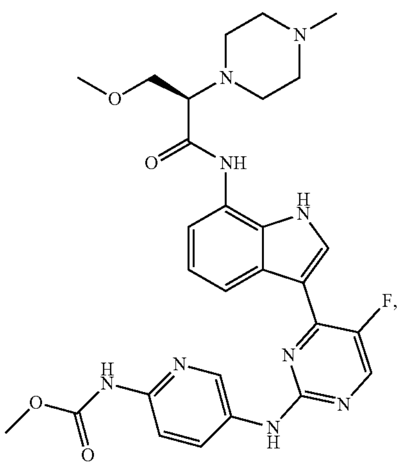
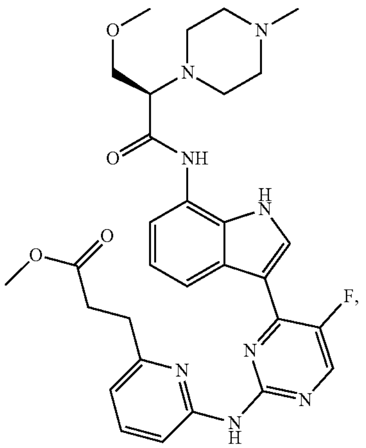
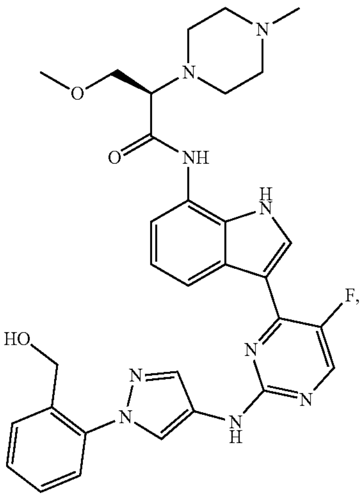
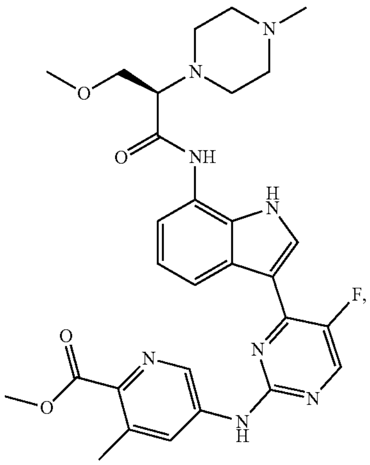
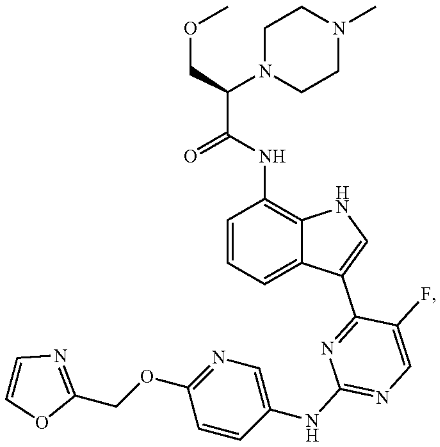
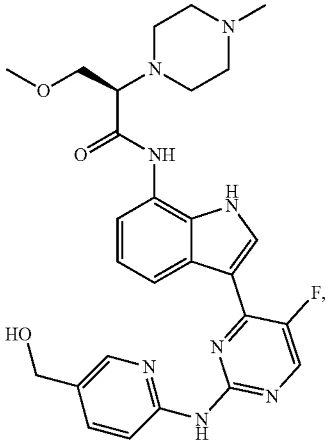

-continued
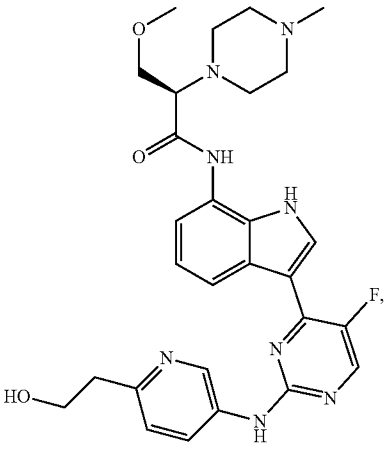
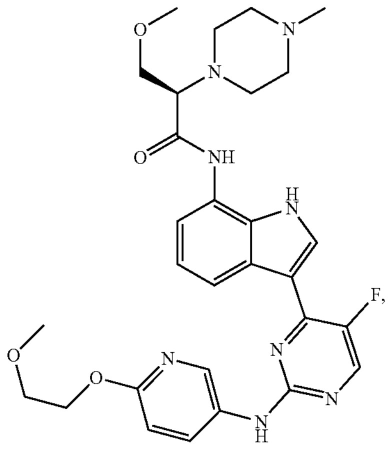
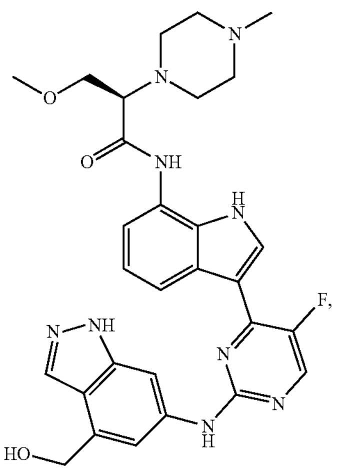
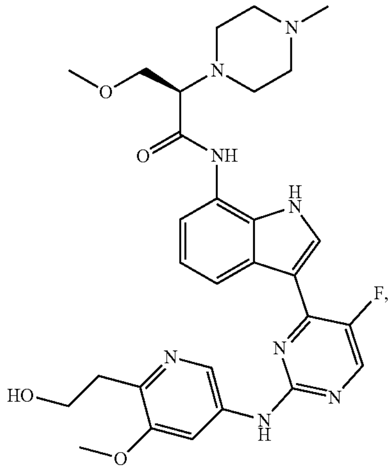
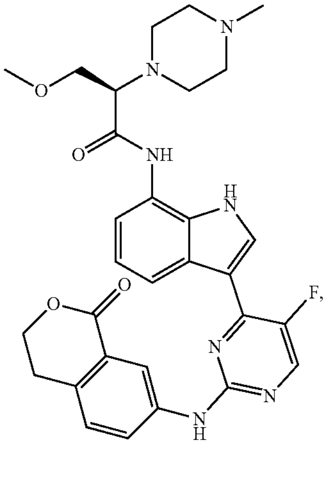
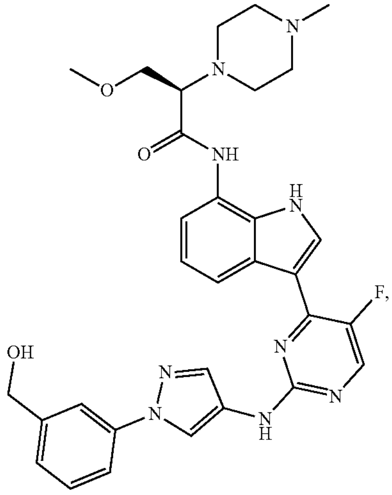
-continued -continued
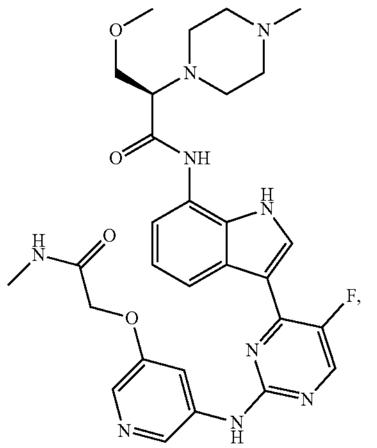
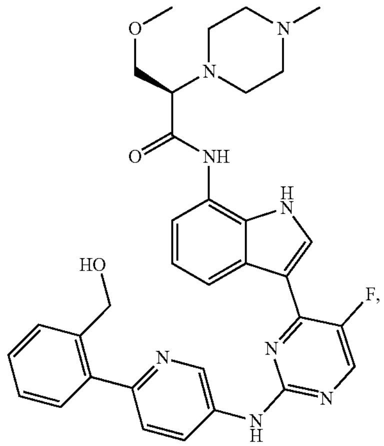
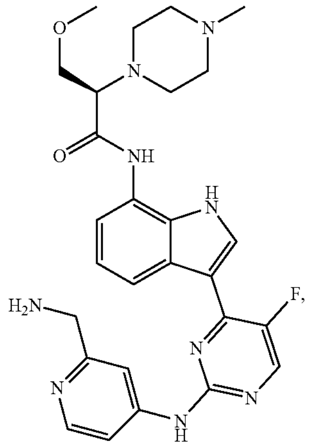
-continued
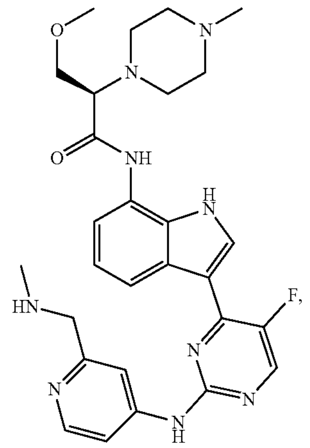
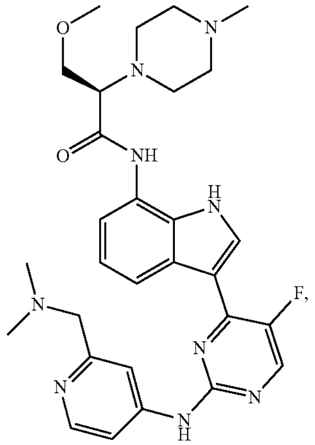
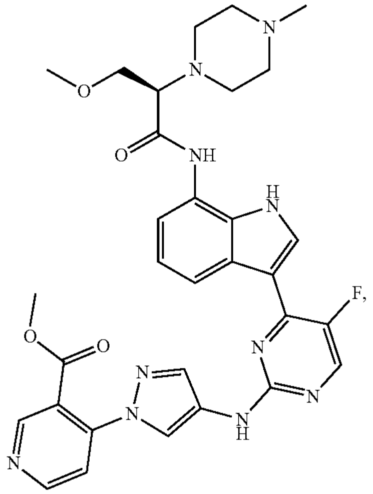

-continued

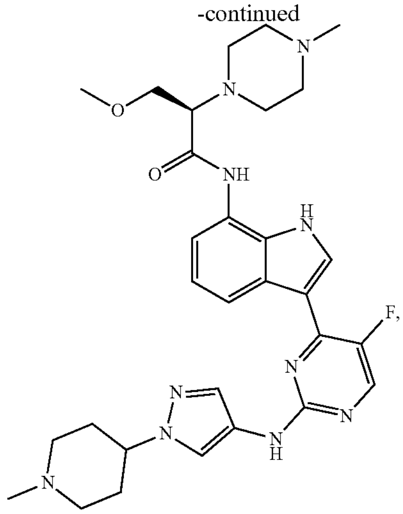

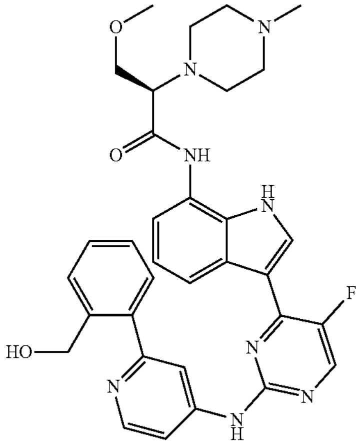

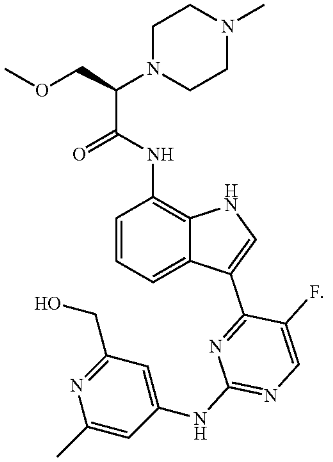 [SMILES: COC[C@H](C(=O)Nc1cccc2c(-c3nc(Nc4cc(C)nc(CO)c4)ncc3F)c[nH]c12)N1CCN(C)CC1]

or a pharmaceutically acceptable salt thereof.

13. The compound of Formula (I), or a pharmaceutically acceptable salt thereof, according to claim 1, in crystalline form.

14. A pharmaceutical composition comprising one or more compounds of Formula (I), or pharmaceutically acceptable salts thereof according to claim 1 as a first active ingredient, and a pharmaceutically acceptable diluent, excipient or carrier.

15. The pharmaceutical composition of claim 14, which is formulated for inhalation.

16. A compound of Formula (I), or a pharmaceutically acceptable salt thereof, according to claim 1, for use as a medicament for inhibiting JAK1.

17. A method of inhibiting JAK1 by using one or more compounds, or pharmaceutically acceptable salts thereof of claim 1.

18. A method of treating a JAK1-related disorder in a subject, comprising administering to the subject an effective amount of one or more compounds, or pharmaceutically acceptable salts thereof of claim 1, wherein the JAK1-related disorder is selected from the group of asthma, chronic constructive pulmonary disease (COPD), psoriasis, scleroderma, rheumatoid arthritis, psoriatic arthritis, juvenile arthritis, myelofibrosis, Castleman's disease, lupus nephritis, systemic lupus erythematosus, Sjogren's syndrome, multiple sclerosis, inflammatory bowel disease, leukemia, glioblastoma, melanoma, osteosarcoma, lymphoma, lung cancer, myeloma, hepatocellular carcinoma, pancreatic cancer, breast cancer, bladder cancer, gastric cancer, colon cancer, colorectal cancer, ovarian cancer, cervical cancer, brain cancer, head and neck cancers, and prostate cancer.

19. The method according to claim 18, wherein the subject is a man.

20. The method according to claim 19, wherein the JAK1-related disorder is asthma or COPD.

21. A combination comprising a compound of Formula (I), or pharmaceutically acceptable salt thereof, as claimed in claim 1, and a second therapeutic agent.

22. The pharmaceutical composition of claim 14, for use as a medicament for inhibiting JAK1.

23. A method of inhibiting JAK1 by using the pharmaceutical composition of claim 14.

24. A method of treating a JAK1-related disorder in a subject, comprising administering to the subject an effective amount of the pharmaceutical composition of claim 12, wherein the JAK1-related disorder is selected from the group consisting of ashtma, chronic obstructive pulmonary disease (COPD), psoriasis, scleroderma, rheumatoid arthritis, psoriatic arthritis, juvenile arthritis, myelofibrosis, Castleman's disease, lupus nephritis, systemic lupus erythematosus, Sjogren's syndrome, multiple sclerosis, inflammatory bowel disease, leukemia, glioblastoma, melanoma, osteosarcoma, lymphoma, lung cancer, myeloma, hepatocellular carcinoma, pancreatic cancer, breast cancer, bladder cancer, gastric cancer, colon cancer, colorectal cancer, ovarian cancer, cervical cancer, brain cancer, head and neck cancers, and prostate cancer.

25. The combination of claim 21, wherein the second therapeutic agent is an anti-inflammatory agent.

* * * * *